United States Patent
Gourdin et al.

(10) Patent No.: US 12,195,555 B2
(45) Date of Patent: Jan. 14, 2025

(54) NATURAL KILLER (NK) CELL ENGAGERS BINDING TO NKp46 AND BCMA VARIANTS WITH Fc-ENGINEERING

(71) Applicants: SANOFI, Paris (FR); INNATE PHARMA, Marseilles (FR)

(72) Inventors: Nicolas Gourdin, Marseilles (FR); Laurent Gauthier, Marseilles (FR); Alexandre Tang, Paris (FR); Marielle Chiron, Paris (FR); Angela Virone-Oddos, Paris (FR); Alessandro Masiero, Paris (FR); Jochen Beninga, Frankfurt am Main (DE); Ingo Focken, Frankfurt am Main (DE); Sambasiva Rao, Cambridge, MA (US); Yanfeng Zhou, Cambridge, MA (US); Leila Sevigny, Cambridge, MA (US)

( * ) Notice: Subject to any disclaimer, the term of this patent is extended or adjusted under 35 U.S.C. 154(b) by 0 days.

(21) Appl. No.: 18/469,947

(22) Filed: Sep. 19, 2023

(65) Prior Publication Data

US 2024/0034816 A1   Feb. 1, 2024

Related U.S. Application Data

(63) Continuation of application No. 18/202,590, filed on May 26, 2023.

(60) Provisional application No. 63/454,158, filed on Mar. 23, 2023, provisional application No. 63/487,470, filed on Feb. 28, 2023, provisional application No. 63/425,639, filed on Nov. 15, 2022, provisional application No. 63/416,081, filed on Oct. 14, 2022.

(30) Foreign Application Priority Data

May 27, 2022  (EP) ..................................... 22305783
Oct. 14, 2022  (EP) ..................................... 22306564

(51) Int. Cl.
C07K 16/46   (2006.01)
A61P 35/00   (2006.01)
C12N 15/63   (2006.01)

(52) U.S. Cl.
CPC ............ *C07K 16/468* (2013.01); *A61P 35/00* (2018.01); *C12N 15/63* (2013.01); *C07K 2317/14* (2013.01); *C07K 2317/31* (2013.01); *C07K 2317/41* (2013.01); *C07K 2317/522* (2013.01); *C07K 2317/524* (2013.01); *C07K 2317/526* (2013.01); *C07K 2317/53* (2013.01); *C07K 2317/565* (2013.01)

(58) Field of Classification Search
None
See application file for complete search history.

(56) References Cited

U.S. PATENT DOCUMENTS

| | | |
|---|---|---|
| 5,288,931 A | 2/1994 | Chang et al. |
| 6,177,078 B1 | 1/2001 | Lopez |
| 6,733,743 B2 | 5/2004 | Jordan |
| 7,112,660 B1 | 9/2006 | Domingues et al. |
| 7,220,829 B2 | 5/2007 | Rossjohn et al. |
| 7,435,549 B1 | 10/2008 | Kufer et al. |
| 7,651,678 B2 | 1/2010 | Jordan |
| 7,919,089 B2 | 4/2011 | Kufer et al. |
| 8,492,119 B2 | 7/2013 | Tawara et al. |
| 8,535,669 B2 | 9/2013 | Vairo et al. |
| 8,569,461 B2 | 10/2013 | Panousis |
| 8,609,149 B2 | 12/2013 | Callahan et al. |
| 8,790,645 B2 | 7/2014 | Kufer et al. |
| 8,852,551 B2 | 10/2014 | Jordan |
| 9,155,802 B2 | 10/2015 | Pedersen et al. |
| 9,217,039 B2 | 12/2015 | Pedersen et al. |
| 9,394,370 B2 | 7/2016 | Tawara et al. |
| 9,540,441 B2 | 1/2017 | Tawara et al. |
| 9,683,048 B2 | 6/2017 | Freeman et al. |
| 9,758,585 B2 | 9/2017 | Vairo et al. |
| 9,815,898 B2 | 11/2017 | Freeman et al. |
| 9,850,310 B2 | 12/2017 | Gaudet et al. |
| 9,879,087 B2 | 1/2018 | Desander et al. |
| 9,944,709 B2 | 4/2018 | Galetto |
| 10,005,832 B2 | 6/2018 | Yoshida et al. |
| 10,047,161 B2 | 8/2018 | Panousis |

(Continued)

FOREIGN PATENT DOCUMENTS

CN    105367657 A    3/2016
EP    1161453 A1    12/2001

(Continued)

OTHER PUBLICATIONS

Mariuzza, R.A. etal. The Structural Basis of Antigen-Antibody Recognition1 Annu. Rev. Biophys. Biphys. Chem. 16:139-159, 1987.*

MacCallum et al. "Antibody-antigen interactions: contact analysis and binding site topography", Journal of Molecular Biology, 1996. vol. 262, pp. 732-745.*

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*

(Continued)

*Primary Examiner* — Nora M Rooney
(74) *Attorney, Agent, or Firm* — LATHROP GPM LLP; James H. Velema, Esq.; Michael J. Spellberg, Esq.

(57) ABSTRACT

The present disclosure relates to multifunctional binding proteins comprising a first and a second antigen binding domains (ABDs) and all or part of an immunoglobulin Fc region or variant thereof, wherein the first ABD binds specifically to human BCMA and the second ABD binds specifically to human NKp46 and wherein all or part of the immunoglobulin Fc region or variant thereof bind to a human Fc-γ receptor.

The disclosure also relates to methods for making said binding proteins, compositions thereof, and their uses, including the treatment or prevention of proliferative disorders, including multiple myeloma (MM).

33 Claims, 42 Drawing Sheets

Specification includes a Sequence Listing.

(56) References Cited

U.S. PATENT DOCUMENTS

| | | |
|---|---|---|
| 10,113,003 B2 | 10/2018 | Gauthier et al. |
| 10,155,818 B2 | 12/2018 | Seibert et al. |
| 10,179,817 B2 | 1/2019 | Sagert et al. |
| 10,221,246 B2 | 3/2019 | Pedersen et al. |
| 10,280,226 B2 | 5/2019 | Seibert et al. |
| 10,508,150 B2 | 12/2019 | Jordan |
| 10,519,234 B2 | 12/2019 | Gauthier et al. |
| 10,611,814 B2 | 4/2020 | Bachmann et al. |
| 10,709,775 B2 | 7/2020 | Dusseaux |
| 11,001,629 B2 | 5/2021 | Gauthier et al. |
| 11,208,480 B2 | 12/2021 | Gauthier et al. |
| 11,267,897 B2 | 3/2022 | Gauthier et al. |
| 11,692,039 B2 | 7/2023 | Chiron et al. |
| 2003/0004547 A1 | 1/2003 | Sailer et al. |
| 2010/0209341 A1 | 8/2010 | Vairo et al. |
| 2011/0052574 A1 | 3/2011 | Dick et al. |
| 2012/0070448 A1 | 3/2012 | Tawara et al. |
| 2013/0230510 A1 | 9/2013 | Dick et al. |
| 2014/0086912 A1 | 3/2014 | Panousis |
| 2014/0154743 A1 | 6/2014 | Levy et al. |
| 2014/0178364 A1 | 6/2014 | Vairo et al. |
| 2015/0017180 A1 | 1/2015 | Vairo et al. |
| 2015/0132315 A1 | 5/2015 | Jordan |
| 2015/0152185 A1 | 6/2015 | Dick et al. |
| 2015/0307615 A1 | 10/2015 | Panousis |
| 2017/0029515 A1 | 2/2017 | Dick et al. |
| 2018/0079818 A1 | 3/2018 | Dick et al. |
| 2018/0244786 A1 | 8/2018 | Lopez et al. |
| 2019/0055315 A1 | 2/2019 | Gauthier et al. |
| 2019/0185573 A1 | 6/2019 | Wilson et al. |
| 2020/0031942 A1 | 1/2020 | Jordan |
| 2020/0048345 A1 | 2/2020 | Gauthier et al. |
| 2020/0131268 A1 | 4/2020 | Gauthier et al. |
| 2020/0207861 A1 | 7/2020 | Dick et al. |
| 2021/0269523 A1 | 9/2021 | Gauthier et al. |
| 2021/0388097 A1 | 12/2021 | Zhou et al. |
| 2022/0135676 A1 | 5/2022 | Gauthier et al. |
| 2022/0213202 A1 | 7/2022 | Amara et al. |
| 2023/0416383 A1 | 12/2023 | Chiron et al. |
| 2024/0117062 A1 | 4/2024 | Beninga et al. |

FOREIGN PATENT DOCUMENTS

| | | |
|---|---|---|
| EP | 1032660 B1 | 11/2009 |
| EP | 1263463 B1 | 5/2011 |
| EP | 2536468 A1 | 12/2012 |
| EP | 2626069 A1 | 8/2013 |
| EP | 2426148 B1 | 8/2015 |
| EP | 2778175 B1 | 3/2016 |
| EP | 2329847 B1 | 11/2016 |
| EP | 2635604 B1 | 11/2016 |
| EP | 2536430 B1 | 12/2016 |
| EP | 2436397 B1 | 5/2017 |
| EP | 2575444 B1 | 5/2017 |
| EP | 3189081 A1 | 7/2017 |
| EP | 1629013 B1 | 1/2018 |
| EP | 3156421 B1 | 6/2018 |
| EP | 2635605 B1 | 7/2018 |
| EP | 3097121 B1 | 12/2018 |
| EP | 3119807 B1 | 4/2019 |
| WO | WO 1997/024373 A1 | 7/1997 |
| WO | WO 1999/025818 A1 | 5/1999 |
| WO | WO 2000/047620 A1 | 8/2000 |
| WO | WO 2001/066139 A1 | 9/2001 |
| WO | WO 2004/106383 A1 | 12/2004 |
| WO | WO 2006/064136 A1 | 6/2006 |
| WO | WO 2009/070844 A1 | 6/2009 |
| WO | WO 2010/094068 A1 | 8/2010 |
| WO | WO 2010/126066 A1 | 11/2010 |
| WO | WO 2010/137654 A1 | 12/2010 |
| WO | WO 2011/100786 A1 | 8/2011 |
| WO | WO 2012/021934 A1 | 2/2012 |
| WO | WO 2012/059857 A2 | 5/2012 |
| WO | WO 2012/059858 A1 | 5/2012 |
| WO | WO 2012/089814 A1 | 7/2012 |
| WO | WO 2014/138805 A1 | 9/2014 |
| WO | WO 2014/138819 A1 | 9/2014 |
| WO | WO 2015/112900 A1 | 7/2015 |
| WO | WO 2015/184099 A1 | 12/2015 |
| WO | WO 2015/193406 A1 | 12/2015 |
| WO | WO 2015/197593 A1 | 12/2015 |
| WO | WO 2015/197598 A2 | 12/2015 |
| WO | WO 2016/030414 A1 | 3/2016 |
| WO | WO 2016/036937 A1 | 3/2016 |
| WO | WO 2016/077526 A1 | 5/2016 |
| WO | WO 2016/116626 A1 | 7/2016 |
| WO | WO 2016/120216 A1 | 8/2016 |
| WO | WO 2016/179257 A2 | 11/2016 |
| WO | WO 2016/201065 A1 | 12/2016 |
| WO | WO 2016/207098 A1 | 12/2016 |
| WO | WO 2016/207273 A2 | 12/2016 |
| WO | WO 2016/207278 A1 | 12/2016 |
| WO | WO 2017/083582 A1 | 5/2017 |
| WO | WO 2017/096179 A1 | 6/2017 |
| WO | WO 2017/096189 A1 | 6/2017 |
| WO | WO 2017/096276 A1 | 6/2017 |
| WO | WO 2017/096281 A1 | 6/2017 |
| WO | WO 2017/114694 A1 | 7/2017 |
| WO | WO 2017/160954 A1 | 9/2017 |
| WO | WO 2017/214433 A1 | 12/2017 |
| WO | WO 2019/101695 A1 | 5/2019 |
| WO | WO 2019/226617 A1 | 11/2019 |
| WO | WO 2022/200525 A1 | 9/2022 |
| WO | WO 2022/212470 A2 | 10/2022 |
| WO | WO 2022/258662 A1 | 12/2022 |

OTHER PUBLICATIONS

Goel et al. Plasticity within the Antigen-Combining Site May Manifest as Molecular Mimicry in the Humoral Immune Response. 1 J. Immunol. 173(12)7358-7367, 2004.*

Kahn et al. 'Adjustable Locks and Flexible Keys: Plasticity of Epitope-Paratope Interactions in Germline Antibodies.' J. Immunol. 192:5398-5405, 2014.*

Poosarla et al. 'Computational De Novo Design of Antibodies Binding to a Peptide With High Affinity.' Biotech. Bioeng. 114(6): 1331-1342, 2017.*

Alaoui-Ismaili, "Design of second generation therapeutic recombinant bone morphogenetic proteins", Cytokine Growth Factor Rev., 2009, 20(5-6): 501-507.

Almagro et al., Humanization of Antibodies, Frontiers in Bioscience, Jan. 2008, 13(5): 1619-1633.

Bachiller et al., "Natural Killer Cells in Immunotherapy: Are We Nearly There?", Cancers, 2020, 12(3139): 1-27.

Bernier et al., "Pharmacological chaperone action on G-protein-coupled receptors", Curr. Opin. Pharmacol., 2004, 4: 528-533.

Bhattacharya et al., "Impact of genetic variation on three dimensional structure and function of proteins", PLoS ONE, 2017, 12(3): e0171355.

Blanchard et al., "Multi-Specific Antibody Technology Engaging NK Cells in Oncology", PEGS Europe, 2018.

Cai et al, "C-terminal lysine processing of human immunoglobulin G2 heavy chain in vivo", Biotechnol. Bioeng. 2011, 108: 404-412.

Demaria , "Harnessing NK Cells in Cancer Therapies by Antibody-Based NK Cell Engager Therapeutics (ANKET)", PEGS Boston, May 4, 2022.

Demaria et al., "Natural killer cell engagers in cancer immunotherapy: Naxt generation of immuno-oncology treatments", Eur. J. Immunol., 2021, 51(8): 1934-1942.

Demaria, "Antitumor immunity induced by antibody-based NK cell engager therapeutics armed with not-alpha IL-2 variant", Cell Reports Medicine, Oct. 18, 2022, 3: 100783.

Dickopf et al., "Format and geometries matter: Structure-based design defines the functionality of bispecific antibodies", Computational and Structural Biotechnology Journal, May 14, 2020, 18: 1221-1227.

Dilillo et al., "A BCMAxCD3 bispecific T cell-engaging antibody demonstrates robust antitumor efficacy similar to that of anti-BCMA CAR T cells", Bllod Advances, Mar. 9, 2021, 5(5): 1291-1304.

(56) References Cited

OTHER PUBLICATIONS

Dondelinger et al., "Understanding the Significance and Implications of Antibody Numbering and Antigen-Binding Surface/Residue Definition", Frontiers in Immunology, Oct., 16, 2018, 9(2278): 1-15.
Ellwanger et al., "Redirected Optimized Cell Killing (Rock®): A highly versatile multispecific fit-for-purpose antibody platform for engaging innate immunity", MABS, Jun. 7, 2019, 11(5): 899-918.
Ernst et al., "Humanized anti-CD123 antibody facilitates NK cell antibody-dependent cell-mediated cytotoxicity (ADCC) of Hodgkin lymphoma targets via ARF6/PLD-1", Blood Cancer Journal, Jan. 15, 2019, 9(6): 1-11.
Extended European Search Report for European Patent Application No. 20306717.8, mailed Jun. 7, 2021.
Extended European Search Report for European Patent Application No. 22305783.7, mailed Nov. 7, 2022.
Extended European Search Report for European Patent Application No. 22305784.5, mailed Nov. 7, 2022.
Fleming et al., "Trifunctional antibodies unleash NK cells", Nature Reviews—Immunology, Jul. 2019, 19: 411.
Gantke et al., "AFM26—Targeting B Cell Maturation Antigen (BCMA) for NK Cell-Mediated Immunotherapy of Multiple Myeloma", Blood, 2017, 130(Suppl. 1): 3082.
Gauthier et al., "#852 Trifunctional NKp46/CD16a-NK cell engager targeting CD123 overcomes acute myeloid leukemia resistance to ADCC", Poster, SITC, Nov. 10-14, 2021.
Gauthier et al., "Abstract 852 Trifunctional NKp46/CD16a-NK cell engager targeting CD123 overcomes acute myeloid leukemia resistance to ADCC", Journal for Immuno Therapy of Cancer, Nov. 2021, 9(Suppl. 2): A893.
Gauthier et al., "Multifunctional Natural Killer Cell Engagers Targeting NKp46 Trigger Protective Tumor Immunity", Cell, Jun. 13, 2019, 177(7): 1701-1713, e16, ePublished May 30, 2019.
Gauthier et al., "Multifunctional Natural Killer Cell Engagers", PEGS Europe Summit, Engineering Biospecific Antibodies, Nov. 4, 2021.
Gauthier et al., "Poster #P776 Multifunctional Natural Killer Cell Engagers Targeting NKp46 Trigger Protective Tumor Immunity", SITC, 2019.
Guo et al., "Protein tolerance to random amino acid change", PNAS USA, 2004, 101(25): 9205-9210.
Hipp et al., "A novel BCMA/CD3 bispecific T-cell engager for the treatment of multiple lyeloma induces lysis in vitro and in vivo", Leukemia, Jan. 13, 2017, 31(8): 1743-1751, online preview Dec. 27, 2016.
Innate Pharma, "Innate's First NK Cell Engager Selected by Sanofi as Drug Candidate for Development", Press Release, Jan. 5, 2021.
International Search Report and Written Opinion for PCT International Patent Application No. PCT/EP2023/64282, mailed Aug. 28, 2023.
International Search Report and Written Opinion for PCT International Patent Application No. PCT/EP2023/64283, mailed Aug. 21, 2023.
International Search Report and Written Opinion for PCT International Patent Application No. PCT/IB2021/062494, mailed Mar. 29, 2022.
Jacobsen et al., "Engineering an IgG Scaffold Lacking Effector Function with Optimized Developability", The Journal of Biological Chemistry, Feb. 3, 2017, 292(5): 1865-1875.
Lazar et al, "Engineered antibody Fc variants with enhanced effector function", PNAS, 2006, vol. 103, No. 11, pp. 4005-4010.
Moraga et al., "Tuning cytokine receptor signaling by re-orienting dimer geometry with surrogate ligands", Cell, Mar. 12, 2015, 160(6): 1196-1208, ePublished Feb. 26, 2015.
Mullard, "FDA approves second BCMA-targeted CAR-T cell therapy", Nature Reviews, Drug Discovery, Apr. 2022, 21(4): 249.
Panowski et al., "Preclinical Efficacy and Safety Comparison of CD3 Bispecific and ADC Modalities Targeting BCMA for the Treatment of Multiple Myeloma", Molecular Cancer Therapeutics, Nov. 2019, 18(11): OF1-OF13, Epub. Aug. 21, 2019.
Shi et al., "A biparatopic agonistic antibody that mimics fibroblast growth factor 21 ligand activity", Journal of Biological Chemistry, Apr. 20, 2018, 293(16): 5909-5919, Published online Feb. 26, 2018.
Stein et al., "Novel conjugates of single-chain Fv antibody fragments specific for stem cell antigen CD123 mediate potent death of acute myeloid leukaemia cells", British Journal of Haematology, Mar. 1, 2010, 148(6): 879-889.
Sun et al., "Monoclonal Antibody 7G3 Recognizes the N-Terminal Domain of the Human Interleukin-3 (IL-3) Receptor a-Chain and Functions as a Specific IL-3 Receptor Antagonist", Blood, Jan. 1, 1996, 87(1): 83-92.
Tokuriki et al., "Stability effects of mutations and protein evolvability", Curr. Opin. Struc. Biol., 2009, 19: 596-604.
Uchanska-Ziegler et al., "Human Single-Chain Fv Fragments Specific for Natural Killer Cell Receptors from Phage Display Libraries", Methods in Molecular Biology, Feb. 2000, 121: 219-237.
Ulloa-Aguirre et al., "Pharmacologic rescue of conformationally-defective proteins: implications for the treatment of human disease", Traffic, 2004, 5: 821-837.
Vidarsson et al, "IgG subclasses and allotypes: from structure to effector functions", Frontiers in Immunology, 2014, vol. 5, Article 521, pp. 1-17.
Vivier, "Natural Killer Cell Engagers", FOCIS—Federation of Clinical Immunology Societies, Jun. 6, 2021.
Vivier, "Targeting Innate Immunity in Cancer", AACR, 2019.
Wang et al., "IgG Fc engineering to modulate antibody effector functions", Protein Cell 2018, vol. 9, No., 1, pp. 63-73.
Wang et al., "BCMA-targeting Bispecific Antibody That Simultaneously Simulates MKG2D-enhanced Efficacy Against Multiple Myeloma", Journal of Immunotherapy, Jul./Aug. 2020, 43(6): 175-188.
Watkins-Yoon et al., "CTX-8573, an Innate-Cell Engager Targeting BCMA, is a Highly Potent Multispecific Antibody for the Treatment of Multiple Myeloma", Blood, American Society of Hematology, Nov. 13, 2019, vol. 134, p. 3182.
Zhou et al., "The landscape of bispecific T cell engager in cancer treatment", Biomarker Research, 2021, 9(38): 1-23.
U.S. Appl. No. 18/324,668, filed May 26, 2023, Jochen Beninga, Anit-BCMA Antibodies.
U.S. Appl. No. 17/566,142 2022/0213202, U.S. Pat. No. 11,692,039, filed Dec. 30, 2021 Jul. 7, 2022 Jul. 4, 2023, Marielle Chiron, Multifunctional Natural Killer (NK) Cell Engagers Binding to NKp46 and CD123.
U.S. Appl. No. 18/308,778 2023/0416383, filed Apr. 28, 2023 Dec. 28, 2023, Marielle Chiron, Multifunctional Natural Killer (NK) Cell Engagers Binding to NKp46 and CD123.
U.S. Appl. No. 18/202,590, filed May 26, 2023, Nicolas Gourdin, Natural Killer (NK) Cell Engagers Binding to NKp46 and Bcma Variants with FC-Engineering.
U.S. Appl. No. 18/469,947 2024/0034816, filed Sep. 19, 2023 Feb. 1, 2024, Nicolas Gourdin, Natural Killer (NK) Cell Engagers Binding to NKp46 and Bcma Variants with FC-Engineering.
U.S. Appl. No. 18/324,668 2024/0117062, filed May 26, 2023 Apr. 11, 2024, Jochen Beninga, Anit-BCMA Antibodies.
Affimed N.V., "Affimed Announces Presentation of Data on Genentech's RO7297089 and AFM24, Both Innate Cell Engagers Developed from Affimed's ROCK® Platform, at AACR Virtual Annual Meeting II", Jun. 22, 2020, Heidelberg, Germany.
Draghi et al., "A Novel Class of Innate Cell Engagers targeting NKp30", Compass Therapeutics, SITC, Nov. 12, 2019.
Draghi et al., "Preclinical characterization of NKp30xBCMA, a novel class of NK-Cell Engagers", Compass Therapeutics, AACR Annual Meeting, Mar. 25, 2019.
Draghi, "A Novel Class of NK-Engagers Targeting NKp30", Compass Therapeutics, Keystone Cancer Immunology Symposium, Mar. 25, 2019, Poster #1010.
Ellwanger et al., "Redirected Optimized Cell Killing (Rock®): A novel multispecific antibody platform for innate immune cell engagement to fight cancer", Oct. 2, 2019, Poster 159.
Gantke et al., "AFM26—Targeting B Cell Maturation Antigen (BCMA) for NK Cell-Mediated Immunotherapy of Multiple Myeloma", 59th ASH Annual Meeting, Dec. 9-12, 2017, Poster 3082.

(56) References Cited

OTHER PUBLICATIONS

Kakiuchi-Kiyota et al., "Abstract 4556: Preclinical pharmacology and safety of RO7297089, a novel anti-BCMA/CD16a bispecific antibody for the treatment of multiple myeloma", Conference Paper: Proceedings: AACR Annual Meeting 2020, Apr. 27-28, 2020 and Jun. 22-24, 2020, Cancer Research, Aug. 2020, 80(16_Supplement): 4556.

Plesner et al., "A Phase I Study of RO7297089, a B-Cell Maturation Antigen (BCMA)-CD16a Bispecific Antibody in Patients with Relapsed/Refractory Multiple Myeloma", ASH Annual Meeting, Dec. 9-12, 2021, Hybrid Format, Poster #2755.

Sanofi, "Core Study Information and Informed Consent Form for SAR445514-TCD17710, First-in-human, open-label Phase 1/2 study to investigate safety and efficacy of SAR445514, an NK cell engager (NKCE) targeting B-cell maturation antigen (BCMA) in monotherapy in participants with relapsed/refractory multiple myeloma (RRMM) and in relapsed/refractory light-chain amyloidosis (RRLCA)", Jan. 22, 2024, Version 2.

Seattle Genetics, Inc., "Seattle Genetics Initiates Phase 1 Clinical Trial of SEA-BCMA for Patients with Relapsed or Refractory Multiple Myeloma", Business Wire, Nov. 14, 2018.

\* cited by examiner

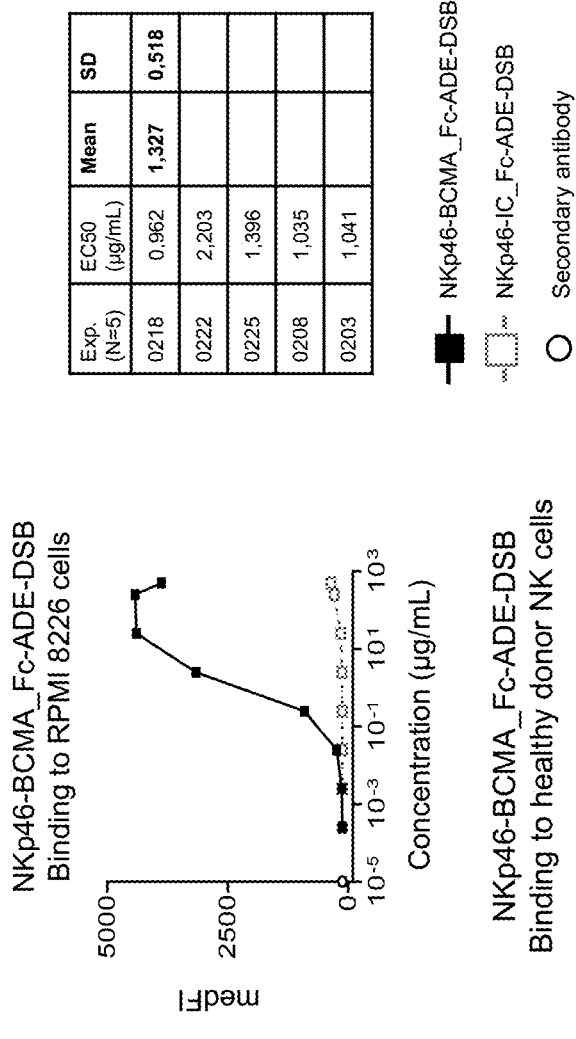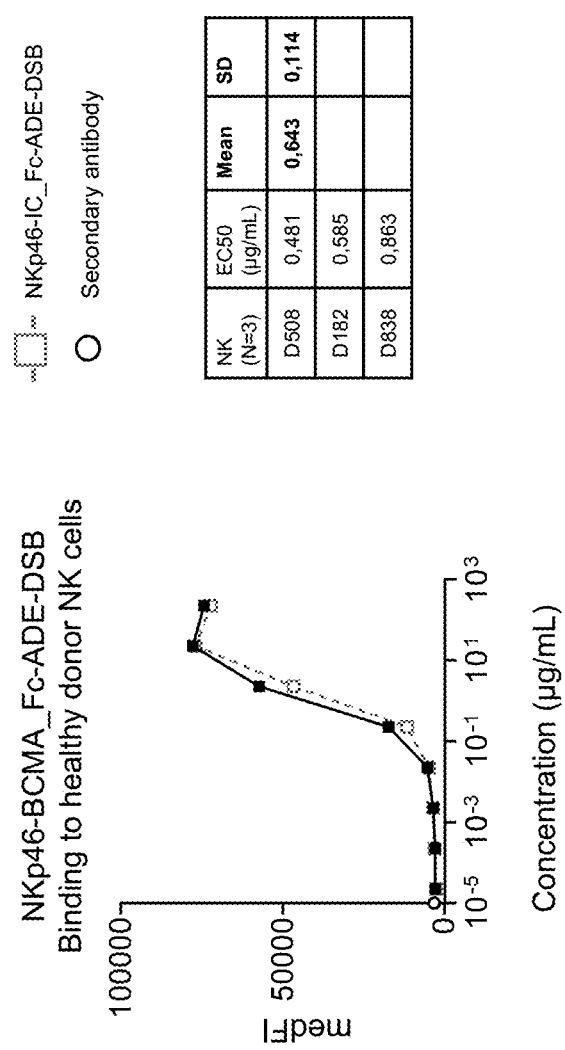
FIG. 3A
FIG. 3B

| Alias | TPP ID | Batch ID | Binding to huCD16a (V176) KD [nM] | Binding to huCD16a (F176) KD [nM] |
|---|---|---|---|---|
| CODV-OL1 | TPP-24383 | EFF-20-017-1 | 705 ± 214 | 1265 ± 287 |
| CODV-OL1-DE | TPP-30387 | FF-20-823-1 | 66 ± 25 | 67.2 ± 11 |
| CODV-OL1-ADE | TPP-24602 | FF-20-821-1 | 113 ± 40 | 87.5 ± 6 |
| CODV-OL1-DE-DSB | TPP-31740 | FF-20-853-1 | 110 | 113 |
| CODV-OL1-ADE-DSB | TPP-31741 | FF-20-854-1 | 165 | 121 |
| CODV-OL1-*afuc* | TPP-24383 | EFF-20-018-1 | 109 ± 27 | 185 ± 72 |
| CODV | TPP-24387 | EFF-20-019-1 | 618 ± 59 | 1376 ± 456 |
| CODV-DE | TPP-30388 | FF-20-824-1 | 87 ± 48 | 63.5 |
| CODV-ADE | TPP-24606 | FF-20-822-1 | 116 ± 37 | 86.9 |
| CODV-DE-DSB | TPP-31742 | FF-20-855-1 | 87 | 80.4 ± 9 |
| CODV-ADE-DSB | TPP-31743 | FF-20-856-1 | 155 | 114 |
| CODV-*afuc* | TPP-24387 | EFF-20-020-1 | 162 ± 19 | 279 ± 154 |
| Adalimumab huIgG1 ctrl | - | - | 467 | n.a. |

FIG. 4

| Format | TPP ID | Batch ID | Binding to huFcRn (KD) at pH6.0 (nM) |
|---|---|---|---|
| CODV-OL1 | TPP-24383 | EFF-20-017-1 | 467 |
| CODV-OL1-DE | TPP-30387 | FF-20-823-1 | 547 |
| CODV-OL1-ADE | TPP-24602 | FF-20-821-1 | 544 |
| CODV-OL1-DE-DSB | TPP-31740 | FF-20-853-1 | 689 |
| CODV-OL1-ADE-DSB | TPP-31741 | FF-20-854-1 | 756 |
| CODV-OL1-*afuc* | TPP-24383 | EFF-20-018-1 | 485 |
| CODV | TPP-24387 | EFF-20-019-1 | 417 |
| CODV-DE | TPP-30388 | FF-20-824-1 | 536 |
| CODV-ADE | TPP-24606 | FF-20-822-1 | 535 |
| CODV-DE-DSB | TPP-31742 | FF-20-855-1 | 697 |
| CODV-ADE-DSB | TPP-31743 | FF-20-856-1 | n.d. |
| CODV-*afuc* | TPP-24387 | EFF-20-020-1 | 342 |
| Adalimumab huIgG1 ctrl | - | - | 154 |

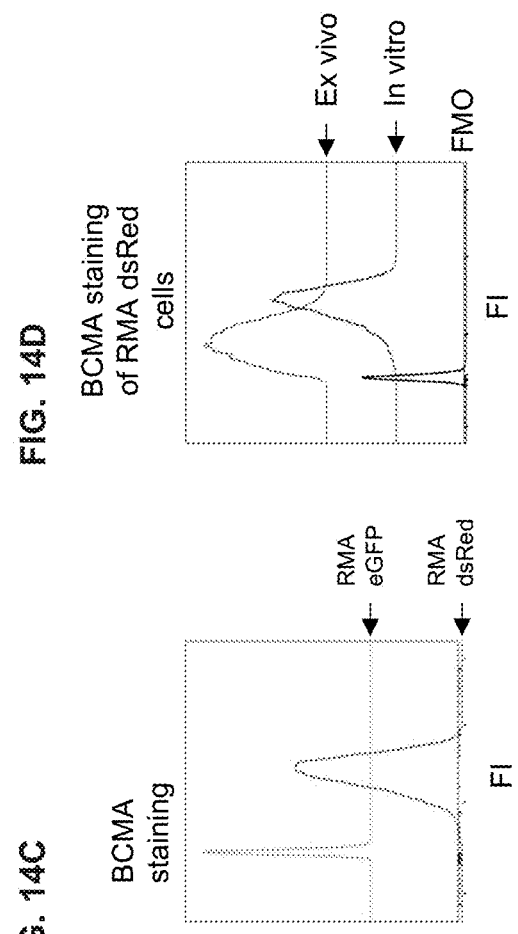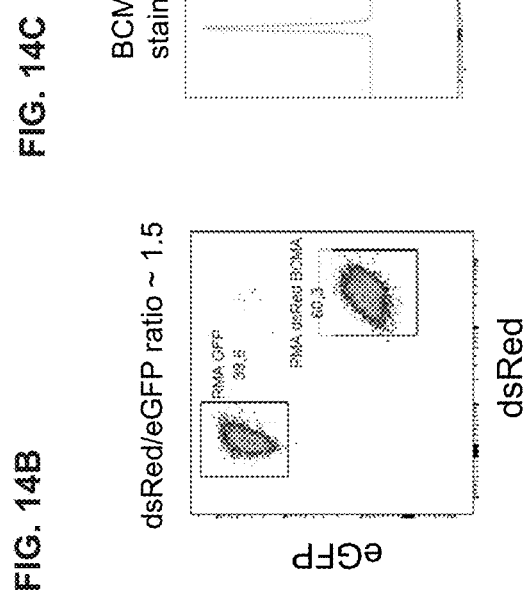

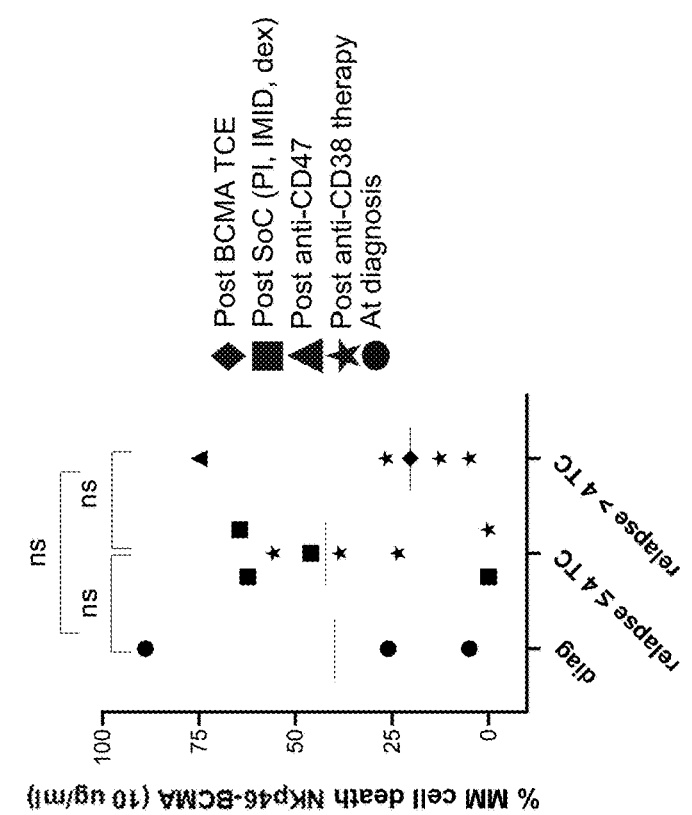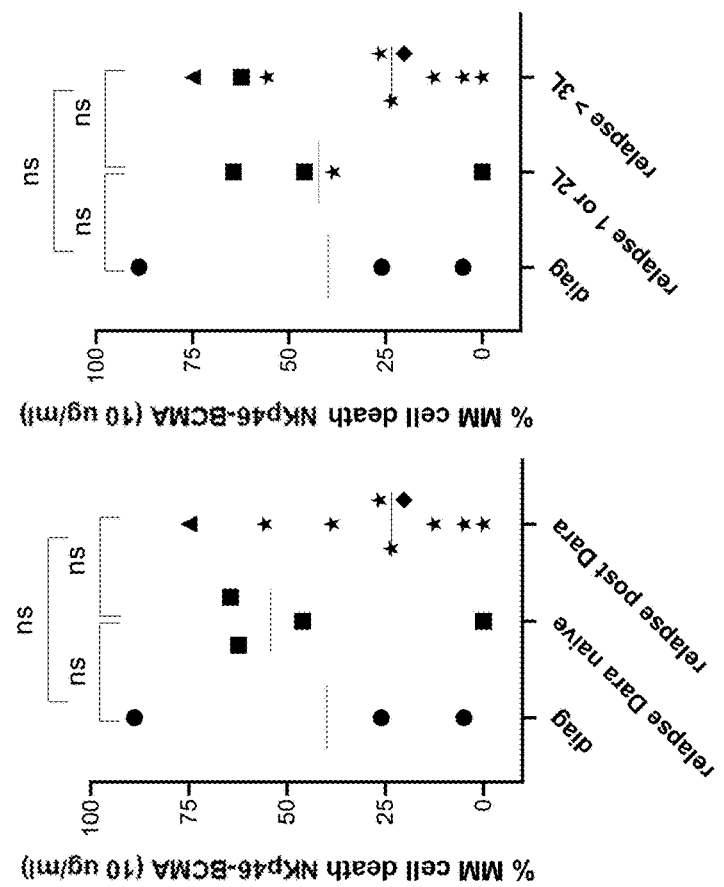

FIG. 20 Kaplan-Meier curves for NKp46-BCMA Fc WT CODV-OL1 and control bispecific antibodies in huNKp46-Tg x Rag mice bearing disseminated EL4-huBCMA tumor cells Kaplan-Meier curves for surrogate muNKp46-huBCMA Fc WT and Fc-ADE CODV-OL1 in huFcgR-Tg mice bearing disseminated EL4-huBCMA tumor cells

NATURAL KILLER (NK) CELL ENGAGERS BINDING TO NKp46 AND BCMA VARIANTS WITH Fc-ENGINEERING

RELATED APPLICATIONS

This application is a continuation of U.S. patent application Ser. No. 18/202,590, filed May 26, 2023, which claims priority to U.S. Provisional Patent Application Ser. No. 63/454,158, filed Mar. 23, 2023, 63/487,470, filed Feb. 28, 2023, 63/425,639, filed Nov. 15, 2022, and 63/416,081, filed Oct. 14, 2022, and European Patent Application Nos. 22306564.0, filed Oct. 14, 2022, and 22305783.7, filed May 27, 2022, the entire disclosures of which are hereby incorporated herein by reference.

SEQUENCE LISTING

The instant application contains a Sequence Listing which has been submitted electronically in XML format and is hereby incorporated by reference in its entirety. Said XML file, created on Sep. 18, 2023, is named 746442_SA9-327CON_ST26.xml and is 102,736 bytes in size.

BACKGROUND

B Cell Maturation Antigen (BCMA) has been implicated in the progression of several B cell cancers (e.g., multiple myeloma) and B cell diseases or disorders (e.g., light chain amyloidosis, or LCA), being expressed on mature B cells and B cell-derived tumor cells. BCMA is thus an attractive target for anti-B cell cancer therapy and therapy for B cell related diseases or disorders. None-the-less, many existing BCMA-targeting therapies, such as anti-CD3×BCMA T cell engagers, elicit potent toxicity issues, such as excessive pro-inflammatory cytokine release.

Natural killer (NK) cells are a subpopulation of lymphocytes that are involved in innate immunity. NK cells provide an efficient immunosurveillance mechanism by which undesired cells such as tumor or virally-infected cells can be eliminated. Characteristics and biological properties of NK cells include the expression of surface antigens including CD16, CD56 and/or CD57, the absence of the $\alpha/\beta$ or $\gamma/\delta$ TCR complex on the cell surface, the ability to bind to and kill cells in a MHC-unrestrictive manner and in particular cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate the immune response. Interest has been growing around natural killer (NK) cells due to their potential anti-tumor properties.

There exists a need in the art for potent anti-BCMA therapies with manageable safety profiles. The instantly claimed anti-BCMA×NKp46 binding proteins provide this need.

SUMMARY

The disclosure relates to multifunctional binding proteins comprising a first and a second antigen binding domains (ABDs) and all or part of an immunoglobulin Fc region or variant thereof, wherein the first ABD binds specifically to human BCMA and the second ABD binds specifically to human NKp46 and wherein all or part of the immunoglobulin Fc region or variant thereof to a human Fc-γ receptor. Particularly, the NKp46-BCMA engagers disclosed have extensive Fc engineering that enhances ADCC activity (via CD16 (FcγRIIIa) binding to constant region (Fc) of antibodies) and/or serum half-life.

The NKp46-BCMA engagers disclosed show a strong potency through the dual NK engagement with NKp46 and CD16, with a good safety profile (minimal pro-inflammatory cytokine release as compared to a T cell engager (TCE) modality) and a long serum half-life.

The disclosure also relates to methods for making said binding proteins, compositions thereof, and their uses.

In one aspect, the disclosure provides a binding protein comprising a first antigen binding domain (ABD) with binding specificity to BCMA and a second ABD with binding specificity to NKp46, wherein:

(a) the first ABD comprises: (a1) a first immunoglobulin heavy chain variable domain (VH1) comprising an HCDR1 sequence comprising the amino acid sequence of GFTFSNFGMH (SEQ ID NO: 1), an HCDR2 sequence comprising the amino acid sequence of VIWSDETNR (SEQ ID NO: 2), and an HCDR3 sequence comprising the amino acid sequence of DQQYCSSDSCFTWFDP (SEQ ID NO: 3); and (a2) a first immunoglobulin light chain variable domain (VL1) comprising an LCDR1 sequence comprising the amino acid sequence of CX$^1$SSTGX$^2$VTPX$^3$X$^4$YAN (SEQ ID NO: 4), wherein X$^1$ is R or A, X$^2$ is T or A, X$^3$ is S or G, and X$^4$ is N or Y, an LCDR2 sequence comprising the amino acid sequence of DNNX$^5$X$^6$PP (SEQ ID NO: 5), wherein X$^5$ is S, I, or N and X$^6$ is R or K, and an LCDR3 sequence comprising the amino acid sequence of ALX$^7$X$^8$GX$^9$QWV (SEQ ID NO: 6), wherein X$^7$ is W or Y, X$^8$ is F or Y, and X$^9$ is N or G; and (b) the second ABD comprises binding specificity to NKp46.

In certain embodiments, (b) the second ABD comprises:

(b1) a second immunoglobulin heavy chain variable domain (VH2) comprising:

an HCDR1 sequence comprising DYVIN (SEQ ID NO: 80), an HCDR2 sequence comprising EIYPGSGTNYYNEKFKA (SEQ ID NO: 81), and an HCDR3 sequence comprising RGRYGLYAMDY (SEQ ID NO: 21); —an HCDR1 sequence comprising GYTFSDYVIN (SEQ ID NO: 19), an HCDR2 sequence comprising EIYPGSGTN (SEQ ID NO: 20), and an HCDR3 sequence comprising RGRYGLYAMDY (SEQ ID NO: 21); —an HCDR1 sequence comprising SDYAWN (SEQ ID NO: 22), an HCDR2 sequence comprising YITYSGSTSYNPSLES (SEQ ID NO: 23), and an HCDR3 sequence comprising GGYYGSSWGVFAY (SEQ ID NO: 24); —an HCDR1 sequence comprising EYTMH (SEQ ID NO: 25), an HCDR2 sequence comprising GISPNIGGTSYNQKFKG (SEQ ID NO: 26), and an HCDR3 sequence comprising RGGSFDY (SEQ ID NO: 27); —an HCDR1 sequence comprising SFTMH (SEQ ID NO: 28), an HCDR2 sequence comprising YINPSSGYTEYNQKFKD (SEQ ID NO: 29), and an HCDR3 sequence comprising GSSRGFDY (SEQ ID NO: 30); or —an HCDR1 sequence comprising SDYAWN (SEQ ID NO: 31), an HCDR2 sequence comprising YITYSGSTNYNPSLKS (SEQ ID NO: 32), and an HCDR3 sequence comprising CWDYALYAMDC (SEQ ID NO: 33); and (b2) a second immunoglobulin light chain variable domain (VL2) comprising:

an LCDR1 sequence comprising RASQDISNYLN (SEQ ID NO: 34), an LCDR2 sequence comprising YTSRLHS (SEQ ID NO: 35), and an LCDR3 sequence comprising QQGNTRPWT (SEQ ID NO: 36); —an LCDR1 sequence comprising RVSENIYSYLA (SEQ ID NO: 37), an LCDR2 sequence comprising NAKTLAE (SEQ ID NO: 38), and an LCDR3 sequence comprising QHHYGTPWT (SEQ ID NO: 39); —an LCDR1 sequence comprising RASQSISDYLH (SEQ ID NO: 40), an LCDR2 sequence comprising YASQSIS (SEQ ID NO: 41), and an LCDR3 sequence comprising QNGHSFPLT (SEQ ID NO: 42); —an LCDR1 sequence comprising RASENIYSNLA (SEQ ID NO: 43), an LCDR2 sequence comprising AATNLAD (SEQ ID NO: 44), and an LCDR3 sequence comprising QHFWGTPRT (SEQ ID NO: 45); or —an LCDR1 sequence comprising RTSENIYSYLA (SEQ ID NO: 46), an LCDR2 sequence comprising NAKTLAE (SEQ ID NO: 47), and an LCDR3 sequence comprising QHHYDTPLT (SEQ ID NO: 48).

In certain embodiments, the VL1 comprises: —an LCDR1 sequence comprising the amino acid sequence of CASSTGTVTPSNYAN (SEQ ID NO: 7), an LCDR2 sequence comprising the amino acid sequence of DNNSRPP (SEQ ID NO: 8), and an LCDR3 sequence comprising the amino acid sequence of ALWFGNQWV (SEQ ID NO: 9); —an LCDR1 sequence comprising the amino acid sequence of CRSSTGTVTPSNYAN (SEQ ID NO: 10), an LCDR2 sequence comprising the amino acid sequence of DNNSRPP (SEQ ID NO: 11), and an LCDR3 sequence comprising the amino acid sequence of ALWFGNQWV (SEQ ID NO: 12); —an LCDR1 sequence comprising the amino acid sequence of CASSTGAVTPSNYAN (SEQ ID NO: 13), an LCDR2 sequence comprising the amino acid sequence of DNNIKPP (SEQ ID NO: 14), and an LCDR3 sequence comprising the amino acid sequence of ALWYGGQWV (SEQ ID NO: 15); or —an LCDR1 sequence comprising the amino acid sequence of CASSTGAVTPGYYAN (SEQ ID NO: 16), an LCDR2 sequence comprising the amino acid sequence of DNNNKPP (SEQ ID NO: 17), and an LCDR3 sequence comprising the amino acid sequence of ALYYGGQWV (SEQ ID NO: 18).

In certain embodiments: —the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 55; —the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 50; —the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 51; —the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 52; —the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 53; or —the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 54.

In certain embodiments: —the VH1 comprises an amino acid sequence of SEQ ID NO: 49, and wherein the VL1 comprises an amino acid sequence of SEQ ID NO: 55; —the VH1 comprises an amino acid sequence of SEQ ID NO: 49, and wherein the VL1 comprises an amino acid sequence of SEQ ID NO: 50; —the VH1 comprises an amino acid sequence of SEQ ID NO: 49, and wherein the VL1 comprises an amino acid sequence of SEQ ID NO: 51; —the VH1 comprises an amino acid sequence of SEQ ID NO: 49, and wherein the VL1 comprises an amino acid sequence of SEQ ID NO: 52; —the VH1 comprises an amino acid sequence of SEQ ID NO: 49, and wherein the VL1 comprises an amino acid sequence of SEQ ID NO: 53; or —the VH1 comprises an amino acid sequence of SEQ ID NO: 49, and wherein the VL1 comprises an amino acid sequence of SEQ ID NO: 54.

In certain embodiments: —the VH2 comprises an amino acid sequence that is at least about 90% identical to the amino acid sequence of SEQ ID NO: 56, and wherein the VL2 comprises an amino acid sequence that is at least about 90% identical to the amino acid sequence of SEQ ID NO: 64; —the VH2 comprises an amino acid sequence that is at least about 90% identical to the amino acid sequence of SEQ ID NO: 57, and wherein the VL2 comprises an amino acid sequence that is at least about 90% identical to the amino acid sequence of SEQ ID NO: 65; —the VH2 comprises an amino acid sequence that is at least about 90% identical to the amino acid sequence of SEQ ID NO: 58, and wherein the VL2 comprises an amino acid sequence that is at least about 90% identical to the amino acid sequence of SEQ ID NO: 66; —the VH2 comprises an amino acid sequence that is at least about 90% identical to the amino acid sequence of SEQ ID NO: 59, and wherein the VL2 comprises an amino acid sequence that is at least about 90% identical to the amino acid sequence of SEQ ID NO: 67; —the VH2 comprises an amino acid sequence that is at least about 90% identical to the amino acid sequence of SEQ ID NO: 60, and wherein the VL2 comprises an amino acid sequence that is at least about 90% identical to the amino acid sequence of SEQ ID NO: 68; —the VH2 comprises an amino acid sequence that is at least about 90% identical to the amino acid sequence of SEQ ID NO: 61, and wherein the VL2 comprises an amino acid sequence that is at least about 90% identical to the amino acid sequence of SEQ ID NO: 69; —the VH2 comprises an amino acid sequence that is at least about 90% identical to the amino acid sequence of SEQ ID NO: 62, and wherein the VL2 comprises an amino acid sequence that is at least about 90% identical to the amino acid sequence of SEQ ID NO: 70; or —the VH2 comprises an amino acid sequence that is at least about 90% identical to the amino acid sequence of SEQ ID NO: 63, and wherein the VL2 comprises an amino acid sequence that is at least about 90% identical to the amino acid sequence of SEQ ID NO: 71.

In certain embodiments: —the VH2 comprises an amino acid sequence of SEQ ID NO: 56, and wherein the VL2 comprises an amino acid sequence of SEQ ID NO: 64; —the VH2 comprises an amino acid sequence of SEQ ID NO: 57, and wherein the VL2 comprises an amino acid sequence of SEQ ID NO: 65; —the VH2 comprises an amino acid sequence of SEQ ID NO: 58, and wherein the VL2 comprises an amino acid sequence of SEQ ID NO: 66; —the VH2 comprises an amino acid sequence of SEQ ID NO: 59, and wherein the VL2 comprises an amino acid sequence of SEQ ID NO: 67; —the VH2 comprises an amino acid sequence of SEQ ID NO: 60, and wherein the VL2 comprises an amino acid sequence of SEQ ID NO: 68; —the VH2 comprises an amino acid sequence of SEQ ID NO: 61, and wherein the VL2 comprises an amino acid sequence of SEQ ID NO: 69; —the VH2 comprises an amino acid sequence of SEQ ID NO: 62, and wherein the VL2 comprises an amino acid sequence of SEQ ID NO: 70; or —the VH2 comprises an amino acid sequence of SEQ ID NO: 63, and wherein the VL2 comprises an amino acid sequence of SEQ ID NO: 71.

In certain embodiments, the binding protein further comprises all or part of an immunoglobulin Fc domain or variant thereof. In certain embodiments, the Fc domain is an IgG1 Fc domain. In certain embodiments, the IgG1 Fc domain is a human IgG1 Fc domain. In certain embodiments, all or part of the immunoglobulin Fc domain or variant thereof binds to a human Fc-γ receptor. In certain embodiments, all or part of the immunoglobulin Fc domain or variant thereof binds to a human CD16A (FcγRIII) polypeptide.

In certain embodiments, the Fc domain comprises a native glycan at amino acid position 297, according to EU numbering.

In certain embodiments, the binding protein is N-glycosylated.

In certain embodiments, the Fc domain or variant thereof comprises a first Fc heavy chain and a second Fc heavy chain.

In certain embodiments, at least one Fc heavy chain comprises an engineered intrachain disulfide bond mediated by a pair of cysteines (C) that substitute for: (i) a leucine (L) at amino acid position 242 and a lysine (K) at amino acid position 334; or (ii) an arginine (R) at amino acid position 292 and a valine (V) at amino acid position 302; wherein the amino acid positions are according to EU numbering.

In certain embodiments, the first Fc heavy chain or the second Fc heavy chain comprises the pair of cysteines. In certain embodiments, the first and the second Fc heavy chain each comprise the pair of cysteines. In certain embodiments, the first and the second Fc heavy chain each comprise the L242C/K334C substitutions. In certain embodiments, the first and the second Fc heavy chain each comprise the R292C/V302C substitutions.

In certain embodiments, at least one Fc heavy chain comprises a substitution at amino acid position 332, according to EU numbering. In certain embodiments, the substitution at amino acid position 332 is a glutamic acid (E).

In certain embodiments, at least one Fc heavy chain further comprises one or more substitutions at amino acid positions 236, 239, or 330, according to EU numbering. In certain embodiments, the substitution at amino acid position 236 is an alanine (A). In certain embodiments, the substitution at amino acid position 239 is an aspartic acid (D). In certain embodiments, the substitution at amino acid position 330 is a leucine (L).

In certain embodiments, at least one Fc heavy chain further comprises an aspartic acid (D) at amino acid position 239, and a glutamic acid (E) at amino acid position 332, according to EU numbering. In certain embodiments, at least one Fc heavy chain further comprises an alanine (A) at amino acid position 236, an aspartic acid (D) at amino acid position 239, and a glutamic acid (E) at amino acid position 332, according to EU numbering. In certain embodiments, at least one Fc heavy chain further comprises an alanine (A) at amino acid position 236, an aspartic acid (D) at amino acid position 239, a leucine (L) at amino acid position 330, and a glutamic acid (E) at amino acid position 332, according to EU numbering.

In certain embodiments, the binding protein comprises at least two polypeptide chains that form at least two antigen-binding sites, wherein at least one polypeptide chain comprises a structure represented by the formula:

VL1-L1-VL2-L2-CL     [I];

and at least one polypeptide chain comprises a structure represented by the formula:

VH2-L3-VH1-L4-CH1     [II];

wherein:
CL is an immunoglobulin light chain constant domain;
CH1 is an immunoglobulin CH1 heavy chain constant domain; and
L1, L2, L3, and L4 are amino acid linkers, wherein any one or more of L1, L2, L3, and L4 are optionally absent, and
wherein the polypeptides of formula I and the polypeptides of formula II form a cross-over light chain-heavy chain pair.

In certain embodiments, the binding protein comprises three polypeptide chains that form two antigen-binding sites, wherein one polypeptide chain comprises a structure represented by the formula:

VL1-L1-VL2-L2-CL     [I];

one polypeptide chain comprises a structure represented by the formula:

VH2-L3-VH1-L4-CH1-hinge-CH2-CH3     [III]; and one polypeptide chain comprises a structure represented by the formula:

hinge-CH2-CH3     [IV]

wherein:
CL is an immunoglobulin light chain constant domain;
CH1 is an immunoglobulin CH1 heavy chain constant domain;
CH2 is an immunoglobulin CH2 heavy chain constant domain;
CH3 is an immunoglobulin CH3 heavy chain constant domain;
hinge is an immunoglobulin hinge region connecting the CH1 and CH2 domains;
and
L1, L2, L3, and L4 are amino acid linkers, wherein any one or more of L1, L2, L3, and L4 are optionally absent, and
wherein the polypeptides of formula I and the polypeptides of formula II form a cross-over light chain-heavy chain pair.

In certain embodiments: (a) L1, L2, L3, and L4 each independently are zero amino acids in length or comprise a sequence selected from the group consisting of GGGGSGGGGS (SEQ ID NO: 78), GGGGSGGGGSGGGGS (SEQ ID NO: 82), S, RT, TKGPS (SEQ ID NO: 83), GQPKAAP (SEQ ID NO: 84), and GGSGSSGSGG (SEQ ID NO: 85); or (b) L1, L2, L3, and L4 each independently comprise a sequence selected from the group consisting of GGGGSGGGGS (SEQ ID NO: 78), GGGGSGGGGSGGGGS (SEQ ID NO: 82), S, RT, TKGPS (SEQ ID NO: 83), GQPKAAP (SEQ ID NO: 84), and GGSGSSGSGG (SEQ ID NO: 85).

In certain embodiments, L1 and L2 each comprise the amino acid sequence GGGGSGGGGS (SEQ ID NO: 78). In certain embodiments, L3 and L4 are each absent.

In certain embodiments, the binding protein comprises: (i) a first polypeptide chain comprising an amino acid sequence of SEQ ID NO: 72; (ii) a second polypeptide chain comprising an amino acid sequence of SEQ ID NO: 73; and (iii) a third polypeptide chain comprising an amino acid sequence of SEQ ID NO: 74.

In another aspect, the disclosure provides a binding protein comprising a first antigen binding domain (ABD) with binding specificity to BCMA and a second ABD with binding specificity to NKp46, wherein: (a) the first ABD comprises a first immunoglobulin heavy chain variable domain (VH1) comprising an amino acid sequence that is at least about 90% identical to the amino acid sequence of SEQ ID NO: 49, and a first immunoglobulin light chain variable domain (VL1) comprising an amino acid sequence that is at least about 90% identical to the amino acid sequence of SEQ ID NO: 55; and (b) the second ABD comprises a second immunoglobulin heavy chain variable domain (VH2) comprising an amino acid sequence that is at least about 90% identical to the amino acid sequence of SEQ ID NO: 56, and a second immunoglobulin light chain variable domain (VL2) comprising an amino acid sequence that is at least about 90% identical to the amino acid sequence of SEQ ID NO: 64.

In certain embodiments: the VH1 comprises an amino acid sequence of SEQ ID NO: 49, and wherein the VL1 comprises an amino acid sequence of SEQ ID NO: 55; and the VH2 comprises an amino acid sequence of SEQ ID NO: 56, and wherein the VL2 comprises an amino acid sequence of SEQ ID NO: 64.

In certain embodiments, the binding protein comprises: (i) a first polypeptide chain comprising an amino acid sequence of SEQ ID NO: 72; (ii) a second polypeptide chain comprising an amino acid sequence of SEQ ID NO: 73; and (iii) a third polypeptide chain comprising an amino acid sequence of SEQ ID NO: 74.

In another aspect, the disclosure provides a binding protein comprising a first antigen binding domain (ABD) with binding specificity to BCMA and a second ABD with binding specificity to NKp46, wherein the binding protein comprises: (i) a first polypeptide chain comprising an amino acid sequence of SEQ ID NO: 72; (ii) a second polypeptide chain comprising an amino acid sequence of SEQ ID NO: 73; and (iii) a third polypeptide chain comprising an amino acid sequence of SEQ ID NO: 74.

In certain embodiments, the binding protein described above is for use as a medicament.

In certain embodiments, the binding protein described above is for use in a method for the treatment of a disease or disorder.

In certain embodiments, the binding protein described above is for use in a method for the treatment or prevention of cancer.

In certain embodiments, the binding protein described above is for use in a method for the treatment or prevention of multiple myeloma.

In certain embodiments, the binding protein described above is for use in a method for the treatment or prevention of light chain amyloidosis (LCA).

In another aspect, the disclosure provides a pharmaceutical composition comprising the binding protein described above and a pharmaceutically acceptable carrier.

In another aspect, the disclosure provides a method of treating or preventing cancer, the method comprising administering to a subject in need of said treatment or prevention the pharmaceutical composition described above.

In another aspect, the disclosure provides an isolated nucleic acid molecule comprising a nucleotide sequence that encodes the binding protein described above.

In another aspect, the disclosure provides an isolated nucleic acid molecule comprising a nucleotide sequence that encodes a first polypeptide chain comprising an amino acid sequence of SEQ ID NO: 72.

In another aspect, the disclosure provides an isolated nucleic acid molecule comprising a nucleotide sequence that encodes a second polypeptide chain comprising an amino acid sequence of SEQ ID NO: 73.

In another aspect, the disclosure provides an isolated nucleic acid molecule comprising a nucleotide sequence that encodes a third polypeptide chain comprising an amino acid sequence of SEQ ID NO: 74.

In another aspect, the disclosure provides an expression vector comprising the nucleic acid molecule described above.

In another aspect, the disclosure provides an isolated cell comprising the nucleic acid molecule described above.

In another aspect, the disclosure provides an isolated cell comprising the expression vector described above. In certain embodiments, the cell is a mammalian cell.

In another aspect, the disclosure provides a method of making the binding protein, comprising culturing the isolated cell under suitable conditions and recovering the binding protein.

In another aspect, the disclosure provides a method for making the binding protein described above, comprising a step of: (a) culturing host cell(s) under conditions suitable for expressing a plurality of recombinant polypeptides, said plurality comprising (i) a polypeptide comprising an amino acid sequence of SEQ ID NO: 72, and (ii) a polypeptide comprising an amino acid sequence of SEQ ID NO: 73, and (iii) a polypeptide comprising an amino acid sequence of SEQ ID NO: 74; (b) optionally recovering the expressed recombinant polypeptides.

In another aspect, the disclosure provides a binding protein produced by the method of making described above. In another aspect, the disclosure provides a method of treating or preventing a disease or disorder, comprising administering to a subject in need thereof the pharmaceutical composition described above.

In another aspect, the disclosure provides a method of treating or preventing a cancer, comprising administering to a subject in need thereof the pharmaceutical composition described above.

In another aspect, the disclosure provides a method of treating or preventing multiple myeloma, comprising administering to a subject in need thereof the pharmaceutical composition described above. In certain embodiments, the multiple myeloma is relapsed multiple myeloma. In certain embodiments, the multiple myeloma is refractory multiple myeloma. In certain embodiments, the multiple myeloma is smoldering multiple myeloma.

In another aspect, the disclosure provides a method of treating or preventing light chain amyloidosis (LCA), comprising administering to a subject in need thereof the pharmaceutical composition described above. In certain embodiments, the LCA is relapsed LCA. In certain embodiments, the LCA is refractory LCA.

In another aspect, the disclosure provides a method of restoring or potentiating the activity of NKp46-expressing cells in a patient in need thereof, comprising administering to the patient the pharmaceutical composition described above.

In another aspect, the disclosure provides a method of eliminating cancer cells in a patient in need thereof, comprising administering to the patient the pharmaceutical composition described above.

In another aspect, the disclosure provides a method of triggering or increasing NK cell-mediated lysis of cancer cells in a patient in need thereof, comprising administering to the patient the pharmaceutical composition described above. In certain embodiments, the cancer cells express BCMA.

In another aspect, the disclosure provides a method of inducing the elimination of cancer cells by NK cells in a patient in need thereof, comprising administering to the patient the pharmaceutical composition described above.

In another aspect, the disclosure provides a binding protein comprising a first antigen binding domain (ABD) with binding specificity to BCMA and a second ABD with binding specificity to NKp46.

In certain embodiments, the binding protein further comprises all or part of an immunoglobulin Fc domain or variant thereof, optionally wherein: all or part of the immunoglobulin Fc domain or variant thereof binds to a human Fc-γ receptor; all or part of the immunoglobulin Fc domain or variant thereof binds to a human CD16a (FcγRIIIa) polypeptide; the Fc domain comprises a native glycan at amino acid position 297, according to EU numbering; and/or the binding protein is N-glycosylated.

In certain embodiments, the Fc domain or variant thereof comprises a first Fc heavy chain and a second Fc heavy chain. In certain embodiments, at least one Fc heavy chain comprises an engineered intrachain disulfide bond mediated by a pair of cysteines (C) that substitute for: (i) a leucine (L) at amino acid position 242 and a lysine (K) at amino acid position 334; or (ii) an arginine (R) at amino acid position 292 and a valine (V) at amino acid position 302; wherein the amino acid positions are according to EU numbering.

In certain embodiments, the first and the second Fc heavy chain each comprise the L242C/K334C substitutions. In certain embodiments, the first and the second Fc heavy chain each comprise the R292C/V302C substitutions.

In certain embodiments, at least one Fc heavy chain comprises a substitution at amino acid position 332, according to EU numbering, optionally wherein the substitution at amino acid position 332 is a glutamic acid (E), optionally further comprising at least one Fc heavy chain further comprises one or more substitutions at amino acid positions 236, 239, or 330, according to EU numbering, optionally wherein the substitution at amino acid position 236 is an alanine (A), the substitution at amino acid position 239 is an aspartic acid (D), and the substitution at amino acid position 330 is a leucine (L).

In certain embodiments, at least one Fc heavy chain further comprises an aspartic acid (D) at amino acid position 239, and a glutamic acid (E) at amino acid position 332, according to EU numbering; at least one Fc heavy chain further comprises an alanine (A) at amino acid position 236, an aspartic acid (D) at amino acid position 239, and a glutamic acid (E) at amino acid position 332, according to EU numbering; or at least one Fc heavy chain further comprises an alanine (A) at amino acid position 236, an aspartic acid (D) at amino acid position 239, a leucine (L) at amino acid position 330, and a glutamic acid (E) at amino acid position 332, according to EU numbering.

BRIEF DESCRIPTION OF THE DRAWINGS

The foregoing and other features and advantages of the present disclosure will be more fully understood from the following detailed description of illustrative embodiments taken in conjunction with the accompanying drawings.

FIG. 1A is a representation of a NKp46 NKCE which binds with one arm to an antigen at the surface of the tumor cell (e.g., BCMA) and with another arm to the NKp46 receptor on NK cells. The Fc domain of the NKCE also binds to CD16 on the NK cell. FIG. 1B depicts a distinct NKp46-BCMA NKCE format that engages BCMA at the surface of the tumor cell while also recruiting NK cells through the dual engagement of both NKp46 and a Fcγ receptor, CD16a, inducing ADCC activity with an enhanced Fc competent format. The enhanced Fc competent format (hereinafter, termed "CODV-OL1-ADE-DSB") includes: (1) ADE mutations (G236A/S239D/I332E) in CH2 to enhance ADCC-activity; (2) DSB (R292C/V302C) in CH2 for thermal stabilization and productivity (e.g., expressability in cells and overall yield); (3) knob-into-hole mutations (KIH) in CH3 to favor heterodimer formation in Fc—(3a) knob (in heavy chain containing the VH/VL domains): S354C/T366W and (3b) hole (in heavy chain lacking the VH/VL domains): Y349C/T366S/L368A/Y407V; and (4) RF mutations (H435R/Y436F) in one CH3 to favor purification of heterodimers in Fc. All Fc domain amino acid numbering is according to EU. This NKp46-BCMA NKCE_Fc CODV-OL1-ADE-DSB additionally contains two linkers GGGGSGGGGS (SEQ ID NO: 78) in the light chain: one between VL anti-BCMA and VL anti-NKp46 and between VL NKp46 and CL. NKp46 binding site: 3D9; BCMA binding site: CA10v7; CD16 binding through ADCC-competent Fc domain.

FIG. 3A is a representative titration of NKp46-BCMA_Fc-ADE-DSB on RPMI 8226 cells. The titration data shown are median fluorescence intensity over a range of doses of antibody concentration. $EC_{50}$ values of 5 independent titrations are indicated.

FIG. 3B is a representative titration of NKp46-BCMA_Fc-ADE-DSB on human NK cells purified from the PBMCs of healthy volunteers. The titration data shown are median fluorescence intensity over a range of doses of antibody concentration. $EC_{50}$ values of 3 NK donors are indicated.

FIG. 4 is a table displaying binding affinities (measured in KD) of 12 distinct Fc formats of NKp46-BCMA-NKCEs to two distinct variants of human CD16a (bearing either a valine (V) or a phenylalanine (F) on amino acid position 176) as quantified by using surface plasmon resonance (SPR).

FIG. 5 is a table displaying binding affinities (measured in KD) of 12 distinct Fc formats of NKp46-BCMA-NKCEs to the human neonatal Fc receptor (FcRn) as quantified by using SPR.

and non-enhanced ADCC (NKp46-BCMA_Fc) at escalating concentrations (nM) incubated with RPMI 8226 cells in the presence of purified resting NK cells from six different donors (D410, D700, D114, D974, D245, and D409) RPMI 8226 cells were used as targets and purified resting NK cells were used as effectors.

Figure 7:
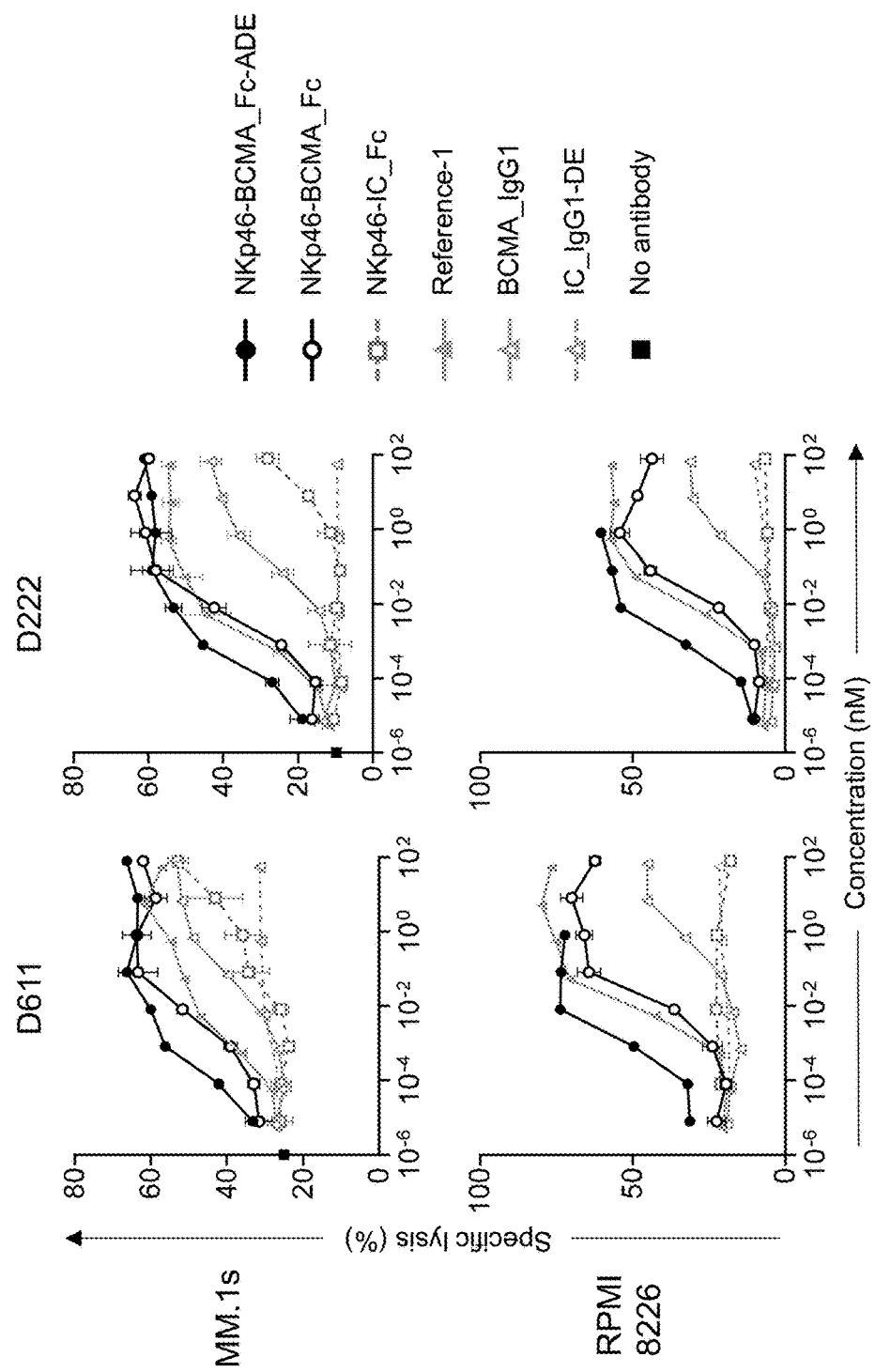

FIG. 7 is an in vitro cell cytotoxicity assay comparing the cytotoxicities of NKp46-BCMA_Fc-ADE, NKp46-BCMA_Fc, Reference-1, BCMA_IgG1, IC_IgG1-DE and NKp46-IC_Fc control at escalating concentrations (nM) incubated with either RPMI 8226 or MM.1s cells in the presence of purified rested NK cells from two distinct donors (D611 and D222). RPMI 8226 and MM.1s cells were used as targets and purified resting NK cells were used as effectors.

Figure 8:
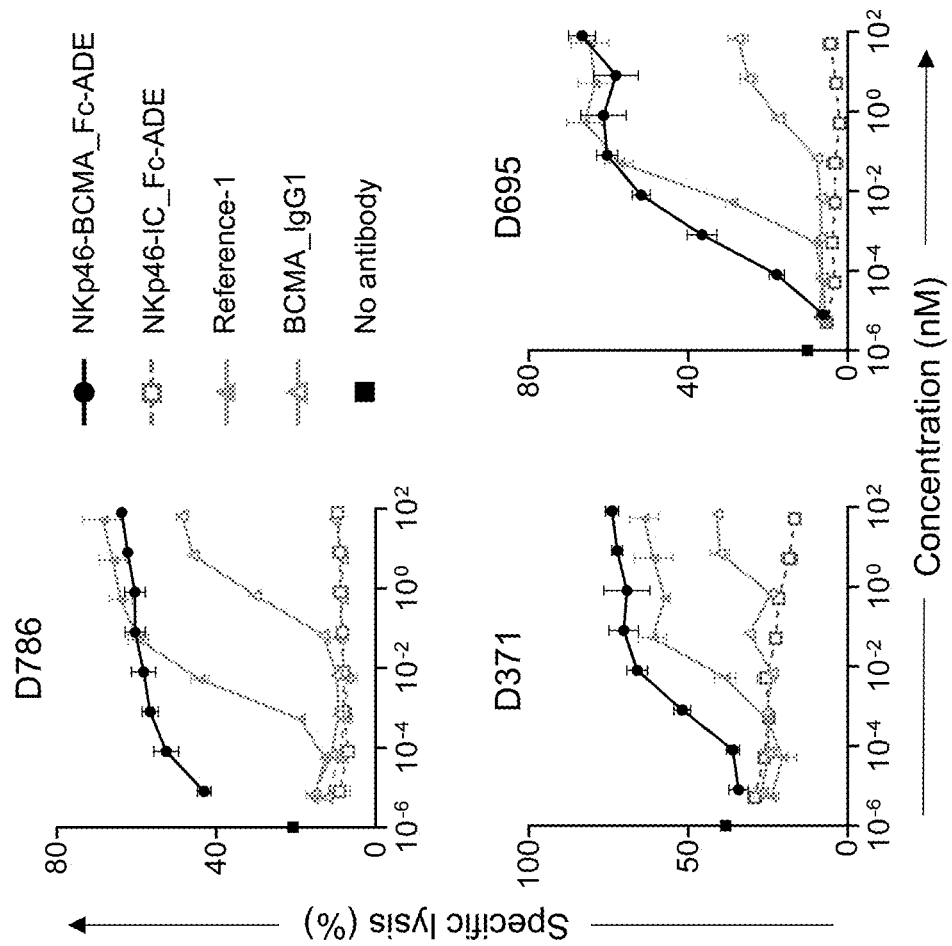

FIG. 8 is an in vitro cell cytotoxicity assay comparing the cytotoxicities of NKp46-BCMA_Fc-ADE, Reference-1, BCMA_IgG1 and NKp46-IC_Fc-ADE control at escalating concentrations (nM) incubated with to RPMI 8226 cells in the presence of purified rested NK cells from three distinct donors (D786, D371, or D695). RPMI 8226 cells were used as targets and purified resting NK cells were used as effectors.

Figure 9:
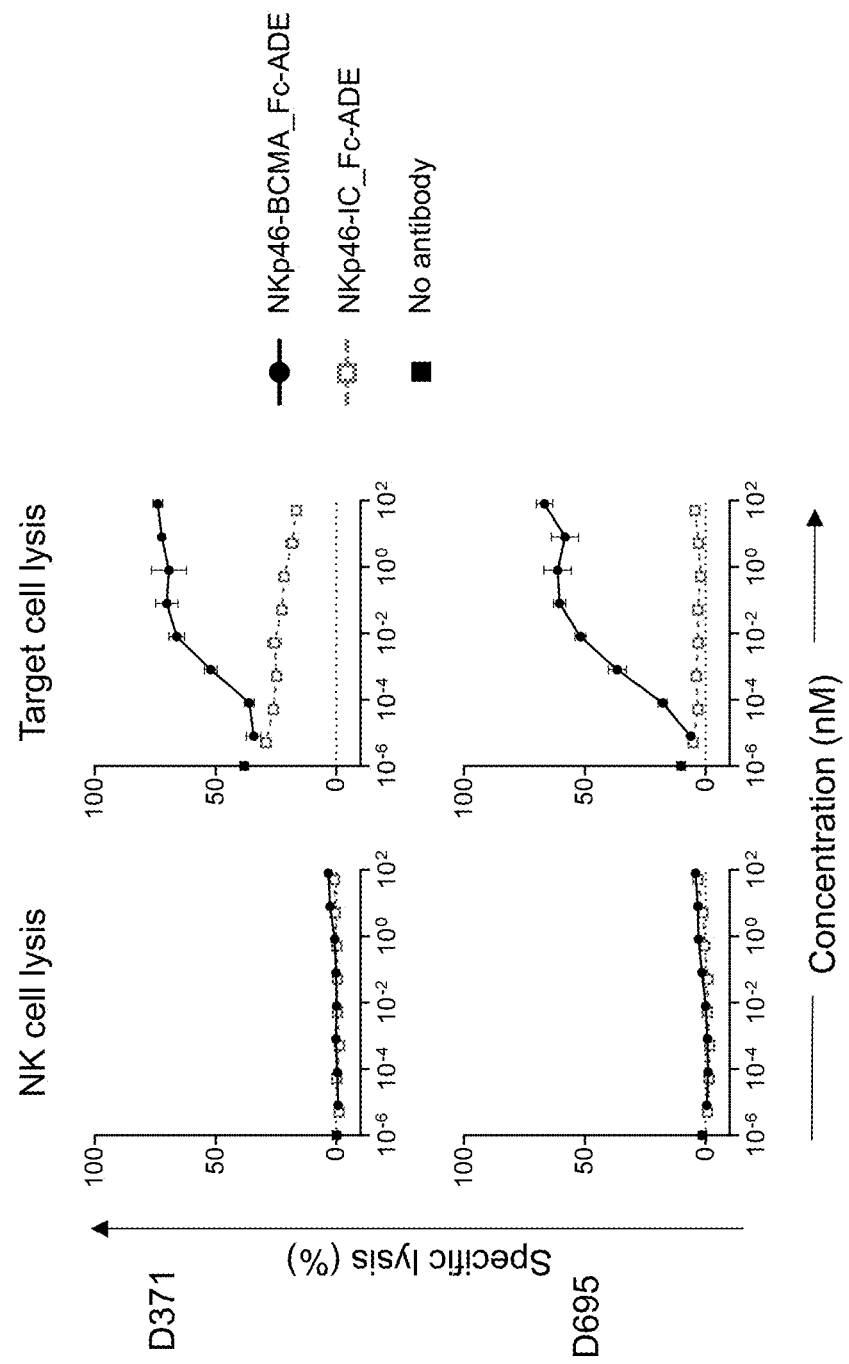

FIG. 9 is an in vitro cell cytotoxicity assay comparing the cytotoxicities of NKp46-BCMA_Fc-ADE and NKp46-IC_Fc-ADE using purified resting NK cells versus RPMI 8226 cells. RPMI 8226 cells were used as targets and purified resting NK cells (left panel) or RPMI 8226 cells (right panel) were loaded with $^{51}$Cr to determine both target cell killing and NK-versus-NK fratricide toxicity in the same assay. (2 NK cell donors are shown).

Figure 10:
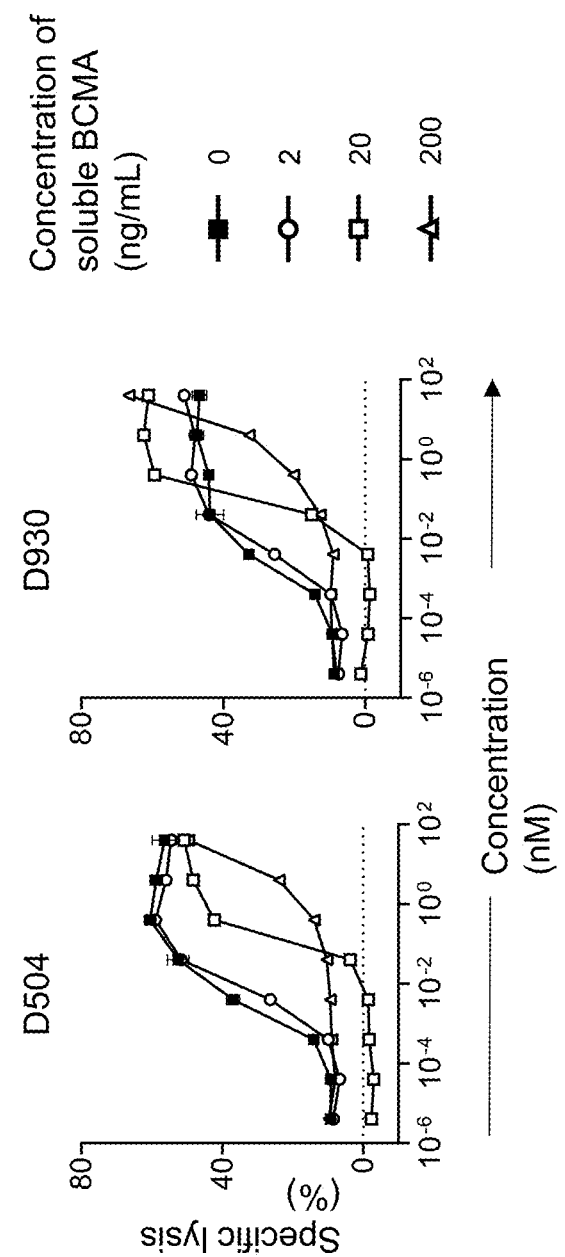

FIG. 10 is an in vitro cell cytotoxicity assay comparing the cytotoxicity of the NKp46-BCMA-NKCE in the presence of various soluble BCMA concentrations. Cytotoxic activities of NKp46-BCMA_Fc-ADE-DSB against RPMI 8226 cells, in presence of increasing concentrations of soluble BCMA recombinant protein (0, 2, 20 and 200 ng/mL). RPMI 8226 were used as targets and purified resting NK cells as effectors (2 NK cell donors, D504 and D930, are shown).

Figure 11:
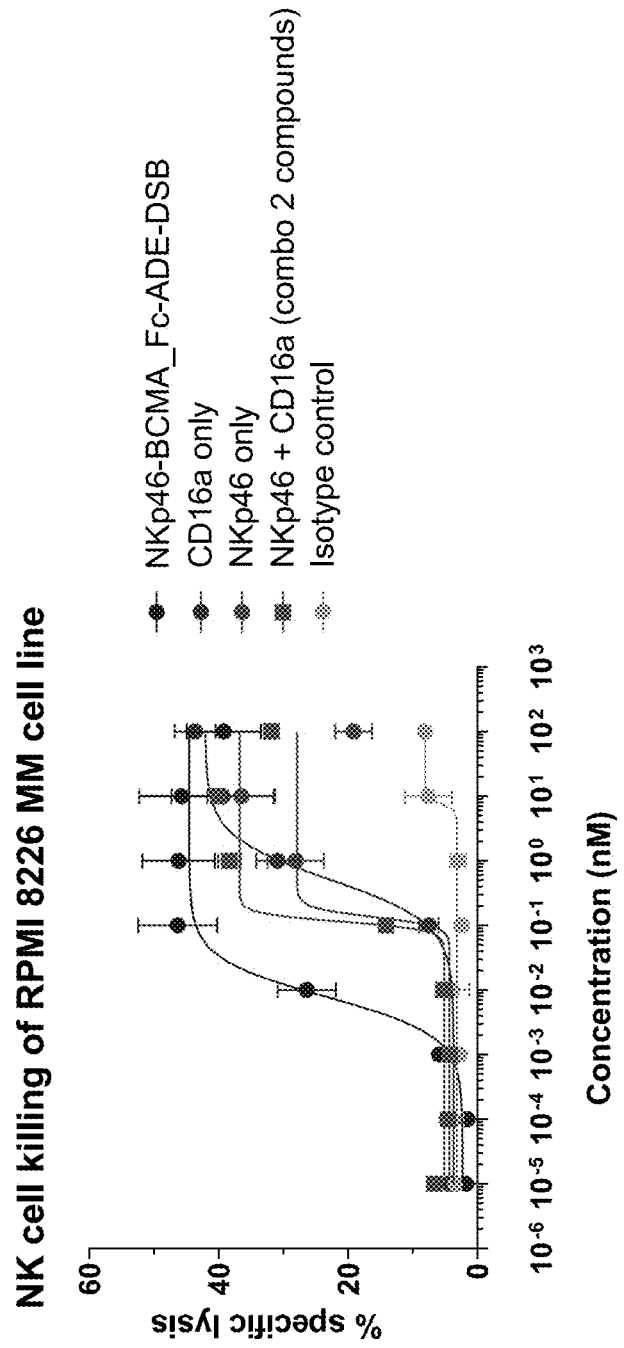

FIG. 11 illustrates that optimal NK cell activation involves dual targeting of NKp46 and CD16a by NKp46-BCMA_Fc-ADE-DSB.

Figure 12:
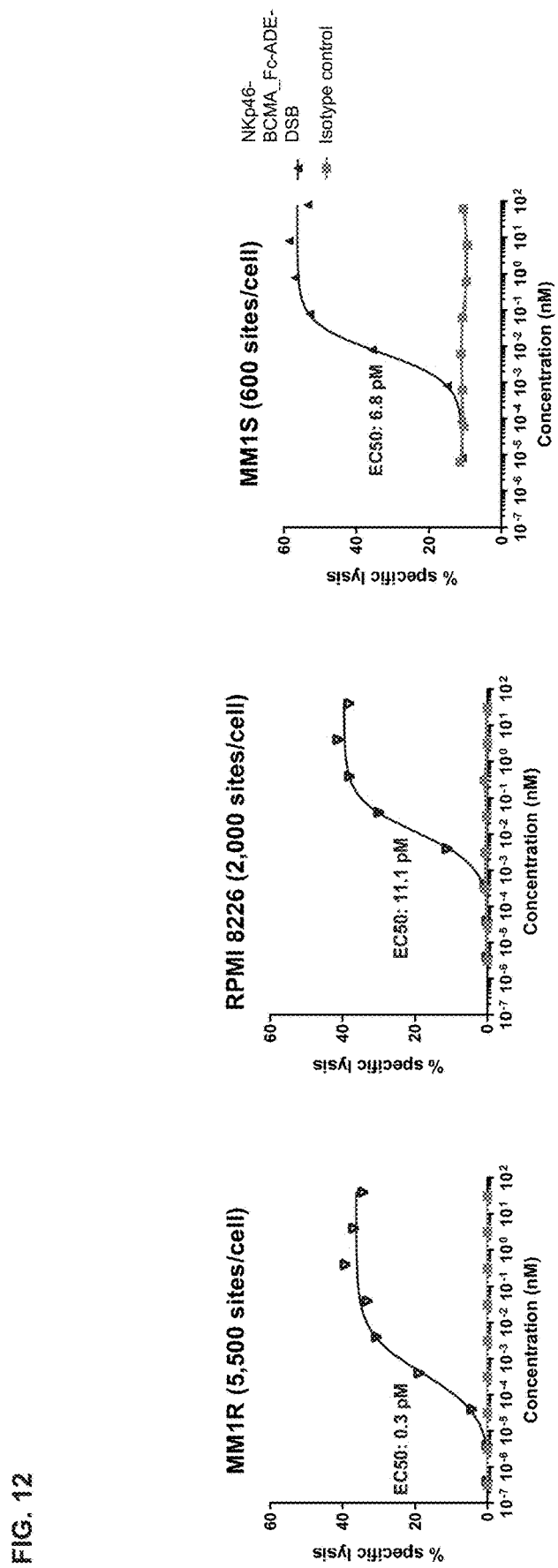

FIG. 12 demonstrations that the high potency of NKp46-BCMA_Fc-ADE-DSB allows for high efficiency in tumor cell killing, even in MM cell models that express low BCMA.

Figure 13:
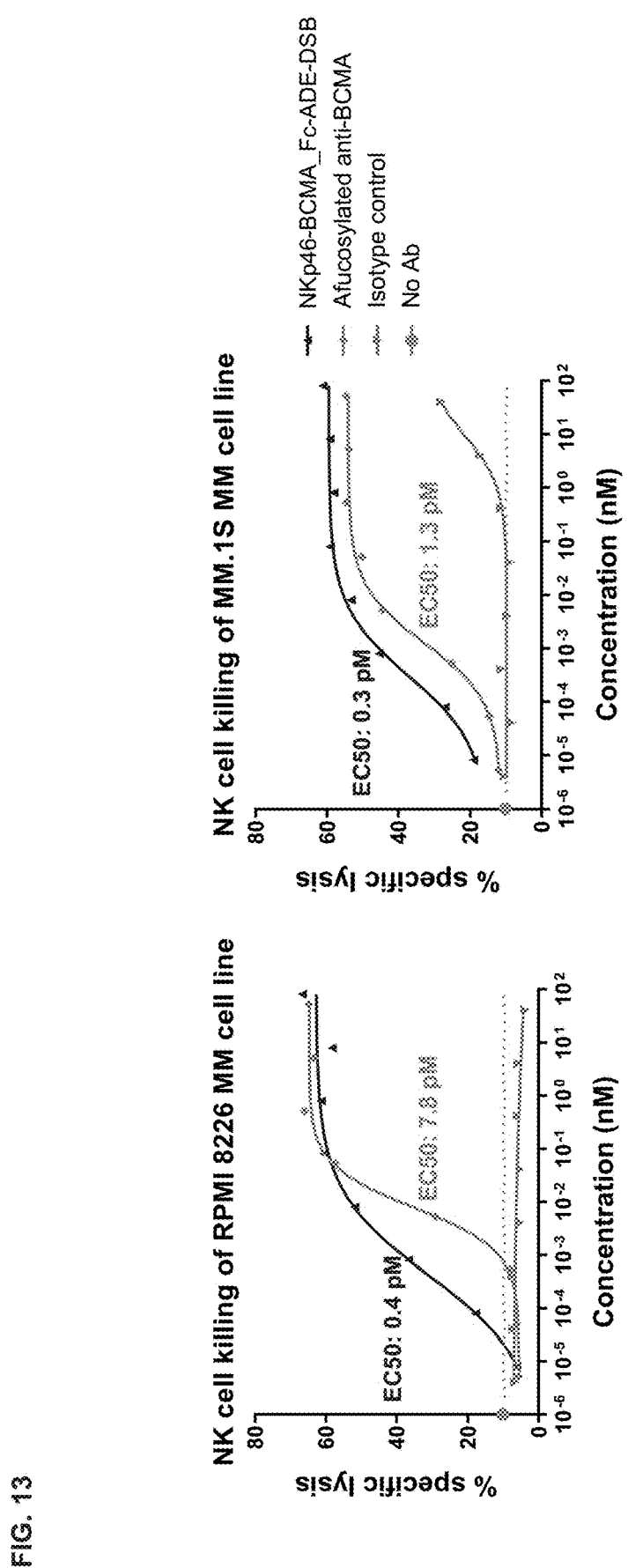

FIG. 13 demonstrates that NKp46-BCMA_Fc-ADE-DSB has enhanced potency over an antibody with enhanced ADCC features.

Figure 14A:
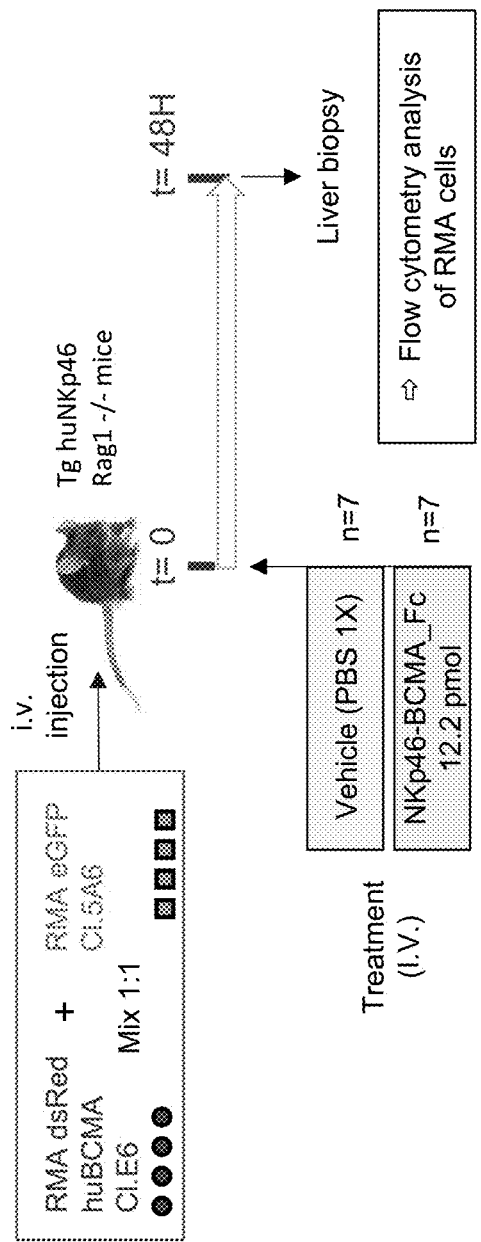
Figure 14E:
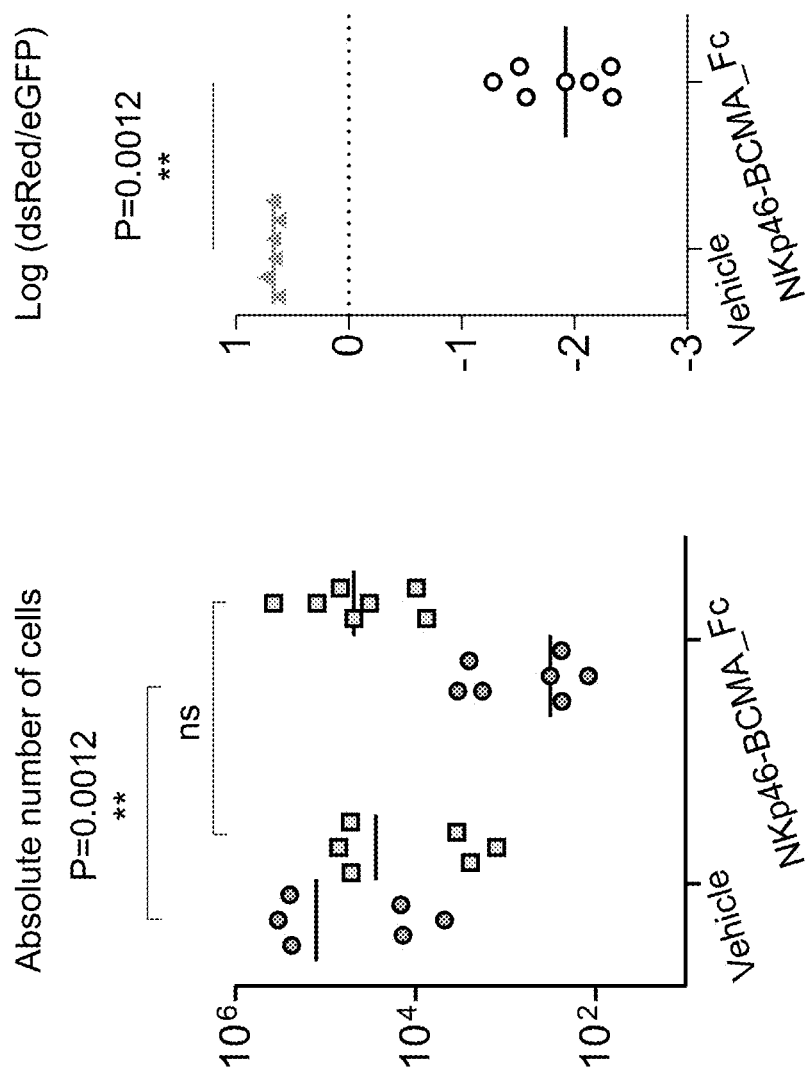

FIG. 14A is a schematic of the experimental mouse model for determining in vivo NKp46-BCMA_Fc anti-tumor activity. A 1:1 mixture of green (eGFP) and red (dsRed) fluorescent mouse lymphoma RMA cells respectively non-expressing and expressing human BCMA were intravenously (i.v.) injected into Rag1 deficient mice transgenic for human NKp46 (Tg huNKp46 Rag1 −/−). Tumor-bearing mice (n=7 for each group) were treated once with a total dose of 12.2 picomoles of NKp46-BCMA_Fc or vehicle as control. The livers of the mice were biopsied 48 h after treatment and the absolute count of infiltrated RMA cells was monitored by flow cytometry as described in FIG. 14B-FIG. 14E. FIG. 14B shows the mixed population of green (eGFP-huBCMA-negative) and red (dsRed-huBCMA-positive) fluorescent mouse lymphoma RMA cells analyzed by flow cytometry before engraftment. FIG. 14C shows the expression of human BCMA by flow cytometry of the green (eGFP) and red (dsRed) fluorescent mouse lymphoma RMA cells. FIG. 14D shows the expression of human BCMA on dsRed RMA cells before engraftment (in vitro) and after engraftment in liver biopsies (ex vivo) analyzed by flow cytometry. FIG. 14E shows the absolute count of liver infiltrating RMA cells (left) and dsRed/eGFP cell ratio (right) analyzed by flow cytometry 48 h after treatment. The statistical test used to analyze the data is the Mann and Whitney Test: non-significant (ns) when p>0.05; significant (**) p<0.01.

Figure 15A:
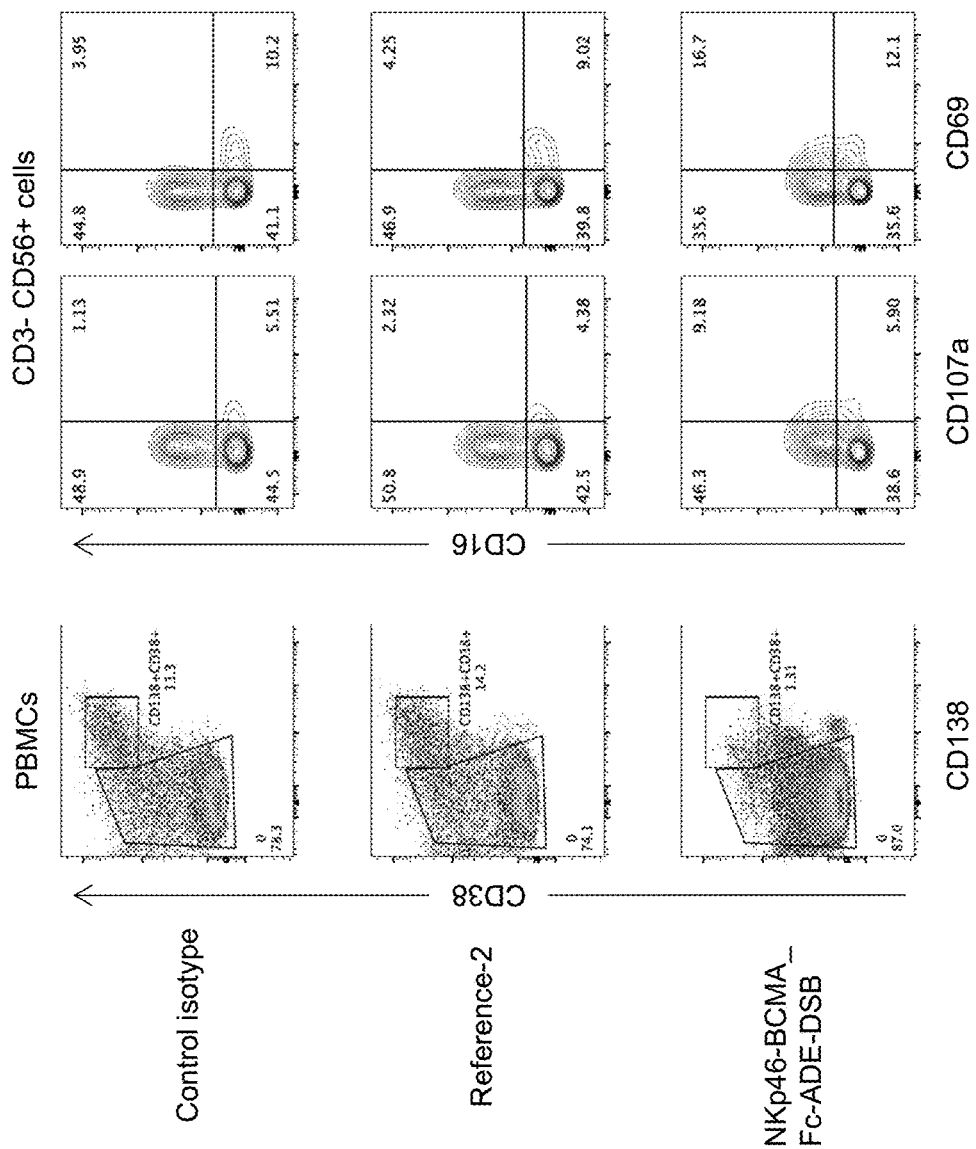
Figure 15B:
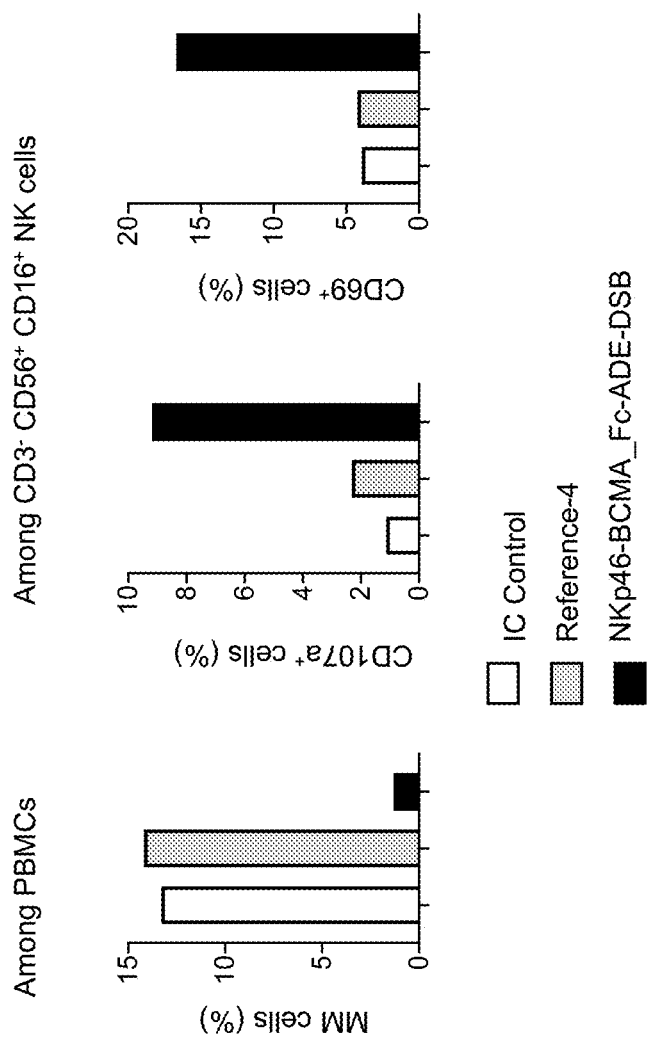

FIG. 15A displays the measurement by flow cytometry of the percentage of multiple myeloma (MM) cells, defined as CD138+ CD38+ cells, and of CD107a and CD69 expression by NK cells, defined as CD3− CD56+ CD16+ cells, after overnight treatment of whole blood-derived PBMCs from one MM patient with 10 μg/mL NKp46-BCMA_Fc-ADE-DSB, or 20 μg/mL of Reference-4 antibody (anti-CD38 IgG1 antibody), or a control isotype (NKp46-IC_Fc-ADE-DSB) in an autologous setting. The left panel are dot plots showing the CD138 and CD38 staining of PBMCs from one MM patient and gating on CD138+ CD38+ (MM) cells. The central panel contour diagrams show the CD107a and CD16 stainings of CD3− CD56+ cells. The right panels contour diagrams show the CD69 and CD16 stainings of CD3− CD56+ cells. FIG. 15B left bar graph represents the percentage of CD38+ CD138+ (MM) cells among PBMCs, the central bar graph represents the percentage of CD3− CD56+ CD16+ NK cells expressing CD107a, and the right bar graph represents the percentage of CD3− CD56+ CD16+ NK cells expressing CD69, after overnight treatment of the whole blood-derived PBMCs from one MM patient with 10 μg/mL NKp46-BCMA_Fc-ADE-DSB (black), or 20 μg/mL of Reference-4 antibody (grey—an anti-CD38 IgG1 antibody), or control isotype (white).

FIG. 16A-16C depict % MM cell death on patient samples treated ex vivo with NKp46-BCMA_Fc-ADE-DSB who are either treatment naïve or those who are relapsed after standard of care therapies. TC=therapeutic classes; ≤4TC: Imid,Dex,PI and anti-CD38mAb; >4TC:previous agents and/or alkylating agent, BH3 mimetic, and/or BCMA or CD38TCE, and/or ant-CD47 mAb, and/or histone deacetylase inhibitor (HDACi).

Figure 17:
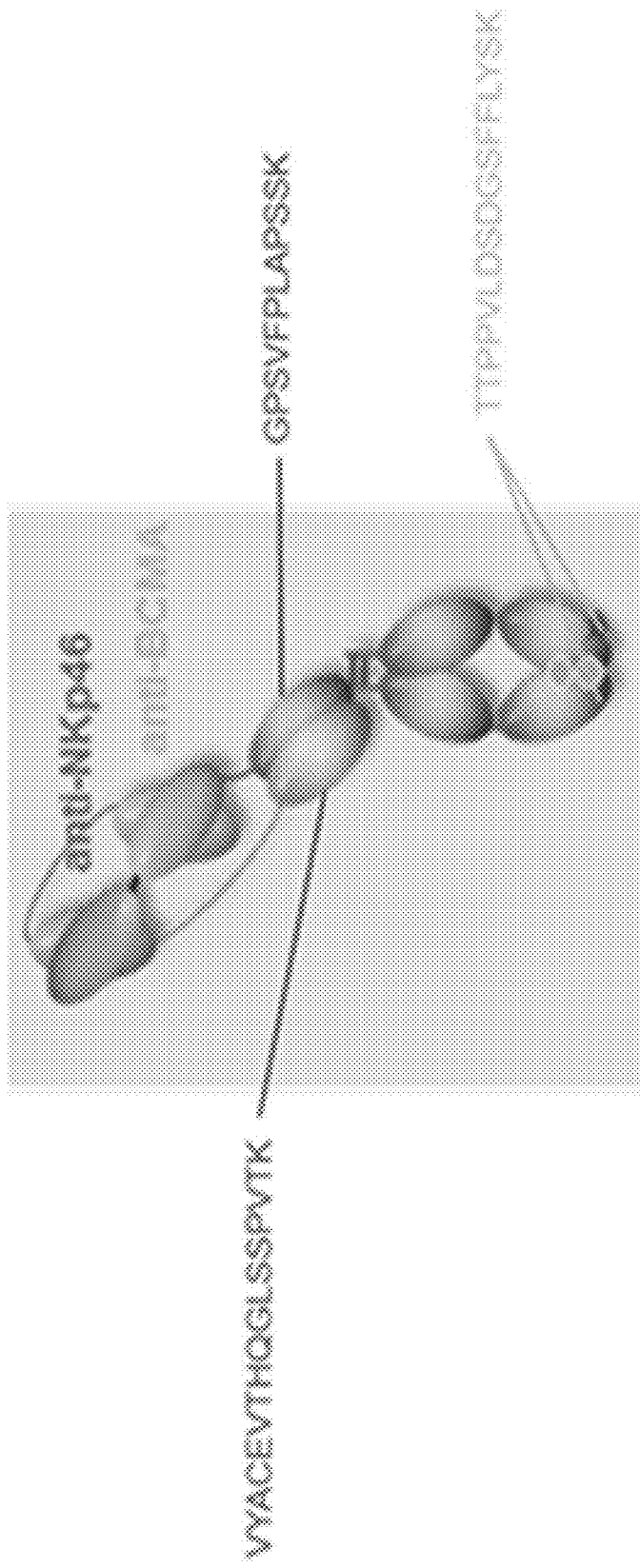

FIG. 17 depicts the location of the VYACE-VTHQGLSSPVTK (SEQ ID NO: 86), GPSVFPLAPSSK (SEQ ID NO: 105), and the TTPPVLDSDGSFFLYSK (SEQ ID NO: 106) peptides on the NKp46-BCMA NKCE_Fc CODV-OL1-ADE-DSB molecule.

Figure 18:
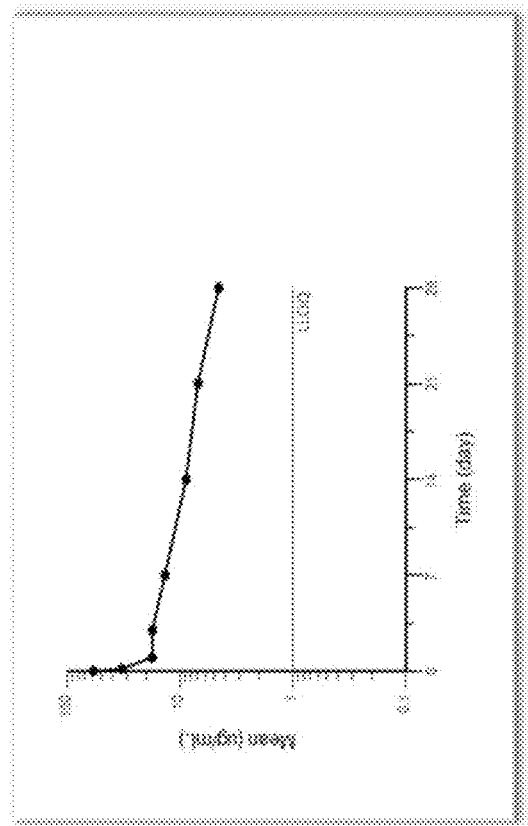

FIG. 18 represents the mean (N=3) plasma concentrations versus time profile of NKp46-BCMA_Fc-ADE-DSB NKCE following a single intravenous (2.5 mg/kg) administration to female huFcRn tg32 transgenic mice.

Figure 19:
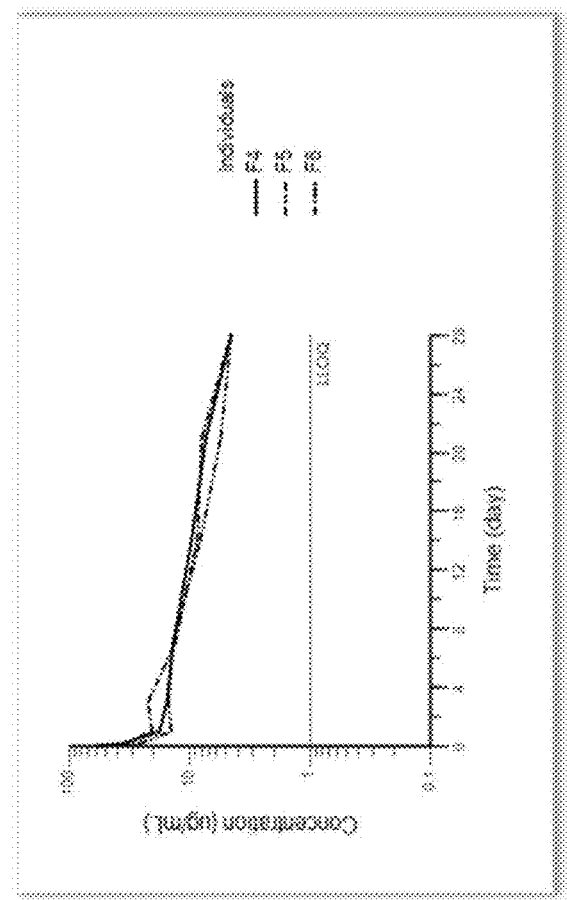

FIG. 19 represents the individual plasma concentrations versus time profile of NKp46-BCMA_Fc-ADE-DSB NKCE following a single intravenous (2.5 mg/kg) administration to female huFcRn tg32 transgenic mice.

Figure 20:
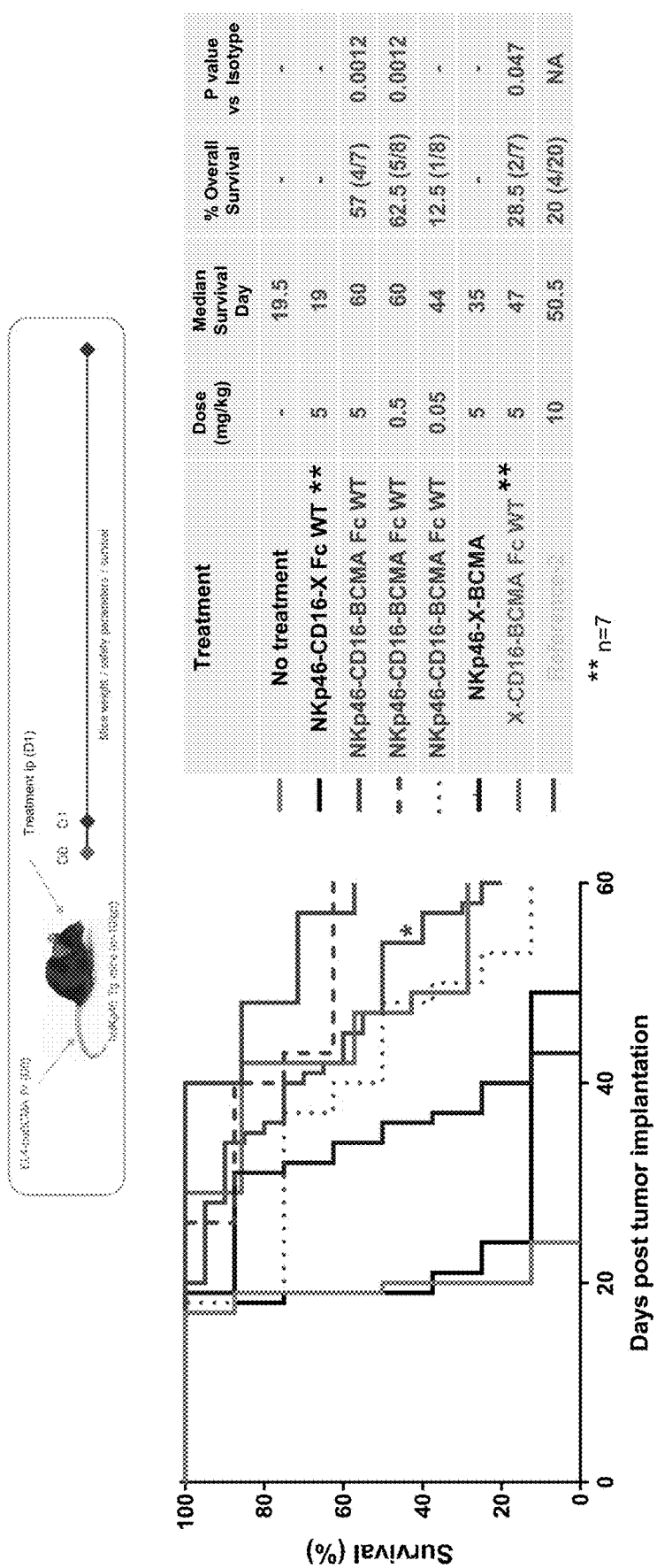

FIG. 20 shows the activity of the NKp46-BCMA Fc WT CODV-OL1 bispecific antibody against disseminated EL4-huBCMA tumor cells in huNKp46-Tg×Rag mice. Graphs represent Kaplan-Meier curves for animals treated by NKp46-BCMA Fc WT CODV-OL1 bispecific antibody at 5, 0.5 and 0.05 mg/kg versus Reference-2 compound, control NKCE invalidated for either CD16 (blue), NKp46 (green) or BCMA binding (black) or untreated group.

Figure 21:
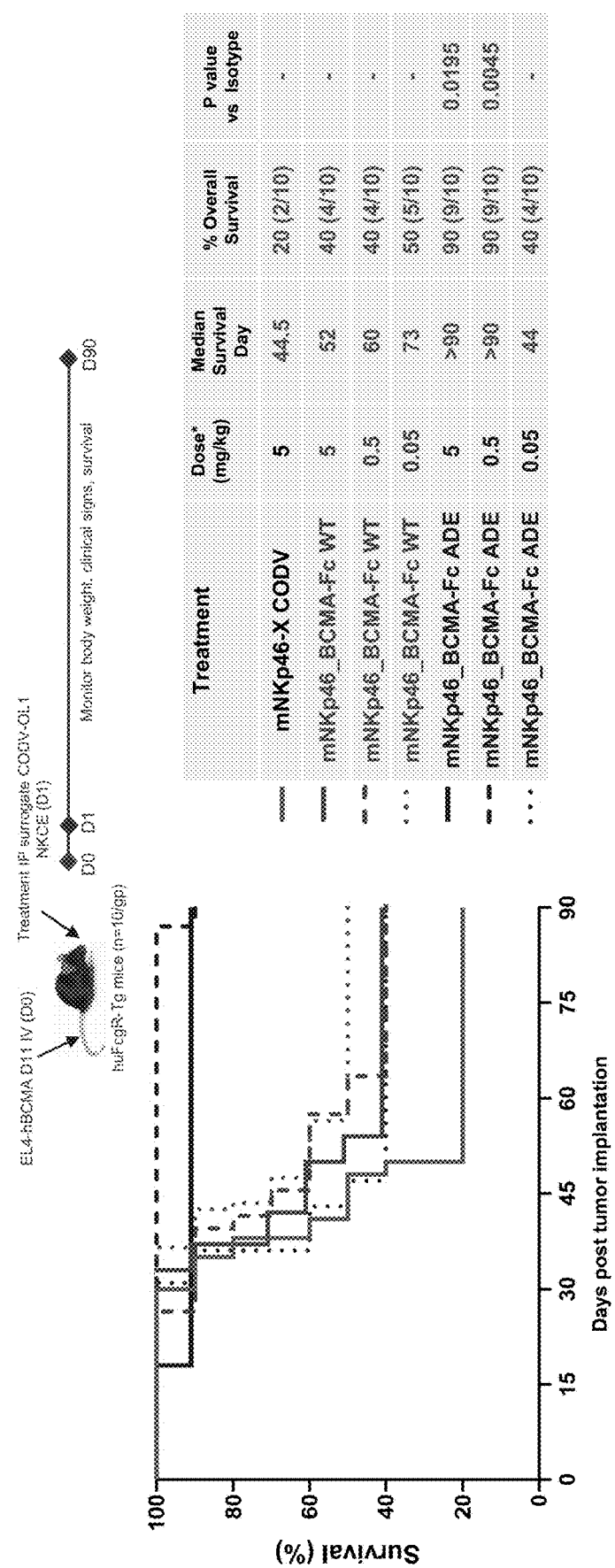

FIG. 21 shows the activity of the surrogate muNKp46-huBCMA CODV-OL1 Fc WT and FC-ADE bispecific antibody against disseminated EL4-huBCMA tumor cells in huFcgR-Tg mice. Graphs represent Kaplan-Meier curves for animals treated with the Fc WT and Fc-ADE muNKp46-huBCMA surrogate bispecific antibodies at 5, 0.5 and 0.05 mg/kg.

Figure 22:
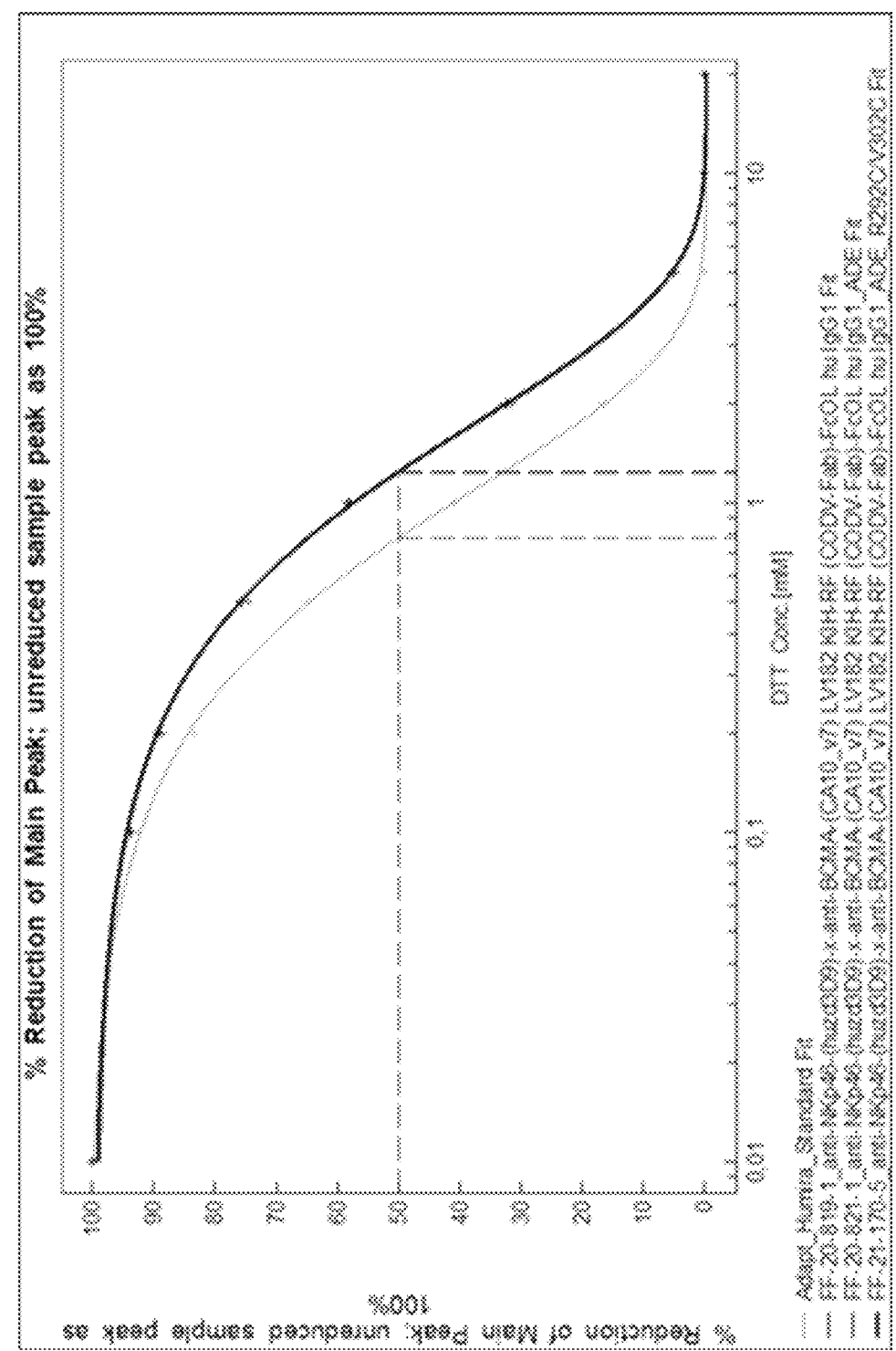

FIG. 22 depicts percent dose response curves of reduction of main peak of unreduced sample by DTT measured by capillary electrophoresis (cGE). mAb ctrl (yellow), CODV-OL1 wt (blue), CODV-OL1 ADE (magenta), CODV-OL1 ADE-DSB (black).

Figure 23A:
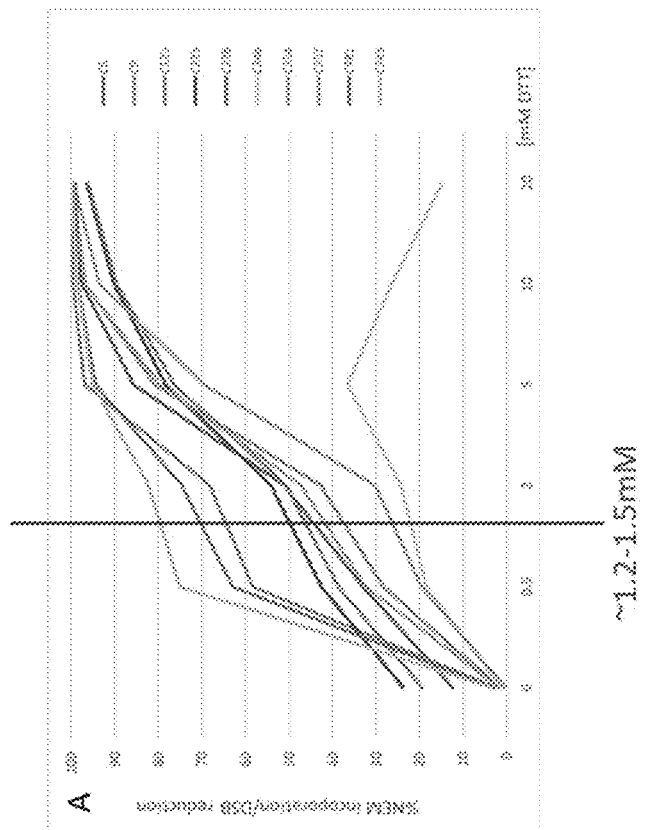
Figure 23B:
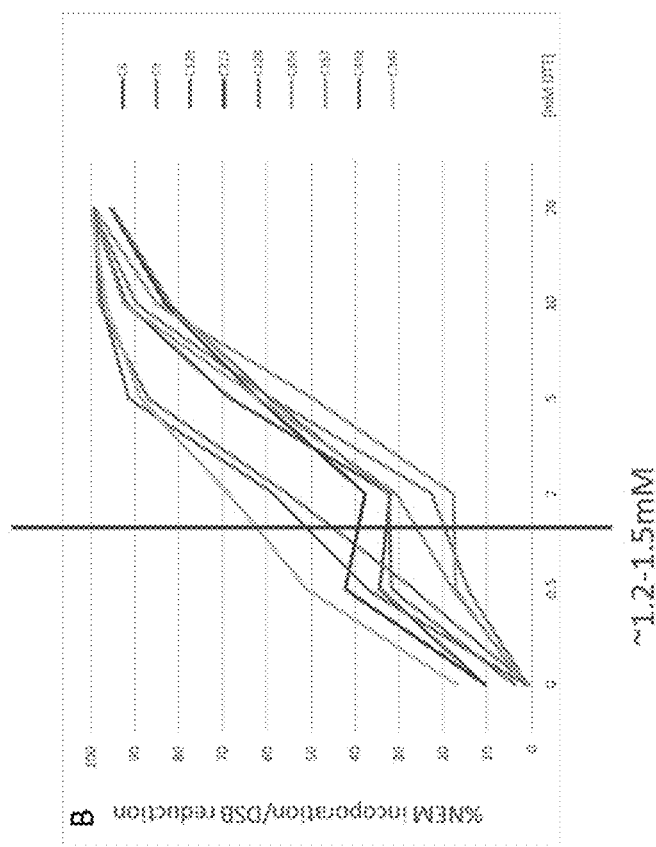
Figure 23C:
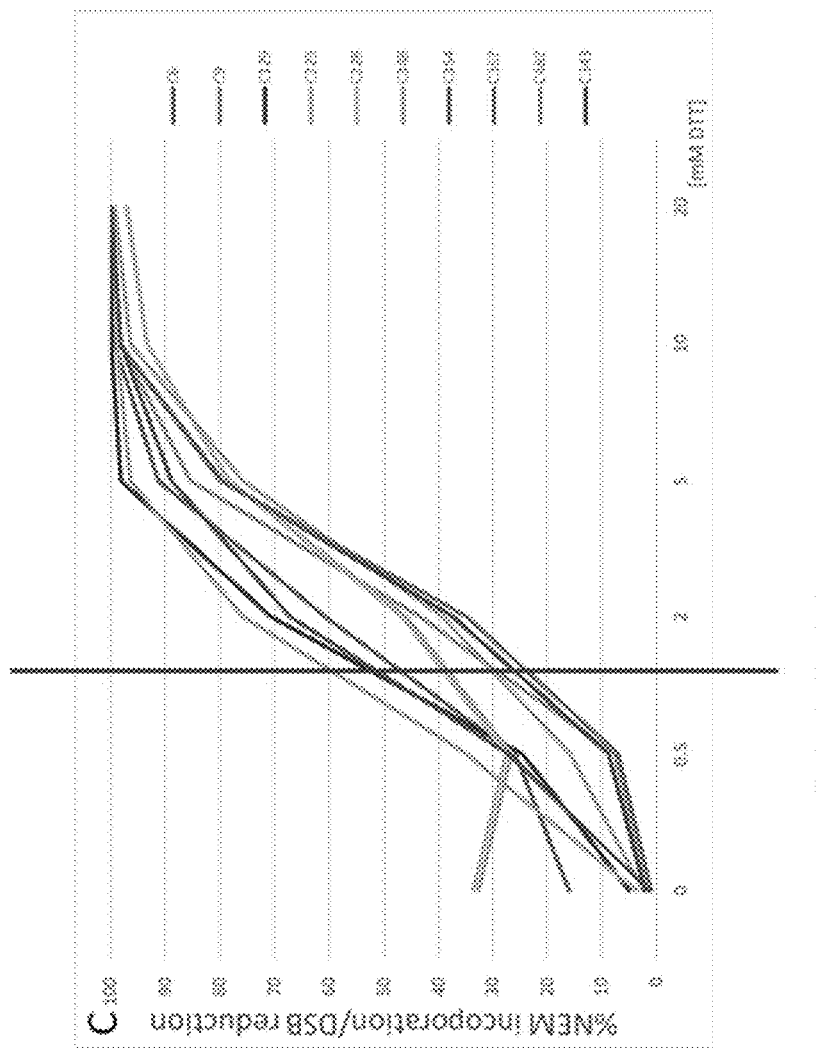

FIG. 23A-FIG. 23C depict dose response curves of % NEM incorporation/DSB reduction of CODV-OL1 wt (FIG. 23A), CODV-OL1 ADE (FIG. 23B), CODV-OL1 ADE-DSB (FIG. 23C). Analyzed cysteine residues are indicated in the figure legends with numbering according to the analyzed proteins.

Figure 24B:
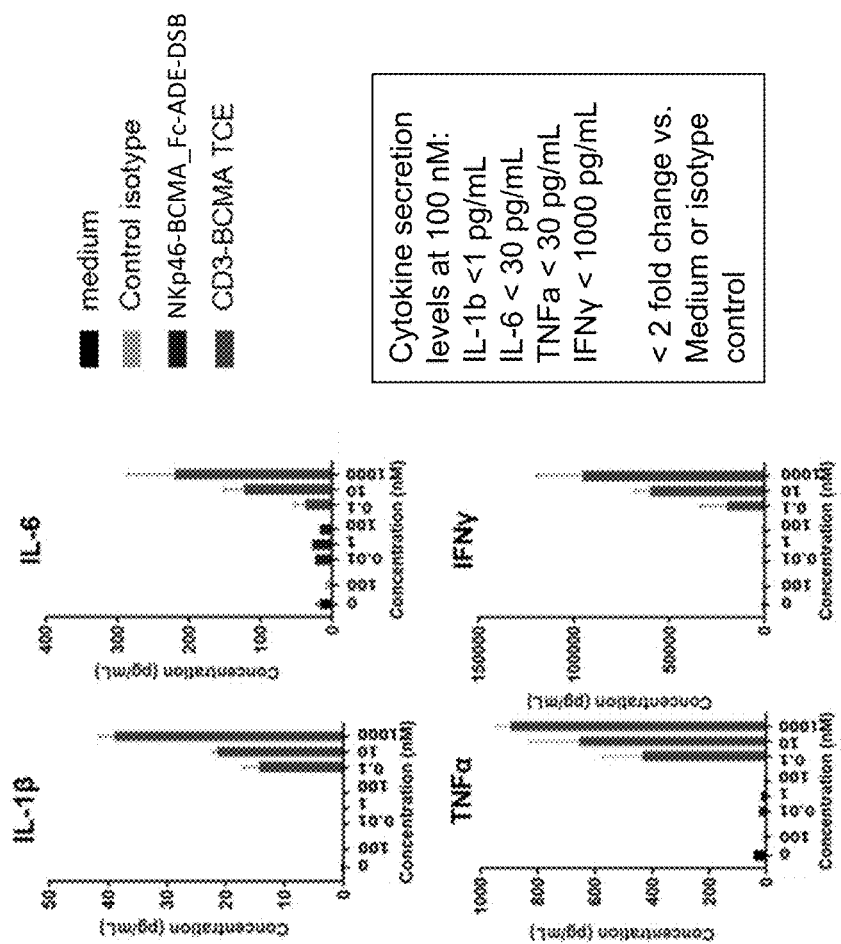
Figure 24A:
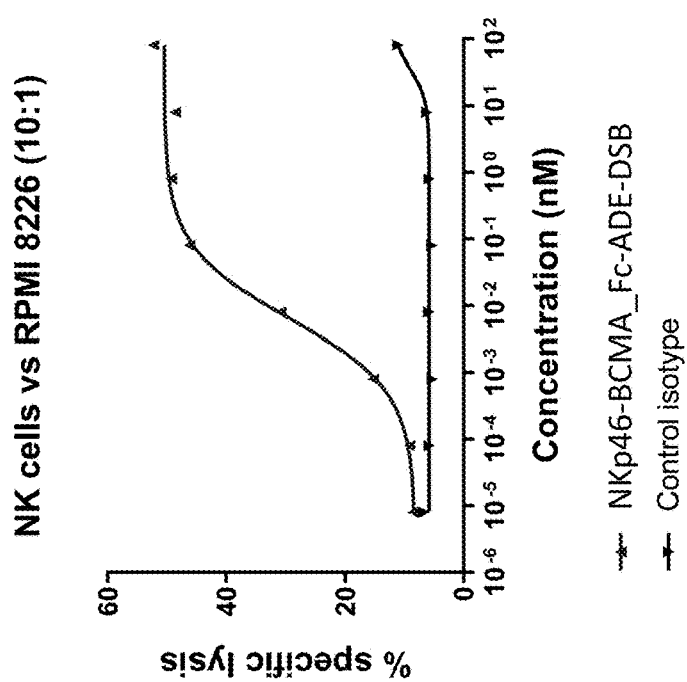

FIG. 24A-FIG. 24B depict cytotoxicity of NKp46-BCMA_Fc-ADE-DSB in an NK cell co-culture with RPMI 8226 cells (FIG. 24A) and pro-inflammatory cytokine release (IL-1-beta, IL-6, TNF-alpha, and IFN-gamma) in said co-culture with PMBCs (FIG. 24B).

Figure 25A:
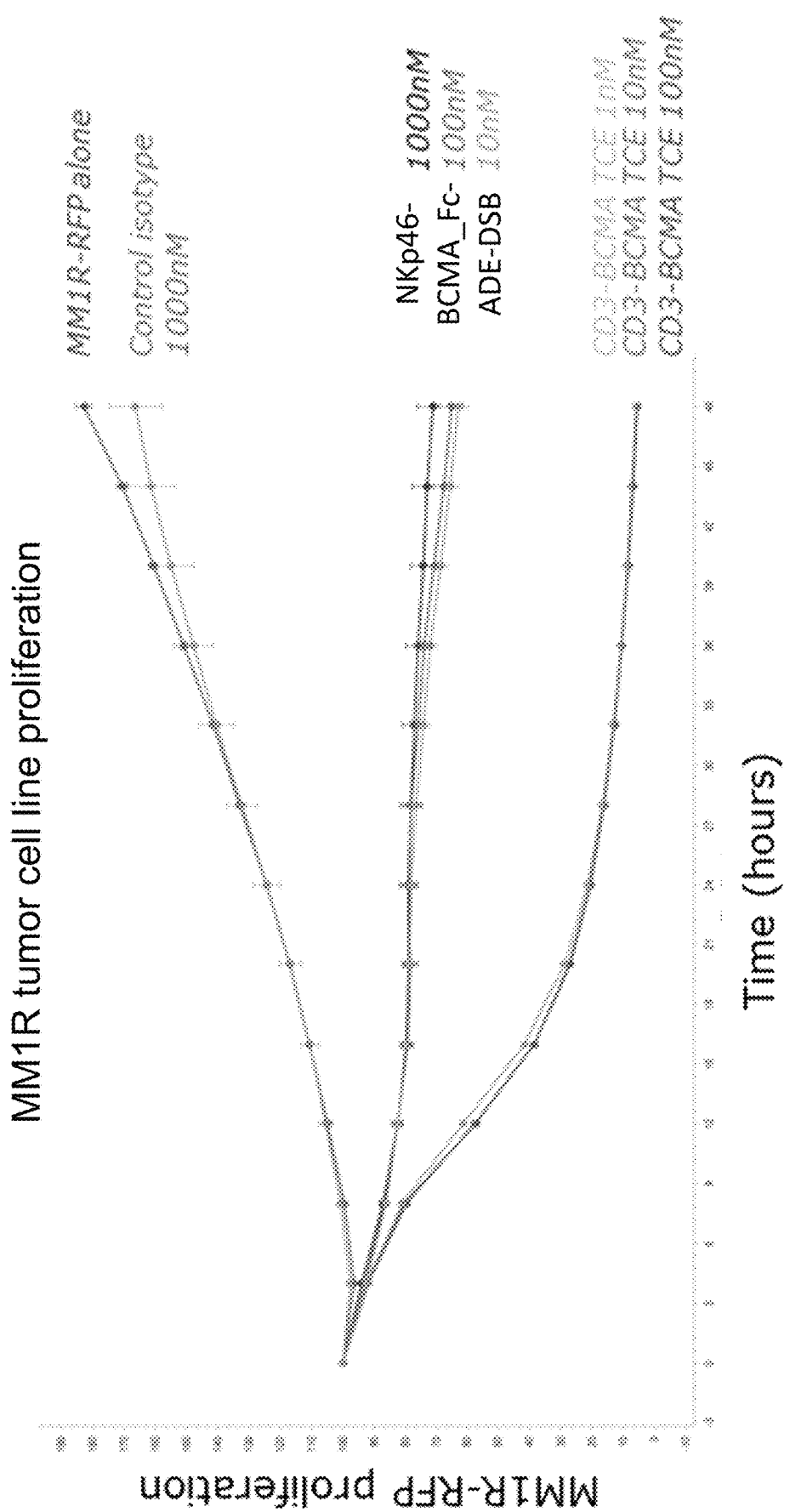
Figure 25B:
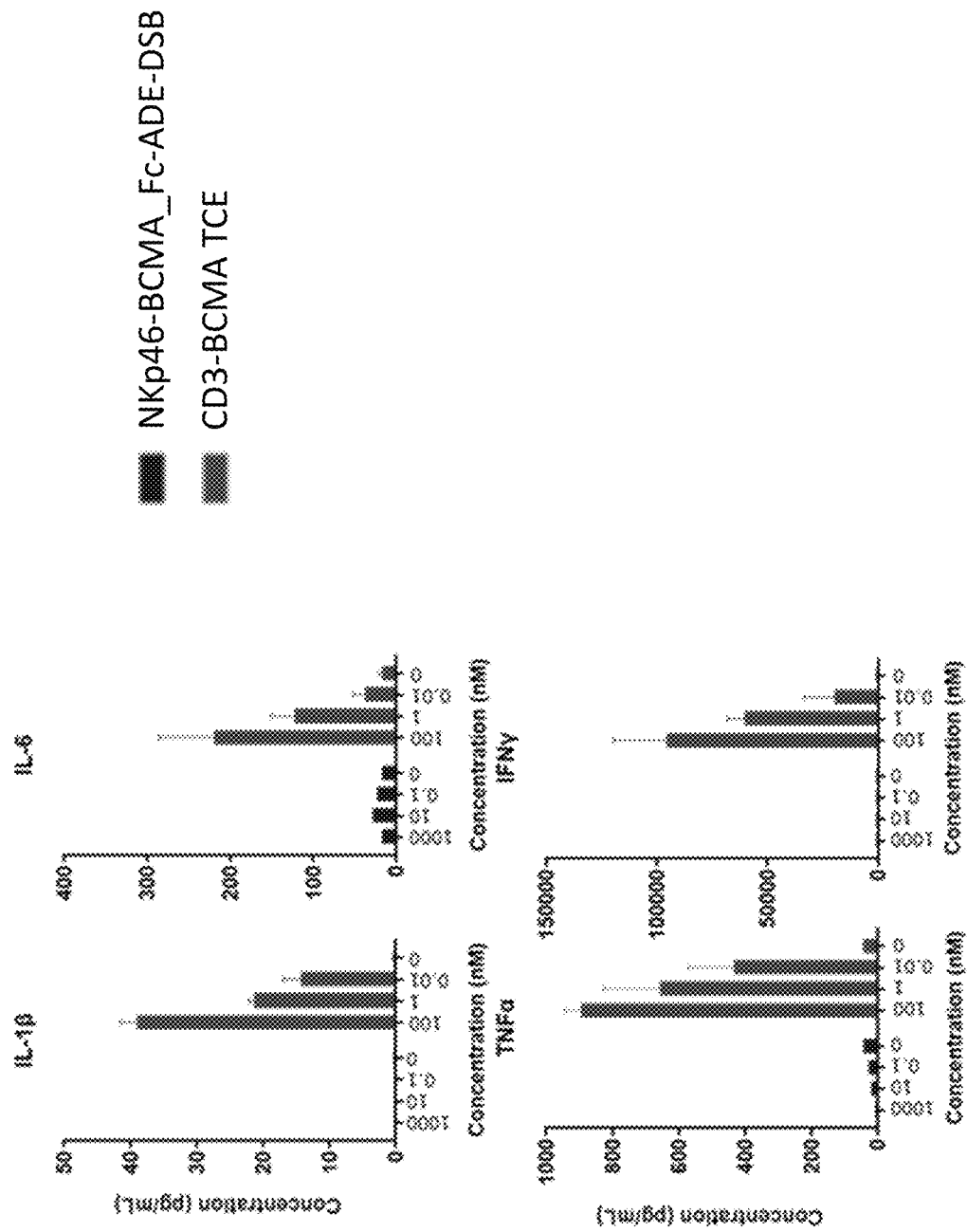
Figures 26A, 26B:
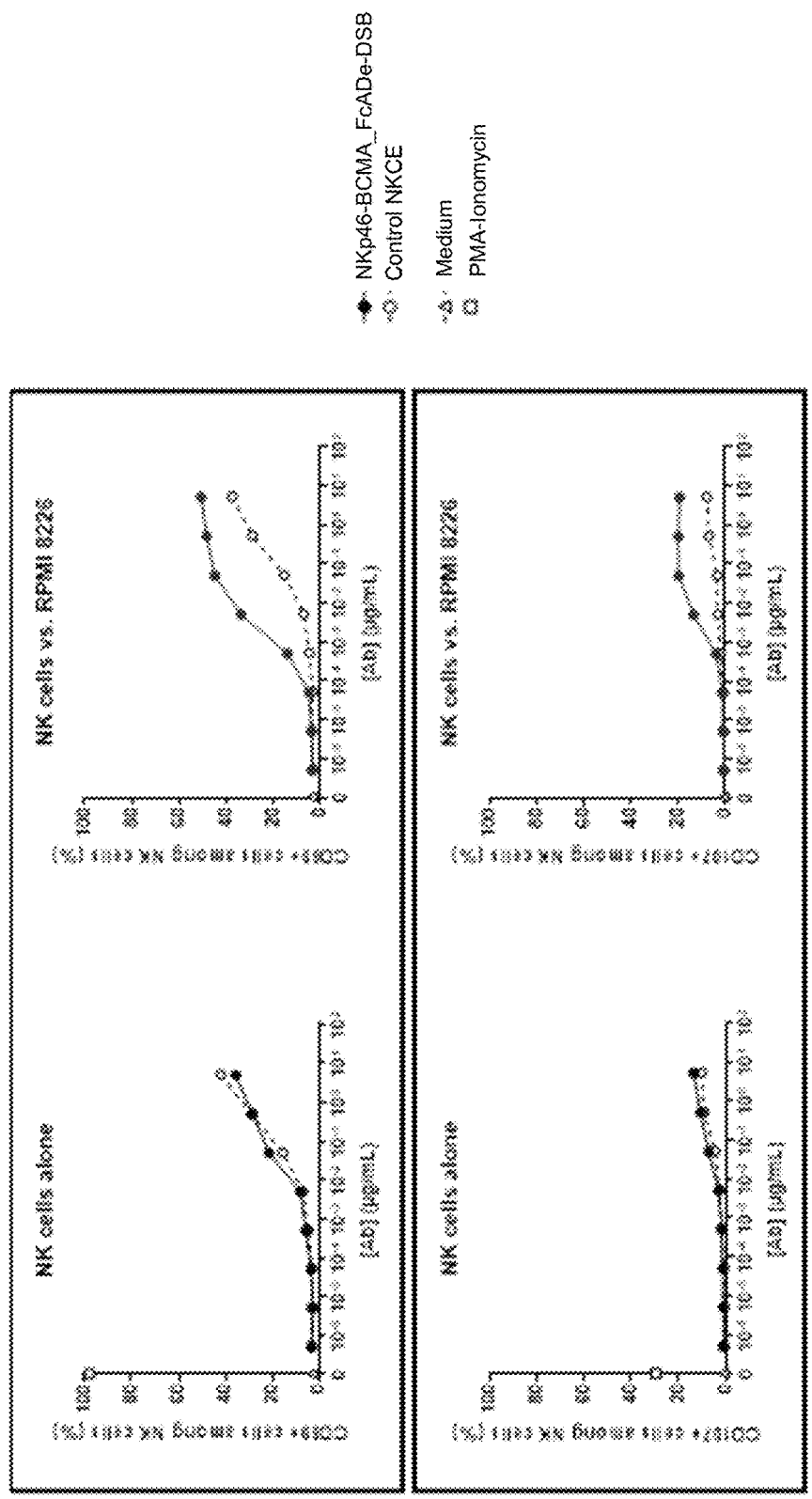
Figures 26C, 26D:
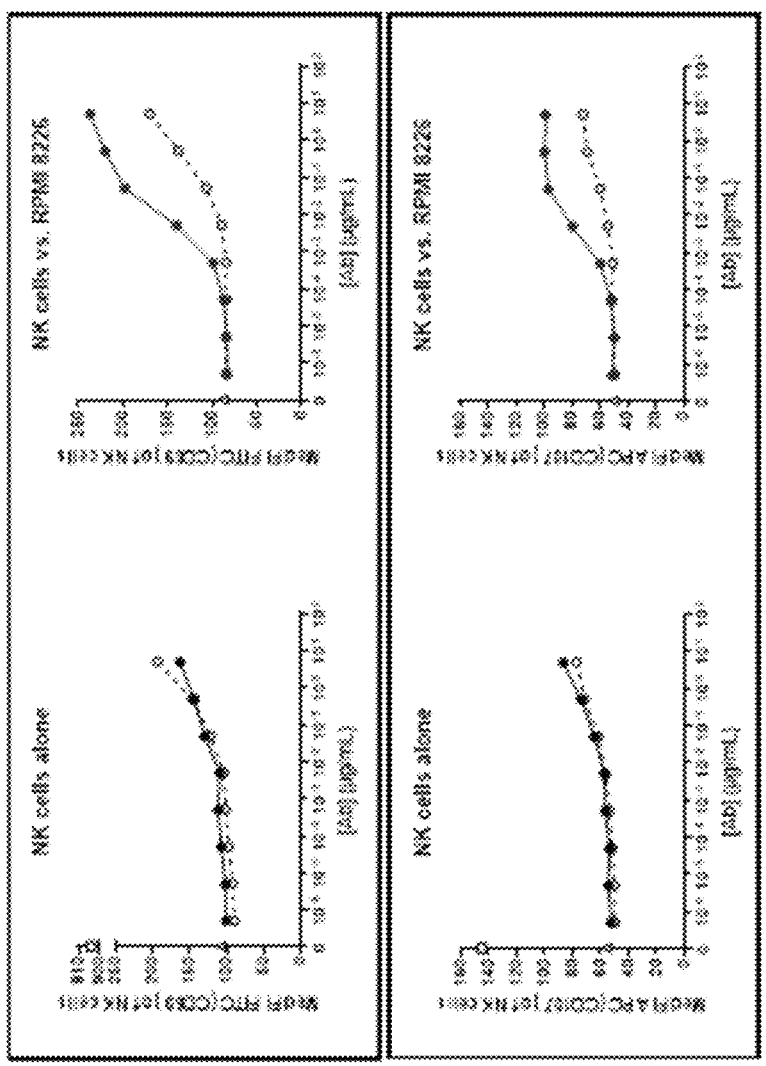
Figures 27A, 27B, 27C:
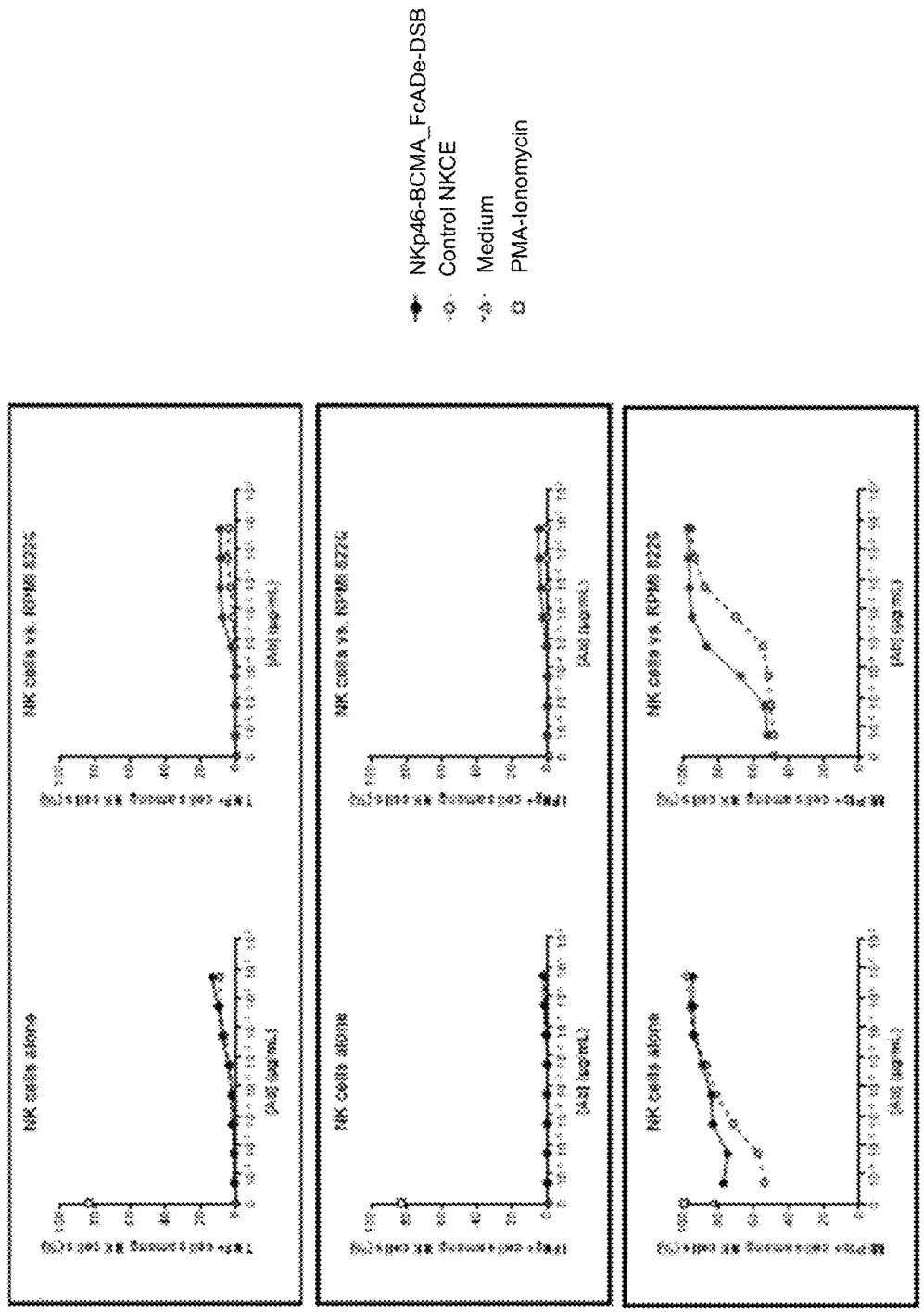
Figures 27D, 27E, 27F:
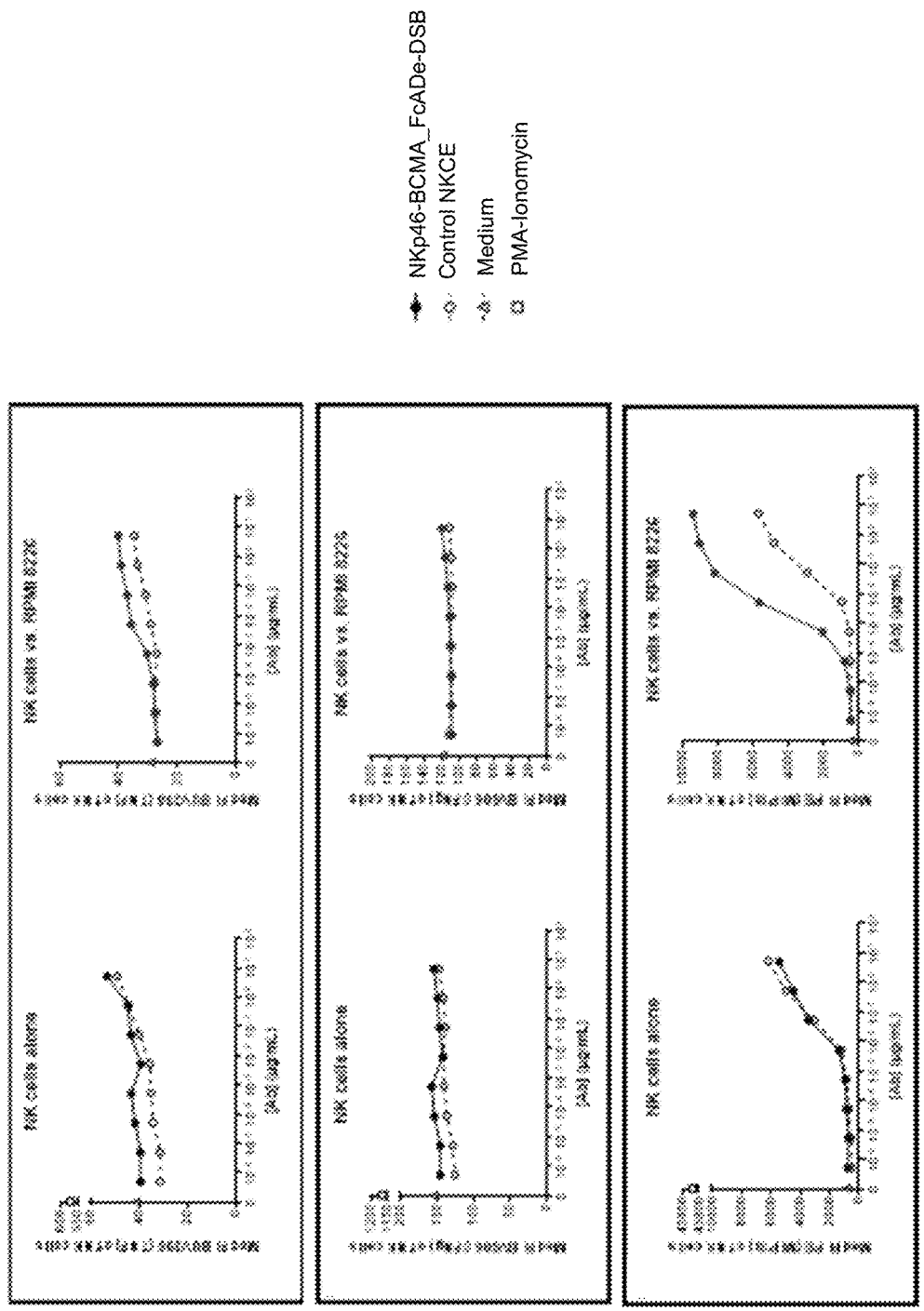

FIG. 25A-FIG. 25B depict MM1R tumor cell line proliferation in the presence of NKp46-BCMA_Fc-ADE-DSB in an NK cell co-culture (FIG. 25A) and pro-inflammatory cytokine release (IL-1-beta, IL-6, TNF-alpha, and IFN-gamma) in said co-culture with PMBCs (FIG. 25B).

FIG. 26A-FIG. 26D depict efficacy of NKp46-BCMA_Fc-ADE-DSB on NK cell activation as indicated by activation markers CD69 (FIG. 26A and FIG. 26C) and CD107a/b (FIG. 26B and FIG. 26D) in the presence or absence of RPMI 8226 MM cells.

FIG. 27A-FIG. 27F depict efficacy of NKp46-BCMA_Fc-ADE-DSB on intracellular production of TFNα (FIG. 27A and FIG. 27D), IFNγ (FIG. 27B and FIG. 27E), and MIP1β (FIG. 27C and FIG. 27F) in by NK cells in the presence or absence of RPMI 8826 MM cells.

Figure 28A:
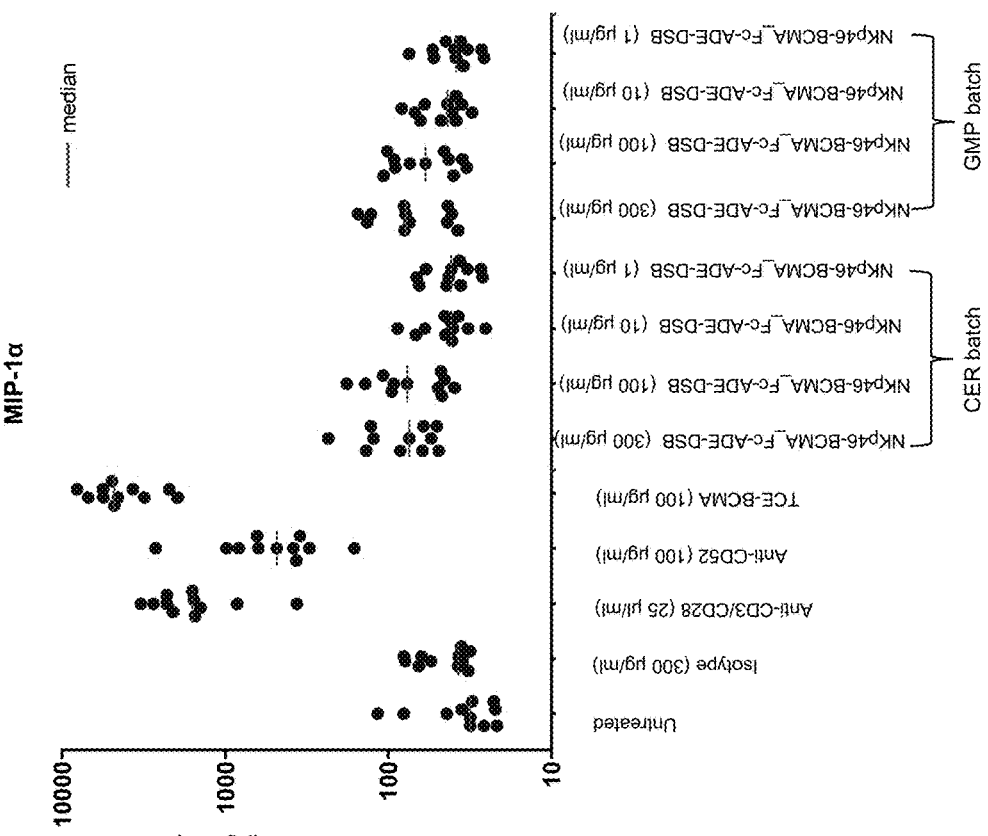
Figure 28B:
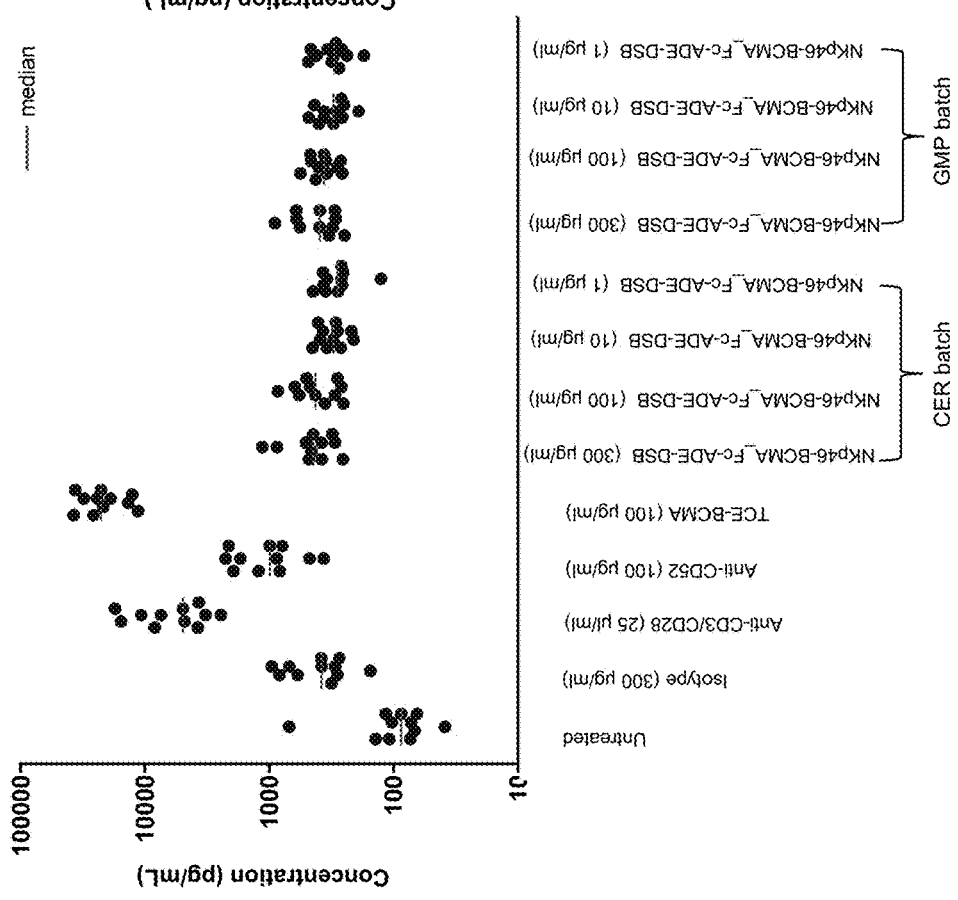

FIG. 28A-FIG. 28B depict IFN-γ (FIG. 28A) and MIP-1α (FIG. 28B) plasma levels following treatment with 1, 10, 100, and 300 ug/mL of NKp46-BCMA_Fc-ADE-DSB prepared from two different batches (CER or GMP) or with negative or positive controls in an in vitro assay with human whole blood co-cultured with RPMI 8226-FRP cells.

Figure 29A:
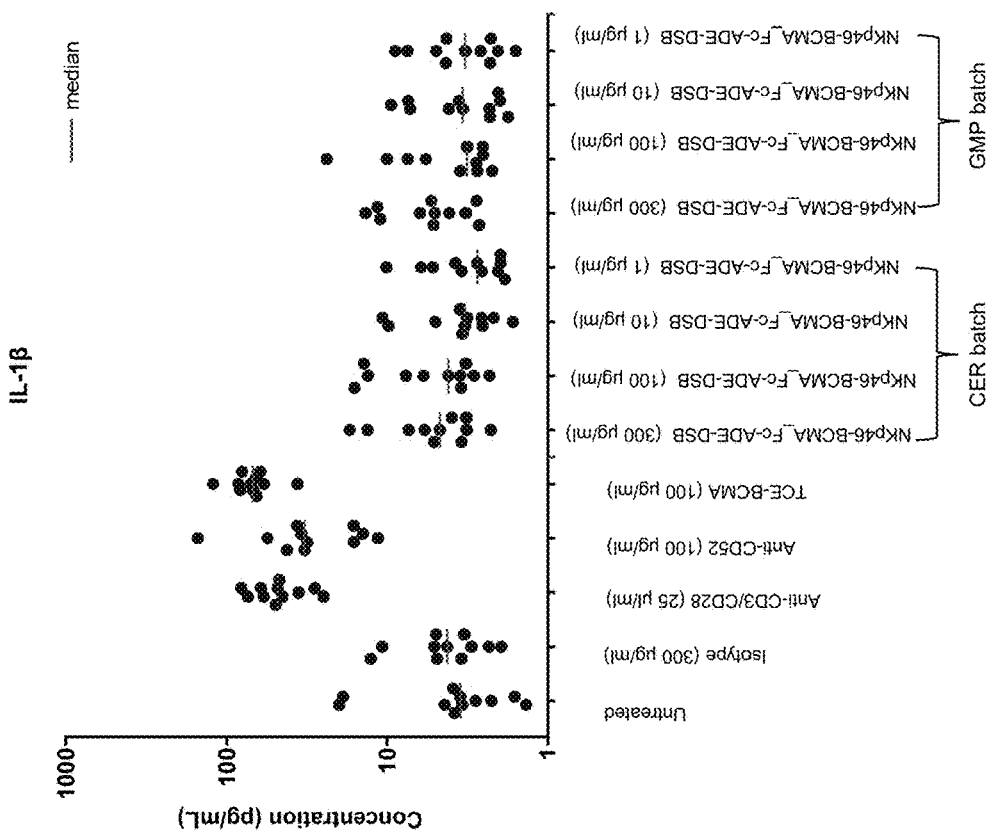
Figure 29B:
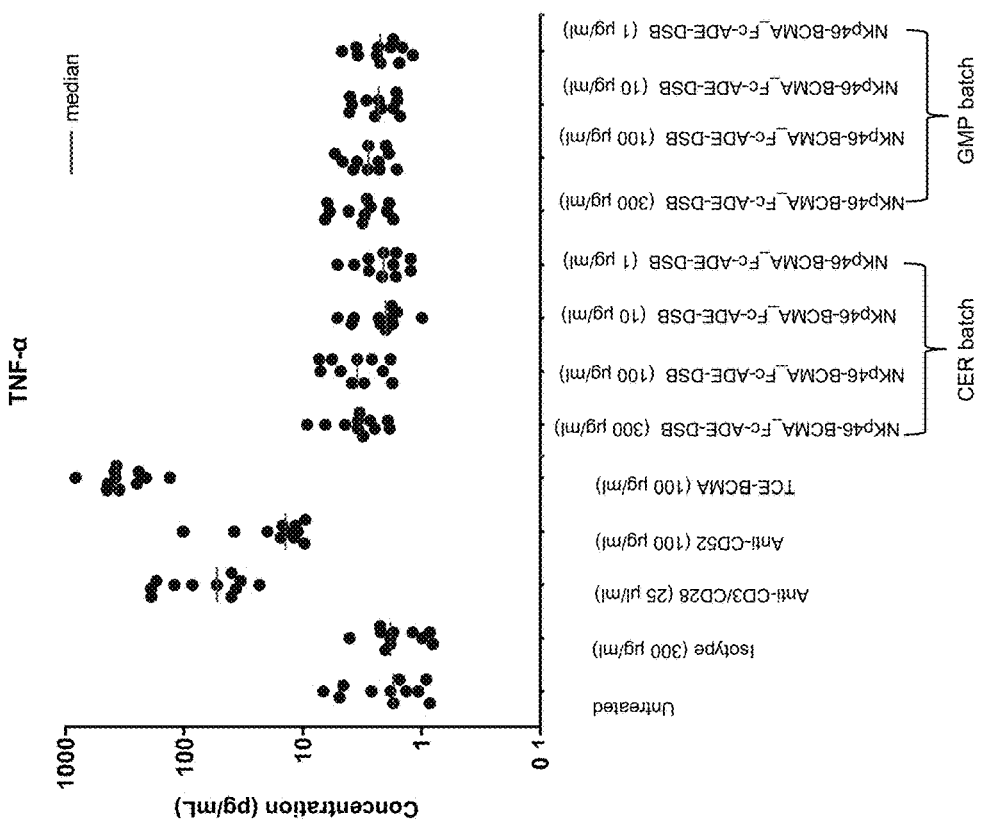

FIG. 29A-FIG. 29B depict TNF-α (FIG. 29A) and IL-1β (FIG. 29B) plasma levels following treatment with 1, 10, 100, and 300 ug/mL of NKp46-BCMA_Fc-ADE-DSB prepared from two different batches (CER or GMP) or with negative or positive controls in an in vitro assay with human whole blood co-cultured with RPMI 8226-RFP cells.

Figure 30A:
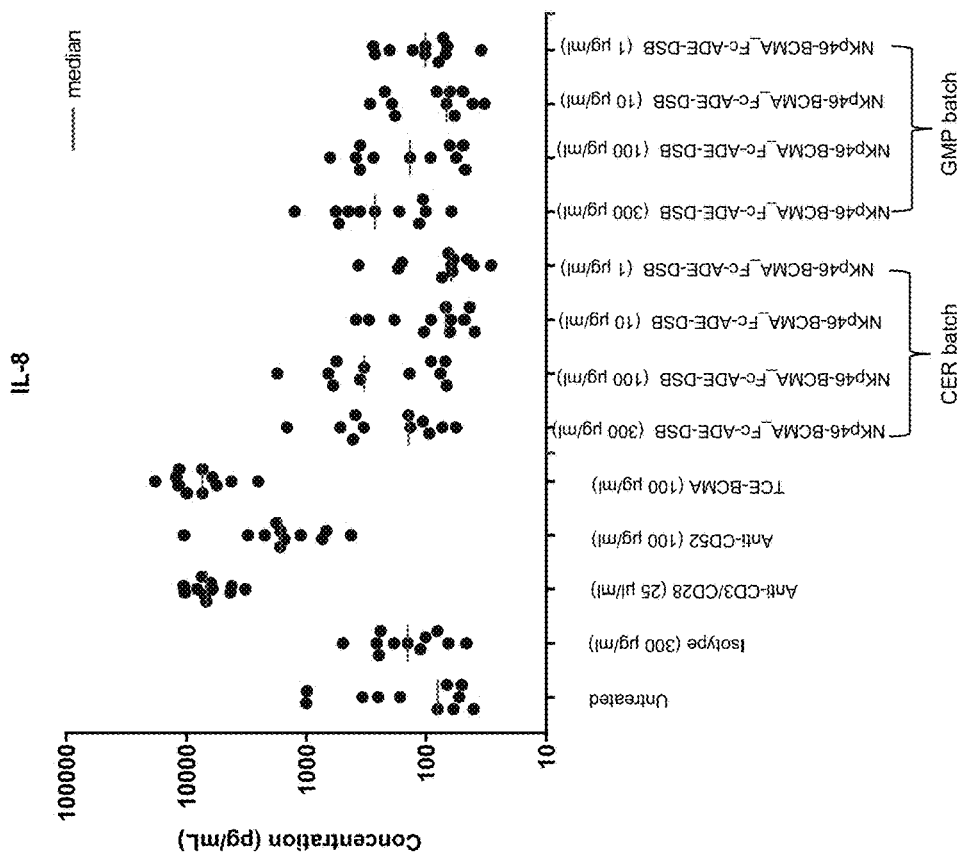
Figure 30B:
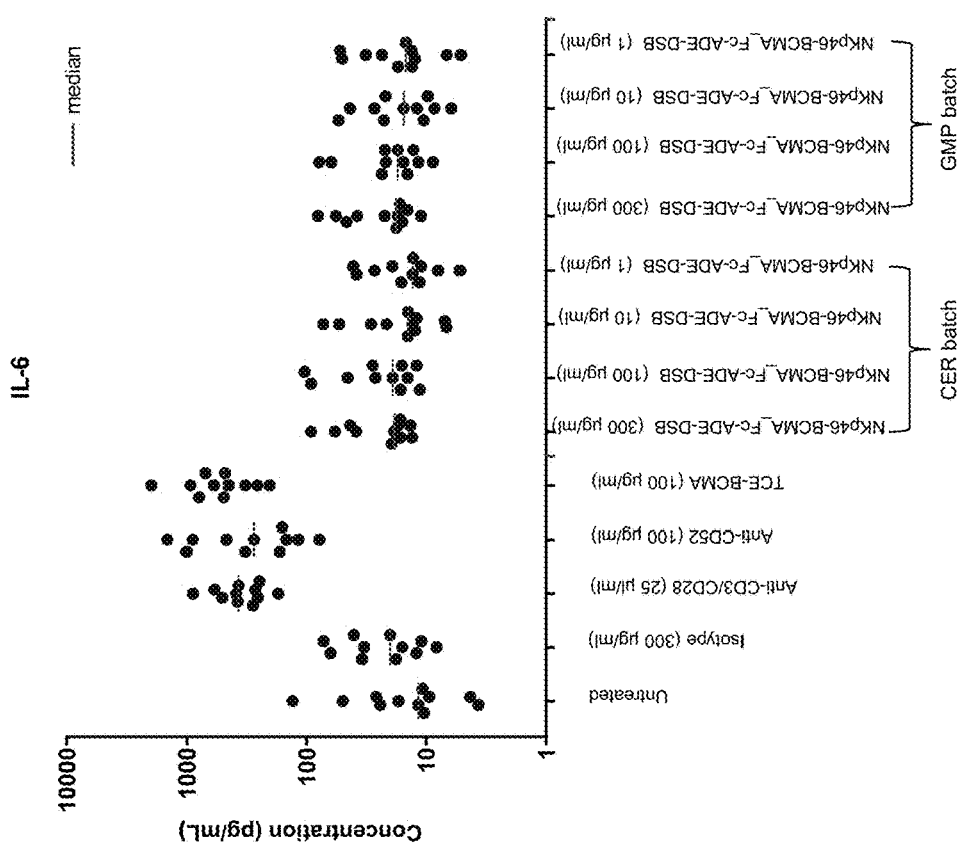

FIG. 30A-FIG. 30B depict IL-6 (FIG. 30A) and IL-8 (FIG. 30B) plasma levels following treatment with 1, 10, 100, and 300 ug/mL of NKp46-BCMA_Fc-ADE-DSB prepared from two different batches (CER or GMP) or with negative or positive controls in an in vitro assay with human whole blood co-cultured with RPMI 8226-RFP cells.

Figure 31B:
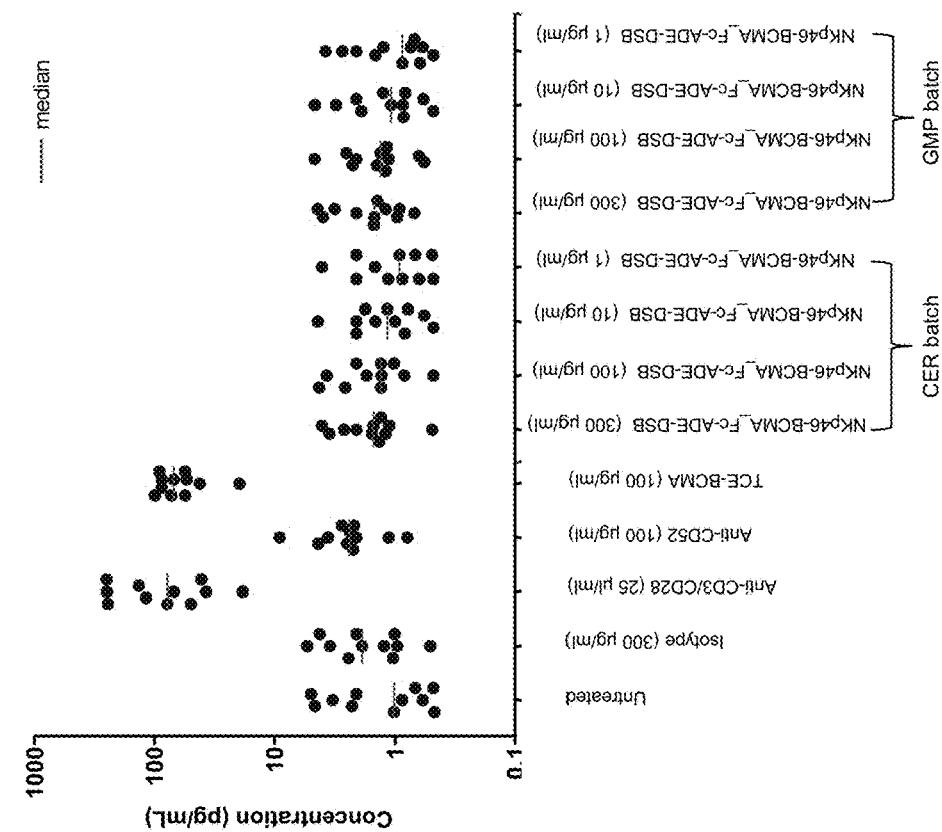
Figure 31A:
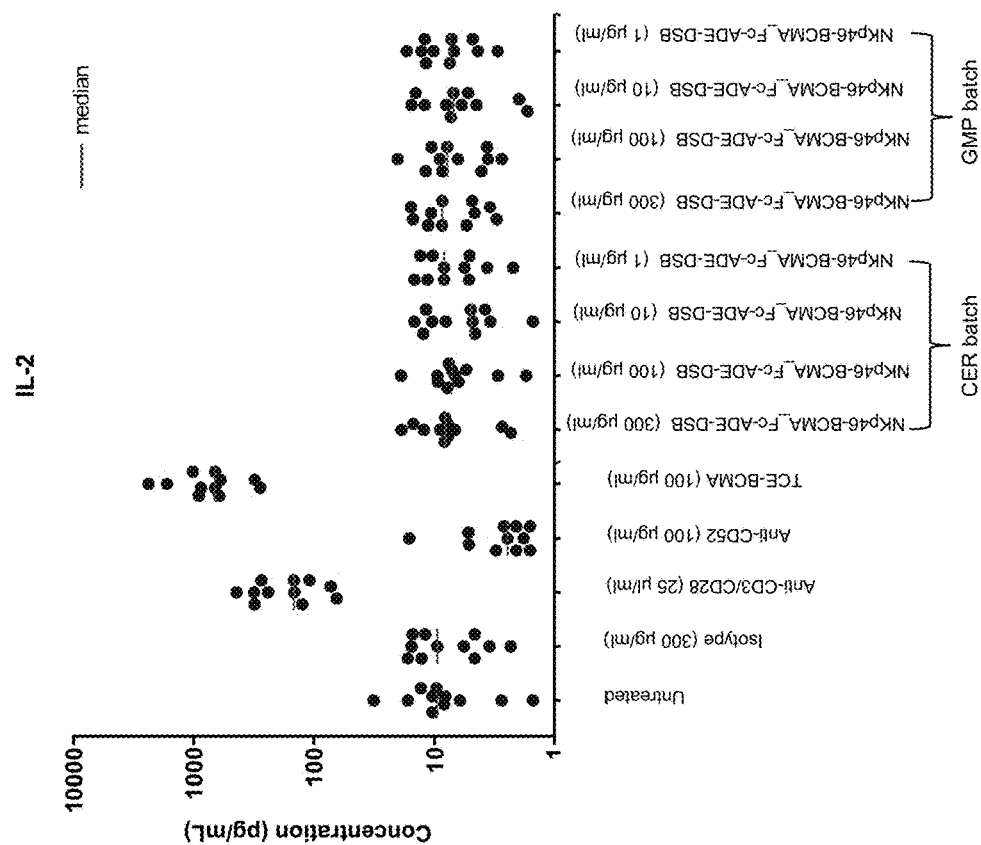

FIG. 31A-FIG. 31B depict IL-2 (FIG. 31A) and GM-CSF (FIG. 31B) plasma levels following treatment with 1, 10, 100, and 300 ug/mL of NKp46-BCMA_Fc-ADE-DSB prepared from two different batches (CER or GMP) or with negative or positive controls in an in vitro assay with human whole blood co-cultured with RPMI 8226-RFP cells.

Figure 32B:
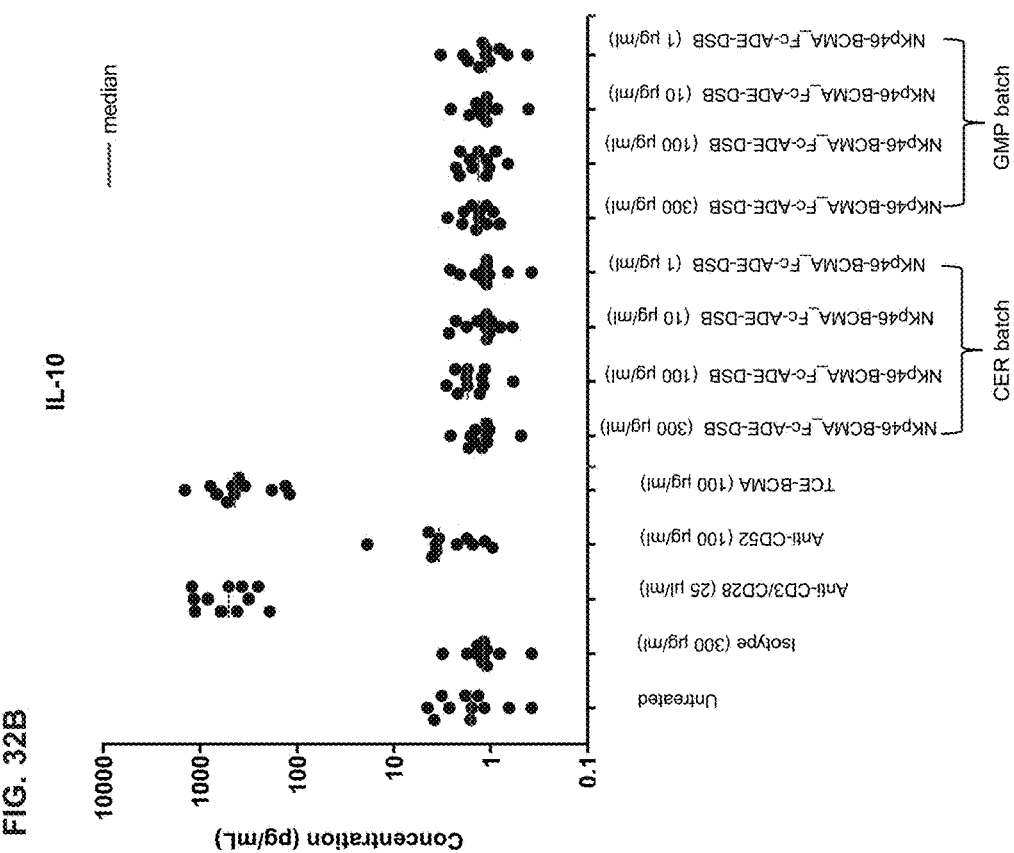
Figure 32A:
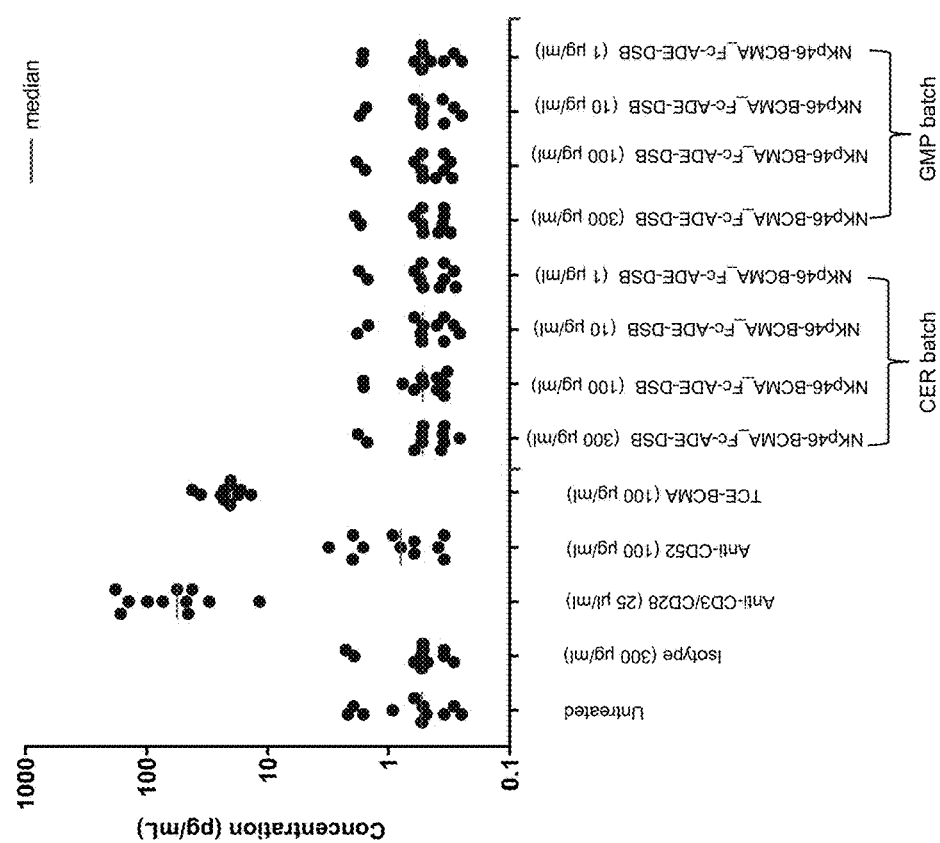

FIG. 32A-FIG. 32B depict IL-4 (FIG. 32A) and IL-10 (FIG. 32B) plasma levels following treatment with 1, 10, 100, and 300 ug/mL of NKp46-BCMA_Fc-ADE-DSB prepared from two different batches (CER or GMP) or with negative or positive controls in an in vitro assay with human whole blood co-cultured with RPMI 8226-RFP cells.

Figures 33A, 33B, 33C:
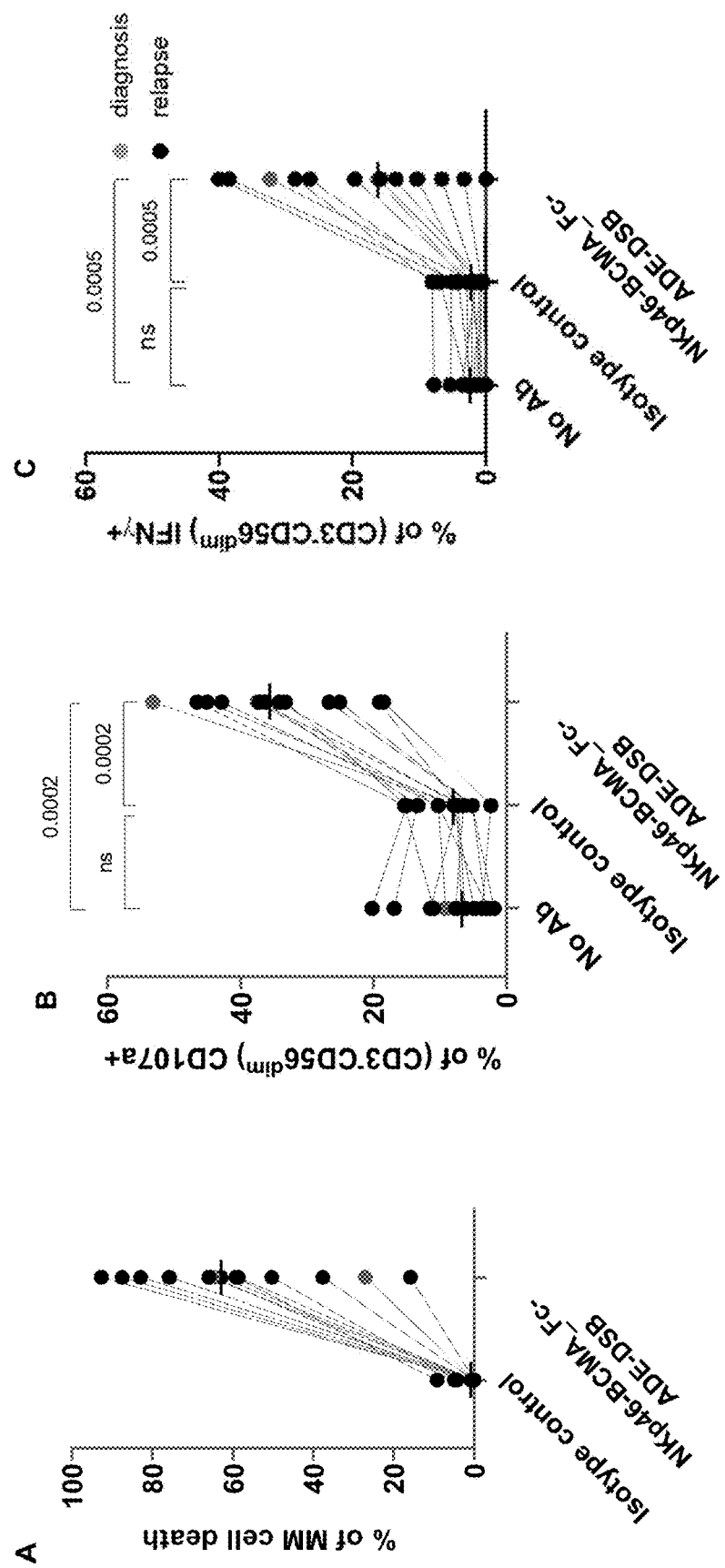

FIG. 33A-FIG. 33C depicts induction of NK cell activation and tumor cell depletion with NKp46-BCMA_Fc-ADE-DSB in vitro and ex vivo with primary patient samples at diagnosis and at relapse. FIG. 33A is % of MM cell death, FIG. 33B is % of CD107+ cells, and FIG. 33C is % of INFγ+ cells.

Figure 34A:
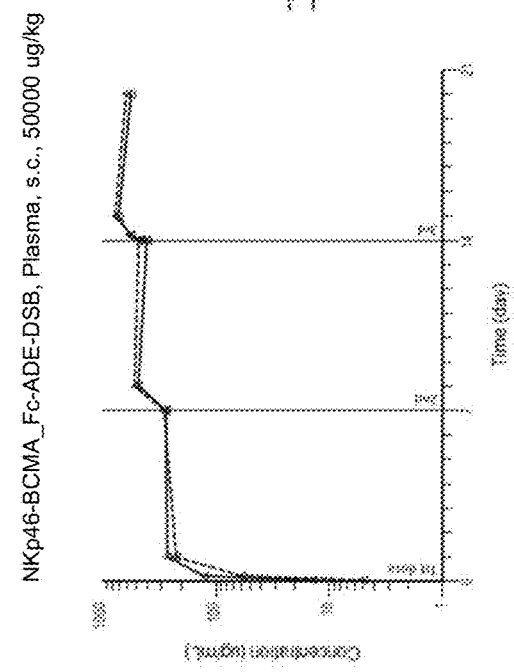
Figure 34B:
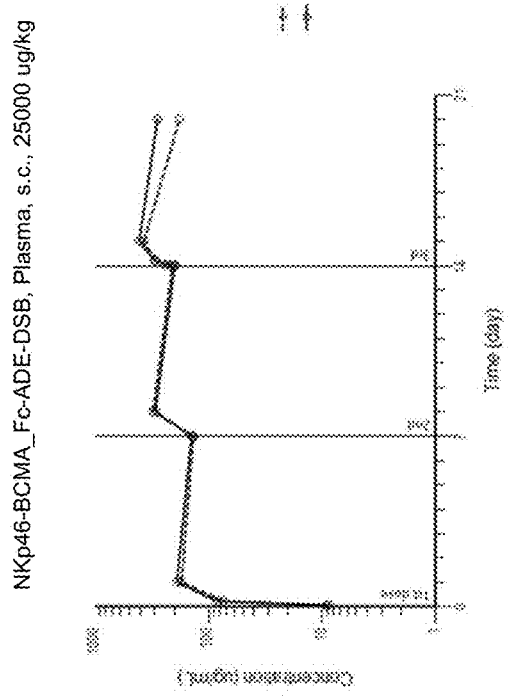

FIG. 34A-FIG. 34B are graphs illustrating plasma NKp46-BCMA_Fc-ADE-DSB concentrations following repeated (once weekly for 3 weeks) subcutaneous injection of NKp46-BCMA_Fc-ADE-DSB in cynomolgus monkeys (2/dose). FIG. 34A depicts plasma concentrations in two males that received 25000 ug/kg/administration. FIG. 34B depicts plasma concentrations in two females that received 50000 ug/kg/administration.

Figure 35:
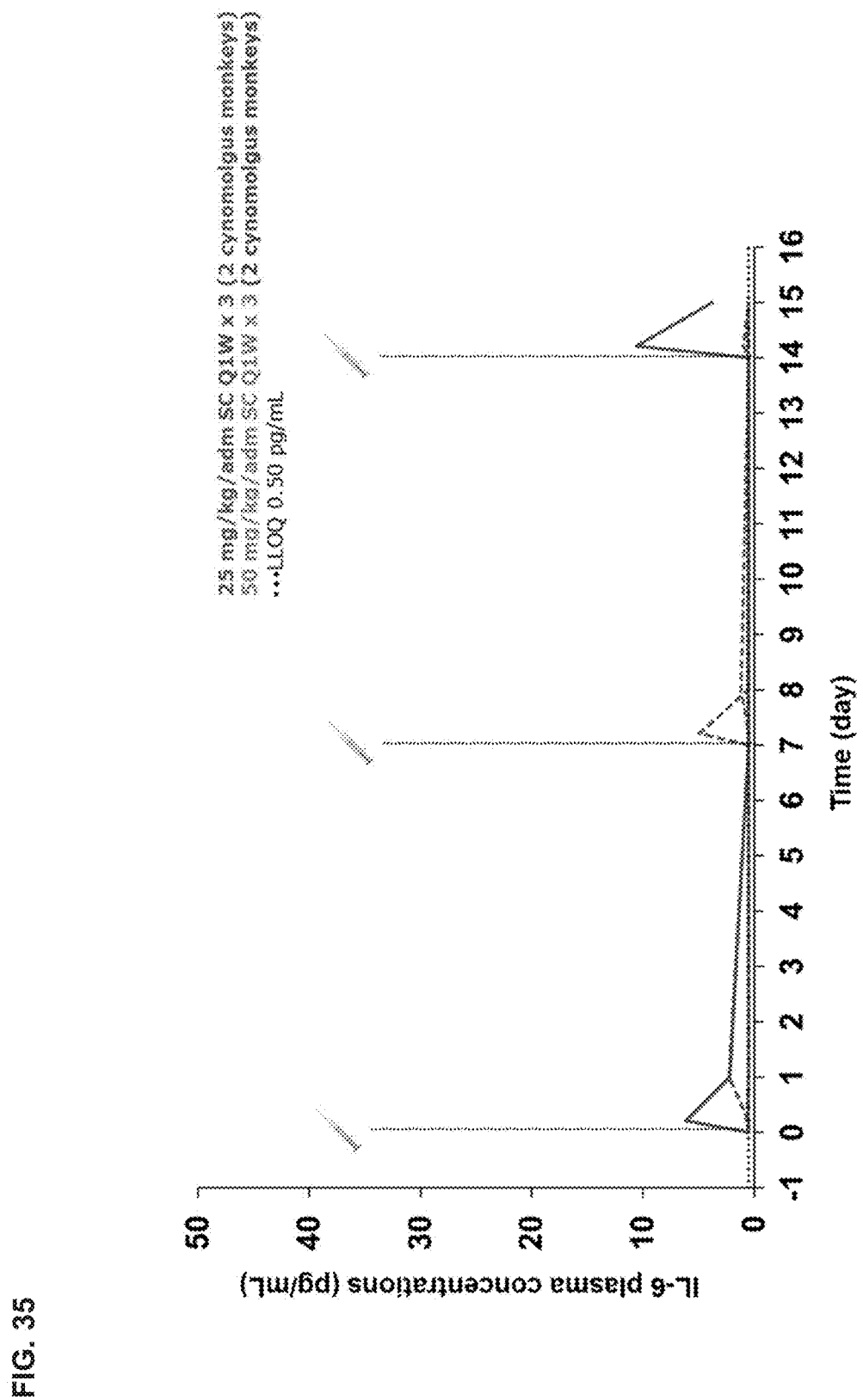

FIG. 35 illustrates plasma IL-6 levels following repeated (once weekly for 3 weeks) subcutaneous injection of NKp46-BCMA_Fc-ADE-DSB at 25 mg/kg/administration or 50 mg/kg/administration in cynomolgus monkeys (2 per dose).

DETAILED DESCRIPTION

The disclosure provides multifunctional binding proteins that bind one surface biomarker on immune NK cells, i.e., NKp46 and one antigen of interest on the cell membrane of normal and malignant plasma cells i.e., BCMA, and is capable of redirecting NK cells to lyse a target cell that expresses the BCMA surface biomarker. The multifunctional binding proteins of the present disclosure further comprises all or part of a Fc region or variant thereof which binds a Fc-γ receptor (FcγR), in particular an activating Fc-γ receptor (FcγR), for example FcγRIIIa also called CD16a.

The present disclosure provides novel Fc domain variants (e.g., novel binding polypeptides comprising Fc domain variants) having improved thermal stability. The present disclosure also provides novel Fc domain variants (e.g., novel binding polypeptides comprising Fc domain variants) having improved binding to Fc receptors. The present disclosure further provides novel Fc domain variants (e.g., binding polypeptides comprising Fc domain variants) comprising a glycosylated Fc domain that enhances interaction with an antibody effector molecule compared to a wild-type (e.g., non-modified) Fc domain. The present disclosure also provides nucleic acids encoding Fc domain variants (e.g., novel binding polypeptides comprising Fc domain variants), recombinant expression vectors and host cells for making Fc domain variants (e.g., novel binding polypeptides comprising Fc domain variants), and pharmaceutical compositions comprising the isolated Fc domain variants (e.g., novel binding polypeptides comprising Fc domain variants). Methods of using the Fc domain variants (e.g., novel binding polypeptides comprising Fc domain variants) of the present disclosure to treat one or more diseases or disorders are also provided.

It is to be understood that the methods described in this disclosure are not limited to particular methods and experimental conditions disclosed herein as such methods and conditions may vary. It is also to be understood that the terminology used herein is for the purpose of describing particular embodiments only and is not intended to be limiting.

Furthermore, the experiments described herein, unless otherwise indicated, use conventional molecular and cellular biological and immunological techniques within the skill of the art. Such techniques are well known to the skilled worker and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2$^{nd}$ edition).

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The term "polypeptide" refers to any polymeric chain of amino acids and encompasses native or artificial proteins, polypeptide analogs or variants of a protein sequence, or fragments thereof, unless otherwise contradicted by context. A polypeptide may be monomeric or polymeric. A polypeptide fragment comprises at least about 5 contiguous amino acids, at least about 10 contiguous amino acids, at least about 15 contiguous amino acids, or at least about 20 contiguous amino acids, for example.

The term "isolated protein" or "isolated polypeptide" refers to a protein or polypeptide that by virtue of its origin or source of derivation is not associated with naturally associated components that accompany it in its native state; is substantially free of other proteins from the same species; is expressed by a cell from a different species; or does not occur in nature. Thus, a protein or polypeptide that is chemically synthesized or synthesized in a cellular system different from the cell from which it naturally originates will be "isolated" from its naturally associated components. A protein or polypeptide may also be rendered substantially free of naturally associated components by isolation using protein purification techniques well known in the art.

As used herein, the term "binding protein" or "binding polypeptide" shall refer to a protein or polypeptide (e.g., an antibody or immunoadhesin) that contains at least one binding site which is responsible for selectively binding to a target antigen of interest (e.g., a human target antigen). Exemplary binding sites include an antibody variable domain, a ligand binding site of a receptor, or a receptor binding site of a ligand. In certain aspects, the binding proteins or binding polypeptides comprise multiple (e.g., two, three, four, or more) binding sites. In certain aspects, the binding protein or binding polypeptide is a therapeutic enzyme.

The term "ligand" refers to any substance capable of binding, or of being bound, to another substance. Similarly, the term "antigen" refers to any substance to which an antibody may be generated. Although "antigen" is commonly used in reference to an antibody binding substrate, and "ligand" is often used when referring to receptor binding substrates, these terms are not distinguishing, one from the other, and encompass a wide range of overlapping chemical entities. For the avoidance of doubt, antigen and ligand are used interchangeably throughout herein. Antigens/ligands may be a peptide, a polypeptide, a protein, an aptamer, a polysaccharide, a sugar molecule, a carbohydrate, a lipid, an oligonucleotide, a polynucleotide, a synthetic molecule, an inorganic molecule, an organic molecule, and any combination thereof.

The dissociation constant ($K_D$) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (Pharmacia Biosensor; Piscataway, NJ). Surface plasmon analysis can also be performed by immobilizing the analyte (binding protein on a biosensor matrix) and presenting the ligand (target antigen). The term "$K_D$" as used herein refers to the dissociation constant of the interaction between a particular binding protein and a target antigen.

The term "specifically binds" as used herein, refers to the ability of an antibody or an immunoadhesin to bind to a target (e.g., an antigen) with a dissociation constant ($K_D$) of at most about $1 \times 10^{-6}$ M, about $1 \times 10^{-7}$ M, about $1 \times 10^{-8}$ M, about $1 \times 10^{-9}$ M, about $1 \times 10^{-10}$ M, about $1 \times 10^{-11}$ M, about $1 \times 10^{-12}$ M or less, and/or to bind to an antigen with an affinity that is at least about two-fold greater than its affinity for a nonspecific antigen. Specific binding of an antibody can be to a target antigen through the CDR sequences. An antibody can also specifically bind to FcRs, such as FcRn or FcγRIIIa through the Fc region.

As used herein, the term "antibody" refers to such assemblies (e.g., intact antibody molecules, immunoadhesins, or variants thereof) which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "antibody" comprises five distinct classes of antibody that can be distinguished biochemically. While all five classes of antibodies are clearly within the scope of the current disclosure, the following discussion will generally be directed to the IgG class of immunoglobulin molecules. With regard to IgG, immunoglobulins comprise two identical light chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Light chains of immunoglobulin are classified as either kappa (κ) or lambda (λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells, or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma (γ), mu (μ), alpha (α), delta (δ), or epsilon (ε), with some subclasses among them (e.g., γI-γ4). It is the nature of this chain that determines the "class" of the antibody as IgG, IgM, IgA, or IgE, respectively. The immunoglobulin isotype subclasses (e.g., IgG1, IgG2, IgG3, IgG4, IgA1, etc.) are well-characterized and are known to confer functional specialization. Modified versions of each of these classes and isotypes are readily discernable to the skilled artisan in view of the instant disclosure and, accordingly, are within the scope of the current disclosure.

Both the light and heavy chains are divided into regions of structural and functional homology. The term "region" refers to a part or portion of an immunoglobulin or antibody chain and includes constant region or variable regions, as well as more discrete parts or portions of said regions. For example, light chain variable regions include "complementarity determining regions" or "CDRs" interspersed among "framework regions" or "FRs," as defined herein.

The regions of an immunoglobulin heavy or light chain may be defined as "constant" (C) region or "variable" (V) regions, based on a relative lack of sequence variation within the regions of various class members in the case of a "constant region," or based on a significant variation within the regions of various class members in the case of a "variable regions." The terms "constant region" and "variable region" may also be used functionally. In this regard, it will be appreciated that the variable regions of an immunoglobulin or antibody determine antigen recognition and specificity. Conversely, the constant regions of an immunoglobulin or antibody confer important effector functions such as secretion, trans-placental mobility, Fc receptor binding, complement binding, and the like. The subunit structures and three-dimensional configurations of the constant regions of the various immunoglobulin classes are well-known.

The constant and variable regions of immunoglobulin heavy and light chains are folded into domains. The term "domain" refers to a globular region of a heavy or light chain comprising peptide loops (e.g., comprising 3 to 4 peptide loops) stabilized, for example, by β-pleated sheet and/or an intra-chain disulfide bond. Constant region domains on the light chain of an immunoglobulin are referred to interchangeably as "light chain constant region domains," "CL regions," "CL domains" or "CK domains." Constant domains on the heavy chain (e.g., hinge, CH1, CH2 or CH3 domains) are referred to interchangeably as "heavy chain constant region domains," "CH" region domains or "CH domains." Variable domains on the light chain are referred to interchangeably as "light chain variable region domains," "VL region domains" or "VL domains." Variable domains on the heavy chain are referred to interchangeably as "heavy chain variable region domains," "VH region domains" or "VH domains."

By convention, the numbering of the amino acids of the variable constant region domains increases as they become more distal from the antigen-binding site or amino-terminus of the immunoglobulin or antibody. The N-terminus of each heavy and light immunoglobulin chain is a variable regin and the C-terminus is a constant region. The CH3 and CL domains comprise the carboxy-terminus of the heavy and light chain, respectively. Accordingly, the domains of a light chain immunoglobulin are arranged in a VL-CL orientation, while the domains of the heavy chain are arranged in the VH-CH1-hinge-CH2-CH3 orientation.

The assignment of amino acids to each variable region domain is in accordance with the definitions of Kabat, Sequences of Proteins of Immunological Interest (National Institutes of Health, Bethesda, M D, 1987 and 1991). Kabat also provides a widely used numbering convention (Kabat numbering) in which corresponding residues between different heavy chain variable regions or between different light chain variable regions are assigned the same number. CDRs 1, 2 and 3 of a VL domain are also referred to herein, respectively, as CDR-L1, CDR-L2 and CDR-L3. CDRs 1, 2 and 3 of a VH domain are also referred to herein, respectively, as CDR-H1, CDR-H2 and CDR-H3. If so noted, the assignment of CDRs can be in accordance with IMGT® (Lefranc et al., Developmental & Comparative Immunology 27:55-77; 2003) in lieu of Kabat. Numbering of the heavy chain constant region is via the EU index as set forth in Kabat (Kabat, Sequences of Proteins of Immunological Interest, National Institutes of Health, Bethesda, M D, 1987 and 1991). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., J. Mol. Biol. 262:732-745 (1996), "Antibody-antigen interactions: Contact analysis and binding site topography," J. Mol. Biol. 262, 732-745. ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Pluckthun A, "Yet another numbering scheme for immunoglobulin variable domains: an automatic modeling and analysis tool," J Mol Biol, 2001 Jun. 8; 309(3):657-70, (AHo numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

As used herein, the CDRs of an antibody can be determined according to the numbering system called, "IMGT" described in Lefranc (1999), The Immunologist, vol. 7:132-136 and Lefranc et al. (1999), Nucleic Acids Res., vol. 27:209-212.

As used herein, the CDRs of an antibody can be determined according to the Chothia numbering scheme, which refers to the location of immunoglobulin structural loops. Chothia and Lesk (1987), J. Mol. Biol., vol. 196:901-917; Al-Lazikani et al. (1997), J. Mol. Biol., vol. 273:927-948;

Chothia et al. (1992), J. Mol. Biol., vol. 227:799-817; Tramontano A et al. (1990), J. Mol. Biol. vol. 215(1):175-82.

As used herein, the CDRs of an antibody can be determined according to the Honegger-Pluckthun numbering scheme described in Honnegger and Pluckthun (2001), J. Mol. Biol., vol. 309(3):657-670.

As used herein, the term "VH domain" includes the amino terminal variable domain of an immunoglobulin heavy chain, and the term "VL domain" includes the amino terminal variable domain of an immunoglobulin light chain.

As used herein, the term "CH1 domain" includes the first (most amino terminal) constant region domain of an immunoglobulin heavy chain that extends, e.g., from about positions 114-223 in the Kabat numbering system (EU positions 118-215). The CH1 domain is adjacent to the VH domain and amino terminal to the hinge region of an immunoglobulin heavy chain molecule and does not form a part of the Fc region of an immunoglobulin heavy chain.

As used herein, the term "hinge region" includes the portion of a heavy chain molecule that joins the CH1 domain to the CH2 domain. The hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998, 161:4083).

As used herein, the term "CH2 domain" includes the portion of a heavy chain immunoglobulin molecule that extends, e.g., from about positions 244-360 in the Kabat numbering system (EU positions 231-340). The CH2 domain is unique in that it is not closely paired with another domain. Rather, two N-linked branched carbohydrate chains are interposed between the two CH2 domains of an intact native IgG molecule. In one embodiment, a binding polypeptide of the current disclosure comprises a CH2 domain derived from an IgG1 molecule (e.g. a human IgG1 molecule).

As used herein, the term "CH3 domain" includes the portion of a heavy chain immunoglobulin molecule that extends approximately 110 residues from N-terminus of the CH2 domain, e.g., from about positions 361-476 of the Kabat numbering system (EU positions 341-445). The CH3 domain typically forms the C-terminal portion of the antibody. In some immunoglobulins, however, additional domains may extend from the CH3 domain to form the C-terminal portion of the molecule (e.g., the CH4 domain in the μ chain of IgM and the e chain of IgE). In one embodiment, a binding polypeptide of the current disclosure comprises a CH3 domain derived from an IgG1 molecule (e.g., a human IgG1 molecule).

As used herein, the term "CL domain" includes the constant region domain of an immunoglobulin light chain that extends, e.g., from about Kabat position 107A to about Kabat position 216. The CL domain is adjacent to the VL domain. In one embodiment, a binding polypeptide of the current disclosure comprises a CL domain derived from a kappa light chain (e.g., a human kappa light chain).

The variable regions of an antibody allow it to selectively recognize and specifically bind epitopes on antigens. That is, the VL domain and VH domain of an antibody combine to form the variable region (Fv) that defines a three dimensional antigen binding site. More specifically, the antigen binding site is defined by three complementary determining regions (CDRs) on each of the heavy and light chain variable regions. As used herein, the term "antigen binding site" includes a site that specifically binds an antigen (e.g., a cell surface or soluble antigen). The antigen binding site includes an immunoglobulin heavy chain and light chain variable region and the binding site formed by these variable regions determines the specificity of the antibody. An antigen binding site is formed by variable regions that vary from one antibody to another. The altered antibodies of the current disclosure comprise at least one antigen binding site.

In certain embodiments, binding polypeptides of the current disclosure comprise at least two antigen binding domains that provide for the association of the binding polypeptide with the selected antigen. The antigen binding domains need not be derived from the same immunoglobulin molecule. In this regard, the variable region may or be derived from any type of animal that can be induced to mount a humoral response and generate immunoglobulins against the desired antigen. As such, the variable region of a binding polypeptide may be, for example, of mammalian origin e.g., may be human, murine, rat, goat, sheep, non-human primate (such as cynomolgus monkeys, macaques, etc.), lupine, or camelid (e.g., from camels, llamas and related species).

In naturally occurring antibodies, the six CDRs present on each monomeric antibody are short, non-contiguous sequences of amino acids that are specifically positioned to form the antigen binding site as the antibody assumes its three-dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to the immunoreactive antigen epitope.

Exemplary binding polypeptides include antibody variants. As used herein, the term "antibody variant" includes synthetic and engineered forms of antibodies which are altered such that they are not naturally occurring, e.g., antibodies that comprise at least two heavy chain portions but not two complete heavy chains (such as, domain deleted antibodies or minibodies); multi-specific forms of antibodies (e.g., bi-specific, tri-specific, etc.) altered to bind to two or more different antigens or to different epitopes on a single antigen); heavy chain molecules joined to scFv molecules and the like. In addition, the term "antibody variant" includes multivalent forms of antibodies (e.g., trivalent, tetravalent, etc., antibodies that bind to three, four or more copies of the same antigen).

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding polypeptides typically has at least one binding site specific for a human antigen molecule. For example, a typical IgG1 monoclonal antibody is specific for one target antigen. A bivalent antibody is one comprising antigen binding domains that targets two different antigens, or two antigen binding domains that target one antigen. Similarly, a trivalent antibody may be a monospecific antibody with three targeting domains to a single antigen. A trivalent antibody may be bispecific if it binds a first antigen with two binding domains and a second antigen with another binding domain. A trivalent antibody maybe trispecific and bind to three different targets.

The term "specificity" refers to the ability to specifically bind (e.g., immunoreact with) a given target antigen (e.g., a human target antigen). A binding polypeptide may be monospecific and contain one or more binding sites which specifically bind a target or a polypeptide may be multi-specific and contain two or more binding sites which specifically bind the same or different targets. In certain embodiments, a binding polypeptide is specific for two different (e.g., non-overlapping) portions of the same target. In certain embodiments, a binding polypeptide is specific for more than one target. Exemplary binding polypeptides (e.g., antibodies) which comprise antigen binding sites that bind to antigens expressed on tumor cells are known in the art and one or more CDRs from such antibodies can be included in an antibody as described herein.

The term "antigen" or "target antigen," as used herein, refers to a molecule or a portion of a molecule that is capable of being bound by the binding site of a binding polypeptide. A target antigen may have one or more epitopes.

The term "about" or "approximately" means within about 20%, such as within about 10%, within about 5%, or within about 1% or less of a given value or range.

As used herein, "administer" or "administration" refers to the act of injecting or otherwise physically delivering a substance as it exists outside the body (e.g., an isolated binding polypeptide provided herein) into a patient, such as by, but not limited to, pulmonary (e.g., inhalation), mucosal (e.g., intranasal), intradermal, intravenous, intramuscular, subcutaneous delivery and/or any other method of physical delivery described herein or known in the art. When a disease, or a symptom thereof, is being managed or treated, administration of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symptoms.

As used herein, the term "composition" is intended to encompass a product containing the specified ingredients (e.g., an isolated binding polypeptide provided herein) in, optionally, the specified amounts, as well as any product which results, directly or indirectly, from combination of the specified ingredients in, optionally, the specified amounts.

"Effective amount" means the amount of active pharmaceutical agent (e.g., an isolated binding polypeptide of the present disclosure) sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject can be a mammal, such as a non-primate (e.g., cows, pigs, horses, cats, dogs, rats, etc.) or a primate (e.g., monkey and human). In certain embodiments, the term "subject," as used herein, refers to a vertebrate, such as a mammal. Mammals include, without limitation, humans, non-human primates, wild animals, feral animals, farm animals, sport animals, and pets.

As used herein, the term "therapy" refers to any protocol, method and/or agent that can be used in the prevention, management, treatment and/or amelioration of a disease or a symptom related thereto. In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, known to one of skill in the art such as medical personnel. In other embodiments, the terms "therapies" and "therapy" refer to a biological therapy, supportive therapy, and/or other therapies useful in the modulation of an immune response to an infection in a subject or a symptom related thereto known to one of skill in the art such as medical personnel.

As used herein, the terms "treat," "treatment" and "treating" refer to the reduction or amelioration of the progression, severity, and/or duration of a disease or a symptom related thereto, resulting from the administration of one or more therapies (including, but not limited to, the administration of one or more prophylactic or therapeutic agents, such as an isolated binding polypeptide provided herein). The term "treating," as used herein, can also refer to altering the disease course of the subject being treated. Therapeutic effects of treatment include, without limitation, preventing occurrence or recurrence of disease, alleviation of symptom (s), diminishment of direct or indirect pathological consequences of the disease, decreasing the rate of disease progression, amelioration or palliation of the disease state, and remission or improved prognosis.

BCMA

As used herein, the term "BCMA" refers to B-cell maturation antigen. BCMA (also known as TNFRSF17, BCM or CD269) is a member of the tumor necrosis receptor (TNFR) family and is predominantly expressed on terminally differentiated B cells, e.g., memory B cells, and plasma cells. Its ligands are called B-cell activator of the TNF family (BAFF) and a proliferation inducing ligand (APRIL). BCMA is involved in mediating the survival of plasma cells for maintaining long-term humoral immunity. The gene for BCMA is encoded on chromosome 16 producing a primary 35 mRNA transcript of 994 nucleotides in length (NCBI accession NM_001192.2) that encodes a protein of 184 amino acids (NP_001183.2). A second antisense transcript derived from the BCMA locus has been described, which may play a role in regulating BCMA expression. (Laabi Y. et al., Nucleic Acids Res., 1994, 22:1147-1154.) Additional transcript variants have been described with unknown significance (Smirnova A S et al. Mol Immunol., 2008, 45(4): 1179-1183 A second isoform, also known as TV4, has been identified (Uniprot identifier Q02223-2). "BCMA" includes proteins comprising mutations, e.g., point mutations, fragments, insertions, deletions, and splice variants of full length wild-type BCMA.

Natural Killer Cells

As used herein, "natural killer cells" or "NK cells" refers to a sub-population of lymphocytes that is involved in innate immunity. NK cells can be identified by virtue of certain characteristics and biological properties, such as the expression of specific surface antigens including CD16, CD56 and/or CD57, NKp46 for human NK cells, the absence of the alpha/beta or gamma/delta TCR complex on the cell surface, the ability to bind to and kill cells that fail to express "self" MHC/HLA antigens by the activation of specific cytolytic machinery, the ability to kill tumor cells or other diseased cells that express a ligand for NK activating receptors, and the ability to release protein molecules called cytokines that stimulate or inhibit the immune response. Any of these characteristics and activities can be used to identify NK cells, using methods well known in the art. Any subpopulation of NK cells will also be encompassed by the term NK cells. Within the context herein "active" NK cells designate biologically active NK cells, including NK cells having the capacity of lysing target cells or enhancing the immune function of other cells. NK cells can be obtained by various techniques known in the art, such as isolation from blood samples, cytapheresis, tissue or cell collections, etc. Useful protocols for assays involving NK cells can be found in Natural Killer Cells Protocols (edited by Campbell K S and Colonna M). Human Press. pp. 219-238 (2000).

NKp46

As used herein, the "NKp46" marker, or "natural cytotoxicity triggering receptor 1," also known as "CD335" or "NKP46" or "NK-p46" or "LY94" refers to a protein or polypeptide encoded by the Ncr1 gene. A reference sequence of full-length human NKp46 protein is available from the NCBI database under the accession number NP_004820. The human NKp46 mRNA sequence is described in NCBI accession number NM_004829.

NK Cell Engager

As used herein, the isolated effector-competent polypeptide comprises a multispecific antibody in an NK cell engager format. An "NK cell engager" refers to binding proteins comprising monoclonal antibody domains targeting activating NK cell receptors, antigen-specific targeting regions, and optionally an Fc region (Gauthier, et al. (2019) Cell, 177: 1701-13). NK cells express CD16a, also known as FcγRIIIa, which binds with low affinity to the Fc parts of antibodies (Cerwenka and Lanier (2018) Science 359:6383). Engagement of CD16a is less demanding compared to CD3 engagement due to lower steric hindrances and is additionally facilitated by the lack of accessory molecules. Upon recognizing a target cell decorated with antibodies, NK cells mediate antibody-dependent cellular cytotoxicity (ADCC) resulting in killing of target cells (Lo Nigro (2019) Ann Transl Med 7:105). This naturally occurring mechanism can be utilized to engage CD16 when in conjunction with NKp46 (another activating NK cell receptor) to generate a trifunctional natural killer cell engager (i.e., NKCE) yielding impressive therapeutic outcomes. For a review of NK cell engagers, see Demaria et al. (2021) Eur. J. Immunology 51(8): 1934, incorporated in its entirety by reference herein.

Trifunctional NKCEs are more potent in vitro than clinical therapeutic antibodies targeting the same antigen and they also have similar in vivo pharmacokinetics to full IgG antibodies and no off-target effects. See International Application No. PCT/1B21/62494 incorporated in its entirety by reference herein.

Fc Domains

In certain aspects of the disclosure, Fc domains, e.g., Fc domain variants, are provided. As used herein, the term "Fc region" or "Fc domain" refers to the portion of a heavy chain constant region beginning in the hinge region just upstream of the papain cleavage site (i.e., residue 216 in IgG, taking the first residue of heavy chain constant region to be 114) and ending at the C-terminus of the antibody. Accordingly, a complete Fc region comprises at least a hinge domain, a CH2 domain, and a CH3 domain.

The Fc region of an antibody is involved in non-antigen binding and can mediate effector function by binding to a Fc receptor. There are several different types of Fc receptors, which are classified based on the type of antibody that they recognize. For example, Fc-gamma receptors (FcγR) bind to IgG class antibodies, Fc-alpha receptors (FcαR) bind to IgA class antibodies, and Fc-epsilon receptors (FcεR) bind to IgE class antibodies. The neonatal Fc receptor (FcRn) interacts with the Fc region of an antibody to promote antibody recycling through rescue of normal lysosomal degradation. The FcγRs belong to a family that includes several members, e.g., FcγRI, FcγRIIa, FcγRIIb, FcγRIIIa, and FcγRIIIb.

The term "native Fc" or "wild-type Fc," as used herein, refers to a molecule corresponding to the sequence of a non-antigen-binding fragment resulting from digestion of an antibody or produced by other means, whether in monomeric or multimeric form, and can contain the hinge region. The original immunoglobulin source of the native Fc is typically of human origin and can be any of the immunoglobulins, such as IgG1 and IgG2. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG. The term "native Fc," as used herein, is generic to the monomeric, dimeric, and multimeric forms.

The term "Fc domain variant," "Fc variant" or "modified Fc," as used herein, refers to a molecule or sequence that is modified from a native/wild-type Fc but still comprises a binding site for a FcR. Thus, the term "Fc variant" can comprise a molecule or sequence that is humanized from a non-human native Fc. Furthermore, a native Fc comprises regions that can be removed because they provide structural features or biological activities that are not required for the antibody-like binding polypeptides described herein. Thus, the term "Fc variant" comprises a molecule or sequence that lacks one or more native Fc sites or residues, or in which one or more Fc sites or residues has been modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to a Fc receptor other than a salvage receptor, or (7) antibody-dependent cellular cytotoxicity (ADCC).

As used herein, an "effector-competent Fc variant" or "effector-competent polypeptide" refers to a Fc domain that has one or more Fc effector functions as described further herein.

In certain exemplary embodiments, a Fc variant featured herein has one or more of increased serum half-life, enhanced FcRn binding affinity, enhanced FcRn binding affinity at acidic pH, enhanced FcγRIIIa binding affinity, and/or similar thermal stability, as compared to a wild-type Fc.

FcγRIIIa V176, or FcγRIIIa V158, or human CD16a-V receptor, or CD16a$^V$, refers to a polypeptide construct comprising a fragment of the CD16 human receptor binding to a Fc region of a natural antibody, mediating antibody-dependent cellular cytotoxicity and bearing a Valine (V) on position 176 or position 158, which is also reported in the literature as allotype CD16a V176 or allotype CD16a V158.

FcγRIIIa F176, or FcγRIIIa F158, or human CD16a-F receptor, or CD16a$^F$, refers to a polypeptide construct comprising a fragment of the CD16 human receptor binding to a Fc region of a natural antibody, mediating antibody-dependent cellular cytotoxicity and bearing a Phenylalanine (F) on position 176 or position 158, which is also reported in the literature as allotype CD16a F176 or allotype CD16a F158.

The term "Fc domain" as used herein encompasses native/wild-type Fc and Fc variants and sequences as defined herein. As with Fc variants and native Fc molecules, the term "Fc domain" includes molecules in monomeric or multimeric form, whether digested from whole antibody or produced by other means.

In certain exemplary embodiments, a Fc domain as described herein is thermally stabilized.

In certain exemplary embodiments, a Fc domain as described herein is glycosylated (e.g., via N-linked glycosylation). In certain exemplary embodiments, a Fc domain comprises N-linked glycosylation, e.g., at an N-linked glycosylation motif that contains the amino acid sequence NXT or NXS (X being any amino acid residue except proline). In certain exemplary embodiments, a Fc domain is glycosylated at amino acid position 297, according to EU numbering.

In certain exemplary embodiments, a Fc domain as described herein is effector-competent.

In certain exemplary embodiments, a Fc domain as described herein is any combination of thermally stabilized, glycosylated, and effector-competent.

Thermally-Stabilized Fc Domain Variants

The structure of constant antibody domains is similar to that of the variable domains consisting of β-strands connected with loops and short helices. The CH2 domain of the heavy constant regions exhibits weak carbohydrate-mediated interchain protein-protein interactions in contrast to the extensive interchain interactions exhibited in other domains. Isolated murine CH2 domains are relatively unstable at physiological temperature (Feige et al., 2004, *J. Mol. Biol.* 344:107-118), but previous efforts demonstrate that the thermostability of CH2 domains may be enhanced with the addition of intrachain disulfide bonds, and that these could be used as scaffolds for binders (Gong et al., 2009, *J. Biol. Chem.* 284:14203-210).

Effector-enhancing Fc domain variants that exhibit increased thermal instability (i.e., decreased thermal stability) relative to a wild-type Fc domain are known. For example, S239D/I332E and S239D/I332E/A330L variants lead to decreased stability of the CH2 domain as indicated by the lowering of melting temperature (Tm) in differential scanning calorimetry (DSC) analysis. G236A/S239D/A330L/I332E has a reduced protein thermal shift measurement when compared to wild-type, as well as a considerably reduced half-life in hFcγR transgenic mice. (See Liu et al. (2014) *J. Biol. Chem.* 289(6): 3571, and Liu et al. (2020) *Antibodies* 9(4): 64 for review.)

Effector-enhancing Fc domain variants having improved FcγR binding wherein stability is not significantly reduced as compared to wild-type are known. (See, e.g., Igawa et al., EP 2 940 135)

It has been further discovered that thermostabilized Fc domain variants may be produced by introducing one or more disulfide bonds in the Fc domain. Accordingly, in one aspect, the present disclosure provides a Fc domain variant comprising one or more engineered (e.g., non-native) disulfide bonds, e.g., intrachain disulfide bonds mediated, e.g., by one or more pairs of cysteines.

In certain exemplary embodiments, a disulfide bond is an intrachain disulfide bond between the two CH2 regions of a Fc domain. In certain exemplary embodiments, a disulfide bond is an intrachain disulfide bond between the two CH3 regions of a Fc domain. In certain exemplary embodiments, two or more intrachain disulfide bonds are present in between the two CH2 regions of a Fc domain and/or between the two CH3 regions of a Fc domain.

Thermal stability, or the propensity of a Fc domain (e.g., a Fc domain with or without a binding polypeptide) to unfold, may be determined using a variety of methods known in the art. For example, the unfolding or denaturation temperature can be measured by nano-format differential scanning calorimetry (nanoDSC) or nano-format differential scanning fluorimetry (nanoDSF) (Wen et al., 2020 *Anal. Biochem.* 593:113581). The detectable temperature at which a protein begins to unfold is the Tonset.

In certain exemplary embodiments, the Tonset of a thermally-stabilized Fc domain variant (e.g., having one or more engineered disulfide bonds) is increased relative to a Fc domain variant that is not thermally stabilized. In certain exemplary embodiments, the Tonset of a thermally-stabilized Fc domain variant is increased by about 1.0° C., about 1.5° C., about 2.0° C., about 2.5° C., about 3.0° C., about 3.5° C., about 4.0° C., about 4.5° C., about 5.0° C., about 5.5° C., about 6.0° C., about 6.5° C., about 7.0° C., about 7.5° C., about 8.0° C., about 8.5° C., about 9.0° C., about 9.5° C., about 10.0° C., about 10.5° C., about 11.0° C., about 11.5° C., about 12.0° C., about 12.5° C., about 13.0° C., about 13.5° C., about 14.0° C., about 14.5° C., about 15.0° C., about 15.5° C., about 16.0° C., about 16.5° C., about 17.0° C., about 17.5° C., about 18.0° C., about 18.5° C., about 19.0° C., about 19.5° C., about 20.0° C., about 20.5° C., about 21.0° C., about 21.5° C., about 22.0° C., about 22.5° C., about 23.0° C., about 23.5° C., about 24.0° C., about 24.5° C. or about 25.0° C. relative to a Fc domain variant that is not thermally stabilized.

In certain exemplary embodiments, a thermally-stabilized Fc domain variant has one or more amino acid substitution pairs selected from the group consisting of cysteine substitutions at: amino acid positions 242 and 334; amino acid positions 240 and 334; amino acid positions 287 and 306; amino acid positions 292 and 302; amino acid positions 323 and 332; amino acid positions 259 and 306; amino acid positions 350 and 441; amino acid positions 343 and 431; amino acid positions 375 and 404; amino acid positions 375 and 396; and amino acid positions 348 and 439, according to EU numbering. (See Wozniak-Knopp et al., 2012, *PLoS One* 7: e30083; Jacobsen et al., 2017 *J. Biol. Chem.* 202: 1865-75; WO2014153063 for reviews.)

In certain exemplary embodiments, a thermally-stabilized Fc domain variant comprises an engineered (e.g., a non-native) intrachain disulfide bond mediated by a pair of cysteines that substitute for (i) a leucine (L) at amino acid position 242 and a lysine (K) at amino acid position 334; (ii) an alanine (A) at amino acid position 287 and a leucine (L) at amino acid position 306; or (iii) an arginine (R) at amino acid position 292 and a valine (V) at amino acid position 302, according to EU numbering.

In certain exemplary embodiments, a thermostabilized Fc domain variant comprises an engineered (e.g., a non-native) intrachain disulfide bond mediated by a pair of cysteines that substitute for (i) a leucine (L) at amino acid position 242 and a lysine (K) at amino acid position 334; (ii) an arginine (R) at amino acid position 292 and a valine (V) at amino acid position 302, according to EU numbering.

In certain exemplary embodiments, a thermally-stabilized Fc domain variant comprises an engineered (e.g., a non-native) intrachain disulfide bond mediated by a pair of cysteines that substitute for a leucine (L) at amino acid position 242 and a lysine (K) at amino acid position 334. In certain exemplary embodiments, a thermally-stabilized Fc domain variant comprises an engineered (e.g., a non-native) intrachain disulfide bond mediated by a pair of cysteines that substitute an alanine (A) at amino acid position 287 and a leucine (L) at amino acid position 306. In certain exemplary embodiments, a thermally-stabilized Fc domain variant comprises an engineered (e.g., a non-native) intrachain disulfide bond mediated by a pair of cysteines that substitute for an arginine (R) at amino acid position 292 and a valine (V) at amino acid position 302. In certain exemplary embodiments, a thermally-stabilized Fc domain variant may comprise at least one engineered intrachain disulfide bond. In certain exemplary embodiments, a thermally-stabilized Fc domain variant may comprise more than one engineered intrachain disulfide bond.

Effector-Enhancing Fc Domain Variants

In one aspect, the present disclosure provides a Fc domain variant comprising effector-enhancing amino acid substitutions.

In one embodiment, a Fc domain variant with altered FcγRIIIa binding comprising one or more amino acid substitutions as disclosed herein. In one embodiment, a Fc domain variant with enhanced FcγRIIIa binding affinity having one or more amino acid substitutions as disclosed herein. In one embodiment, a Fc domain variant with enhanced FcγRIIIa binding affinity comprises two or more amino acid substitutions as disclosed herein. In one embodiment, a Fc domain variant with enhanced FcγRIIIa binding affinity comprises three or more amino acid substitutions as disclosed herein. In one embodiment, a Fc domain variant with enhanced FcγRIIIa binding affinity comprises four or more amino acid substitutions as disclosed herein.

In one embodiment, a Fc domain variant with altered FcRn binding comprises a Fc domain having one or more amino acid substitutions as disclosed herein. In one embodiment, a Fc domain variant with enhanced FcRn binding affinity comprises a Fc domain having one or more amino acid substitutions as disclosed herein. In one embodiment, a Fc domain variant with enhanced FcRn binding affinity comprises a Fc domain having two or more amino acid substitutions as disclosed herein. In one embodiment, a Fc domain variant with enhanced FcRn binding affinity comprises a Fc domain having three or more amino acid substitutions as disclosed herein.

In some embodiments, a Fc domain variant may exhibit a species-specific FcRn binding affinity. In one embodiment, a Fc domain variant may exhibit hum a FcRn binding affinity. In one embodiment, a Fc domain variant may exhibit cyno FcRn binding affinity. In some embodiments, a Fc domain variant may exhibit cross-species FcRn binding affinity. Such a Fc domain variants are said to be cross-reactive across one or more different species. In one embodiment, a Fc domain variant may exhibit both human and cyno FcRn binding affinity.

The neonatal Fc receptor (FcRn) interacts with the Fc region of antibodies to promote recycling through rescue of normal lysosomal degradation. This process is a pH-dependent process that occurs in the endosomes at acidic pH (e.g., a pH less than 6.5) but not under the physiological pH conditions of the bloodstream (e.g., a non-acidic pH). In some embodiments, a Fc domain variant has enhanced FcRn binding affinity at an acidic pH compared to a wild-type Fc domain. In some embodiments, a Fc domain variant has enhanced FcRn binding affinity at pH less than 7.0, e.g., at about pH 6.5, at about pH 6.0, at about pH 5.5, at about pH 5.0, compared to a wild-type Fc domain. In some embodiments, a Fc domain variant has enhanced FcRn binding affinity at pH less than 7.0, e.g., at about pH 6.5, at about pH 6.0, at about pH 5.5, at about pH 5.0, compared to the FcRn binding affinity of a wild-type Fc domain at an elevated non-acidic pH. An elevated non-acidic pH can be, e.g., pH greater than 7.0, about pH 7.0, about pH 7.4, about pH 7.6, about pH 7.8, about pH 8.0, about pH 8.5, about pH 9.0.

In certain embodiments, it may be desired for a Fc domain variant to exhibit approximately the same FcRn binding affinity at non-acidic pH as a wild-type Fc domain. In some embodiments, it may be desired for a Fc domain variant to exhibit less FcRn binding affinity at non-acidic pH than a binding polypeptide comprising a modified Fc domain having the double amino acid substitution M428L/N434S, according to EU numbering (See U.S. Pat. No. 8,088,376). Accordingly, it may be desired a Fc domain variant to exhibit minimal perturbation to pH-dependent FcRn binding.

In some embodiments, a Fc domain variant having enhanced FcRn binding affinity at an acidic pH, has a reduced (i.e., slower) FcRn off-rate as compared to a wild-type Fc domain. In some embodiments, a Fc domain variant having enhanced FcRn binding affinity at an acidic pH compared to the FcRn binding affinity of the binding polypeptide at an elevated non-acidic pH, has a slower FcRn off-rate at the acidic pH compared to the FcRn off-rate of a wild-type Fc domain at the elevated non-acidic pH.

Certain embodiments include Fc domain variants in which at least one amino acid in one or more of the constant region domains has been deleted or otherwise altered so as to provide desired biochemical characteristics such as reduced or enhanced effector functions, the ability to non-covalently dimerize, increased ability to localize at the site of a tumor, reduced serum half-life, or increased serum half-life when compared with a whole, unaltered antibody of approximately the same immunogenicity.

In certain other embodiments, a Fc domain variant comprises constant regions derived from different antibody isotypes (e.g., constant regions from two or more of a human IgG1, IgG2, IgG3, or IgG4). In other embodiments, a Fc domain variant comprises a chimeric hinge (i.e., a hinge comprising hinge portions derived from hinge domains of different antibody isotypes, e.g., an upper hinge domain from an IgG4 molecule and an IgG1 middle hinge domain). In certain embodiments, the Fc domain may be mutated to increase or decrease effector function using techniques known in the art.

In some embodiments, a Fc domain variant has altered binding affinity to a Fc receptor. There are several different types of Fc receptors, which are classified based on the type of antibody that they recognize. For example, Fc-gamma receptors (FcγR) bind to IgG class antibodies, Fc-alpha receptors (FcαR) bind to IgA class antibodies, and Fc-epsilon receptors (FcεR) bind to IgE class antibodies. The FcγRs belong to a family that includes several members, e.g., FcγRI, FcγRIIa, FcγRIIb, FcγRIIIa, and FcγRIIIb. In some embodiments, a Fc domain variant has altered FcγRIIIa binding affinity, compared to a wild-type Fc domain. In some embodiments, a Fc domain variant has reduced FcγRIIIa binding affinity, compared to a wild-type Fc domain. In some embodiments, a Fc domain variant has enhanced FcγRIIIa binding affinity, compared to a wild-type Fc domain. In some embodiments, a Fc domain variant modified Fc domain has approximately the same FcγRIIIa binding affinity, compared to a wild-type Fc domain.

In certain embodiments, a Fc domain variant comprises an antibody constant region (e.g., an IgG constant region e.g., a human IgG constant region, e.g., a human IgG1 constant region) which mediates one or more effector functions. For example, binding of the C1-complex to an antibody constant region may activate the complement system. Activation of the complement system is important in the opsonization and lysis of cell pathogens. The activation of the complement system also stimulates the inflammatory response and may also be involved in autoimmune hypersensitivity. Furthermore, antibodies bind to receptors on various cells via the Fc domain (Fc receptor binding sites on the antibody Fc region bind to Fc receptors (FcRs) on a cell). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In some embodiments, a Fc domain variant, e.g., a binding polypeptide (e.g., an antibody, immunoadhesin or an antibody variant) binds to a Fc-gamma receptor. In alternative embodiments, a Fc domain variant comprised a constant region which is devoid of one or more effector functions (e.g., ADCC activity) and/or is unable to bind Fcγ receptor.

In certain exemplary embodiments, an effector-enhancing Fc domain variant has one or more amino acid substitutions selected from the group consisting of: an aspartic acid (D) at amino acid position 221; a cysteine (C) at amino acid position 222; a tyrosine (Y) at amino acid position 234; an alanine (A) at amino acid position 236; a tryptophan (W) at amino acid position 236; an aspartic acid (D) at amino acid position 239; a leucine (L) at amino acid position 243; a glutamic acid (E) at amino acid position 267; a phenylalanine (F) at amino acid position 268; a proline (P) at amino acid position 292; an alanine (A) at amino acid position 298; a leucine (L) at amino acid position 300; an isoleucine (I) at amino acid position 305; a threonine (T) at amino acid position 324; a tryptophan (W) at amino acid position 326; an alanine (A) at amino acid position 326; a leucine (L) at amino acid position 330; a glutamic acid (E) at amino acid position 332; an alanine (A) at amino acid position 333; a serine (S) at amino acid position 333; an alanine (A) at amino acid position 334; an alanine (A) at amino acid position 336; an arginine (R) at amino acid position 345; and a leucine (L) at amino acid position 396, according to EU numbering. (See Saunders, 2009, *Front. Immunol.* doi: 10.3389/fimmu.2019.01296, for a review.)

In some embodiments, a Fc domain variant may comprise an amino acid substitution at positions selected from amino acid positions 236, 239, 330, and 332, according to EU numbering. In some embodiments, the substitutions may comprise an alanine (A) at amino acid position 236, an aspartic acid (D) at amino acid 239, a leucine (L) at amino acid position 330, and a glutamic acid (E) at amino acid position 332, according to EU numbering. In some embodiments, a Fc domain variant may comprise a double amino acid substitution at any two amino acid positions selected from an alanine (A) at amino acid position 236, aspartic acid (D) at amino acid 239, a leucine (L) at amino acid position 330, and a glutamic acid (E) at amino acid position 332. In some embodiments, a Fc domain variant may comprise a triple amino acid substitution at any three amino acid positions selected from an alanine (A) at amino acid position 236, an aspartic acid (D) at amino acid 239, a leucine (L) at amino acid position 330, and a glutamic acid (E) at amino acid position 332. In some embodiments, a Fc domain variant may comprise a quadruple amino acid substitution at any four amino acid positions selected from an alanine (A) at amino acid position 236, an aspartic acid (D) at amino acid 239, a leucine (L) at amino acid position 330, and a glutamic acid (E) at amino acid position 332. In some embodiments, a Fc domain variant may comprise the combination of amino acid substitutions comprising an aspartic acid (D) at amino acid 239 and a glutamic acid (E) at amino acid position 332. In some embodiments, a Fc domain variant may comprise the combination of amino acid substitutions comprising an alanine (A) at amino acid position 236, an aspartic acid (D) at amino acid position and a glutamic acid at position 332.

In some embodiments, a Fc domain variant may further comprise an amino acid substitution at amino acid positions 256 and/or 307, according to EU numbering. In some embodiments, a Fc domain variant may comprise the combination of amino acid substitutions comprising an aspartic acid (D) at amino acid positions 256 and a glutamine (Q) at amino acid position 307 (See Mackness et al., 2019 MAbs 11:1276-88; WO2019147973A1, incorporated in its entirety by reference herein).

Glycosylated Fc Domain Variants

In certain exemplary embodiments, a binding protein is glycosylated. Glycosylation of antibodies at conserved positions in their constant regions is known to have a profound effect on antibody function, particularly effector functioning such as those described above, see for example, Boyd et al (Mol. Immunol, 32: 1311-1318, 1996). Glycosylation of a binding protein of the present disclosure wherein one or more carbohydrate moiety is added, substituted, deleted or modified are contemplated. In some embodiments, the glycosylation of the Fc domain of the binding protein is an N-linked glycosylation. Introduction of an asparagine-X-serine or asparagine-X-threonine motif creates a potential site for enzymatic attachment of carbohydrate moieties and may therefore be used to manipulate the glycosylation of a Fc domain variant. In Raju et al. (Biochemistry 40: 8868-8876, 2001) the terminal sialylation of a TNFR-IgG immunoadhesin was increased through a process of re-galactosylation and/or re-sialylation using β-1,4-galactosyltransferace and/or alpha, 2,3 sialyltransferase. Increasing the terminal sialylation is believed to increase the half-life of the immunoglobulin.

Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms (see Zhang et al. 2004, Science 303: 371; Sears et al, 2001, Science 291: 2344; Wacker et al., 2002, Science 298: 1790; Davis et al. 2002, Chem. Rev. 102: 579; Hang et al., 2001, Acc. Chem. Res. 34: 727). In some embodiments, the glycosylated Fc domain comprises a native glycan at amino acid position 297, according to EU numbering. Glycosylation of the asparagine at amino acid position 297 in the CH2 domain of IgG1 is known to facilitate interaction between the Fc domain and FcγR. Elimination of this glycosylation site eliminates effector function (Leabman, et al., 2013, MAbs 5:896-903). In particularly exemplary embodiments, a Fc domain comprises wild-type levels, or near wild-type levels, of glycosylation at amino acid position 297, according to EU numbering.

In some embodiments, the glycosylated Fc domain variant comprises an engineered or non-native glycan. In some embodiments, the engineered or non-native glycan is a modified glycan that can be conjugated to a therapeutic molecule (e.g., antibody-drug conjugate).

Fc-Containing Binding Polypeptides

In one aspect, the present disclosure provides an isolated Fc domain variant comprising or complexed with (e.g., fused to) at least one binding domain (e.g., at least one binding polypeptide). In certain embodiments, the binding domain comprises one or more antigen binding domains. The antigen binding domains need not be derived from the same molecule as the parental Fc domain. In certain embodiments, the Fc domain variant is present in an antibody.

In one embodiment, a Fc domain variant is present in an antibody or is complexed with an antibody. Any antibody from any source or species can be employed with a Fc domain variant disclosed herein. Suitable antibodies include without limitation, chimeric antibodies, humanized antibodies, or human antibodies. Suitable antibodies include without limitation, full-length antibodies, monoclonal antibodies, polyclonal antibodies, or single-domain antibodies, such as VHH antibodies.

In certain exemplary embodiments, a Fc domain variant may be bound to or complexed with an antigen-binding fragment of an antibody. The term "antigen-binding fragment" refers to a polypeptide fragment of an immunoglobulin or antibody which binds antigen or competes with intact antibody (i.e., with the intact antibody from which they were derived) for antigen binding (i.e., specific binding). Antigen-binding fragments can be produced by recombinant or biochemical methods that are well known in the art. Exemplary antigen-binding fragments include Fv, Fab, Fab', and (Fab')2. In certain exemplary embodiments, a binding polypeptide of the current disclosure comprises at least one antigen-binding fragment and a Fc domain variant.

In some embodiments, the binding polypeptide comprises a single chain variable region sequence (ScFv). Single chain variable region sequences comprise a single polypeptide having one or more antigen binding sites, e.g., a VL domain linked by a flexible linker to a VH domain. ScFv molecules can be constructed in a VH-linker-VL orientation or VL-linker-VH orientation. The flexible hinge that links the VL and VH domains that make up the antigen binding site includes from about 10 to about 50 amino acid residues. Connecting peptides are known in the art. Binding polypeptides may comprise at least one scFv and/or at least one constant region. In one embodiment, a binding polypeptide of the current disclosure may comprise at least one scFv linked or fused to a Fc domain variant.

In some embodiments, a binding polypeptide of the current disclosure is a multivalent (e.g., tetravalent) antibody which is produced by fusing a DNA sequence encoding an antibody with a ScFv molecule (e.g., an altered ScFv molecule). For example, in one embodiment, these sequences are combined such that the ScFv molecule (e.g., an altered ScFv molecule) is linked at its N-terminus or C-terminus to a Fc domain variant via a flexible linker (e.g., a gly/ser linker). In another embodiment a tetravalent antibody of the current disclosure can be made by fusing a ScFv molecule to a connecting peptide, which is fused to a Fc domain variant to construct a ScFv-Fab tetravalent molecule.

In another embodiment, a binding polypeptide of the current disclosure is an altered minibody. An altered minibody of the current disclosure is a dimeric molecule made up of two polypeptide chains each comprising a ScFv molecule which is fused to a Fc domain variant via a connecting peptide. Minibodies can be made by constructing a ScFv component and connecting peptide components using methods described in the art (see, e.g., U.S. Pat. No. 5,837,821 or WO 94/09817AI). In another embodiment, a tetravalent minibody can be constructed. Tetravalent minibodies can be constructed in the same manner as minibodies, except that two ScFv molecules are linked using a flexible linker. The linked scFv-scFv construct is then joined to a Fc domain variant.

In another embodiment, a binding polypeptide of the current disclosure comprises a diabody. Diabodies are dimeric, tetravalent molecules each having a polypeptide similar to scFv molecules, but usually having a short (less than 10, e.g., about 1 to about 5) amino acid residue linker connecting both variable domains, such that the VL and VH domains on the same polypeptide chain cannot interact. Instead, the VL and VH domain of one polypeptide chain interact with the VH and VL domain (respectively) on a second polypeptide chain (see, for example, WO 02/02781). Diabodies of the current disclosure comprise a scFv-like molecule fused to a Fc domain variant.

In another embodiment, a binding polypeptide of the current disclosure comprises a single-domain antibody (sdAb), also referred to as a VHH or a nanobody. Nanobody® is registered trademark of Ablynx. VHHs comprise variable heavy chain domains devoid of light chains. Similar to conventional VH domains, VHHs contain four FRs and three CDRs. VHHs have advantages over conventional antibodies. As they are about ten times smaller than IgG molecules, properly folded functional VHHs can be produced by in vitro expression while achieving high yield. Furthermore, VHHs are very stable, and resistant to the action of proteases. The properties and production of VHHs have been reviewed by Harmsen and De Haard H J (Appl. Microbiol. Biotechnol. 2007 November; 77(1):13-22).

In certain exemplary embodiments, a Fc domain is fused with one or more VHHs.

In other embodiments, binding polypeptides comprise multi-specific or multivalent antibodies comprising one or more variable domain in series on the same polypeptide chain, e.g., tandem variable domain (TVD) polypeptides. Exemplary TVD polypeptides include the "double head" or "dual-Fv" configuration described in U.S. Pat. No. 5,989,830. In the dual-Fv configuration, the variable domains of two different antibodies are expressed in a tandem orientation on two separate chains (one heavy chain and one light chain), wherein one polypeptide chain has two VH domains in series optionally separated by a peptide linker (VH1-linker-VH2) and the other polypeptide chain consists of complementary VL domains optionally connected in series by a peptide linker (VL1-linker-VL2). In the cross-over double head configuration, the variable domains of two different antibodies are expressed in a tandem orientation on two separate polypeptide chains (one heavy chain and one light chain), wherein one polypeptide chain has two VH domains in series optionally separated by a peptide linker (VH1-linker-VH2) and the other polypeptide chain consists of complementary VL domains optionally connected in series by a peptide linker in the opposite orientation (VL2-linker-VL1). Additional antibody variants based on the "dual-Fv" format include the dual-variable-domain IgG (DVD-IgG) bispecific antibody (see U.S. Pat. No. 7,612,181 and the TBTI format (see US 2010/0226923 A1). In some embodiments, binding polypeptides comprise multi-specific or multivalent antibodies comprising one or more variable domain in series on the same polypeptide chain fused to a Fc domain variant.

In another embodiment, a binding polypeptide comprises a cross-over dual variable domain IgG (CODV-IgG) bispecific antibody based on a "double head" configuration (see US20120251541 A1, which is incorporated by reference herein in its entirety).

In other embodiments, a binding polypeptide comprises a CrossMab or a CrossMab-Fab multispecific format (see WO2009080253 and Schaefer, et al., PNAS (2011), 108: 11187-1191). Antibody variants based on the CrossMab format have a crossover of antibody domains within one arm of a bispecific IgG antibody enabling correct chain association.

In other embodiments, the glycosylated effector-competent polypeptide comprises a multispecific antibody in a T cell engager format. A "T cell engager" refers to binding proteins directed to a host's immune system, more specifically the T cells' cytotoxic activity as well as directed to a tumor target protein. In some embodiments, the isolated effector-competent polypeptide comprises a multispecific antibody in a NK cell engager format. A "NK cell engager" refers to binding proteins comprising monoclonal antibody fragments targeting activating NK cell receptors, antigen-specific targeting regions, and a Fc region (Gauthier, et al. Cell (2019), 177: 1701-13).

A binding polypeptide of the present disclosure, comprising a Fc domain variant described herein, can include the CDR sequences or the variable domain sequences of a known "parent" antibody. In some embodiments, the parent antibody and the antibody of the disclosure can share similar or identical sequences except for modifications to the Fc domain as disclosed herein.

Cross-Over Dual Variable

In a particular embodiment, "cross-over dual variable" or "CODV" refers to an antigen-binding domain that specifically binds to at least one target antigen or at least one target epitope, and comprises at least two polypeptide chains that form at least two antigen-binding sites, wherein at least one polypeptide chain comprises a structure represented by the formula:

VL1-L1-VL2-L2-CL     [I]

and at least one polypeptide chain comprises a structure represented by the formula:

VH2-L3-VH1-L4-CH1     [II]

wherein:
VL1 is a first immunoglobulin light chain variable domain;
VL2 is a second immunoglobulin light chain variable domain;
VH1 is a first immunoglobulin heavy chain variable domain;
VH2 is a second immunoglobulin heavy chain variable domain;
CL is an immunoglobulin light chain constant domain;
CH1 is an immunoglobulin CH1 heavy chain constant domain; and
L1, L2, L3, and L4 are amino acid linkers, wherein any one or more of L1, L2, L3, and L4 are optionally absent, and
wherein the polypeptides of formula I and the polypeptides of formula II form a cross-over light chain-heavy chain pair.

In certain exemplary embodiments, the binding protein of the disclosure comprises a "CODV-OL1" format, comprising three polypeptide chains that form two antigen-binding sites, wherein one polypeptide chain comprises a structure represented by the formula:

VL1-L1-VL2-L2-CL     [I];

one polypeptide chain comprises a structure represented by the formula:

VH2-L3-VH1-L4-CH1-hinge-CH2-CH3     [III]; and one polypeptide chain comprises a structure represented by the formula:

hinge-CH2-CH3     [IV]

wherein:
CL is an immunoglobulin light chain constant domain;
CH1 is an immunoglobulin CH1 heavy chain constant domain;
CH2 is an immunoglobulin CH2 heavy chain constant domain;
CH3 is an immunoglobulin CH3 heavy chain constant domain;
hinge is an immunoglobulin hinge region connecting the CH1 and CH2 domains; and
L1, L2, L3, and L4 are amino acid linkers, wherein any one or more of L1, L2, L3, and L4 are optionally absent, and
wherein the polypeptides of formula I and the polypeptides of formula II form a cross-over light chain-heavy chain pair.

In a particular embodiment, a CODV antigen-binding domain specifically binds to at least one target antigen or at least one target epitope, and comprises four polypeptide chains that form four antigen-binding sites, wherein two polypeptide chains each comprises a structure represented by the formula:

VL1-L1-VL2-L2-CL     [I]

and two polypeptide chains each comprises a structure represented by the formula:

VH2-L3-VH1-L4-CH1-Fc     [II]

wherein:
VL1 is a first immunoglobulin light chain variable domain;
VL2 is a second immunoglobulin light chain variable domain;
VH1 is a first immunoglobulin heavy chain variable domain;
VH2 is a second immunoglobulin heavy chain variable domain;
CL is an immunoglobulin light chain constant domain;
CH1 is an immunoglobulin CH1 heavy chain constant domain;
Fc is an immunoglobulin hinge region and CH2 and CH3 immunoglobulin heavy chain constant domains; and
L1, L2, L3, and L4 are amino acid linkers, wherein any one or more of L1, L2, L3, and L4 are optionally absent, and
wherein the polypeptides of formula I and the polypeptides of formula II form a cross-over light chain-heavy chain pair,
wherein the VH1/VL1 pair comprises a first antigen binding specificity and the VH2/VL2 pair comprises a second antigen binding specificity.

In a particular embodiment, an antigen-binding protein described herein is a trispecific and/or a trivalent antigen-binding protein comprising four polypeptide chains that form three antigen-binding sites that specifically bind to one or more different antigen targets, wherein the first polypeptide chain comprises a structure represented by the formula:

VL2-L1-VL1-L2-CL     [I]

the second polypeptide chain comprises a structure represented by the formula:

VH1-L3-VH2-L4-CH1-hinge-CH2-CH3   [II]

the third polypeptide chain comprises a structure represented by the formula:

VH3-CH1-hinge-CH2-CH3   [III]

and the fourth polypeptide chain comprises a structure represented by the formula:

VL3-CL   [IV], wherein:
VL1 is a first immunoglobulin light chain variable domain;
VL2 is a second immunoglobulin light chain variable domain;
VL3 is a third immunoglobulin light chain variable domain;
VH1 is a first immunoglobulin heavy chain variable domain;
VH2 is a second immunoglobulin heavy chain variable domain;
VH3 is a third immunoglobulin heavy chain variable domain;
CL is an immunoglobulin light chain constant domain;
CH1 is an immunoglobulin CH1 heavy chain constant domain;
CH2 is an immunoglobulin CH2 heavy chain constant domain;
CH3 is an immunoglobulin CH3 heavy chain constant domain;
hinge is an immunoglobulin hinge region connecting the CH1 and CH2 domains; and
L1, L2, L3, and L4 are amino acid linkers, wherein any one or more of L1, L2, L3, and L4 are optionally absent, and
wherein the polypeptides of formula I and the polypeptides of formula II form a cross-over light chain-heavy chain pair.

In certain embodiments, the first polypeptide chain and the second polypeptide chain have a cross-over orientation that forms two distinct antigen-binding sites. In some embodiments, the VH1 and VL1 form a binding pair and form the first antigen-binding site. In some embodiments, the VH2 and VL2 form a binding pair and form the second antigen-binding site. In some embodiments, the third polypeptide and the fourth polypeptide form a third antigen-binding site. In some embodiments, the VH3 and VL3 form a binding pair and form the third antigen-binding site.

Such antigen-binding protein comprises at least three antigen-binding sites. It is at least a trivalent antigen-binding molecule. In a particular embodiment, it specifically binds to one antigen target, i.e., it is a monospecific antigen-binding molecule. In another embodiment, it specifically binds to two different antigen targets, i.e., it is a bispecific antigen-binding molecule. In another embodiment, it specifically binds to three different antigen targets, i.e., it is a trispecific antigen-binding molecule.

The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the antibody-like binding proteins described herein.

In certain embodiments of the binding protein, (a) L1, L2, L3, and L4 each independently are zero amino acids in length or comprise a sequence selected from the group consisting of GGGGSGGGGS (SEQ ID NO: 78), GGGGSGGGGSGGGGS (SEQ ID NO: 82), S, RT, TKGPS (SEQ ID NO: 83), GQPKAAP (SEQ ID NO: 84), and GGSGSSGSGG (SEQ ID NO: 85); or (b) L1, L2, L3, and L4 each independently comprise a sequence selected from the group consisting of GGGGSGGGGS (SEQ ID NO: 78), GGGGSGGGGSGGGGS (SEQ ID NO: 82), S, RT, TKGPS (SEQ ID NO: 83), GQPKAAP (SEQ ID NO: 84), and GGSGSSGSGG (SEQ ID NO: 85).

In certain embodiments, L1 and L2 each comprise the amino acid sequence GGGGSGGGGS (SEQ ID NO: 78).

In certain embodiments, wherein L3 and L4 are each absent.

The CODV antibody format, the various permutations of the CODV antibody format, and additional details regarding linkers is further described in WO 2012/135345A1, and WO 2017/180913A2, which are incorporated herein by reference in their entireties.

Nucleic Acids and Vectors

In one aspect, polynucleotides encoding the binding proteins disclosed herein are provided. Methods of making a binding protein comprising expressing these polynucleotides are also provided.

Polynucleotides encoding the binding proteins disclosed herein are typically inserted in an expression vector for introduction into host cells that may be used to produce the desired quantity of the claimed binding proteins. Accordingly, in certain aspects, the disclosure provides expression vectors comprising polynucleotides disclosed herein and host cells comprising these vectors and polynucleotides.

The term "vector" or "expression vector" is used herein for the purposes of the specification and claims, to mean vectors used for introducing into and expressing a desired gene in a cell. As known to those skilled in the art, such vectors may easily be selected from the group consisting of plasmids, phages, viruses and retroviruses. In general, a vector will comprise a selection marker, appropriate restriction sites to facilitate cloning of the desired gene and the ability to enter and/or replicate in eukaryotic or prokaryotic cells.

Numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed or introduced into the same cell by co-transformation. Additional elements may also be needed for optimal synthesis of mRNA. These elements may include signal sequences, splice signals, as well as transcriptional promoters, enhancers, and termination signals. In some embodiments the cloned variable region genes are inserted into an expression vector along with the heavy and light chain constant region genes (such as human genes) synthesized as discussed above.

In other embodiments, a glycosylated effector-competent polypeptide as described herein may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980 which is incorporated by reference herein. Those skilled in the art will appreciate that such expression systems may be used to effectively produce the full range of polypeptides disclosed in the instant application.

More generally, once a vector or DNA sequence encoding a binding protein of the present disclosure has been prepared, the expression vector may be introduced into an appropriate host cell. That is, the host cell may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, e.g., Ridgway, A. A. G. "Mammalian Expression Vectors" Chapter 24.2, pp. 470-472 Vectors, Rodriguez and Denhardt, Eds. (Butterworths, Boston, M A 1988). The transformed cells are grown under conditions appropriate to the production of the light chains and heavy chains, and assayed for heavy and/or light chain protein synthesis.

Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refer to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, the host cell line used for expression of a binding protein is of eukaryotic or prokaryotic origin. In one embodiment, the host cell line used for expression of a binding protein is of bacterial origin. In one embodiment, the host cell line used for expression of a binding protein is of mammalian origin. Those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1 BPT (bovine endothelial cells), RAJI (human lymphocyte), 293 (human kidney). In one embodiment, the cell line provides for altered glycosylation, e.g., afucosylation, of the antibody expressed therefrom (e.g., PER.C6® (Crucell) or FUT8-knock-out CHO cell lines (POTELLIGENT™ cells) (Biowa, Princeton, NJ)). In one embodiment NSO cells may be used. Host cell lines are typically available from commercial services, the American Tissue Culture Collection or from published literature.

In vitro production allows scale-up to give large amounts of the desired binding protein. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

One or more genes encoding glycosylated binding proteins can also be expressed in non-mammalian cells such as bacteria or yeast or plant cells. In this regard, it will be appreciated that various unicellular non-mammalian microorganisms such as bacteria can also be transformed, i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the Fc domain variants and/or binding polypeptides can become part of inclusion bodies. The binding proteins must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

Methods of Use/Treatment

In one aspect, the disclosure provides methods of treating a disease or disorder in a subject in need thereof comprising administering to the subject an effective amount of a binding protein disclosed herein. In certain embodiments, the present disclosure provides kits and methods for the treatment of diseases and disorders, e.g., cancer in a mammalian subject in need of such treatment. In certain embodiments, the present disclosure provides kits and methods for the treatment of diseases and disorders, e.g., amyloidosis or multiple myeloma, in a mammalian subject in need of such treatment.

In certain embodiments, the disease is cancer. In certain embodiments, the cancer is a hematological cancer. In certain embodiments, the hematological cancer is a plasma cells malignancy. In certain embodiments, the plasma cell malignancy is multiple myeloma. In certain embodiments, the multiple myeloma is relapse/refractory multiple myeloma, newly diagnosed multiple myeloma, or smoldering multiple myeloma. In certain other embodiments, the disease is light chain amyloidosis (LCA). In certain embodiments, the LCA is relapse/refractory LCA, newly diagnosed LCA, or smoldering LCA. The binding proteins of the current disclosure are useful in a number of different applications. For example, in one embodiment, the subject binding proteins are useful for reducing or eliminating cells bearing an epitope recognized by the binding protein. In another embodiment, the subject binding proteins are effective in reducing the concentration of or eliminating soluble antigen in the circulation. In another embodiment, the subject binding proteins are effective as NK-cell engagers. In one embodiment, the Fc domain variants may reduce tumor size, inhibit tumor growth, and/or prolong the survival time of tumor-bearing animals. Accordingly, this disclosure also relates to a method of treating tumors in a human or other animal by administering to such human or animal an effective, non-toxic amount of the binding protein of the disclosure.

In another embodiment, the subject binding proteins are useful for the treatment of other disorders, including, without limitation, infectious diseases, autoimmune disorders, inflammatory disorders, or cancer. Diseases can optionally be specified as being characterized by cells (e.g., disease-causing cells, disease causing B-lymphocytes or other immune cells) expressing BCMA. For example, cancer cells, particularly hematological cancers or plasma cell malignancies, can be characterized as expressing BCMA at the surface of the cancer cell. Accordingly, this disclosure relates to a method of treating various conditions that would benefit from using a subject effector-competent polypeptide having, e.g., enhanced half-life.

One skilled in the art would be able, by routine experimentation, to determine what an effective, non-toxic amount of the binding protein would be for the purpose of treating malignancies. For example, a therapeutically active amount of a binding protein of the present disclosure may vary according to factors such as the disease stage (e.g., stage I versus stage IV), age, sex, medical complications (e.g., immunosuppressed conditions or diseases) and weight of the subject, and the ability of the modified antibody to elicit a desired response in the subject.

In general, the compositions provided in the current disclosure may be used to prophylactically or therapeutically treat any neoplasm comprising an antigenic marker that allows for the targeting of the cancerous cells by the binding protein.

Method of Treatment/Use for Multiple Myeloma

In one aspect, the disclosure is directed to the treatment and prevention of multiple myeloma.

The term "Multiple Myeloma (MM)" (also known as plasma cell myeloma, myelomatosis, or Kahler's disease) is a progressive hematologic cancer of the plasma cell, a type of white blood cell normally responsible for producing antibodies. The condition is characterized by excessive numbers of plasma cells in the bone marrow and overproduction of intact monoclonal immunoglobulin or free monoclonal light chains. Clinically the disease is diagnosed, staged, and treated based on a variety of parameters which include the myeloma tumor cell mass on the basis of the amount of monoclonal (or myeloma) protein (M protein) in the serum and/or urine, along with hemoglobin and serum calcium concentrations, the number of lytic bone lesions based on a skeletal survey, and the presence or absence of renal failure. Additional approaches to characterizing the condition include the detection of greater than ten percent (10%) of plasma cells on a bone marrow examination, the presence of soft tissue plasmacytomas and the detection of free kappa and lambda serum immunoglobulin light chain. Bone marrow examination is done using standard histology and immunohistochemistry techniques. Additional cytogenetics of bone marrow samples may be conducted to determine prognosis. Follow up surveillance consists of chemistry and bone marrow evaluations if clinically indicated due to its invasive nature.

In certain embodiments, the methods of the invention include treatment of patients having relapsed and/or refractory MM or patients having MM who have received one or more prior therapies for MM. In certain embodiments, the multiple myeloma is relapsed/refractory multiple myeloma (RR/MM). In some embodiments, the patient has received at least one or two previous therapies for multiple myeloma (e.g., a thalidomide analog such lenalidomide, a proteasome inhibitor, or autologous stem cell transplant (ASCT), and had demonstrated disease progression on last therapy or after completion of the last therapy.

"Relapsed MM" refers to multiple myeloma which has been previously treated and which progresses and requires the initiation of additional treatment but does not meet the criteria for either primary 'refractory' or relapsed and refractory MM. Clinical criteria for determining relapse are well known to those of skill in the art. For example, clinical criteria developed by the International Myeloma Working Group (IMWG) include serum M-component increases of >1 gm/dL, development of new soft tissue plasmacytomas or bone lesions, and increases in the size of existing plasmacytomas or bone lesions.

"Refractory MM" refers to multiple myeloma which is non-responsive (e.g., fails to achieve a minimal response or develops progressive disease while on therapy). In certain embodiments, the multiple myeloma is non-responsive while on primary or salvage therapy, or progresses within 60 days of the last therapy.

In certain embodiments, the MM is "relapsed and refractory MM" "Relapsed and refractory MM" is non-responsive while on salvage therapy (e.g., therapy that is administered after treatment with first line of therapy has failed) or disease that progresses within 60 days of last therapy in patients who have achieved minimal response or better at some point prior to progressing in their current disease course.

In certain embodiment, the MM is Primary Refractory MM. Primary refractory MM is MM disease that is non-responsive in patients who have never achieved minimal response or better with any therapy.

In certain embodiments, the MM is precancerous or "smoldering" MM. Smoldering multiple myeloma is a pre-cancerous condition that alters certain proteins in blood and/or increases plasma cells in bone marrow, but it does not cause symptoms of disease. About half of those diagnosed with the condition, however, will develop multiple myeloma within 5 years. Patients are closely monitored for evidence of progression to active multiple myeloma. Patients are diagnosed with smoldering multiple myeloma if they meet certain criteria: a blood test showing an M protein of >3 g/dl of blood or a 24-hour urine test showing 500 mg or more of protein or a bone marrow biopsy that shows that plasma cells make up between 10% and 59% of blood cells in the bone marrow; and no sign of abnormal bone lesions or kidney damage that active myeloma may cause. There are currently no approved treatments for smoldering multiple myeloma.

"Disease response" may be determined according to standard criteria for hematological malignancies and staging. Methods to evaluate the disease response of a hematological malignancy are known to persons skilled in the art. For example, methods to evaluate the disease response include performance status evaluations such as Eastern Cooperative Oncology Group (ECOG) performance status and International Myeloma Working Group Response Criteria (see Oken, et al. Am. J. Clin. Oncol. 1982; 5(6):649-655 and Kumar, et al., Lancet Oncol. 2016; 17(8):328-346, respectively) Methods to evaluate disease response can also include quantification of disease markers, bone marrow biopsy and/or aspiration, radiologic imaging of plasmacytoma, bone skeletal survey, M-protein quantification (serum and/or 24-hr urine) and serum free light chain levels or urinary light chain levels, serum b2-microglobulin, lymph node biopsy, radiologic tumor assessment (by X-ray, computed tomography (CT) scan, PET scan, or magnetic resonance imaging (MRI)), and blood count including blast count. This list of evaluation methods is to be understood as being non-limiting.

Based on the results obtained from the evaluation of the disease response, the disease response may then be stratified according to the standard criteria for underlying disease and classified into complete response or complete remission (CR), partial response (PR), stable disease (SD), or progressive disease (PD).

In another aspect, the disclosure provides a method of treating or preventing multiple myeloma in a subject in need thereof, the method comprising administering to the subject a binding protein as disclosed herein, comprising a first antigen binding domain with binding specificity to BCMA and a second antigen binding domain with binding specificity to a Natural Killer (NK) cell marker.

In an aspect, the disclosure provides a method of treating or preventing multiple myeloma in a subject in need thereof, the method comprising administering to the subject a binding protein comprising a first antigen binding domain with binding specificity to BCMA and a second antigen binding domain with binding specificity to a Natural Killer (NK) cell marker, wherein the first antigen binding domain comprises:
  a. a first immunoglobulin heavy chain variable domain (VH1) comprising an HCDR1 sequence comprising the amino acid sequence of GFTFSNFGMH (SEQ ID NO: 1), an HCDR2 sequence comprising the amino acid sequence of VIWSDETNR (SEQ ID NO: 2), and an HCDR3 sequence comprising the amino acid sequence of DQQYCSSDSCFTWFDP (SEQ ID NO: 3); and
  b. a first immunoglobulin light chain variable domain (VL1) comprising an LCDR1 sequence comprising the amino acid sequence of CX1SSTGX2VTPX3X4YAN (SEQ ID NO: 4), wherein X1 is R or A, X2 is T or A, X3 is S or G, and X4 is N or Y; an LCDR2 sequence comprising the amino acid sequence of DNNX5X6PP (SEQ ID NO: 5), wherein X5 is S, I, or N and X6 is R or K, and an LCDR3 sequence comprising the amino acid sequence of ALX7X8GX9QWV (SEQ ID NO: 6), wherein X7 is W or Y, X8 is F or Y, and X9 is N or G.

In certain embodiments, the first antigen binding domain with binding specificity to BCMA comprises:
  a. a first immunoglobulin heavy chain variable domain (VH1) comprising an HCDR1 sequence comprising the amino acid sequence of GFTFSNFGMH (SEQ ID NO: 1), an HCDR2 sequence comprising the amino acid sequence of VIWSDETNR (SEQ ID NO: 2), and an HCDR3 sequence comprising the amino acid sequence of DQQYCSSDSCFTWFDP (SEQ ID NO: 3); and
  b. a first immunoglobulin light chain variable domain (VL1) comprising an LCDR1 sequence comprising the amino acid sequence of CX1SSTGX2VTPX3X4YAN (SEQ ID NO: 4), wherein X1 is R or A, X2 is T or A, X3 is S or G, and X4 is N or Y; an LCDR2 sequence comprising the amino acid sequence of DNNX5X6PP (SEQ ID NO: 5), wherein X5 is S, I, or N and X6 is R or K, and an LCDR3 sequence comprising the amino acid sequence of ALX7X8GX9QWV (SEQ ID NO: 6), wherein X7 is W or Y, X8 is F or Y, and X9 Is N or G.

In certain embodiments, the VL1 comprises:
  a. an LCDR1 sequence comprising the amino acid sequence of CASSTGTVTPSNYAN (SEQ ID NO: 7), an LCDR2 sequence comprising the amino acid sequence of DNNSRPP (SEQ ID NO: 8), and an LCDR3 sequence comprising the amino acid sequence of ALWFGNQWV (SEQ ID NO: 9);
  b. an LCDR1 sequence comprising the amino acid sequence of CRSSTGTVTPSNYAN (SEQ ID NO: 10), an LCDR2 sequence comprising the amino acid sequence of DNNSRPP (SEQ ID NO: 11), and an LCDR3 sequence comprising the amino acid sequence of ALWFGNQWV (SEQ ID NO: 12);
  c. an LCDR1 sequence comprising the amino acid sequence of CASSTGAVTPSNYAN (SEQ ID NO: 13), an LCDR2 sequence comprising the amino acid sequence of DNNIKPP (SEQ ID NO: 14), and an LCDR3 sequence comprising the amino acid sequence of ALWYGGQWV (SEQ ID NO: 15); or
  d. an LCDR1 sequence comprising the amino acid sequence of CASSTGAVTPGYYAN (SEQ ID NO: 16), an LCDR2 sequence comprising the amino acid sequence of DNNNKPP (SEQ ID NO: 17), and an LCDR3 sequence comprising the amino acid sequence of ALYYGGQWV (SEQ ID NO: 18).

In certain embodiments:
  a. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 55;
  b. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 50;
  c. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 51;
  d. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 52;
  e. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 53; or
  f. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 54.

In certain embodiments:
  a. the VH1 comprises an amino acid sequence of SEQ ID NO: 49, and wherein the VL1 comprises an amino acid sequence of SEQ ID NO: 55;
  b. the VH1 comprises an amino acid sequence of SEQ ID NO: 49, and wherein the VL1 comprises an amino acid sequence of SEQ ID NO: 50;

c. the VH1 comprises an amino acid sequence of SEQ ID NO: 49, and wherein the VL1 comprises an amino acid sequence of SEQ ID NO: 51;
d. the VH1 comprises an amino acid sequence of SEQ ID NO: 49, and wherein the VL1 comprises an amino acid sequence of SEQ ID NO: 52;
e. the VH1 comprises an amino acid sequence of SEQ ID NO: 49, and wherein the VL1 comprises an amino acid sequence of SEQ ID NO: 53; or
f. the VH1 comprises an amino acid sequence of SEQ ID NO: 49, and wherein the VL1 comprises an amino acid sequence of SEQ ID NO: 54.

In certain embodiments, the second antigen binding domain with binding specificity to a NK cell marker comprises:
a. a second immunoglobulin heavy chain variable domain (VH2) comprising:
  i. an HCDR1 sequence comprising the amino acid sequence of DYVIN (SEQ ID NO: 80), an HCDR2 sequence comprising the amino acid sequence of EIYPGSGTNYYNEKFKA (SEQ ID NO: 81), and an HCDR3 sequence comprising the amino acid sequence of RGRYGLYAMDY (SEQ ID NO: 21);
  ii. an HCDR1 sequence comprising SDYAWN (SEQ ID NO: 22), an HCDR2 sequence comprising YITYSGSTSYNPSLES (SEQ ID NO: 23), and an HCDR3 sequence comprising GGYYGSSWGVFAY (SEQ ID NO: 24);
  iii. an HCDR1 sequence comprising EYTMH (SEQ ID NO: 25), an HCDR2 sequence comprising GISPNIGGTSYNQKFKG (SEQ ID NO: 26), and an HCDR3 sequence comprising RGGSFDY (SEQ ID NO: 27);
  iv. an HCDR1 sequence comprising SFTMH (SEQ ID NO: 28), an HCDR2 sequence comprising YINPSSGYTEYNQKFKD (SEQ ID NO: 29), and an HCDR3 sequence comprising GSSRGFDY (SEQ ID NO: 30); or
  v. an HCDR1 sequence comprising SDYAWN (SEQ ID NO: 31), an HCDR2 sequence comprising YITYSGSTNYNPSLKS (SEQ ID NO: 32), and an HCDR3 sequence comprising CWDYALYAMDC (SEQ ID NO: 33); and
b. a second immunoglobulin light chain variable domain (VL2) comprising:
  i. an LCDR1 sequence comprising the amino acid sequence of RASQDISNYLN (SEQ ID NO: 34), an LCDR2 sequence comprising the amino acid sequence of YTSRLHS (SEQ ID NO: 35), and an LCDR3 sequence comprising the amino acid sequence of QQGNTRPWT (SEQ ID NO: 36);
  ii. an LCDR1 sequence comprising RVSENIYSYLA (SEQ ID NO: 37), an LCDR2 sequence comprising NAKTLAE (SEQ ID NO: 38), and an LCDR3 sequence comprising QHHYGTPWT (SEQ ID NO: 39);
  iii. an LCDR1 sequence comprising RASQSISDYLH (SEQ ID NO: 40), an LCDR2 sequence comprising YASQSIS (SEQ ID NO: 41), and an LCDR3 sequence comprising QNGHSFPLT (SEQ ID NO: 42);
  iv. an LCDR1 sequence comprising RASENIYSNLA (SEQ ID NO: 43), an LCDR2 sequence comprising AATNLAD (SEQ ID NO: 44), and an LCDR3 sequence comprising QHFWGTPRT (SEQ ID NO: 45); or
  v. an LCDR1 sequence comprising RTSENIYSYLA (SEQ ID NO: 46), an LCDR2 sequence comprising NAKTLAE (SEQ ID NO: 47), and an LCDR3 sequence comprising QHHYDTPLT (SEQ ID NO: 48).

In certain embodiments:
a. the VH2 comprises an amino acid sequence that is at least about 90% identical to the amino acid sequence of SEQ ID NO: 56, and wherein the VL2 comprises an amino acid sequence that is at least about 90% identical to the amino acid sequence of SEQ ID NO: 64;
b. the VH2 comprises an amino acid sequence that is at least about 90% identical to the amino acid sequence of SEQ ID NO: 57, and wherein the VL2 comprises an amino acid sequence that is at least about 90% identical to the amino acid sequence of SEQ ID NO: 65;
c. the VH2 comprises an amino acid sequence that is at least about 90% identical to the amino acid sequence of SEQ ID NO: 58, and wherein the VL2 comprises an amino acid sequence that is at least about 90% identical to the amino acid sequence of SEQ ID NO: 66;
d. the VH2 comprises an amino acid sequence that is at least about 90% identical to the amino acid sequence of SEQ ID NO: 59, and wherein the VL2 comprises an amino acid sequence that is at least about 90% identical to the amino acid sequence of SEQ ID NO: 67;
e. the VH2 comprises an amino acid sequence that is at least about 90% identical to the amino acid sequence of SEQ ID NO: 60, and wherein the VL2 comprises an amino acid sequence that is at least about 90% identical to the amino acid sequence of SEQ ID NO: 68;
f. the VH2 comprises an amino acid sequence that is at least about 90% identical to the amino acid sequence of SEQ ID NO: 61, and wherein the VL2 comprises an amino acid sequence that is at least about 90% identical to the amino acid sequence of SEQ ID NO: 69;
g. the VH2 comprises an amino acid sequence that is at least about 90% identical to the amino acid sequence of SEQ ID NO: 62, and wherein the VL2 comprises an amino acid sequence that is at least about 90% identical to the amino acid sequence of SEQ ID NO: 70; or
h. the VH2 comprises an amino acid sequence that is at least about 90% identical to the amino acid sequence of SEQ ID NO: 63, and wherein the VL2 comprises an amino acid sequence that is at least about 90% identical to the amino acid sequence of SEQ ID NO: 71.

In certain embodiments:
a. the VH2 comprises an amino acid sequence of SEQ ID NO: 56, and wherein the VL2 comprises an amino acid sequence of SEQ ID NO: 64;
b. the VH2 comprises an amino acid sequence of SEQ ID NO: 57, and wherein the VL2 comprises an amino acid sequence of SEQ ID NO: 65;
c. the VH2 comprises an amino acid sequence of SEQ ID NO: 58, and wherein the VL2 comprises an amino acid sequence of SEQ ID NO: 66;
d. the VH2 comprises an amino acid sequence of SEQ ID NO: 59, and wherein the VL2 comprises an amino acid sequence of SEQ ID NO: 67;
e. the VH2 comprises an amino acid sequence of SEQ ID NO: 60, and wherein the VL2 comprises an amino acid sequence of SEQ ID NO: 68;
f. the VH2 comprises an amino acid sequence of SEQ ID NO: 61, and wherein the VL2 comprises an amino acid sequence of SEQ ID NO: 69;
g. the VH2 comprises an amino acid sequence of SEQ ID NO: 62, and wherein the VL2 comprises an amino acid sequence of SEQ ID NO: 70; or h. the VH2 comprises an amino acid sequence of SEQ ID NO: 63, and wherein the VL2 comprises an amino acid sequence of SEQ ID NO: 71.

In certain embodiments, the method further comprises all or part of an immunoglobulin Fc domain or variant thereof.

In certain embodiments, the Fc domain is an IgG1 Fc domain. In certain embodiments, the Fc domain or variant thereof comprises a first Fc heavy chain and a second Fc heavy chain. In certain embodiments, the first Fc heavy chain or the second Fc heavy chain comprises the pair of cysteines.

In certain embodiments, the subject has received treatment or therapy prior to treatment with an NKCE as disclosed herein. In certain embodiments, the multiple myeloma is relapsed/refractory multiple myeloma.

Method of Treatment/Use for Light Chain Amyloidosis

In one aspect, the disclosure is directed to the treatment and prevention of light chain amyloidosis (LCA).

In certain embodiments, the present disclosure provides kits and methods for the treatment of diseases and disorders, e.g., an amyloidosis in a mammalian subject in need of such treatment. Current standards of care for LCA are limited due to tolerability in this population with frequent organ dysfunction. As such, there is still an unmet need for additional therapeutics for LCA that are effective and safe.

In another aspect, the disclosure provides a method of treating or preventing light chain amyloidosis in a subject in need thereof, the method comprising administering to the subject a binding protein as disclosed herein, comprising a first antigen binding domain with binding specificity to BCMA and a second antigen binding domain with binding specificity to a Natural Killer (NK) cell marker.

In an aspect, the disclosure provides a method of treating or preventing LCA in a subject in need thereof, the method comprising administering to the subject a binding protein comprising a first antigen binding domain with binding specificity to BCMA and a second antigen binding domain with binding specificity to a Natural Killer (NK) cell marker, wherein the first antigen binding domain comprises:
 a. a first immunoglobulin heavy chain variable domain (VH1) comprising an HCDR1 sequence comprising the amino acid sequence of GFTFSNFGMH (SEQ ID NO: 1), an HCDR2 sequence comprising the amino acid sequence of VIWSDETNR (SEQ ID NO: 2), and an HCDR3 sequence comprising the amino acid sequence of DQQYCSSDSCFTWFDP (SEQ ID NO: 3); and
 b. a first immunoglobulin light chain variable domain (VL1) comprising an LCDR1 sequence comprising the amino acid sequence of CX1SSTGX2VTPX3X4YAN (SEQ ID NO: 4), wherein X1 is R or A, X2 is T or A, X3 is S or G, and X4 is N or Y; an LCDR2 sequence comprising the amino acid sequence of DNNX5X6PP (SEQ ID NO: 5), wherein X5 is S, I, or N and X6 is R or K, and an LCDR3 sequence comprising the amino acid sequence of ALX7X8GX9QWV (SEQ ID NO: 6), wherein X7 is W or Y, X8 is F or Y, and X9 is N or G.

In certain embodiments, the first antigen binding domain with binding specificity to BCMA comprises:
 a. a first immunoglobulin heavy chain variable domain (VH1) comprising an HCDR1 sequence comprising the amino acid sequence of GFTFSNFGMH (SEQ ID NO: 1), an HCDR2 sequence comprising the amino acid sequence of VIWSDETNR (SEQ ID NO: 2), and an HCDR3 sequence comprising the amino acid sequence of DQQYCSSDSCFTWFDP (SEQ ID NO: 3); and
 b. a first immunoglobulin light chain variable domain (VL1) comprising an LCDR1 sequence comprising the amino acid sequence of CX1SSTGX2VTPX3X4YAN (SEQ ID NO: 4), wherein X1 is R or A, X2 is T or A, X3 is S or G, and X4 is N or Y; an LCDR2 sequence comprising the amino acid sequence of DNNX5X6PP (SEQ ID NO: 5), wherein X5 is S, I, or N and X6 is R or K, and an LCDR3 sequence comprising the amino acid sequence of ALX7X8GX9QWV (SEQ ID NO: 6), wherein X7 is W or Y, X8 is F or Y, and X9 is N or G.

In certain embodiments, the VL1 comprises:
a. an LCDR1 sequence comprising the amino acid sequence of CASSTGTVTPSNYAN (SEQ ID NO: 7), an LCDR2 sequence comprising the amino acid sequence of DNNSRPP (SEQ ID NO: 8), and an LCDR3 sequence comprising the amino acid sequence of ALWFGNQWV (SEQ ID NO: 9);
b. an LCDR1 sequence comprising the amino acid sequence of CRSSTGTVTPSNYAN (SEQ ID NO: 10), an LCDR2 sequence comprising the amino acid sequence of DNNSRPP (SEQ ID NO: 11), and an LCDR3 sequence comprising the amino acid sequence of ALWFGNQWV (SEQ ID NO: 12);
c. an LCDR1 sequence comprising the amino acid sequence of CASSTGAVTPSNYAN (SEQ ID NO: 13), an LCDR2 sequence comprising the amino acid sequence of DNNIKPP (SEQ ID NO: 14), and an LCDR3 sequence comprising the amino acid sequence of ALWYGGQWV (SEQ ID NO: 15); or
d. an LCDR1 sequence comprising the amino acid sequence of CASSTGAVTPGYYAN (SEQ ID NO: 16), an LCDR2 sequence comprising the amino acid sequence of DNNNKPP (SEQ ID NO: 17), and an LCDR3 sequence comprising the amino acid sequence of ALYYGGQWV (SEQ ID NO: 18).

In certain embodiments:
a. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 55;
b. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 50;
c. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 51;
d. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 52;
e. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 53; or
f. the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 54.

In certain embodiments:
a. the VH1 comprises an amino acid sequence of SEQ ID NO: 49, and wherein the VL1 comprises an amino acid sequence of SEQ ID NO: 55;
b. the VH1 comprises an amino acid sequence of SEQ ID NO: 49, and wherein the VL1 comprises an amino acid sequence of SEQ ID NO: 50;
c. the VH1 comprises an amino acid sequence of SEQ ID NO: 49, and wherein the VL1 comprises an amino acid sequence of SEQ ID NO: 51;
d. the VH1 comprises an amino acid sequence of SEQ ID NO: 49, and wherein the VL1 comprises an amino acid sequence of SEQ ID NO: 52;
e. the VH1 comprises an amino acid sequence of SEQ ID NO: 49, and wherein the VL1 comprises an amino acid sequence of SEQ ID NO: 53; or
f. the VH1 comprises an amino acid sequence of SEQ ID NO: 49, and wherein the VL1 comprises an amino acid sequence of SEQ ID NO: 54.

In certain embodiments, the second antigen binding domain with binding specificity to a NK cell marker comprises:
a. a second immunoglobulin heavy chain variable domain (VH2) comprising:
 i. an HCDR1 sequence comprising the amino acid sequence of DYVIN (SEQ ID NO: 80), an HCDR2 sequence comprising the amino acid sequence of EIYPGSGTNYYNEKFKA (SEQ ID NO: 81), and an HCDR3 sequence comprising the amino acid sequence of RGRYGLYAMDY (SEQ ID NO: 21);
 ii. an HCDR1 sequence comprising SDYAWN (SEQ ID NO: 22), an HCDR2 sequence comprising YITYSGSTSYNPSLES (SEQ ID NO: 23), and an HCDR3 sequence comprising GGYYGSSWGVFAY (SEQ ID NO: 24);
 iii. an HCDR1 sequence comprising EYTMH (SEQ ID NO: 25), an HCDR2 sequence comprising GISPNIGGTSYNQKFKG (SEQ ID NO: 26), and an HCDR3 sequence comprising RGGSFDY (SEQ ID NO: 27);
 iv. an HCDR1 sequence comprising SFTMH (SEQ ID NO: 28), an HCDR2 sequence comprising YINPSSGYTEYNQKFKD (SEQ ID NO: 29), and an HCDR3 sequence comprising GSSRGFDY (SEQ ID NO: 30); or
 v. an HCDR1 sequence comprising SDYAWN (SEQ ID NO: 31), an HCDR2 sequence comprising YITYSGSTNYNPSLKS (SEQ ID NO: 32), and an HCDR3 sequence comprising CWDYALYAMDC (SEQ ID NO: 33); and
b. a second immunoglobulin light chain variable domain (VL2) comprising:
 i. an LCDR1 sequence comprising the amino acid sequence of RASQDISNYLN (SEQ ID NO: 34), an LCDR2 sequence comprising the amino acid sequence of YTSRLHS (SEQ ID NO: 35), and an LCDR3 sequence comprising the amino acid sequence of QQGNTRPWT (SEQ ID NO: 36);
 ii. an LCDR1 sequence comprising RVSENIYSYLA (SEQ ID NO: 37), an LCDR2 sequence comprising NAKTLAE (SEQ ID NO: 38), and an LCDR3 sequence comprising QHHYGTPWT (SEQ ID NO: 39);
 iii. an LCDR1 sequence comprising RASQSISDYLH (SEQ ID NO: 40), an LCDR2 sequence comprising YASQSIS (SEQ ID NO: 41), and an LCDR3 sequence comprising QNGHSFPLT (SEQ ID NO: 42);
 iv. an LCDR1 sequence comprising RASENIYSNLA (SEQ ID NO: 43), an LCDR2 sequence comprising AATNLAD (SEQ ID NO: 44), and an LCDR3 sequence comprising QHFWGTPRT (SEQ ID NO: 45); or
 v. an LCDR1 sequence comprising RTSENIYSYLA (SEQ ID NO: 46), an LCDR2 sequence comprising NAKTLAE (SEQ ID NO: 47), and an LCDR3 sequence comprising QHHYDTPLT (SEQ ID NO: 48).

In certain embodiments:
a. the VH2 comprises an amino acid sequence that is at least about 90% identical to the amino acid sequence of SEQ ID NO: 56, and wherein the VL2 comprises an amino acid sequence that is at least about 90% identical to the amino acid sequence of SEQ ID NO: 64;
b. the VH2 comprises an amino acid sequence that is at least about 90% identical to the amino acid sequence of SEQ ID NO: 57, and wherein the VL2 comprises an amino acid sequence that is at least about 90% identical to the amino acid sequence of SEQ ID NO: 65;
c. the VH2 comprises an amino acid sequence that is at least about 90% identical to the amino acid sequence of SEQ ID NO: 58, and wherein the VL2 comprises an amino acid sequence that is at least about 90% identical to the amino acid sequence of SEQ ID NO: 66;
d. the VH2 comprises an amino acid sequence that is at least about 90% identical to the amino acid sequence of SEQ ID NO: 59, and wherein the VL2 comprises an amino acid sequence that is at least about 90% identical to the amino acid sequence of SEQ ID NO: 67;
e. the VH2 comprises an amino acid sequence that is at least about 90% identical to the amino acid sequence of SEQ ID NO: 60, and wherein the VL2 comprises an amino acid sequence that is at least about 90% identical to the amino acid sequence of SEQ ID NO: 68;
f. the VH2 comprises an amino acid sequence that is at least about 90% identical to the amino acid sequence of SEQ ID NO: 61, and wherein the VL2 comprises an amino acid sequence that is at least about 90% identical to the amino acid sequence of SEQ ID NO: 69;
g. the VH2 comprises an amino acid sequence that is at least about 90% identical to the amino acid sequence of SEQ ID NO: 62, and wherein the VL2 comprises an amino acid sequence that is at least about 90% identical to the amino acid sequence of SEQ ID NO: 70; or
h. the VH2 comprises an amino acid sequence that is at least about 90% identical to the amino acid sequence of SEQ ID NO: 63, and wherein the VL2 comprises an amino acid sequence that is at least about 90% identical to the amino acid sequence of SEQ ID NO: 71.

In certain embodiments:
a. the VH2 comprises an amino acid sequence of SEQ ID NO: 56, and wherein the VL2 comprises an amino acid sequence of SEQ ID NO: 64;
b. the VH2 comprises an amino acid sequence of SEQ ID NO: 57, and wherein the VL2 comprises an amino acid sequence of SEQ ID NO: 65;
c. the VH2 comprises an amino acid sequence of SEQ ID NO: 58, and wherein the VL2 comprises an amino acid sequence of SEQ ID NO: 66;
d. the VH2 comprises an amino acid sequence of SEQ ID NO: 59, and wherein the VL2 comprises an amino acid sequence of SEQ ID NO: 67;
e. the VH2 comprises an amino acid sequence of SEQ ID NO: 60, and wherein the VL2 comprises an amino acid sequence of SEQ ID NO: 68;

f. the VH2 comprises an amino acid sequence of SEQ ID NO: 61, and wherein the VL2 comprises an amino acid sequence of SEQ ID NO: 69;

g. the VH2 comprises an amino acid sequence of SEQ ID NO: 62, and wherein the VL2 comprises an amino acid sequence of SEQ ID NO: 70; or h. the VH2 comprises an amino acid sequence of SEQ ID NO: 63, and wherein the VL2 comprises an amino acid sequence of SEQ ID NO: 71.

In certain embodiments, the method further comprises all or part of an immunoglobulin Fc domain or variant thereof.

In certain embodiments, the Fc domain is an IgG1 Fc domain. In certain embodiments, the Fc domain or variant thereof comprises a first Fc heavy chain and a second Fc heavy chain. In certain embodiments, the first Fc heavy chain or the second Fc heavy chain comprises the pair of cysteines.

In certain embodiments, the NK cell marker is selected from NKp46, NKp30, NKp44, CD16, CD56, CD57, a KIR receptor (e.g., KIR2DL1, KIR2DL2, KIR2DL3, KIR2DL5A, KIR2DL5B, KIR3DL1, KIR3DL2, and KIR3DL3), CD94, and NKG2. In certain embodiments, the NK cell marker is NKp46.

In certain embodiments, the method further comprises selection of a subject with light chain amyloidosis, wherein the selection comprises:
a. diagnosing the subject with light chain amyloidosis;
b. determining the staging of disease based on a prognostic system as disclosed herein; and/or
c. determining that the subject has not received a prior diagnosis of multiple myeloma.

In certain embodiments, the subject is treatment-naïve.

In certain embodiments, the subject has received or is receiving one or more therapeutics for light chain amyloidosis (e.g., chemotherapy, autologous stem cell transplant, immunomodulatory drugs, immunotherapies, proteasome inhibitors and any combinations thereof). In certain embodiments, the subject has received at least one proteasome inhibitor.

In certain embodiments, the LCA is relapsed/refractory LCA.

In one aspect, the disclosure provides a method of treating or preventing LCA in a subject in need thereof, the method comprising administering to the subject a binding protein comprising a first antigen binding domain with binding specificity to BCMA and a second antigen binding domain with binding specificity to NKp46, wherein:
a. the first antigen binding domain comprises:
i. a first immunoglobulin heavy chain variable domain (VH) comprising an HCDR1 sequence comprising the amino acid sequence of GFTFSNFGMH (SEQ ID NO: 1), an HCDR2 sequence comprising the amino acid sequence of VIWSDETNR (SEQ ID NO: 2), and an HCDR3 sequence comprising the amino acid sequence of DQQYCSSDSCFTWFDP (SEQ ID NO: 3); and
ii. a first immunoglobulin light chain variable domain (VL1) comprising an LCDR1 sequence comprising the amino acid sequence of CX1SSTGX2VTPX3X4YAN (SEQ ID NO: 4), wherein X1 is R or A, X2 is T or A, X3 is S or G, and X4 is N or Y; an LCDR2 sequence comprising the amino acid sequence of DNNX5X6PP (SEQ ID NO: 5), wherein X5 is S, I, or N and X6 is R or K, and an LCDR3 sequence comprising the amino acid sequence of ALX7X8GX9QWV (SEQ ID NO: 6), wherein X7 is W or Y, X8 is F or Y, and X9 is N or G; and b. the second antigen binding domain comprises:
i. an HCDR1 sequence comprising DYVIN (SEQ ID NO: 19), an HCDR2 sequence comprising EIYPGSGTNYYNEKFKA (SEQ ID NO: 20), and an HCDR3 sequence comprising RGRYGLYAMDY (SEQ ID NO: 21); and
ii. an LCDR1 sequence comprising RASQDISNYLN (SEQ ID NO: 34), an LCDR2 sequence comprising YTSRLHS (SEQ ID NO: 35), and an LCDR3 sequence comprising QQGNTRPWT (SEQ ID NO: 36);

In one aspect, the disclosure provides a method of treating or preventing LCA in a subject in need thereof, the method comprising administering to the subject a binding protein comprising a first antigen binding domain with binding specificity to BCMA and a second antigen binding domain with binding specificity to NKp46, wherein:
a. the first antigen binding domain comprises:
i. a VH1 comprising an amino acid sequence that is at least about 90% identical to the amino acid sequence of SEQ ID NO: 49; and
ii. a VL1 comprising an amino acid sequence that is at least about 90% identical to the amino acid sequence of SEQ ID NO: 55; and
b. the second antigen binding domain comprises:
i. a VH2 comprising an amino acid sequence that is at least about 90% identical to the amino acid sequence of SEQ ID NO: 56; and
ii. a VL1 comprising an amino acid sequence that is at least about 90% identical to the amino acid sequence of SEQ ID NO: 64.

In certain embodiments, the binding protein is administered through intraarterial, intraperitoneal, intramuscular, subcutaneous, rectal, or vaginal administration. In certain embodiments, the binding protein is administered through subcutaneous administration.

In certain embodiments, the Fc domain variant comprises ADE mutations (G236/S239D/I332E) in CH2 to enhance ADCC-activity.

In certain embodiments, the F domain variant comprises disulfide bond substitutions (R292C/V302C) in CH2 for stabilization.

In certain embodiments, the Fc domain variant comprises knob-into-hole mutations (KIH) in CH3 to favor heterodimer formation in the Fc domain. In certain embodiments the "knob" mutations are at positions C482/W494 and the "hole" mutations are at positions C129/S146/A148/V187. In some embodiments, the Fc domain variant comprises RF mutations (H435R/Y436F) in one CH3 to favor purification of heterodimers in the Fc domain.

In certain embodiments, the disease is an amyloidosis or an amyloid disease. The term "amyloidosis" or "amyloid disease", as used herein, refers to diseases or disorders that fall under the umbrella of plasma cell dyscrasias. Amyloidosis or amyloid disease occurs when amyloid builds up in organs and interferes with normal physiological function. The term "amyloid", as used herein, refers to the abnormal fibrous, extracellular, proteinaceous deposits found in organs and tissues. Amyloid is not normally found in the body, but it can be formed from several different types of protein. Amyloid is typically insoluble and is structurally dominated a by β-sheet structure. Organs that may be affected include the heart, kidneys, liver, spleen, nervous system, skin, and digestive tract. The term "amyloidosis" is used to refer to a cluster of diseases which share a common feature, i.e., the extracellular deposition of pathologic insoluble fibrillar proteins in organs and tissues.

A hallmark feature of amyloid disease is the production of amyloids characterized by a fibrillar morphology of about 5-15 nm in diameter which bind the dye congo red and display fluorescence birefringence when bound to the dye thioflavin T. The fibers can form secondary structures called protofilaments made of pleated β-sheets which make them resistant to degradation. Toyama and Weissman (2011), Annu Rev Biochem, 80:557-585; Picken (2020), Acta Haematol, vol. 143: 322-334.

In certain embodiments, the amyloidosis or the amyloid disease is light chain amyloidosis or amyloid light-chain amyloidosis. The current classification of amyloid is based on the type of amyloid protein. For instance, amyloid is termed "A" (for amyloid) followed by an abbreviation of the protein type: AL (amyloid derived from immunoglobulin light chain). The term "amyloid light-chain amyloidosis" or "light chain amyloidosis" or "LCA"; also called AL amyloidosis, AL, ALA, or AL primary amyloidosis, is the most common form of systemic amyloidosis in the United States and in developed countries. Picken (2020), Acta Haematol, vol. 143: 322-334. The patient may present with a first instance of LCA (newly diagnosed LCA), or the LCA may be relapsed and/or refractory (relapsed/refractory LCA). LCA is the most common form of systemic amyloidosis and is associated with an underlying plasma cell dyscrasia. Aberrant plasma cells are derived from a single plasma cell source and secrete toxic fibril-forming free light chains. These plasma cells have been shown to be BCMA-positive (Godara et al. 2019. Blood 134 (Supplement_1): 4409). In certain embodiments, the patient with LCA is treatment-naïve. In some embodiments, the patient with LCA has received or is receiving one or more therapeutics for light chain amyloidosis (e.g., chemotherapy, autologous stem cell transplant, immunomodulatory drugs, immunotherapies, proteasome inhibitors and any combinations thereof).

In certain embodiments, the binding protein, including those comprising Fc domain variants, are useful in a number of different applications. For example, in one embodiment, the subject binding proteins are useful for reducing or eliminating cells bearing an epitope recognized by the binding domain of the Fc domain variant. In another embodiment, the subject Fc domain variants are effective in reducing the concentration of or eliminating soluble antigen in the circulation. In another embodiment, the subject Fc domain variants are effective as T-cell engagers.

In another embodiment, the subject binding proteins, including those comprising Fc domain variants, are useful for the treatment of diseases or disorders associated with an aberrant monoclonal B-cell or a plasma cell. In one embodiment, the aberrant monoclonal B-cell or plasma cell expresses BCMA.

The binding proteins can be particularly useful in the treatment of a disease or disorder within the category of plasma cell dyscrasias. In one embodiment, the plasma cell dyscrasia is not multiple myeloma. In one embodiment, the plasma cell dyscrasia is an amyloidosis, e.g., LCA (also called, light chain amyloidosis, AL (primary) amyloidosis, systemic amyloidosis, AL, or ALA).

LCA is a hematological disorder caused primarily by clonal plasma cells that produce misfolded immunoglobulin light chains. These aberrant light chains form a toxic aggregate in plasma cells and deposit fibrils (amyloids) in organs and tissue which result in significant and sometimes permanent organ dysfunction. LCA can impact any organ other than the brain. Li et al. (2019), J Int Med Res., 47(4): 1778-1786. The mechanisms by which amyloidogenic immunoglobulin light chains result in organ dysfunction are not well characterized but likely due to both amyloid deposits and prefibrillar aggregates cytotoxic effects on the underlying organ(s). Primary LCA is that which is neither associated with nor considered a complication of multiple myeloma.

Symptoms depend on the underlying organ impacted and are generally recognized late in disease progression. Early signs and symptoms of LCA include but are not limited to swelling of the ankles and legs; severe fatigue and weakness (e.g., shortness of breath; numbness, tingling or pain in the hands or feet), diarrhea or constipation, unintentional, significant weight loss; an enlarged tongue, changes to skin (such as, thickening or easy bruising, or purplish patches around the eyes), an irregular heartbeat, or difficulty swallowing. Clinical features of more severe LCA include cardiac, renal, hepatic, and gastrointestinal involvement and/or dysfunction, as well as neuropathies and macroglossia. Cardiac involvement (e.g., heart failure and arrhythmias) is the most common LCA symptom and represents the single most adverse prognostic feature. Bianchi et al. (2021), Cardiooncology, vol. 3: 4.

The diagnostic criteria for LCA include (1) the presence of a systemic syndrome, (2) histological documentation of amyloid, (3) evidence of a monoclonal plasma cell disorder (e.g., based on bone marrow or fat aspirate and/or target biopsy and serologic parameters), and (4) amyloidosis typing for identification of Ig light chain (via e.g., LC-MS or immunoelectron microscopy). Koh (2020) Blood Res., 55(Suppl): S54-S57. The outcome of the disease for LCA patients can be predicted based on a multi-stage prognostic system. There are currently four different prognostic models: (1) Mayo Model 2004 (Dispenzieri et al. (2004), J Clin Oncol., vol. 22:3751-7); (2) Mayo Model 2012 (Kumar et al. (2012), J Clin Oncol., vol. 30:989-95); (3) European Model 2015 (Muchtar et al. (2019), Leukemia, vol. 33:811-4); (4) Boston University Score 2019 (Lilleness et al. (2019), Blood, vol. 133:215-23). The Mayo Model 2012 and the European Model 2015 have shown the best predictive performance in recent validation studies. Vaxman et al. (2020) Blood Rev, 40: 100636.

Autologous stem cell transplant (ASCT) is the most effective treatment for patients with LCA. Sanchorawala (2020), Acta Haematol, vol. 143: 381-387. Cardiac biomarkers for the assessment of ASCT eligibility are often tested as Troponin T levels >0.06 ng/ml or NT-proBNP levels >5000 ng/L are associated with high transplant related mortality. Gavriatopoulou et al. (2018), Leukemia, vol. 32:1183-1898. The majority of LCA patients are ineligible for stem cell transplantation, may receive single or combination chemotherapy and/or immunotherapy regimens to eradicate the underlying plasma-cell. For intermediate-risk patients standard treatment has been oral melphalan/dexamethasone (Mdex), bortezomib-based regimen (BMDex, or VCD). However, treatment related mortality is substantial (24%). Id. Patients who fail to achieve rapid-response rates are considered for second-line treatments, namely, immunomodulatory drugs (IMIDs). IIMIDs include thalidomide, lenalidomide, and pomalidomide, and combinations thereof with alkylating agents. However, immunotherapies are poorly tolerated in patients, particularly those with cardiac LCA. Sidiqi & Gertz (2021), Blood Cancer Journal, vol. 11: 90. Overall, the LCA treatment regimens in current use are often difficult for the patient to tolerate with patients often succumbing to the lasting side effects of the treatments that frequently enhance disease symptoms. Hassan and Sanchorawala (2022), Hemato, vol. 3: 38-46. More recently, daratumumab (anti-CD38)-VCD has been approved as standard therapy in newly diagnosed LCA patients, based on the Phase 3 ANDROMEDA study (NCT03201965) (Kastritis et al. 2021. NEJM, 385:46-58).

A therapeutically effective amount of the NK cell engager disclosed herein may be the dose or amount sufficient to induce a "therapeutic response" in a subject, such as an improvement in at least one measure of amyloid disease, such as a reduction in the size of existing amyloid deposits or plaques, a decrease in the rate of amyloid deposition, or improved organ function as measured by standard techniques. Examples of common presenting signs specific to common target organs and examples of improved organ function are summarized below.

Heart

Common presenting signs of amyloid deposits are dyspnea on exertion, orthopnea, paroxysmal nocturnal dyspnea, lower extremity edema, pleural effusions, jugular venous distention, arrhythmia, syncope, angina. A decrease in the level of the patient's N-terminal pro b-type natriuretic peptide (NT-proBNP) or a decrease in the patient's New York Heart Association (NYHA) Functional Classification level may be indications of cardiac improvement. Palladini et al. (2003), Circulation, vol. 107: 2440-2445. Improved heart function may also be evaluated by measuring cardiac troponin levels, by analyzing cardiac MRI and echocardiogram.

Kidney

Common presenting signs of amyloid deposits in the kidneys are lower extremity edema, anasarca, and uremia. A decrease in proteinuria or the rate of protein output in the urine and estimated glomerular filtration rate (eGFR) may be indications of improved kidney function. Kidney Int. Suppl (2011), vol. 3(1): 19-62.

Liver

Common presenting signs of amyloid deposits in the liver are right upper quadrant tenderness, hepatomegaly, ascites, and/or oliguria. Improved alkaline phosphatase (ALP) levels, serum y-glutamyltransferase (GGT) levels, may be indications of improved liver function. Improvement of other metrics, such as hyperlipidemia, coagulation abnormalities, thrombocytopenia, prothrombin time (PT), erythrocyte sedimentation rate, alanine aminotransferase (ALT) and/or aspartate aminotransferase (AST), serum albumin and complement fragment levels can also indicate improvement of liver function, when those parameters were evaluated prior to any treatment, as they lack specificity for hepatic amyloidosis. Park et al. (2003), Medicine, vol. 82(5): 291-298.

GI Tract

Common presenting symptoms of amyloid deposits in the gastrointestinal (GI) tract are loss of motility, gastrointestinal bleeding, malabsorption, weight loss, anorexia, vomiting, nausea, hematomas, erosions and ulcerations, or a nodular gastritis. Improved GI tract function may be evaluated using conventional imaging (e.g., echography, computed tomography scanner, X-ray, endoscopy).

Nervous System

Common presenting symptoms of amyloid deposits in proximity to or in the nerves are sensorimotor polyneuropathy, characterized by symptoms of neuropathic pain, numbness, and in advanced cases weakness. Improvement of nervous system function may be evaluated by electrophysiologic tests such nerve conduction studies (NCS), electromyography (EMG), autonomic function testing (AFT), and quantitative sudomotor axon reflex testing (QSART).

One skilled in the art would be able, by routine experimentation, to determine what an effective, non-toxic amount of binding protein or Fc domain variant would be for the purpose of treating LCA. For example, a therapeutically active amount of a binding protein, including those comprising an Fc domain variant of the present disclosure may vary according to factors such as the prognostic staging system, age, sex, medical complications (e.g., immunosuppressed conditions or diseases) and weight of the subject, and the ability of the modified antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation.

In general, the compositions provided in the current disclosure may be used to prophylactically or therapeutically treat any neoplasm comprising an antigenic marker that allows for the targeting of the cancerous cells by the binding protein, including those comprising an Fc domain variant.

Binding proteins of the current disclosure can be administered on multiple occasions. Intervals between single dosages can be weekly, monthly or yearly. Intervals can also be irregular as indicated by measuring blood levels of binding protein or antigen in the patient. In some methods, dosage is adjusted to achieve a plasma modified binding polypeptide concentration of about 1-1000 µg/ml and in some methods about 25-300 µg/ml. Alternatively, binding proteins can be administered as a sustained release formulation, in which case less frequent administration is required. For antibodies, dosage and frequency vary depending on the half-life of the antibody in the patient. In general, humanized antibodies show the longest half-life, followed by chimeric antibodies and nonhuman antibodies.

The dosage and frequency of administration can vary depending on whether the treatment is prophylactic or therapeutic. In prophylactic applications, compositions containing the present polypeptides or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from about 0.1 to about 25 mg per dose, especially about 0.5 to about 2.5 mg per dose. A relatively low dosage is administered at relatively infrequent intervals over a long period of time. Some patients continue to receive treatment for the rest of their lives. In therapeutic applications, a relatively high dosage (e.g., from about 1 to 400 mg/kg of antibody per dose, with dosages of from about 5 to 25 mg being more commonly used for radioimmunoconjugates and higher doses for cytotoxin-drug modified antibodies) at relatively short intervals is sometimes required until progression of the disease is reduced or terminated, or until the patient shows partial or complete amelioration of disease symptoms. Thereafter, the patient can be administered a prophylactic regime.

Binding proteins, including those comprising Fc variants, of the current disclosure can optionally be administered in combination with other agents that are effective in treating the disorder or condition in need of treatment (e.g., prophylactic or therapeutic). Effective single treatment dosages (i.e., therapeutically effective amounts) of 90Y-labeled modified antibodies of the current disclosure range from between about 5 and about 75 mCi, such as between about 10 and about 40 mCi. Effective single treatment non-marrow ablative dosages of 131I-modified antibodies range from between about 5 and about 70 mCi, or between about 5 and about 40 mCi. Effective single treatment ablative dosages (i.e., may require autologous bone marrow transplantation)

of 131I-labeled antibodies range from between about 30 and about 600 mCi, such as between about 50 and less than about 500 mCi. In conjunction with a chimeric antibody, owing to the longer circulating half-life I murine antibodies, an effective single treatment of non-marrow ablative dosages of iodine-131 labeled chimeric antibodies range from between about 5 and about 40 mCi, such as less than about 30 mCi. Imaging criteria for, e.g., the 111In label, are typically less than about 5 mCi.

While the binding proteins may be administered as described immediately above, it must be emphasized that in other embodiments the polypeptide may be administered to otherwise healthy patients as a first line therapy. In such embodiments, the binding proteins may be administered to patients having normal or average red marrow reserves and/or to patients that have not, and are not, undergoing treatment. As used herein, the administration of the polypeptides in conjunction or combination with an adjunct therapy means the sequential, simultaneous, coextensive, concurrent, concomitant, or contemporaneous administration or application of the therapy and the disclosed antibodies. Those skilled in the art will appreciate that the administration or application of the various components of the combined therapeutic regimen may be timed to enhance the overall effectiveness of the treatment.

As previously discussed, the binding proteins, including those comprising Fc variants, of the present disclosure, antibodies, therapeutic polypeptides, or Fc variant-fusion polypeptides thereof, may be administered in a pharmaceutically effective amount for the in vivo treatment of mammalian disorders. In this regard, it will be appreciated that the disclosed binding proteins will be formulated to facilitate administration and promote stability of the active agent.

Pharmaceutical Compositions and Administration Thereof

Methods of preparing and administering the binding protein of the current disclosure to a subject are well known to or are readily determined by those skilled in the art. The route of administration of the binding polypeptides of the current disclosure may be oral, parenteral, by inhalation or topical. The term parenteral as used herein includes intravenous, intraarterial, intraperitoneal, intramuscular, subcutaneous, rectal or vaginal administration. While all these forms of administration are clearly contemplated as being within the scope of the current disclosure, a form for administration would be a solution for injection, in particular for intravenous or intraarterial injection or drip or for subcutaneous administration. Usually, a suitable pharmaceutical composition for injection may comprise a buffer (e.g., acetate, phosphate or citrate buffer), a surfactant (e.g., polysorbate), optionally a stabilizer agent (e.g., human albumin), etc. In some embodiments, Fc domain variants can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Aqueous carriers include water, alcoholic/aqueous solutions, emulsions or suspensions, including saline and buffered media. In the compositions and methods of the current disclosure, pharmaceutically acceptable carriers include, but are not limited to, 0.01-0.1 M, e.g., 0.05 M phosphate buffer, or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will typically be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

In many cases, isotonic agents will be included, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a binding protein of the disclosure) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, exemplary methods of preparation include vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will typically have labels or package inserts indicating that the associated compositions are useful for treating a subject suffering from, or predisposed to autoimmune or neoplastic disorders.

Effective doses of the compositions of the present disclosure, for the treatment of the above-described conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

A pharmaceutical composition in accordance with the present disclosure can comprise a pharmaceutically acceptable, non-toxic, sterile carrier such as physiological saline, nontoxic buffers, preservatives and the like. For the purposes of the instant application, a pharmaceutically effective amount of the binding protein shall be held to mean an amount sufficient to achieve effective binding to an antigen and to achieve a benefit, e.g., to ameliorate symptoms of a disease or disorder or to detect a substance or a cell. In the case of tumor cells, the polypeptide can interact with selected antigens on neoplastic or immunoreactive cells and provide for an increase in the death of those cells. Of course, the pharmaceutical compositions of the present disclosure may be administered in single or multiple doses to provide for a pharmaceutically effective amount of the modified binding polypeptide.

In keeping with the scope of the present disclosure, the binding proteins of the disclosure may be administered to a human or other animal in accordance with the aforementioned methods of treatment in an amount sufficient to produce a therapeutic or prophylactic effect. The binding proteins of the disclosure can be administered to such human or other animal in a conventional dosage form prepared by combining the antibody of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of binding polypeptides described in the current disclosure may prove to be particularly effective.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present disclosure has been described with reference to the specific embodiments thereof, it should be understood by those skilled in the art that various changes may be made and equivalents may be substituted without departing from the true spirit and scope of the disclosure. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present disclosure. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The present disclosure is further illustrated by the following examples, which should not be construed as further limiting.

Example 1: Design of NKp46-BCMA NKCE Binding Proteins

Introduction

To date, anti-tumor therapy has focused on manipulating effector T cells. T cell engager formats are in clinical development, but their use is limited to hematological diseases because of the potential toxicity. In contrast, the manipulation of NK cells in cancer via NKCEs is a therapeutic alternative due to NK cells anti-tumor effector potential yet favorable toxicity profile when compared to effector T cells. FIG. 1A schematizes the NKp46 NKCE which binds with one arm to an antigen at the surface of the tumor cell and with another arm to the NKp46 receptor on NK cells.

Figure 1B:
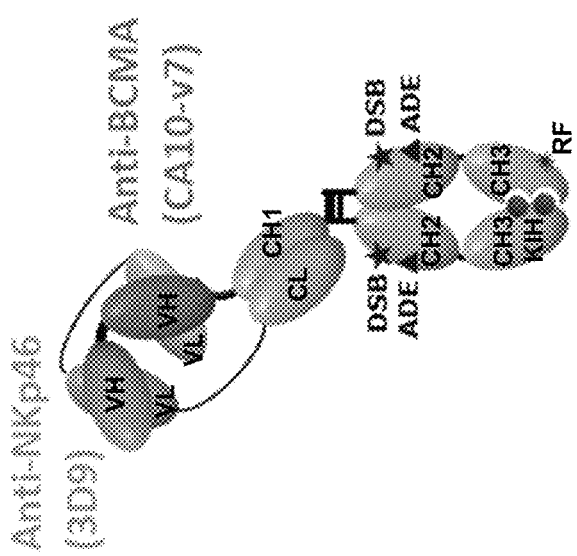
FIG. 1A-FIG. 1B are schematics of NKp46 multi-specific NK cell engagers (NKCE).
Figure 1A:
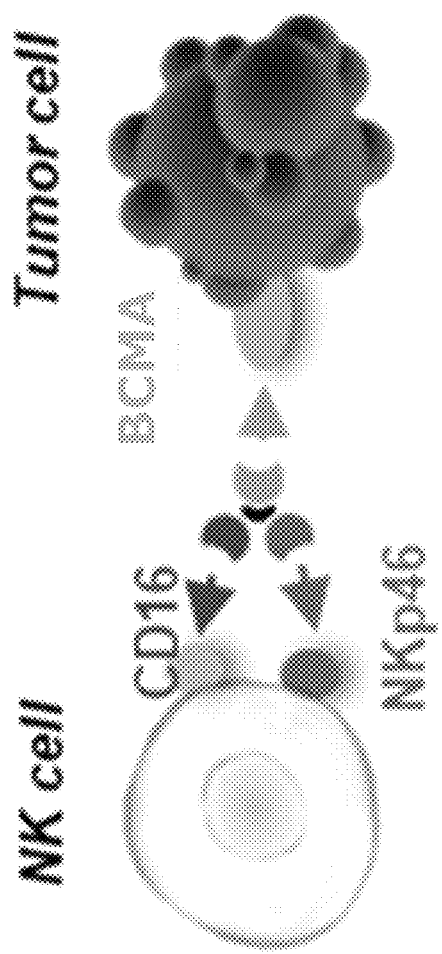

A NKp46 NKCE engineered with a unique Fc format (i.e., a NKp46-BCMA_CODV-OL1_Fc-ADE-DSB) as shown in FIG. 1B engages BCMA at the surface of the tumor cell while also engaging both NKp46 and a Fcγ receptor, CD16a. ADCC activity is induced with its novel enhanced Fc competent format. The novel enhanced Fc competent format (hereinafter, termed "CODV-OL1-ADE-DSB") includes: (1) ADE mutations (G236A/S239D/I332E) in CH2 to enhance ADCC-activity; (2) DSB (R292C/V302C) in CH2 for thermal stabilization; (3) knob-into-hole mutations (KIH) in CH3 to favor heterodimer formation in Fc—(3a) knob (in heavy chain containing the VH/VL domains): S354C/T366W and (3b) hole (in heavy chain lacking the VH/VL domains): Y349C/T366S/L368A/Y407V; and (4) RF mutations (H435R/Y436F) in one CH3 to favor purification of heterodimers in Fc. This NKp46-BCMA NKCE_Fc CODV-OL1-ADE-DSB additionally contains two linkers GGGGSGGGGS (SEQ ID NO: 78) in the light chain: one between VL anti-BCMA and VL anti-NKp46 and between VL NKp46 and CL.

Materials and Methods—Human Recombinant Protein, Cloning, Production, Purification Recombinant Human NKp46—Cloning, Production, and Purification The sequence encoding the Extracellular Domain (ECD) of human NKp46 (Gln22-Asn255, NCBI Reference: NM_004829.5) was inserted into the expression vector and a C-terminal 6×His tag was added for purification. The following primers were used for PCR on human PBMCs: 5' TACGACTCACAAGCTTGCCGCCACCATGTCTTC-CACACTCCCTGC 3' (SEQ ID NO: 107) and 5' CCGCCCCGACTCTAGATCAATGGTGATGGTGGT-GATGATTCTGGGCAGTGTGAT CCC 3' (SEQ ID NO: 108). The sequence of the amplicon was checked. The vector was then used to transfect a CHO cell line and a clone producing the protein was selected. The protein was purified from the culture supernatant with Ni-NTA beads (Qiagen, #1018244) and S200 size exclusion chromatography was performed to ensure the elimination of aggregates prior to characterization of downstream interrogation of binding kinetics with surface plasmon resonance (SPR).

The sequence encoding the ECD of Cynomolgus NKp46 (Pro22-Asn254, NP_001271509.1) was cloned into an expression vector and a C-terminal Flag-M2 tag was added for purification. The primers used to amplify the expected sequence from cynomolgus PBMC were: 5' TACGACT-CACAAGCTTGCCGCCACCATGTCTTC-CACACTCCGTGC 3' (SEQ ID NO: 109) and 5' CCGCCCCGACTCTAGATCACTTGTCATCGT-CATCTTTGTAATCATTCTGGGCAGTGTGGTCC 3' (SEQ ID NO: 110). After sequence validation, the vector was used to transfect the CHO-K1 SV cell line and a producing cell clone was selected. The first three batches were purified by M2 affinity chromatography. The beads were incubated with the supernatant containing the recombinant protein overnight. The beads were then washed with PBS1× and the elution is performed with elution peptide at 150 ng/µl in PBS1×. The proteins are then dialyzed against PBS1×. The next batches were purified by affinity chromatography by coupling an anti-NKp46 antibody to the AminoLink Coupling Resin according to the manufacturer's instructions (GE Healthcare, #20381, batch QB213815). The beads were then incubated with the supernatant containing the recombinant protein overnight. The beads were then washed with PBS1× and the elution is performed using Glycine 0.1M pH2.5. The proteins are then dialyzed against TBS buffer pH7.5 and concentrated to perform a preparative size exclusion chromatography on a Superdex 200 Increase 10/300 GL column.

Recombinant human BCMA—Cloning, Production, and Purification

For the generation of recombinant human BCMA(TN-FRSF17) a synthetic, HEK293-codon optimized DNA fragment coding for the extracellular domain of human BCMA fused to diphtheria toxin fragment A (DTA) and a His6 purification tag was ordered from Atum (Newark, CA, USA). The synthetic DNA fragment was then cloned into a pTT5 mammalian expression vector using Gateway® Cloning technology (Life Technologies—ThermoFisher Scientific, Carlsbad, CA, USA) to generate a recombinant plasmid for heterologous expression in mammalian cells.

Expi293F cells (ThermoFisher) were transfected with the plasmid DNA using the commercially available protocol. Cells were harvested after 6 days of growth and conditioned media (CM) was collected by centrifugation. Protein was purified using Ni-NTA agarose (Qiagen). Resin was equilibrated in PBS pH 7.2 three times by spinning for 5 min at 1000×g and decanting/adding fresh PBS each time. Equilibrated resin was added to a roller bottle with the CM and rotated for 1 hour at room temperature. 1 ml of resin was used for every 200 ml of conditioned media. After incubation, the CM/resin slurry was poured into a gravity drop column and washed with 10CV of PBS pH 7.2. Protein was eluted with 10CV of 600 mM imidazole in PBS. Eluate was buffer exchanged into PBS pH 7.2 and concentrated using an Amicon Ultra-15 centrifugal filter (Millipore). Preparative SEC was preformed using a Superdex 200 (16/60) column (Cytiva Life Sciences) run in PBS. The final sample was pooled and concentrated in PBS to a final concentration of >5 mg/ml.

CODV-OL1 Molecules—Production and Purification

The expression plasmids encoding the different chains of the corresponding constructs were propagated in *E. coli* DH5a. Plasmids used for transfection were prepared from *E. coli* with EndoFree Plasmid Mega kits (Qiagen).

HEK 293-FS cells growing in F17 serum free suspension culture (Invitrogen) were transfected with indicated plasmids using Polyethyleneimine transfection reagent. After 6 days of cultivation at 37° C. with 8% $CO_2$ cells were removed by centrifugation and the supernatant was passed over a 0.22 μm filter to remove particles.

The proteins were captured on MabSelect SuRe (Cytiva) and eluted with 0.1 M Citrate buffer pH 3.0 and neutralized with 1M Tris pH9. After polishing the proteins by size exclusion chromatography (SEC) using a Superdex200 26/60 (Cytiva) and 0.22 μm filtration and UV280 concentration determination the proteins were used for further characterization.

Recombinant Control Samples

The human and cynomolgus recombinant proteins listed below were produced and purified at Innate Pharma as previously described (LG Cell 2019): human NKp46 (Gln22-Asn255, NCBI Reference: NM_004829.5), human neonatal Fc receptor (FcRn, NCBI Reference: P55899), human CD16a (human FcγRIIIA V and F isoforms, NCBI reference: AAH36723), human CD32a (human FcγRIIA, NCBI reference: AAH20823), human CD32b (human FcγRIIB, NCBI reference: NP_003992), human CD16b (human FcgRIIIB, NCBI reference: AA128563), human CD64 (human FcγRI, NCBI reference: P12314), cynomolgus NKp46 (Gln17-Asn254, NP_001271509.1), cynomolgus FcRn (NCBI reference: Q8SPV9), cynomolgus CD16 (NCBI reference: NP_001270121.1), cynomolgus CD32a (NCBI reference: NP_001270598.1), cynomolgus CD32b (NCBI reference: NP_001271060.1), and cynomolgus CD64 (NCBI reference: AAL92095.1). The recombinant human BCMA was purchased from ACRO Biosystems.

TABLE 1

Example Anti-NKp46-1 CDRs

| | Kabat | IMGT | Chothia | Honegger |
|---|---|---|---|---|
| CDRL1 | RASQDISNYLN (SEQ ID NO: 34) | QDISNY (SEQ ID NO: 96) | SQDISNY (SEQ ID NO: 97) | ASQDISNY (SEQ ID NO: 98) |
| CDRL2 | YTSRLHS (SEQ ID NO: 35) | YTS (SEQ ID NO: 99) | YTS (SEQ ID NO: 100) | YTSRLHSGVPSR (SEQ ID NO: 101) |
| CDRL3 | QQGNTRPWT (SEQ ID NO: 36) | QQGNTRPWTF (SEQ ID NO: 102) or QQGNTRPWT (SEQ ID NO: 111) | GNTRPW (SEQ ID NO: 103) | GNTRPW (SEQ ID NO: 104) |
| CDRH1 | DYVIN (SEQ ID NO: 80) | GYTFSDYV (SEQ ID NO: 87) | GYTFSDY (SEQ ID NO: 88) | ASGYTFSDYV (SEQ ID NO: 89) |
| CDRH2 | EIYPGSGTNYYNEKFKA (SEQ ID NO: 81) | IYPGSGTN (SEQ ID NO: 90) | PGSG (SEQ ID NO: 91) | IYPGSGTNYYNEKFKAK (SEQ ID NO: 92) |
| CDRH3 | RGRYGLYAMDY (SEQ ID NO: 21) | ARRGRYGLYAMDY SEQ ID NO: 93) | GRYGLYAMD (SEQ ID NO: | RGRYGLYAMD (SEQ ID NO: 95) |

Example 2: Determination of BCMA Receptor Density on a Panel of Myeloid Myeloma Cell Lines Introduction B-cell maturation antigen (BCMA) expression has been proposed as a marker for the identification of malignant plasma cells in patients with multiple myeloma (MM).

Nearly all MM tumor cells express BCMA, while normal tissue expression is restricted to plasma cells and a subset of mature B cells. Friedman et al. (2018) Hum Gene Ther. 29(5): 585-601. In order to determine the number of BCMA molecules per cell, a flow cytometry based BCMA receptor assay was used to quantify BCMA surface expression and subsequently select MM cell lines that would be suitable choices for downstream analysis of BCMA antibodies.

A list of the MM cell lines used in this study are shown in Table 2 below.

TABLE 2

Panel of MM cell lines

| MM Cell line Name | Cell Bank |
|---|---|
| H929 | ATCC |
| U266 | DSMZ |
| OPM2 | DSMZ |
| MM1R | ATCC |
| JJN3 | DSMZ |
| KMS12BM | DSMZ |
| L363 | DSMZ |
| RPMI 8226 | ATCC |
| LP1 | DSMZ |
| MOLP8 | Immunogen |
| MM1S | ATCC |
| KMS11 | JCRB |
| EJM | DSMZ |

Materials and Methods—Analytical Procedure for Determination of the Antigen Binding Capacity for BCMA Expression on MM Cell Lines Surface by Flow Cytometry.

Experimental Set-up

For BCMA density determination, the CELLQUANT Calibrator (Biocytex, ref:7208) was used. First, 200,000 MM cells (see list below for all tested cell lines) were seeded in 96-well round bottom plates (TPP, Trasadingen, ref 92097) in 100 mL Reagent 1 at 1× (diluted at $\frac{1}{10}^{th}$ in distilled water)+10 mL FcR Blocking Reagent, human (Miltenyi Biotec, Bergisch Gladbach, ref 130-059-901) for 15 min at 4° C.

Then, MM cells were spun down for 5 min at 300 g before removing supernatant. 50 mL of mouse anti-human BCMA antibody at 10 mg/mL were added before 30 min incubation at 4° C. (BD BioLegend, clone 19F2 ref 357502, stock concentration at 0.5 mg/mL, dilution at $\frac{1}{50}^{th}$ by mixing 5 mL anti-BCMA with 245 mL Reagent 1 at 1×).

For control isotype, 50 mL of purified mouse IgG2a kappa isotype control at 10 mg/mL were added instead before 30 min incubation at 4° C. (BD BioLegend, ref 400201, stock concentration at 0.5 mg/mL, dilution at $\frac{1}{50}^{th}$ by mixing 5 mL IgG2a with 245 mL Reagent 1 at 1×).

Two consecutive washing steps were performed by adding 200 mL of Reagent 1 at 1× in the wells followed by centrifugation at 2000 rpm for 1 min at 4° C. After removing supernatant, cells were resuspended in 50 mL anti-mouse IgG FITC secondary antibody (Reagent 3 in the Biocytex kit, ref 7208, for 15 mL use 1.5 mL Reagent 3+13.5 mL Reagent 1), previously diluted at $\frac{1}{10}^{th}$ in Reagent 1 at 1×. 50 mL containing calibration beads were added on wells dedicated to calibration (Reagent 2 in the Biocytex kit) and 5 mL of Reagent 3 were finally added to the calibration wells (non-diluted) to be in the same staining conditions as with cells. The 96-well plate was then incubated for 20 min at 4° C., protected from light.

Three consecutive washing steps were performed by adding 200 mL of Reagent 1 at 1× in the wells followed by centrifugation at 2000 rpm for 1 min at 4° C. After removing supernatant, cells were resuspended in 100 mL cold PBS before reading with MACSQuant Analyzer 10 or MACSQuant VYB (Miltenyi Biotec, Bergisch Gladbach).

Acquisition is done on a B1 channel for FITC staining and V1 channel for DAPI staining (cell viability marker).

Calculation of BCMA Density

To determine BCMA density on MM cell lines based on FITC fluorescence, calibration beads information was used to generate a linear calibration curve as shown in Table 3 below.

TABLE 3

Antigen Binding Capacity Bead Staining to create standard curve

| Beads | Number of sites | MFI FITC |
|---|---|---|
| A | 770 | 386.87 |
| B | 5 500 | 2996.01 |
| C | 33 000 | 18861.1 |
| D | 173 000 | 103844.3 |

| Beads | Log (FITC) | Log (Nb of sites) |
|---|---|---|
| A | 2.59 | 2.89 |
| B | 3.48 | 3.74 |
| C | 4.28 | 4.52 |
| D | 5.02 | 5.24 |

| Curve data (y = ax + b) | |
|---|---|
| Slope (a) | 0.9686 |
| Intercept (b) | 0.3772 |
| r² | 0.9998 |

For the analysis, the BCMA density per cell was calculated using the following formula:

$$\text{BCMA density} = 10^{(\log(FITC\ BCMA)*a+b)} - 10^{(\log(FITC\ isotype)*a+b)}$$

Results

Figures 2A, 2B:
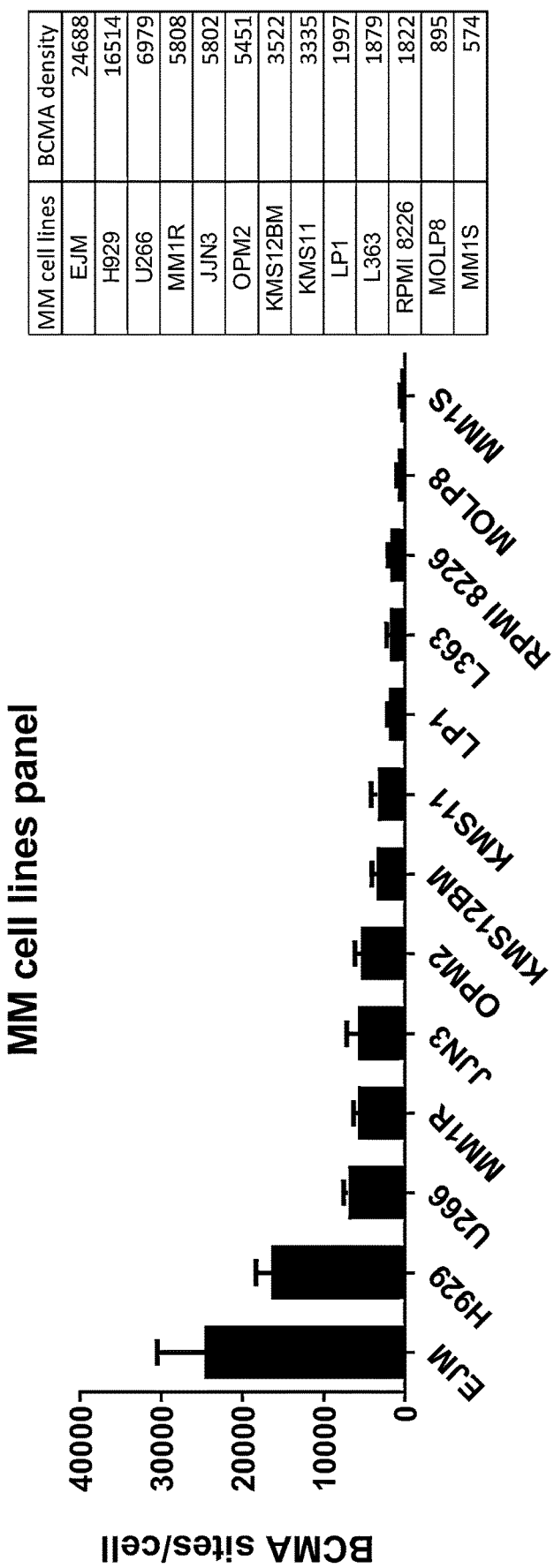
FIG. 2A is a bar graph representing the BCMA density on a panel of multiple myeloma cell lines based on cell-surface FITC fluorescence emission.
FIG. 2B is the corresponding table recording the BCMA density on each cell line ranked in descending order.

The calculation of BCMA density per cell on the panel of MM cell lines revealed that the EJM cell line had the highest level of BCMA density and the MM1S cell line had the lowest level of BCMA density at the cell surface relative to other MM cell lines used in the panel. FIG. 2 shows the ranking of the MM cell lines in descending order of BCMA density per cell. Based on these results, cell lines were selected for use in downstream studies that interrogate NKp46-BCMA_Fc binding affinities to BCMA and cell lytic activity on MM cells. In particular, RPMI 8226 has a BCMA density of about 2000 sites/cell, which is close to the average in multiple myeloma cells. MM1S has a BCMA density of about 800 sites/cell, which corresponds almost to the level of BCMA expression in healthy plasma cells. MM1R has a BCMA density of about 5500 sites/cell, useful for determining efficiency of the binding proteins of the disclosure at high expression levels.

Example 3: Binding Characterization of NKp46-BCMA Fc Format Variants

Introduction

The NKp46-BCMA_Fc-ADE-DSB NKCE was titrated on RPMI cells to determine $K_D$ value for binding to MM tumor cells as well as donor NK cells. Subsequently, distinct Fc format variants of NKp46-BCMA-NKCEs were tested by SPR in order to confirm affinity to FcRn as well as two variants of the CD16a receptor.

Materials and Methods

Cells

RPMI 8226 multiple myeloma cell lines were purchased at ATCC. Cells were cultured in complete RPMI medium (RPMI-1640 containing 10% FBS, 2 mM L-glutamine, 1 mM sodium pyruvate and 1× non-essential amino acids).

Titration Assay

Resting NK cells and RPMI 8226 cells ($1·10^5$ cells/well) were stained for 1 hour in a U-bottom 96-well plate with 1/10 serial dilution range of unconjugated molecules starting at 225 and 500 µg/mL respectively. Staining with secondary antibody was performed with goat anti-human IgG, Fcγ fragment specific PE (Jackson Immunoresearch 109-116-170). After staining, cells were resuspended in BD Cellfix and analyzed by flow cytometry. Parameters were recorded and analysed with FlowJo software. Staining EC50 values were calculated with GraphPad prism using 4 parameter logistics non-linear regression model.

SPR Binding Experiment—CD16a

For binding affinity measurements with CD16a, HBS-EP+ buffer (Cytiva, Uppsala, Catalog No. BR1006-69) was prepared by mixing 100 mL 10×HBS-EP+ buffer with 900 mL of purified water.

Affinity capture of the human CD16a proteins was achieved using the His capture kit (Cytiva, Uppsala, Catalog No. 28995056). The anti-His capture antibody was diluted in running buffer 1:20 and coupled to the CM5 chip (Cytiva, Uppsala, Catalog No. 29149603) using standard amine coupling to yield approximately 8000 response units (RU) using the amine coupling kit (Cytiva, Uppsala, Catalog No. BR-100-50).

Ten serial 1:1 dilutions of the bispecific antibody in HBS-EP+ assay buffer were prepared to concentrations of 5.8 nmol/L, 11.7 nmol/L, 23.4 nmol/L, 46.8 nmol/L, 93.75 nmol/L, 187.5 nmol/L, 375 nmol/L, 750 nmol/L, 1500 nmol/L and 3000 nmol/L. The CD16a (V/F) proteins were diluted with HBS-EP+ buffer to a concentration of 0.1 ng/mL and used at this concentration in the experiments. CD16a (V176) and CD16a (V176F) were captured at a flow rate of 10 µL/min for 30 sec on flow cells 2 and 4, respectively to yield maximal response (Rmax) values of approximately 30 RU.

Measurements were performed in multicycle kinetics experiments. In each multicycle experiment CD16a was captured via an anti-His antibody immobilized on a series S CM5 sensor chip (human antibody capture kit, Cytiva, Uppsala, Catalog No. BR1008-39). The bispecific antibody diluted into HBS-EP+ buffer, was injected in a 1:1 dilution series from 5.8 nmol/L to 3000 nmol/L for 120 sec at a flow rate of 30 µL/min followed by a dissociation phase of 120 sec. All analyte concentrations were run in duplicate together with multiple buffer blanks for double referencing. Regeneration of the capture surface was performed with two consecutive injects of regeneration solution (10 mmol/L Glycine pH 1.5) for 30 sec at 30 µL/min. Binding affinities (KD values) of the bispecific antibody to human CD16a were evaluated with the Biacore T200 Evaluation Software version 3.0 (Cytiva, Uppsala) using a steady state fit of the SPR response for the measured antibody concentrations.

SPR Binding Experiment—huNKp46 and BCMA

For binding affinity measurements with huNKp46 and BCMA, serial two-fold dilutions of human NKp46 (concentration range 50 nM to 0.1 nM), cyno NKp46 (concentration range 50 nM to 0.1 nM), human BCMA (concentration range 50 nM to 0.1 nM) and cyno BCMA (PPB-17990; concentration range 50 nM to 0.1 nM) were prepared in HBS-EP+ assay buffer.

Affinity capture of the mAb samples (FF-20-1319-1, FF-20-1320-1, FF-20-1634-1, FF-20-1635-1, EFF-20-106-1, EFF-20-107-1) was achieved using the Human antibody capture kit (Cytiva, Uppsala, Catalog No. BR1008-39) according to the manufacturer's instructions. The anti-Fc capture antibody was diluted in running buffer 1:20 and coupled to the CM5 chip (Cytiva, Uppsala, Catalog No. 29149603) using standard amine coupling to yield approximately 8000 response units (RU) using the amine coupling kit (Cytiva, Uppsala, Catalog No. BR-100-50).

The antibodies (were diluted with HBS-EP+ buffer to a concentration of 0.1 to 0.4 µg/mL and used at this concentration in the experiments. The antibodies were captured at a flow rate of 10 µL/min for 120 sec to yield maximal response (Rmax) values of approximately 30 RU.

Measurements were performed in multicycle kinetics experiments for each antibody using a Biacore 8K instrument. In each multicycle experiment the antibodies were captured via an anti-hum a Fc antibody immobilized on a series S CM5 sensor chip (human antibody capture kit, Cytiva, Uppsala, Catalog No. BR1008-39).

The antigens, diluted as described above (concentration range 0.1 nM to 50 nM), were injected at a flow rate of 60 µL/min for 240 sec followed by a dissociation phase of 400 sec. All analyte concentrations were run in duplicate together with multiple buffer blanks for double referencing. Regeneration of the capture surface was performed with regeneration solution (3 mol/L $MgCl_2$) for 60 sec at 30 µL/min. Binding kinetics data were evaluated with the Biacore 8K Evaluation Software version 1.1.1.7442 using a 1:1 binding model with mass transport limitation.

Results

The titration of NKp46-BCMA_Fc-ADE-DSB on RPMI cells and donor NK cells demonstrated that NKp46-BCMA in a Fc format which enhanced ADCC still retained affinity for NKp46 and BCMA targets as shown in FIG. 3A and FIG. 3B.

SPR binding analysis on a larger panel of 12 distinct Fc formats of NKp46-BCMA-NKCEs confirmed the affinity to CD16a and FcRn as shown in FIG. 4 and FIG. 5, respectively. Notably, all ADCC enhanced molecules demonstrated increased binding to CD16 (V176) and (F176) variants as shown in FIG. 4.

Binding kinetics to NKp46 (human and cynomolgus monkey), BCMA (human and cynomolgus monkey), and FcγR for the NKp46-BCMA_Fc-ADE-DSB NKCE were also calculated, and results are displayed in Tables 4, 5, and 6 below.

TABLE 4

Affinity of NKp46-BCMA_Fc-ADE-DSB and control
NKCE for human and cynomolgus FcγRs: KD values (nM)

| FcγR | Fitting model | NKp46-BCMA_Fc-ADE-DSB KD (nM) | | | NKp46-BCMA_Fc-ADE-DSB (nM) | | HUX1-IC-3H4 Mean KD (nM) |
|---|---|---|---|---|---|---|---|
| | | Exp No 1 | Exp No 2 | Exp No 3 | Mean KD | SD | S239D/I332E |
| HuFcγRI | 1:1 Binding | 0.32 | 0.27 | 0.38 | 0.32 | 0.06 | 0.06 |
| HuFcγRIIa | Steady State Affinity | 415 | 656 | 963 | 678 | 275 | 833 |
| HuFcγRIIb | Steady State Affinity | 1348 | 1062 | 1415 | 1275 | 187 | 916 |
| HuFcγRIIIaF | Two State Reaction | 18.0 | 20.4 | 29.7 | 22.7 | 6.2 | 93.3 |
| HuFcγRIIIaV | Two State Reaction | 11.7 | 12.1 | 16.5 | 13.4 | 2.7 | 18.3 |
| HuFcγRIIIb | Steady State Affinity | 1259 | 1692 | 2327 | 1759 | 537 | 1639 |
| CyFcγRI | 1:1 Binding | 30.0 | 24.9 | 29.0 | 28.0 | 2.7 | 25.7 |
| CyFcγRIIa | Steady State Affinity | 1346 | 1440 | 1699 | 1495 | 183 | 1489 |
| CyFcγRIIb | Steady State Affinity | 884 | 1066 | 1295 | 1082 | 206 | 748 |
| CyFcγRIII | Two State Reaction | 10.0 | 9.3 | 15.7 | 11.7 | 3.5 | 15.7 |

TABLE 5

Affinity of NKp46-BCMA_Fc-ADE-DSB for human
and cynomolgus NKp46: ka, kd, and KD values (nM)

| | Experiment No 1 | | | Experiment No 2 | | | Experiment No 3 | | | Mean | |
|---|---|---|---|---|---|---|---|---|---|---|---|
| | $K_D$ (nM) | ka ($M^{-1}s^{-1}$) | kd ($s^{-1}$) | KD (nM) | ka ($M^{-1}s^{-1}$) | kd (s-1) | $K_D$ (nM) | ka ($M^{-1}s^{-1}$) | kd ($s^{-1}$) | $K_D$ (nM) | SD |
| Human | 11.8 | $1.6^E+05$ | $1.9^E-03$ | 13.2 | $1.4^E+05$ | $1.8^E-03$ | 12.5 | $1.4^E+05$ | $1.8^E-03$ | 12.5 | 0.7 |
| Cyno | 16.6 | $2.1^E+05$ | $3.0^E-03$ | 16.2 | $2.1^E+05$ | $3.4^E-03$ | 17.8 | $1.9^E+05$ | $3.3^E-03$ | 16.9 | 0.8 |

TABLE 6

Affinity of NKp46-BCMA_Fc-ADE-DSB for human
and cynomolgus BCMA: ka, kd, and KD values (nM)

| | Experiment No 1 | | | Experiment No 2 | | | Experiment No 3 | | | Mean | |
|---|---|---|---|---|---|---|---|---|---|---|---|
| | $K_D$ (nM) | ka ($M^{-1}s^{-1}$) | kd ($s^{-1}$) | KD (nM) | ka ($M^{-1}s^{-1}$) | kd ($s^{-1}$) | $K_D$ (nM) | ka ($M^{-1}s^{-1}$) | kd ($s^{-1}$) | $K_D$ (nM) | SD |
| Human | 0.2 | $2.8^E+05$ | $6.1^E-05$ | 0.2 | $3.2^E+05$ | $6.9^E-05$ | 0.3 | $1.9^E+05$ | $5.7^E-05$ | 0.2 | 0.1 |
| Cyno | 0.4 | $1.7^E+05$ | $7.2^E-05$ | 0.3 | $1.8^E+05$ | $5.8^E-05$ | 0.3 | $1.8^E+05$ | $6.0^E-05$ | 0.3 | 0.1 |

Example 4: Fc-Engineered NKp46-BCMA NKCEs Demonstrate Enhanced In Vitro Cell Cytotoxic Activity Introduction The NKp46-BCMA NKCEs engineered in different Fc formats, with either enhanced ADCC (Fc-DE, Fc-DE-DSB, Fc-ADE, and Fc-ADE-DSB) or non-enhanced ADCC (NKp46-BCMA_Fc) were evaluated for their ability to promote lysis of MM tumor cells in the presence of NK donor cells as well as for evaluation of potential off-target NK cell toxicity. Further, NKp46-BCMA NKCEs were compared to anti-BCMA antibody controls to assess their MM tumor-killing potential.

Materials and Methods

Cells

Human NK cells. Healthy human buffy coats were provided by the Etablissement Français du Sang (EFS, the French blood service, Marseille; AC-2019-3428). Peripheral mononuclear cells (PBMC) were isolated from buffy coats by Ficoll density gradient centrifugation. Human NK cells were purified from PBMC with a bead-based negative selection kit from STEMCELL Technologies or Miltenyi Biotec.

MM cell lines. RPMI 8226 and MM1.S multiple myeloma cell lines were purchased at ATCC. Cells were cultured in complete RPMI medium (RPMI-1640 containing 10% FBS, 2 mM L-glutamine, 1 mM sodium pyruvate and 1× non-essential amino acids).

NK Cell-Based Cytotoxicity Assay

For cytotoxic assays performed on MM cell lines, target cells were alternatively loaded with Cr-51. 1/10 serial dilution ranges were performed for test and control items, starting from 5, 10 or 15 µg/mL depending on experiment. The molecules tested, the labeled target cells (~3,000 cells) and the human NK cells (~30,000 cells) from healthy donors (fresh or allowed to rest overnight) were successively added to each well of round-bottomed 96-well plates to obtain a 10:1 (E:T) ratio. After 4 h of co-incubation, the supernatant was transferred to a Lumaplate (for Cr-51). In the Cr-51-based cytotoxicity assay, the Cr-51 released from dead target cells was determined with a TopCount NXT™ (Microplate Scintillation and Luminescence Counter; Perkin Elmer). Radioactivity was measured by counting γ-emission for 60 s for each well. The results are expressed in cpm=counts per minute. The percent specific lysis was calculated with the following formula:

Specific lysis (%)=(ER (cpm)–SR (cpm))/(MR (cpm)–SR (cpm))×100 where ER=experimental release, SR=spontaneous release and MR=maximal release.

The $EC_{50}$ was determined for each molecule by drawing an appropriate non-linear regression curve (choice of "log (agonist) vs. response—variable slope (four parameters)" model) with Graphpad Prism Software.

Results

Figure 6:
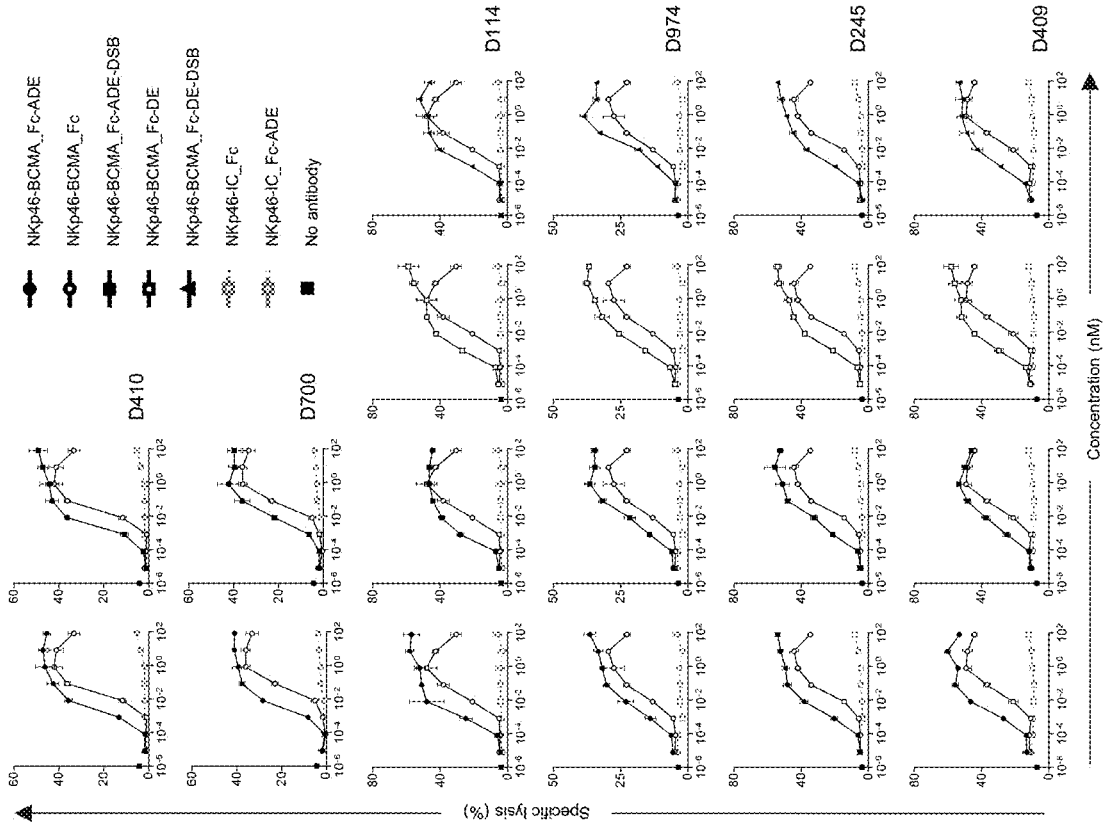
FIG. 6 is an in vitro cell cytotoxicity assay comparing the cytotoxicities of NKp46-BCMA-NKCEs, with enhanced ADCC (Fc-DE, Fc-DE-DSB, Fc-ADE, and Fc-ADE-DSB)

The NKp46-BCMA NKCEs engineered in the Fc formats which enhanced ADCC (Fc-DE, Fc-DE-DSB, Fc-ADE, and Fc-ADE-DSB) promoted NK cell mediated MM tumor-cell cytotoxic activity more effectively than the non-enhanced ADCC format, NKp46-BCMA_Fc as shown in FIG. 6. The cytotoxic activity was not impaired by the introduction of the DSBs, which stabilize the molecule. Both NKp46-IC_Fc-ADE and NKp46-BCMA_Fc mediated MM tumor-cell death in the presence of NK cell effectors to a similar level or with superior cytotoxic activity to an anti-BCMA antibody in IgG1 format (BCMA_IgG1) or an anti-BCMA antibody in an afucosylated IgG1 format (Reference-1) as shown in FIG. 7 and FIG. 8.

Although both NKp46-IC_Fc-ADE and NKp46-BCMA_Fc had superior cytotoxic activity on MM tumor cells in the presence of NK cells, no fratricidal NK cell killing was observed indicating that NKp46-BCMA NKCEs do not induce potential toxic off-target effects (FIG. 9).

The presence of soluble BCMA in the serum of MM patients has been described. Hipp et al. (2017) Leukemia 31: 1743-1751. Soluble BCMA titrated at escalating concentrations in cytotoxic assays with MM cells and NK cell co-cultures demonstrate that soluble BCMA slightly influenced the potency of the NKp46-BCMA NKCE but not the maximal level of MM cell lysis as shown in FIG. 10.

Example 5: In Vitro Cytotoxicity Assay Using Calcein Release as an Indicator

Materials and Methods

Whole blood samples: Fresh human peripheral blood mononuclear cells (PBMC) were isolated from healthy donors' whole blood samples supplied by EFS IIe de France following the "terms & conditions" described in the agreement No 12/EFS/131 established between EFS IIe de France and Sanofi-Aventis Recherche et Développement.

Human PBMC isolation from whole blood: Human PBMC were isolated from whole blood of healthy donors (HD) through a density gradient centrifugation.

The whole blood was recovered from the blood bag and diluted with 40 mL of sterile Phosphate Buffer Solution (PBS). Fifteen mL of Ficoll-Paque Plus Cytiva (Sigma Aldrich, ref #17-1440-02) was dispensed into the center of four sepMate-50 tubes (Stemcell ref #85450). Then, 80 mL of the diluted blood were gently added on the edge of each sepMate-50 tube containing Ficoll solution (20 ml per tube). The tubes were centrifuged at 1 200 g for 20 minutes at room temperature (RT) without brake. The four buffy coat layers were recovered and collected in two 50 mL tubes. The leucocytes solution was completed with sterile PBS up to 50 mL final volume. The two tubes were centrifuged twice (in between each centrifugation, the supernatant was discarded, and 50 mL of PBS added) at 400 g for 10 minutes at RT with brake. After the last centrifugation, the pellets were mixed, and the volume completed to 10 mL by RPM11640 medium supplemented with 10% Fetal Bovin Serum (FBS) and 2 mM L-Glutamine (complete culture medium). The total viable PBMC number was defined by Vicell XR counting (Beckman Coulter cell counter instrument).

NK Cell collection: Human NK cells were purified from PBMCs using MACSxpress® Whole Blood NK Cell Isolation Kit (Miltenyi) according to supplier recommendations. NK cells were then cultured in complete medium at 5×106 cells/mL at +37° C. at 5% CO2 (so called "resting" NK cells) overnight before to be used in the activation assay. $1\times10^6$ cells were kept aside to assess their NKp46 and CD16 expression by flow-cytometry.

Cell line: RPM18226 (ATCC CCL-155), MM.1R (ATCC CRL-2975) and MM.1S (ATCC CRL-2974) cells are a Multiple myeloma cell line (plasmacytoma). They growth mostly in suspension, while some cells may grow adherent (occasionally up to 50%). For maintenance, cells were resuspended in fresh complete medium at $0.3\times10^6$ cells/mL for 3 or 4 days.

Stock solutions: Stock solution of each antibody was stored in PBS at 4° C. On the day of the assay, the products were vortexed to eliminate potential aggregates before cascade dilution. A dilution range from 200 nM (twice concentrated) to 0.02 pM (1/10 serial dilution) was performed in complete culture medium.

Of these serial dilutions 100 μL were added to each well that will contain cells suspension (50 μl of BCMA+ RPM18226 target cells and 50 μl of NK) to obtain a final concentration of 100, 10, 1, 0.1, 0.01, 0.001, 0.0001, 0.00001 nM.

For the conditions of combination antibodies (not binding NKp46 or CD16) the first concentration was 4 times concentrated and 50 μl of NKp46-BCMA-Fc ADE-DSB to reach the same concentration of the other antibodies tested.

Cytotoxic Assay: BCMA+RPM18226 (or MM.1R, or MM.1S) target cells were counted the day of the assay and the amount of cell needed for the experiment was evaluated (5000 cells/well). Target cells at the concentration of $1\times10^6$/ml were resuspended in 4 ml of complete medium containing 10 μl calcein-AM (50 μg) previously reconstituted in 25 μl of DMSO. Labeled cells were incubated at 37° C. in the presence of 5% C02 (carbon dioxide) for 30 minutes.

Antibody serial dilutions were prepared and added to a U-bottom 96-well plate (100 μl/well) (Corning® Costar® Ultra-Low Attachment Multiple 96-Well Plate; Thermo Scientific).

Target cells were washed 3 times with 5 ml of complete medium (every washed was followed by a centrifugation of 300 g for 5 minutes and supernatant discard). Final wash was performed in complete medium containing Probenecid (4× concentrated) (ThermoFisher Scientific. Target cells were counted and seeded at 5000 cells/50 μl per well. Finally, NK cells at E/T ratio of 10:1 were added to the suspensions of target cells and antibodies. As controls, target cells alone and target cells with NK, but without antibodies, were added. Moreover, to reach maximal target cell death, 2% of Triton X was considered. Each condition was performed in duplicate. Culture plates were incubated at 37° C. in the presence of 5% C02 for 4 hours at the end of which 100 μl of supernatant was collected, transferred to a black 96-well microplates flat-bottom med binding, to assess the calcein release from dead target cells at TECAN 1000Pro machine.

Data analysis: To convert the concentration of antibodies from mg/ml to M the following formula was used:

Concentration (mg/ml)/Molecular Weight (Da)=Molar Concentration (M)

For the killing analysis, the percent specific lysis was calculated using the following formula:

% Cytotoxicity=[(ER−SR)*100/(MR−SR)]

ER=experimental release (target cell+NK+[Antibody])
SR=spontaneous release (target cell alone)
MR=maximal release (target cells+2% Triton X)

Statistical analysis: The analyses were performed with GraphPad prism 9.1.2. Top of lysis values corresponded to the observed maximum lysis (mean of duplicate values). Half maximal effective concentration ($EC_{50}$) values were expressed in pM and calculated using 4 parameter logistics non-linear regression model, according to Ratkowsky and Reedy.

Results

NK cell activation was determined by measuring % specific lysis of RPMI 8226 cells by NK cells and one of the following: NKp46-BCMA_Fc-ADE-DSB, which engages both NKp46 and CD16a; an NKp46-BCMA-Fc incompetent-DSB (a molecule that binds NKp46 only); X-BCMA-ADE-DSB (a molecule that binds CD16a only); a combination of the NKp46-only binder and CD16a-only binder or isotype control antibodies (X-BCMA-Fc incompetent-DSB that only binds to BCMA on tumor cells and not on NK cells, and the NKp46-X-ADE-DSB which binds to NKp46 and CD16a on NK cells but not on tumor cells). Optimal NK cell activation occurred with NKp46-BCMA_Fc-ADE-DSB as compared to the other four antibodies and the combination of single targeting agents, indicating that: (1) dual targeting of NKp46 and CD16a results in a higher potency and efficacy in tumor cell killing than single engagement and (2) the importance of having the NKp46 arm and CD16a arm on the same molecule for optimized potency (FIG. 11).

Additionally, it was found that the high potency of NKp46-BCMA_Fc-ADE-DSB allowed for strong efficiency in tumor cell killing even in MM cell models that express low levels of BCMA (e.g., MM1S cells) (FIG. 12).

NKp46-BCMA_Fc-ADE-DSB was also compared to an anti-BCMA monoclonal antibody that had enhanced ADCC features (e.g., afucosylated anti-BCMA antibody). NKp46-BCMA_Fc-ADE-DSB demonstrated comparable maximum lysis and better potency when compared to the afucosylated anti-BCMA antibody in both RPMI 8226 cells and MM1S cells (FIG. 13).

Example 6: Fc-Engineered NKp46-BCMA NKCEs Demonstrate Strong and Specific In Vivo Anti-Tumor Activity Introduction To assess the in vivo efficacy of NKp46-BCMA NKCE against tumor cells a xenograft mouse model not expressing CD16 was established. FIG. 14A is a schematic of the experimental set for determining in vivo NKp46-BCMA_Fc anti-tumor activity in the xenograft mouse model. Briefly, a 1:1 mixture of green (eGFP) and red (dsRed) fluorescent mouse lymphoma RMA cells respectively non-expressing and expressing human BCMA were intravenously (i.v.) injected into Rag1 deficient mice transgenic for human NKp46 (Tg huNKp46 Rag1−/−). Tumor-bearing mice (n=7 for each group) were treated once with a total dose of 12.2 picomoles of NKp46-BCMA_Fc or vehicle as control. The livers of mice were biopsied 48 h after treatment and the absolute count of infiltrated RMA cells was monitored by flow cytometry. The livers of mice were biopsied 48 hours after treatment and the absolute count of infiltrated RMA cells was monitored by flow cytometry as described below and shown in corresponding FIG. 14B-FIG. 14E.

Materials and Methods

Antitumor Activity In Vivo in Short Term Model

The activity of the BCMA-NKCE molecule was evaluated in a disseminated tumor model using mouse RMA leukemia cells, transduced RMA-dsRed-huBCMA Cl.E6 (BCMA-positive) or not RMA-eGFP Cl.5A6 (BCMA-negative) for the expression of human BCMA and mixed at 1:1 ratio for injection in the tails vein on day 0 of immunodeficient mice expressing human NKp46 on NK cells (HuNKp46 Tg Rag1−/−) (N=14). Mice were divided in two groups, treated at day 0 with the vehicle (N=7) or with NKp46-BCMA_Fc molecule (N=7) at a flat dose of 12.3 picomoles per mice.

Mice were sacrificed on day 2 (48 h after treatment) and disseminated RMA cells extracted from liver by crushing with OctoMacs® and Percoll gradient isolation. RMA cells infiltrating the liver were analyzed and counted by flow cytometry.

Quantification and Statistical Analysis

Sequential statistical analysis of obtained data was performed using GraphPad Prism V7. A logarithmic transformation was applied on obtained ratio data to perform statistical analysis. A normality test (d'Agostino-Pearson) was performed to confirm the use of non-parametric test (Kruskal-Wallis followed by a comparison post-test). Each treated groups were systematically compared with the control vehicle group. If the data were not normally distributed, the statistical significance of differences between paired sample populations was determined with the Wilcoxon matched-pair signed rank test. N is the number of samples used in the experiments. The means or medians are shown, with or without error bars indicating the SD. Significance is indicated as follows: *p≤0.05; p≤0.01; *p≤0.001, ****p≤0.0001. Four-parameter non-linear regression analysis was used to calculate the NKp46-BCMA_Fc NKCE $EC_{50}$.

Results

Before engraftment, there was relatively 1.5 times more dsRed-huBCMA RMA cells than eGFP-huBCMA-negative cells as analyzed by flow cytometry and only RMA dsRed cells expressed BCMA (FIG. 14B-14C). The expression of human BCMA on dsRed RMA cells before engraftment (in vitro) and after engraftment in liver biopsies (ex vivo) as analyzed by flow cytometry could also be detected (FIG. 14D). After 48 hours of treatment with NKp46-BCMA-FC or vehicle control the absolute count of liver infiltrated RMA cells (left) and dsRed/eGFP cell ratio (right) analyzed by flow cytometry demonstrated that NKp46-BCMA_Fc tumor killing was specific for tumor cells expressing BCMA (FIG. 14E).

Example 7: NKp46-BCMA Fc-ADE-DSB Promotes Autologous NK-Cell Activation and Multiple Myeloma (MM) Cell Killing Ex-Vivo Introduction Bone marrow and peripheral blood samples containing multiple myeloma cells and autologous immune effector cells were obtained from untreated or standard of care treated diagnosed patients with either de novo or relapsed multiple myeloma to assess the cumulative impact of a NKp46-BCMA_Fc-ADE-DSB NKCE ex vivo.

Material and Methods

Cells and Staining

Bone marrow and peripheral blood samples were obtained from MYRACLE cohort (Benaniba et al., BMC Cancer, 2019). Peripheral blood mononuclear cells (PBMC) and bone marrow mononuclear cells (BMMC) were isolated by gradient density centrifugation using Ficoll-Hypaque. The sample from the patient who underwent standard treatment of care had been previously treated with Daratumumab, Carfilzomib, Dexamethasone, and Revlimid.

Cells ($4 \times 10^5$ cells/well) were incubated in RPMI containing 5% FCS and 3 ng/ml IL-6, in the presence of CTL-NKCE2, NKCE2 (10 ug/ml), Reference-4 (20 ug/ml) or Obinutuzumab (10 ug/ml) for 24 hours. At the end of the incubation, cells were transferred into V bottom plates and plates was centrifuged for 1 min at 3000 rpm and washed once in PBS. Panel of antibodies in BD pharmingen Stain Buffer BSA/Brilliant Stain buffer were added in each condition as described in the table below.

Cells were resuspended in FACs buffer and analyzed by flow cytometry using a FACS Symphony. NK cell activation as described further below was assessed by CD107a and CD69 expression on CD3–/CD56+NK cells and myeloma cell death was assessed by disappearance of CD138+/CD38+ cells.

TABLE 7

Antibodies used for NK activation and myeloma cell death

| Reagent | Supplier | Reference | Comments |
|---|---|---|---|
| Anti-human CD56-BUV737 | BD Biosciences | 612767 | Clone NCAM16.2, 1/200 dilution |
| Anti-human CD107a(LAMP-1)-APC | Biolegend | 328620 | Clone H4A3, 1/100 dilution |
| Anti-human CD69-BV650 | Biolegend | 310934 | Clone FN50, 1/100 dilution |
| Anti-human CD3-PB | BD Biosciences | 625565 | Clone SP34-2, 1/100 dilution |
| Anti-human CD138-PerCP-eF710 | ThermoFisher | 46-1388-41 | Clone MI15, 1/50 dilution |
| Anti-human CD38-FITC | Cytognos/Med Tech | CYT-38F2 | polyclonal, 1/100 dilution |

NK Cell Activation Assay

Molecules were added in U bottom 96-well plates. Then 50,000 resting NK cells and 50,000 RPMI 8226 cells were successively added in each well to obtain a 1:1 effector to target (E:T) ratio. Control conditions were performed by adding only 50,000 resting NK cells by well. BD GolgiSTOP™ solution (BD Biosciences, 554724) was added at a final dilution of 1/6000e in each well (control and experimental). A positive control of NK cell activation was performed by using 125 ng/mL final of Phorbol 12-myristate 13-acetate (PMA, SIGMA, P8139) and 1 µg/mL final of Ionomycin (IONO, SIGMA, 10634) added on 50,000 resting NK cells by well. Each condition was performed in duplicate. After 4 h of co-incubation at 37±1C and 5±1% C02, an extracellular staining was performed for CD3, CD56, CD69, CD107a, and CD107b markers. After fixation and permeabilization of the cells, an intracellular staining was performed for measurement of intracellular IFNg, TNFα and MIP1β production. Mixes of antibodies were centrifuged at 16 000 g for 10 min at +4° C. to eliminate potential aggregates. Cells were resuspended in Staining Buffer (PBS, 0.2% BSA, 2 mM EDTA, 0.02% azide) after last staining and analyzed by flow cytometry (FC).

Flow cytometric data were analyzed with FlowJo software. Analysis of percent NK cell activation were done with GraphPad prism. Top of activation values corresponded to the observed maximum activation. Half maximal effective concentration (EC50) values were calculated using 4 parameter logistics non-linear regression model corresponding to the following equation:

$$NK \text{ cell activation } (\%) = \text{calculated bottom} + \frac{\text{calculated top} - \text{calculated bottom}}{1 + 10^{(log(EC50)-log(concentration))^{slope}}}$$

Calculated bottom of activation, calculated top of activation, slope and 95% confidence interval (CI) values were calculated using the same model as EC50

Results

Flow cytometric analysis of MM patient PBMCs which were treated with NKp46-BCMA_Fc-ADE-DSB NKCE showed a decrease in frequency of myeloma cells marked by the disappearance of CD138+/CD38+ cells (FIG. 15A left panel) and an increase in activated NK cells as assessed by CD107a and CD69 expression on CD3-/CD56+NK cells (FIG. 15A central and right panel) relative to anti-BCMA IgG1 DE antibody or no antibody controls. These difference in expression levels of markers were quantified in the corresponding bar graphs as shown in FIG. 15B. FIG. 16 depicts the ex vivo characterization of NKp46-BCMA_Fc-ADE-NKCE tumor killing activity in an autologous setting with bone marrow aspirates from MM patients either at diagnosis or that have failed diverse therapies (TC; therapeutic class) including standard of care (SoC) treatments (Daratumumab, Isatuximab, proteasome inhibitors, IMIDs, dexamethasone, alkylating agent, BH3 mimetic, histone deacetylase inhibitor), anti-CD47, CD3-CD38 or CD3-BCMA T cell engagers. samples demonstrating 510% lysis were associated with very low E:T ratio.

NKp46-BCMA_Fc-ADE-DSB NKCE shows a similar ex-vivo anti-myeloma activity (autologous setting) in samples of patients at diagnosis or at relapse. No decrease of the anti-myeloma activity is observed at relapse.

These data demonstrate that NKp46-BCMA_Fc-ADE-DSB NKCE activate ex vivo NK cells in primary samples from MM patients in an autologous assay, e.g., with multiple myeloma cells and NK cells from the same patient.

Example 8: Fc Engineered NKp46-BCMA NKCEs Demonstrate Strong and Specific In Vivo Anti-Tumor Activity and with Favorable Elimination Half-Life Introduction This example evaluates pharmacokinetic (PK) profile and parameters of NKp46-BCMA_Fc-ADE-DSB NKCE after a single intravenous (2.5 mg/kg) administration to female huFcRn Tg32 transgenic mice.

Material and Methods

PK Studies in hFcRn Transgenic Mice

The mice experiments were performed in transgenic Tg32 (B6.Cg-Fcgrttm,1 Dcr Tg(FCGRT)32Dcr/DcrJ) mice derived from C57BL/6 mice and purchased from The Jackson Laboratory (Bar Harbor, Maine). FcRn−/− hFcRn (line 32) Tg mice carry a null mutation for the mouse gene and a transgene expressing the hFcRn α-chain transgene under the control of its natural human promoter. Three Tg32 homozygous naïve adult female mice (mean body weight of 21.4 g) were used at study start.

For dosing regimen, NKp46-BCMA_Fc-ADE-DSB NKCE (stock solution: 1.5 mg/ml) was prepared in 10 mM His, 150 mM NaCl, pH6 buffer diluted in the same buffer extemporaneously and administered as single intravenous doses of 2.5 mg/kg into the tail vein with a dose volume of 10 mL/kg. Animals were evaluated utilizing a serial sampling approach 0.083, 4, 24, 72, 168, 336, 504 and 672 hours after the dosing across the study duration of 28 days. At each time point, blood samples (~20 µL—serial sampling) were withdrawn from saphenous vein into K3-EDTA collecting devices. Immediately after collection, blood samples were placed on wet ice and then centrifuged. 4 µL of plasma was then diluted into 60 µl DPBS (phosphate buffer saline).

The analytical method was the following:

The concentration at each time point, was determined by a bottom-up LC-MS/MS assay using the following generic method: After precipitation of a plasma aliquot, the plasma pellet was subjected to protein denaturation, reduction, alkylation, trypsin digestion, and solid-phase extraction prior to analysis of surrogate peptide. The surrogate peptide VYACEVTHQGLSSPVTK (SEQ ID NO: 86), belonging to Fab regions (light chain), was selected for each antibody for quantification, depending on its selectivity and response factor. Calibration standards were prepared by spiking the antibody into the plasma at 1, 2.8, 7, 14, 40, 80 and 100 µg/mL. Peptide separation was performed on a Shimadzu UHPLC system with a reverse phase Xbridge BEH C18 column (2.1×150 mm, 3.5 µM, 300 Å, Waters) at a flow rate of 600 µL/min in a stepwise gradient of 0.1% formic acid in water and 0.1% formic acid in acetonitrile. For detection, a Sciex API6600 TripleTOF mass spectrometer was used in positive product ion mode, with the source temperature at 500° C., the ionspray voltage at 5500 V, curtain gas at 35 and nebulizer gases at 50. Dwell time was 15 ms for each experiment. Declustering Potential was 90 V and Collision Energy was 26 V. The 807.4098 m/z fragment of the 626.0 m/z parent ion of the unique surrogate peptide of the antibodies was used for concentration determination relative to the standards and controls, using the peak area from the MQ4 integration algorithm of the MultiQuant software.

Assay Method

NKp46-BCMA_Fc-ADE-DSB NKCE concentrations were determined in plasma using an exploratory LBA method. NKp46-BCMA_Fc-ADE-DSB NKCE was captured by biotin-BCMA antigen bound on the streptavidin-beads of Gyrolab microstructured discs and detected using goat anti-human IgGFcg Alexa-tag tracer. The Lower Limit of Quantification (LLOQ) value was of 1.00 µg/mL.

Statistical Analysis

Individual plasma concentration values of NKp46-BCMA_Fc-ADE-DSB NKCE (expressed in µg/mL) were summarized by descriptive statistics (mean, standard deviation (SD) and coefficient of variation (CV %)) and tabulated by sampling time. All results were reported with three significant figures, except CV % with no decimal place.

Individual PK parameters were summarized by descriptive statistics as described above. Individual and mean values were expressed with three significant figures (except tmax and tlast rounded appropriately to the time value, with only the median and the range [min-max] values reported).

Results

No clinical signs or symptoms were observed during study.

Mean and individual values (N=3) of NKp46-BCMA_Fc-ADE-DSB NKCE plasma concentrations (ug/ml) obtained after a single IV (2.5 mg/kg) administration of NKp46-BCMA_Fc-ADE-DSB NKCE to female huFcRn tg32 mice are reported below in Table 8 and corresponding mean and individual plasma concentrations versus time profiles are shown in FIG. 18 and FIG. 19, respectively.

TABLE 8

NKp46-BCMA_Fc-ADE-DSB NKCE concentrations in plasma following administration NKp46-BCMA_Fc-ADE-DSB NKCE to huFcRn tg32 mice

| Route | Dose (mg/kg) | Animal Id. | Time (day) | | | | | | | |
|---|---|---|---|---|---|---|---|---|---|---|
| | | | 0.0035 | 0.17 | 1 | 3 | 7 | 14 | 21 | 28 |
| | | | Concentrations (ug/mL) | | | | | | | |
| i.v. | 2.5 | 1 | 61.0 | 36.2 | 17.9 | 15.6 | 13.8 | 9.71 | 7.37 | 4.54 |
| | | 2 | 56.9 | 26.4 | 14.3 | 15.1 | 13.9 | 8.21 | 5.56 | 4.55 |
| | | 3 | 56.9 | 35.2 | 20.7 | 22.3 | 13.3 | 8.71 | 7.98 | 4.60 |
| | | Mean | 58.3 | 32.6 | 17.6 | 17.7 | 13.7 | 8.88 | 6.97 | 4.56 |
| | | SD | 2.37 | 5.39 | 3.21 | 4.02 | 0.321 | 0.764 | 1.26 | 0.0321 |
| | | CV % | 4 | 17 | 18 | 23 | 2 | 9 | 18 | 1 |

Mean and individual values (N=3) pharmacokinetic parameters of NKp46-BCMA_Fc-ADE-DSB NKCE in plasma after a single intravenous (2.5 mg/kg) administration of NKp46-BCMA_Fc-ADE-DSB NKCE are presented below in Table 9.

TABLE 9

PK parameters of NKp46-BCMA_Fc-ADE-DSB NKCE in plasma following administration
of NKp46-BCMA_Fc-ADE-DSB NKCE to huFcRn tg32 mice

| Animal ID. | $C_0$ (ug/mL) | $AUC_{last}$ (day*ug/mL) | $t_{last}$ (day) | AUCall (day*ug/mL) | AUC (day*ug/mL) | $AUC_{Extrap}$ (%) | CL (mL/day/kg) | $V_{ss}$ (mL/kg) | $t_{1/2z}$ (day) | $\lambda_z$ lower (day) | $\lambda_z$ upper (day) |
|---|---|---|---|---|---|---|---|---|---|---|---|
| 1 | 61.7 | 307 | 28 | 307 | 395 | 22.3 | 6.33 | 118 | 13.4 | 7 | 28 |
| 2 | 57.8 | 272 | 28 | 272 | 357 | 23.8 | 6.99 | 132 | 13.0 | 7 | 28 |
| 3 | 57.5 | 325 | 28 | 325 | 423 | 23.3 | 5.91 | 113 | 14.8 | 7 | 28 |
| Mean | 59.0 | 301 | 28 | 301 | 392 | NA | 6.41 | 121 | 13.7 | NA | NA |
| SD | 2.33 | 26.6 | [28-28] | 26.6 | 32.9 | NA | 0.546 | 9.82 | 0.964 | NA | NA |
| CV % | 4 | 9 | — | 9 | 8 | NA | 9 | 8 | 7 | NA | NA |

After 2.5 mg/kg intravenous administration, NKp46-BCMA_Fc-ADE-DSB NKCE concentrations were quantifiable in plasma up to 28 days (last sampling time), Plasma clearance was estimated to 6.4±0.546 mL/day/kg and volume of distribution at steady state was 121±9.82 mL/kg leading to a terminal elimination half-life (t½) around 14 days.

Example 9: NKp46-BCMA Fc WT CODV-OL1 Shows Strong Anti-Tumoral Activity in a Dose-Response Manner and Demonstrates a Better Activity by Co-Engaging Both CD16 and NKp46 on NK Cells Introduction The efficacy of NKp46-BCMA Fc WT CODV-OL1 was evaluated in huNKp46-TgxRag mice engrafted with disseminated murine EL4 cells expressing human BCMA. IgG1 competent Fc domain is able to bind to all activating murine FcγRs, to recruit murine effector cells and to induce ADCC with murine NK cells.

Material and Methods

Mice were intravenously inoculated with $0.5 \times 10^6$ tumor cells on day 0. Treatments were administered IP on day 1 post tumor implantation. The following control antibodies were administered at 5 mg/kg: NKp46-CD16-X Fc WT binding huNKp46 and murine FcγRs but not huBCMA; NKp46-X-BCMA binding huNKp46 and BCMA but with LALA Fc mutation inhibiting binding to murine FcγRs and recruitment of murine effector cells through CD16; X-CD16-BCMA binding huBCMA and murine FcγRs but not huNKp46. NKp46-BCMA Fc WT CODV-OL1 was administered at 5, 0.5, and 0.05 mg/kg. The control group was left untreated.

Mice were checked daily, and adverse clinical reactions noted. Individual mice were weighed daily until the end of the experiment (day 60). Mice were euthanized when turning moribund according to predefined criteria to avoid animal suffering. Clinical signs related to the pathology, considered as critical are limb paralysis, ascites, palpable internal tumor mass, morbidity or weight loss superior or equal to 20%.

The primary efficacy endpoints were the median survival time (MST) in day, the percent increased lifespan (% ILS), and the long-term survivor rate.

Individual days of death (if any) of each mouse was reported. MST was determined for each group and the ratio ILS was calculated and expressed as percentage:

$$\% \, ILS = 100 \times (T-C)/C$$

where T=MST of treated group and C=MST of control group.

A dose is considered as therapeutically active when % ILS is superior to 25% and highly active when % ILS is superior to 50% (Johnson J I et al. (2001) Br J Cancer 84(10):1424-1431). Relationships between drug activity in NCI preclinical in vitro and in vivo models and early clinical trials. Id.

Long term survivor rate is defined as the number of mice with survival duration superior or equal to 2 times the MST of control group on the total number of mice in the group expressed in percentage.

Results

The results are presented on FIG. 20 and Table 10.

The NKp46-BCMA Fc WT NKCE induced a statistically significant activity at the doses of 5, 0.5, and 0.05 mg/kg in EL4-huBCMA disseminated model, with an ILS compared to control of 215% and 57% of long-term survivors for the dose of 5, an ILS of 215% and 62.5% of long-term survivors at the dose of 0.5 and an ILS of 132% and 12.5% of long-term survivors at the dose of 0.25 mg/kg.

The control X-CD16-BCMA NKCE induced a statistically significant activity at the dose of 5 mg/kg in EL4-huBCMA disseminated model, with an ILS of 147% and 28.6% of long-term survivors, while the control NKp46-X-BCMA NKCE did not induce a significant activity at the dose of 5 mg/kg with an ILS of 84% without any long term survivor.

In conclusion, NKp46-BCMA CODV-OL1 NKCE showed a dose-dependent activity with a robust activity from 0.05 mg/kg and activity with the NKp46-X-BCMA and X-CD16-BCMA NKCE controls demonstrated the benefit of co-engaging NK cells with both NKp46 and FcγRs leading to an improved in vivo efficacy.

TABLE 10

Activity of NKp46-BCMA Fc WT CODV-OL1 and control bispecific antibodies in huNKp46-Tg × Rag mice bearing disseminated EL4-huBCMA tumor cells

| Group | Long term survivors | Median Survival Time in days | Increase of lifespan |
|---|---|---|---|
| NKp46-BCMA at 5 mg/kg | 57% | >60 | 215% |
| NKp46-BCMA at 0.5 mg/kg | 62.5% | >60 | 215% |
| NKp46-BCMA at 0.05 mg/kg | 12.5% | 44 | 132% |
| X-CD16-BCMA at 5 mg/kg | 28.6% | 47 | 147% |
| NKp46-X-BCMA at 5 mg/kg | 0% | 35 | 84% |
| NKp46-CD16-X at 5 mg/k | 0% | 19 | — |
| Control | 0% | 19.5 | — |

Example 10: ADCC Enhanced NKCE Shows Clear Superiority In Vivo as Compared to Fc WT NKCE Introduction The efficacy of surrogate muNKp46-huBCMA Fc WT and Fc-ADE CODV-OL1 was evaluated in huFcgR-Tg mice engrafted with disseminated murine EL4 cells expressing human BCMA. The huFcgR-Tg mice have been generated by the Rockefeller Institute (Smith P et al. (2012) PNAS, 109(16):6181-6186), these mice express all 5 human Fc γ receptors. The ADE mutation enhances affinity of Fc receptor for the human FcgRIIIA receptor expressed by NK cells but does not enhance affinity to the mouse ortholog FcgRIV. The huFcgR-Tg mice were used to assess the potential enhanced activity of the ADE versus WT NKCE. The control surrogate contains a IgG1 competent Fc domain.

Material and Methods

Mice were intravenously inoculated with 5×10⁶ tumor cells on day 0. Treatments were administered IP on day 1 post tumor implantation. A control antibody binding muNKp46 but not huBCMA (muNKp46-X) was administered at 5 mg/kg. muNKp46-BCMA Fc WT and Fc-ADE CODV-OL1 were administered at 5, 0.5, and 0.05 mg/kg.

Mice were checked daily, and adverse clinical reactions noted. Individual mice were weighed daily until the end of the experiment (day 60). Mice were euthanized when turning moribund according to predefined criteria to avoid animal suffering. Clinical signs related to the pathology, considered as critical are limb paralysis, ascites, palpable internal tumor mass, morbidity or weight loss superior or equal to 20%.

The primary efficacy endpoints were the Median Survival Time (MST) in day, the percent Increased Lifespan (% ILS), and the long-term survivor rate.

Individual days of death (if any) of each mouse was reported. MST was determined for each group and the ratio ILS was calculated and expressed as percentage:

$$\% ILS = 100 \times (T-C)/C$$

where T=MST of treated group and C=MST of control group.

A dose is considered as therapeutically active when % ILS is superior to 25% and highly active when % ILS is superior to 50% (Johnson J I et al. (2001), Br. J. Cancer, 84(10): 1424-31).

Long term survivor rate is defined as the number of mice with survival duration superior or equal to 2 times the MST of control group on the total number of mice in the group expressed in percentage.

Results

The results are presented on FIG. 21 and Table 11.

The surrogate muNKp46-huBCMA Fc WT NKCE did not induce a statistically significant activity at the doses of 5, 0.5, and 0.05 mg/kg in EL4-huBCMA disseminated model (compared to control NKCE group). In contrast, the surrogate muNKp46-huBCMA Fc ADE NKCE induced a statistically significant activity at the doses of 5 and 0.5 mg/kg, with an ILS>100% and 90% of long-term survivor. The lower dose of 0.05 mg/kg did not induce a statistically significant activity.

In conclusion, muNKp46-huBCMA Fc ADE surrogate NKCE showed a better activity than the WT Fc surrogate, in a dose-dependent manner.

TABLE 11

Kaplan-Meier curves for surrogate muNKp46-huBCMA Fc WT and Fc-ADE CODV-OL1 in huFcgR-Tg mice bearing disseminated EL4-huBCMA tumor cells

| Group | Long term survivors | Median Survival Time in days | Increase of lifespan |
|---|---|---|---|
| muNKp46-huBCMA Fc WT at 5 mg/kg | 40% | 52 | 17% |
| muNKp46-huBCMA Fc WT at 0.5 mg/kg | 40% | 60 | 35% |
| muNKp46-huBCMA Fc WT at 0.05 mg/kg | 50% | 73 | 64% |
| muNKp46-huBCMA Fc ADE at 5 mg/kg | 90% | >90 | 102% |
| muNKp46-huBCMA Fc ADE at 0.5 mg/kg | 90% | >90 | 102% |
| muNKp46-huBCMA Fc ADE at 0.05 mg/kg | 40% | 43 | — |
| muNKp46-X Control Fc WT at 5 mg/kg | 20% | 44.5 | — |

Example 11: Chemical Stability/Integrity of Disulfide Bond R292C_V302C within the NKp46-BCMA CODV-OL1 Molecule in Reduction Conditions Introduction Engineering of disulfide bonds (DSB) on the Fc CH2 domain increases stability. See U.S. Provisional Patent Application Ser. No. 63/193,665 incorporated in its entirety by reference herein. To ensure that the engineered DSB, R292C_V302C, and the ADE mutations (G236A/S239D/I332E) within the NKp46-BCMA CODV-OL1 molecule do not aberrantly influence DSB reduction behavior the rate of reduction was measured by DTT and subsequent tryptic peptide mapping.

Material and Methods

Reduction Sensitivity Assay

A serial dilution of DTT in PBS-E was performed (final DTT concentrations in assay: 20, 10, 5, 2, 1, 0.5, 0.2 and 0.1 mM). The protein batches FF-20-819-1, FF-20-821-1 and FF-21-170-5 were dialyzed into PBS-E buffer using spin-desalting columns to ensure pH 7.2 was obtained during reduction. The protein samples were normalized to 1.5 mg/mL in PBS-E. Two parts of normalized sample were added to one part of each DTT dilution into a PCR plate and were mixed after addition. This step was performed from lowest to highest concentration DTT concentration within one minute. Reduction was performed by incubation at 25° C. for 10 minutes on a Thermostat C Thermoblock. The reaction was quenched by the addition of 3 parts of NEM stock solution to all wells. To ensure assay consistency the NEM addition was conducted from lowest to highest DTT concentration within one minute and mixed after addition. The prepared plate was stored at room temperature until measurement by capillary gel electrophoresis (cGE) and mass spectrometry (peptide mapping).

Table 12 and Table 13 below contain the reagent and material list for the reduction sensitivity assay and capillary gel electrophoresis, respectively.

TABLE 12

Reagent and material list for the reduction sensitivity assay

| Reagent/material | Manufacturer | Catalog# | Stock conc. |
|---|---|---|---|
| PBS Buffer pH 7.2 | Gibco/Thermo-Fisher | 20012043 | 1x |
| Dithiothreitol (DTT) | Pierce/Thermo-Fisher | A39255 | solid, resolved in PBS-E to 100 mM |
| N-ethylmaleimide (NEM) | Pierce/Thermo-Fisher | 23030 | solid, resolved in PBS-E to 200 mM |
| Invitrogen EDTA, pH 8.0 | Thermo-Fisher | AM9260G | 0.5M |
| Hard-shell 96 well plate | Bio-Rad | HSP9601 | / |
| Spin Desalting Columns, 7 K MWCO | ZEBA | 89883 | / |

| Instrument | Manufacturer | Catalog # |
|---|---|---|
| Thermostat C Thermoblock | Eppendorf | 5383000027 |

| Assay buffer | Composition |
|---|---|
| PBS-E | Gibco 1X PBS Buffer pH 7.2 + 1 mM EDTA |

TABLE 13

Reagent and material list for capillary gel electrophoresis (cGE)

| Reagent/material | Manufacturer | Catalog # | Stock conc. |
|---|---|---|---|
| Water MS grade | Thermo | #51140 | / |
| Iodoacetamide (IAM) | Thermo-Fisher | #A39271 | solid, resolved in water to 250 mM |
| Hard-shell 96 well plate | Bio-Rad | #HSP9601 | / |
| Protein Clear HR Assay Kit | PerkinElmer | #CLS960014 | / |
| Protein Clear HR Chip | PerkinElmer | #CLS148695 | / |

| Instrument | Manufacturer | Catalog # |
|---|---|---|
| LabChip GXII Touch | PerkinElmer | CLS138160 |
| Thermostat C Thermoblock | Eppendorf | 5383000027 |

| Assay buffer | Composition/concentration |
|---|---|
| Non-reducing sample buffer | Protein Express Sample Buffer + 8.75 mM IAM |

After the reduction sensitivity assay was performed the samples were measured by use of the non-reducing protocol of the Protein Clear HR Assay according to the manufacturer's instructions.

To prepare the chip, all assay components were allowed to equilibrate to room temperature. Protein Clear HR Gel matrix was mixed with Protein Clear HR Dye solution and filtered before adding to rinsed chip wells according to the manufacturer's instructions.

The provided assay control VeriMAb-standard was diluted in non-reducing sample buffer, denatured at 70° C. for 10 minutes and mixed with water according to the manufacturer's instructions and placed in the LabChip GXII Touch instrument for assay calibration. After 1:10 dilution of Protein Clear HR Ladder in water the indicated volumes of the ladder solution and Protein Clear HR Wash buffer were transferred into corresponding tubes and placed in LabChip GXII Touch instrument. Calibration process was finished successfully before measuring the samples.

To prepare the samples, 5 µL of each sample coming from the reduction sensitivity assay was added to 18 µL of non-reducing sample buffer in a PCR plate, which was sealed, and samples were denatured at 70° C. for 10 min on a Thermostat C Thermoblock. After denaturation, the samples were diluted with 35 µL water. The prepared assay plate was stored at room temperature until it was measured with the LabChip GXII Touch instrument.

After measurement, the data was analyzed using the LabChip Reviewer Software. All peaks with ≥0.85% of relative peak area were integrated. The relative peak area [%] of the remaining intact molecule was plotted against the DTT concentrations and the curve was fitted by a 4 Parameter Logistic Model/Sigmoidal Dose-Response Model (XIfit, Dose Response One Site, Model 205). The area of the sample without DTT addition was used for standardization and was set to 100%. The DTT concentration of each sample where 50% of the intact molecule was remaining was used as EC50 value to evaluate the molecule's sensitivity towards reduction.

Antibody Sample Preparation after Reduction Assay for Tryptic Peptide Mapping Experiments After performing the reduction sensitivity assay samples were subjected to the digestion procedure. 100 µg per antibody sample were denatured using 0.2 mol/L histidine chloride, 5.6 mmol/L guanidinium hydrochloride pH 6 by buffer exchange with 0.5 mL Zeba Spin Desalting Columns (Thermo Fisher Scientific, Catalog No. 89883). Buffer exchange was repeated once to ensure complete removal of NEM. Then, samples were reduced by addition of 10 mmol/L TCEP (tris(2-carboxyethyl)phosphine, Thermo Fisher Scientific, Catalog No. T2556) for 1 h at 37° C. Subsequently, buffer was exchanged to 20 mmol/L histidine chloride, 0.5 mmol/L TCEP, pH 6 with 0.5 mL Zeba Spin Desalting Columns (Thermo Fisher Scientific, Catalog No. 89883). Antibodies were digested with trypsin overnight at 37° C. at an enzyme to substrate ratio of 1:20. Digestion was stopped by addition of 7 µL of 10% formic acid solution and samples were frozen at −80° C. until further analysis.

Detection of Modified Peptides by Liquid-Chromatography Tandem Mass-Spectrometry Peptides were analyzed using a Vanquish™ Flex UHPLC System coupled to an orbitrap Fusion™ Lumos™ Tribrid™ mass spectrometer equipped with the EASY-ETD ion source (Thermo Fisher Scientific, San Jose, CA, USA).

For peptide separation a binary solvent system was used: (A) 0.1% formic acid and (B) 90% acetonitrile, 0.1% formic acid. 2 µg of tryptic digested sample was separated with a 1 h gradient with linearly increasing concentrations of solvent B for 50 min, followed by 5 min at 95% B washing and 5 min re-equilibration to 5% solvent B on a Hypersil GOLD™ C18 LC-column (150 mm×2.1 mm with 1.9 µm particle size, Thermo Fisher Scientific, Catalog No. 25003-152130-V). Peptides separated on the column were detected with the following crucial settings: full MS spectra were acquired at a resolution of 120,000 (defined at 200 m/z) with the mass range set to 375-2000, an automated gain control (AGC) target of 4.0e5, a maximum injection time of 50 ms and 1 µscan. Data-dependent (MS/MS) spectra were acquired in a top 5 data-dependent mode using a resolution of 15,000 (defined at 200 m/z) after accumulation of 5.0e4 AGC targets within an injection time of 200 ms. Ions were isolated at a 1.6 Th isolation window and fragmented using HCD, EthcD or EtciD at 30% normalized collision energy. Dynamic exclusion was set to 10 s.

Data Processing

Acquired MS data was processed using Expressionist software (GeneData version 13.5) and manually inspected to ensure correct assignment and relative quantification accuracy. Mass spectra were searched against the amino acid sequence of the sample molecule. Crucial settings are the mass tolerances for MS and MS/MS spectra which was set to 10 ppm, respectively. Post-translational modifications considered within the search parameters were NEM modification on cysteines and common N-terminal glycosylations using the IgG N-glycan library from Expressionist.

Results

EC50 values were calculated from the dose response curves as displayed in FIG. 22. The reductions of main peak of unreduced sample by DTT measured by capillary electrophoresis (cGE) were identical for CODV-OL1 wt, CODV-OL1 ADE and CODV-OL1 ADE-DSB, indicating that neither the ADE mutation nor the engineered disulfide bond in the CH2 domain have an influence on the reduction sensitivity of the protein.

The proteins, CODV-OL1 wt, CODV-OL1 ADE, and CODV-OL1 ADE-DSB, from the reduction sensitivity assay analyzed by peptide mapping exhibit similar reduction behavior of reduction sensible intermolecular disulfide bonds (DSBs) as shown in FIG. 23A (CODV-OL1 wt), FIG. 23B (CODV-OL1 ADE), and FIG. 23C (CODV-OL1 ADE-DSB). Based on the dose response curves EC50 values were estimated for the three proteins to be in the range of 1.2-1.5 mM DTT indicating that the engineered DSB is similarly reduction stable as a typical intermolecular DSB.

CODV-OL1 wt, CODV-OL1 ADE and CODV-OL1 ADE-DSB—Expression Yields

The antibodies were produced as follows:

The expression plasmids encoding the different chains of the corresponding constructs were propagated in *E. coli* DH5a. Plasmids used for transfection were prepared from *E. coli* with EndoFree Plasmid Mega kits (Qiagen). HEK 293-FS cells growing in F17 serum free suspension culture (Invitrogen) were transfected with indicated plasmids using polyethyleneimine transfection reagent. After 6 days of cultivation at 37° C. with 8% C02 cells were removed by centrifugation and the supernatant was passed over a 0.22 µm filter to remove particles. The Proteins were captured on MabSelect SuRe (Cytiva) and eluted with 0.1 M Citrate buffer pH 3.0 and neutralized with 1 M Tris pH 9. After polishing the proteins by size exclusion chromatography (SEC) using a Superdex200 26/60 (Cytiva) and 0.22 µm filtration and UV280 concentration determination the proteins were used for further characterization. The yields are reported below in Table 14.

TABLE 14

Yield of antibodies with a wild-type IgG1 or with enhanced Fc domain, with or without disulfide bond

| Clone | Sample Yield (mg/L) |
| --- | --- |
| CODV-OL1-WT | 25.2 |
| CODV-OL1-DE-R292C/V302C | 21.7 |
| CODV-OL1-ADE-R292C/V302C | 25.7 |

The antibody with a normal IgG1 Fc backbone demonstrated a sample yield of 25.2 mg/L while the antibodies with ADE or DE mutations in the Fc backbone show a strong reduction below 5 mg/L in the sample yields. The antibodies with an IgG1 Fc with ADE or DE mutations and with the disulfide-bond demonstrated a sample yield similar to WT.

Example 12: In Vitro Cytokine Release in PBMC in Coculture with BCMA-Positive RPMI 8226 MM Tumor Cells with the NKp46-BCMA Fc-ADE-DSB Material and Methods In vitro safety procedure for IncuCyte S3 (PBMC+ MM1R-RFP, Effector:Target ratio=3:1)

One day after PBMC purification, both PBMCs and MM1R-RFP were counted at Vi-Cell XR (Beckman Coulter, Brea).

Target cells: MM1R cell line was purchased from ATCC/Northwestern University BDW and transfected with Incucyte Nuclight Red lentivirus (EssenBiosciences, ref #4476) in order to express mKate2 Red Fluorescent Protein (RFP) that can be followed over several days with the Incucyte incubator. The selection of MM1R-RFP cell was obtained through the addiction of Puromycin dihychloride hydrate (Thermo Scientific, Denmark, ref #10781691) at the final concentration of 1 µg/ml in the culture medium [RPMI Medium 1640 (1×) (GIBCO, Denmark, ref #31870-025) with 20% of Fetal Bovine Serum Heat Inactivated FBS (Biowest, ref #S140H-100) and 1% of L-Glutamine 200 mM (100×) (GIBCO, Denmark, ref #25030-024)].

Since MM1R-RFP are semi-adherent cells, the culture medium was removed and put in a 50 ml falcon tube together with the 5 ml of PBS 1× used to wash the Nunc EasY Flask 75 cm² (Thermo Scientific, Denmark). The remaining adherent cells were detached by adding 1 ml/75 cm² flask of Accutase Cell Detachment Solution (Corning, ref #25-058-CI). The action of accutase was stopped after 5 min at 37° C. with 9 ml of culture medium (RPMI+20% FBS, final volume of 10 ml) and the MM1R-RFP cells were counted at Vi-Cell XR. The proper number of cells was prepared and seeded at density of 30 000 cells/well (50 µl/well) to have an E:T ratio of 3:1.

Antibodies: all the Abs are prepared 2× concentrated (since 50 µl target cells+100 µl Ab 2X+50 µl PBMC were added for each well) in RPMI culture medium. The antibodies used for the experiment were diluted 1/100 times in culture medium in Deepwell plates (Axigen, ref #P-DW-11-C-S). The starting concentration for all the Abs was 1000 nM (so 2000 nM was calculated), except for the CD3-BCMA T cell engager whose initial concentration was at 100 nM (so 200 nM) and 3 dilutions were performed.

Effector cells: Total PBMCs were prepared at density of 300 000 cells/well (50 µl/well) (E:T ratio of 3:1). After counting, needed number of PBMCs were centrifuged at 300 g for 5 min (acceleration=9, brake=9) and resuspended in proper volume of RPMI culture medium with the human IgG at concentration of 4 mg/ml (Sigma-Aldrich, ref #14506) so that the final concentration was 1 mg/ml in 200 µl of final volume/well: [50 µl MM1R-RFP+100 µl Antibodies (2×)+50 µl PBMCs].

Cells were seeded in 96-well plate poly D (Greiner bio-one, ref #655946) and the external wells were filled with 200 µl of PBS 1×.

After seeding tumoral cells (50 µl/well)+Ab (100 µl/well)+PBMC (50 µl/well), the plate was centrifuged at 100 g for 1 min at RT and placed in the incubator of IncuCyte S3 (Essen BioScience) but the plate was read only after at least 30 min to avoid differences in the temperature.

The following parameters were used to read the plate on Incucyte S3: analyse type (Basic Analyzer), RED, Objectif 10×, 4 images/well, time points 48 h (images every 4 h), acquisition time 400 ms.

After 48 h the Incucyte scanner was stopped and the plate was centrifuged at 300 g for 5 min, then 100 µl of supernatant/well were collected to perform the analysis of cytokine release by Human Proinflammatory I (4-Plex) Kit V-Plex.

Procedure for the Analysis of Cytokine Release by Human Proinflammatory I (4-Plex) Kit V-Plex For the analysis of cytokine release, the Human Proinflammatory I (4-Plex) Kit V-Plex was used (MSD, ref #K15052D-1).

First, the control ranges were prepared: the lyophilized tube was resumed with 1000 µl of Diluent 2 (Calibrator, ref #C0049-2) and left to rest for 30 min. 7 successive dilutions of 4 were made in Diluent 2 (i.e. 75 µl Cx+225 µl diluent 2); the last tube n.8 was considered as negative control (Diluent 2 alone=Zero), while in the tube n. 1 the starting solution was not diluted.

Successively, samples were prepared with a dilution of 1/100 for DART (i.e. 50 µl/well, preparation of 5 µl DART/concentration+495 µl Diluent 2) and 1/5 (i.e. 50 µl/well, preparation of 100 µl Ab/concentration+400 µl Diluent 2) for the other antibodies.

The secondary antibody was prepared in Diluent 3: 100 µl IFNγ+100 µl IL1β+100 µl IL6+100 µl TNFα+4600 µl Diluent 3 (final volume 5 ml) and then 25 µl of the secondary Ab mix was distributed in every well.

Before adding the samples to the plate, the latter was washed 3 times with 150 µl of PBS 1× tween 0.05% (Washing Buffer prepared with: 500 µl of Tween20 in 1 L of PBS 1×). Then, 50 µl/well of the diluted samples to be tested and 50 µl/well of the standard range were added. The plate was covered with a film and left for 2 hours under stirring at RT.

The plate was washed 3 times with 150 µl of washing buffer and 25 µl of secondary Ab was added to the samples (the plate was tapped for a better distribution of the secondary Ab) and the plate was covered again with film and left for 2 hours under stirring at RT. 3 steps of washing with 150 µl of washing buffer were made and 150 µl of reading buffer were added in all wells [reading buffer (4×) prepared by a 1% dilution in H2O]. The plate was read to MSD instrument 1250.

Results:

As shown in FIG. 24A and FIG. 24B, NKp46-BCMA_Fc-ADE-DSB mediated potent cytotoxicity of BCMA-expressing cells, yet led to minimal cytokine release from PBMCs in a co-culture. As shown in FIG. 25A and FIG. 25B, NKp46-BCMA_Fc-ADE-DSB also mediated reduced MM1R tumor cell proliferation while minimally triggering cytokine release. The reduced cytokine release in vitro is indicative of a favorable safety profile.

Example 13. In Vitro Characterization of NKCE on NK Cell Activation and Cytokine/Chemokine Production by Resting NK Cells in the Presence of MM Cells This example is drawn to characterizing the in vitro efficacy of NKp46-BCMA_Fc-ADE-DSB on activation and cytokine/chemokine production of NK cells in the presence of a BCMA-positive cell line (RPMI 8226 multiple myeloma cells).

Material and Methods

Peripheral blood mononuclear cells: To isolate peripheral blood mononuclear cells (PBMCs), buffy coats were diluted at ~1/5 in RPMI and transferred in Pancoll tubes at room temperature. Tubes were centrifugated at 800 g for 20 min without brake. The first cell wash was performed in RPMI with a centrifugation at 400 g for 10 min. at room temperature with brake. A second wash of the cells was performed in RPMI with a centrifugation at 130 g for 10 min. at room temperature with brake.

NK cell collection: Human NK cells were purified from a PBMC sample with an NK cell isolation kit (Miltenyi) by negative selection using manual magnetic labeling and subsequent manual separation with LS columns according to the protocol recommended by the supplier. The NK cells were then cultured in complete RPMI at $1 \times 10^6$ cells/mL for about 24 hours at 37±1° C. at 5±1% C02 before to be used in an activation assay (so called "resting" NK cells).

The viability criterion for effector cells was set to 90%. The cell surface expression of both CD16a and NKp46 on resting NK cells was monitored by flow cytometry the day of the experiment.

NK Cell Activation Assay

NKCE molecules were added to wells of a U-bottom 96-well plate. 50,000 resting (e.g., not activated) NK cells and 50,000 RPMI 8226 MM cells were successively added to each well to obtain an effector:target (E:T) ratio of 1:1. Control conditions were performed by adding only 50,000 resting NK cells to each well. GolgiStop™ (BD Biosciences) solution was added at a final dilution of 1/1500 in each well (control and experimental) to block intracellular protein transport outside of cells resulting the accumulation of cytokines in the Golgi complex. A positive control of NK cell activation was performed by using 125 ng/mL final concentration of phorbol 12-myristate 13-acetate (PMA) and 1 µg/mL final concentration of Ionomycin added to 50,000 resting NK cells. Each condition was performed in simplicate.

After 4 hours of co-incubation at 37±1° C., cells were stained by performing staining for extracellular markers (CD3, Cd56, CD69, CD107a, and CD107b) for flow cytometry analysis. After fixation and permeabilization steps, an intracellular staining was performed for IFNγ, TNFα, and MIP1β. Cells were fixed using Cytofix (BD Biosciences) for 15 minutes after the last staining and analyzed by flow cytometry with a LSR Fortessa™ X-20. FSC-A, FSC-H, FSC-W, SSC-A, SSC-H, SSC-W, FL-1, FL-3, FL-6, FL-7, FL-9, FL-13 and FL-16 parameters were recorded with BD FACSDiva software and the analyses were done with FlowJo software.

Analysis of the percent of NK cell activation and median fluorescence intensity (MedFI) of activation markers were done with GraphPad Prism. Top of activation values corresponded to the observed maximum activation. Half maximal effective concentration ($EC_{50}$) values were calculated using a 4 parameter logistics non-linear regression model corresponding to the following equation:

$$NK \text{ cell activation } (\%) = \text{calculated bottom} + \frac{\text{calculated top} - \text{calculated bottom}}{1 + 10^{(log(EC50)-log(concentration))slope}}$$

Calculated bottom of activation, calculated top of activation, slope and 95% confidence interval (CI) values were calculated using the same model as $EC_{50}$.

Flow Cytometry Analysis for Purity and Phenotype of Resting NK Cells and Target Cells The resting NK cells, used for NK cell activation experiments, were analyzed in terms of purity, expression of CD16a, and NKp46. RPMI 8226 MM cells were analyzed for expression of CD32 and BCMA.

Staining of resting NK cells and target cells was performed on the day of the experiment. $1\times10^5$ cells/well were stained in a U-bottom 96-well plate with antibodies coupled to dyes (allophycocyanin, Pacific blue, or phycoerythrin).

Results:

NK cell activation was evaluated by: 1) expression of activation markers (CD69 and CD107a/b) at the cell surface and 2) intracellular production of cytokines (IFNγ, TNFα) and chemokines (MIP1β). Seven NK cell donors were evaluated in the study.

As shown in FIG. 26A-FIG. 26D in the absence of RPMI 8226 MM cells, PMA-Ionomycin, a positive control, activated NK cells by inducing expression of CD69 and CD107a/b. In contrast, NKp46-BCMA_Fc-ADE-DSB and control NKCE induced a non-sigmoid dose response activation from 4.88 ng/mL to reach at the highest concentration (4.88 µg/mL) around 40% of CD69 positive cells (CD69 MedFI around 150) and 14% of CD107 positive cells (CD107 MedFI around 90).

In the presence of RPMI 8226 MM cells, NK cells were not activated in the absence of the molecule. Addition of the control NKCE induced a low level of activation of NK cells similar to the activation obtained in the absence of target cells. Addition of NKp46-BCMA_Fc-ADE-DSB induced a sigmoidal dose response for NK cell activation higher than activation obtained with the control NKCE. More precisely, a saturation phase was observed for NKp46-BCMA_Fc-ADE-DSB at around 48.8 ng/mL for CD69 expression (around 60% of positive cells and a MedFI of 351 on NK cells) and CD107a/b expression (around 22% of positive cells and a MedFI of 132 on NK cells) (Table 15).

TABLE 15

Observed top of NK cell activation values obtained for CD69 and CD107a/b expression in NK cell activation assay in the presence of NKp46-BCMA_Fc-ADE-DSB and RPMI 8226 MM cells.

| NK cell activation marker | Molecule | Top of activation (% of positive NK cells) | | | | | | | Mean top of activation (% of positive NK cells) | SD top of activation (% of positive NK cells) |
|---|---|---|---|---|---|---|---|---|---|---|
| | | D091 | D584 | D819 | D018 | D042 | D101 | D236 | | |
| CD69 | ESB1 | 68 | 51 | 72 | 70 | 43 | 70 | 45 | 60 | 13 |
| CD107a/b | | 25 | 20 | 14 | 24 | 24 | 30 | 18 | 22 | 5 |

| NK cell activation marker | Molecule | Top of activation (MedFI on NK cells) | | | | | | | Mean top of activation (MedFI on NK cells) | SD top of activation (MedFI on NK cells) |
|---|---|---|---|---|---|---|---|---|---|---|
| | | D091 | D584 | D819 | D018 | D042 | D101 | D236 | | |
| CD69 | ESB1 | 398 | 237 | 428 | 572 | 208 | 390 | 223 | 351 | 134 |
| CD107a/b | | 133 | 100 | 91 | 191 | 149 | 145 | 117 | 132 | 34 |

As saturation phase and sigmoid dose-response were obtained for NKp46-BCMA_Fc-ADE-DSB for 0069 expression, the $EC_{50}$ was extracted from the seven selected donors (Table 16). Given the level of production of CD107a/b (around or below 20% of positive cells for 3 out of the 7 donors), no $EC_{50}$ was estimated for the CD107a/b activation marker.

TABLE 16

EC$_{50}$ values obtained in the NK cell activation assay for CD69 expression
in the presence of NKp46-BCMA_Fc-ADE-DSB and RPMI 8226 MM cells.

| NK cell activation marker | Molecule | EC$_{50}$ (pg/mL) [95% CI] | | | | | | | GeoMean EC$_{50}$ (pg/mL) [95% CI] |
|---|---|---|---|---|---|---|---|---|---|
| | | D091 | D584 | D819 | D018 | D042 | D101 | D236 | |
| CD69 (% of positive NK cells) | ESB1 | 1394 [525, 4467] | 2229 [1657, 3011] | 1420 [865, 2365] | 1096 [1023, 1175] | 3511 [1873, 7161] | 894 [592, 1384] | 2644 [979, 9969] | 1695 [1072, 2679] |
| CD69 (MedFI on NK cells) | ESB1 | 12510 [2485, 6.67$^E$+11] | 10510 [7041, 16320] | 2882 [1290, 7171] | 3507 [3179, 3847] | 9867 [3754, 50980] | 2585 [1126, 7443] | 39430 [5128, ND] | 7501 [3014, 18670] |

| NK cell activation marker | Molecule | EC$_{50}$ (pM) | | | | | | | GeoMean EC$_{50}$ (pM) [95% CI] |
|---|---|---|---|---|---|---|---|---|---|
| | | D091 | D584 | D819 | D018 | D042 | D101 | D236 | |
| CD69 (% of positive NK cells) | ESB1 | 11.2 | 17.8 | 11.4 | 8.8 | 28.1 | 7.2 | 21.2 | 13.6 [8.6, 21.4] |
| CD69 (MedFI on NK cells) | ESB1 | 100.1 | 84.1 | 23.1 | 28.1 | 78.9 | 20.7 | 315.4 | 60.1 [24.1, 149.4] |

IFNγ, TNFα, and MIP1β Secretion by NK Cells

In the same experiment, production of intracellular cytokines (IFNγ and TNFα) and the chemokine MIP1@ by NK cells was measured. TNFα, IFNγ, and MIP1@ release were proportional to NK cell activation: higher NK cell activation resulted in higher cytokine/chemokine production (FIG. 27A-FIG. 27F).

In the absence of RPMI 8226 MM cells and NKp46-BCMA_Fc-ADE-DSB, no detectable TNFα and IFNγ were produced by NK cells, however MIP1p was produced by around 80% of NK cells. Addition of a positive control (PMA-Ionomycin) induced production of TNFα (~84% for D584), IFNγ (~83% for D584) and increased MIP1β (~100% for D584) by NK cells. In contrast, addition of NKp46-BCMA_Fc-ADE-DSB induced very low target dependent expression of IFNγ and TNFα, in a dose dependent manner with observed top of activation below 20% of positive cells (8±5% for IFNγ and 12±7% for TNFα). MIP1β was produced by NK cells form 4.88 ng/mL to reach around 95% of positive cells (MIP1β MedFI around 5400 on NK cells) in a dose response of the two molecules.

Results showed that the presence of RPMI 8226 MM cells alone was not enough to induce cytokine secretion by NK cells in the absence of NKCE molecules. Addition of control NKCE molecules at high concentrations induced a low or very low production of cytokines by NK cells and induced high production of MIP1β with a sigmoid dose-response. Addition of NKp46-BCMA_Fc-ADE-DSB induced cytokine and chemokine production. For the three cytokines/chemokine, the maximal level of production was reached at a concentration ranging between 4.88 and 48.8 ng/mL of NKp46-BCMA_Fc-ADE-DSB according to the donor. For the seven tested donors, the percent NK cells producing TNFα or IFNγ was about 12±7 (TNFα MedFI on NK cells: 39±7) and 8±5 (IFNγ MedFI on NK cells: 137±30), respectively, and the percent NK cells producing MIP1 was about 94±2 (MIPβ MedF on NK cells: 10145±4416) at the highest NKp46-BCMA_Fc-ADE-DSB concentrations (Table 17).

As saturation phase and sigmoid dose-response were obtained for NKp46-BCMA_Fc-ADE-DSB for TNFα, IFNγ and MIP1β production, the observed top of activation (TNFα, IFNγ, and MIP1 P) and the EC$_{50}$ for MIP1 P from the seven tested donors were observed. Given the level of TNFα and IFNγ production (below 20% of positive cells), no EC$_{50}$ was estimated for these two cytokines (Table 18).

TABLE 17

Observed top of NK cell activation values obtained in NK cell activation
assay in the presence of NKp46-BCMA_Fc-ADE-DSB and RPMI 8226 MM cells.

| NK cell activation marker | Molecule | Top of activation (% of positive NK cells) | | | | | | | Mean top of activation (% of positive NK cells) | SD top of activation (% of positive NK cells) |
|---|---|---|---|---|---|---|---|---|---|---|
| | | D091 | D584 | D819 | D018 | D042 | D101 | D236 | | |
| TNFα | NKp46- | 14 | 9 | 9 | 0 | 13 | 15 | 23 | 12 | 7 |
| IFNγ | BCMA_Fc- | 12 | 5 | 4 | 0 | 6 | 16 | 11 | 8 | 5 |
| MIP1β | ADE-DSB | 97 | 97 | 95 | 94 | 90 | 93 | 94 | 94 | 2 |

TABLE 17-continued

Observed top of NK cell activation values obtained in NK cell activation assay in the presence of NKp46-BCMA_Fc-ADE-DSB and RPMI 8226 MM cells.

| NK cell activation marker | Molecule | Top of activation (MedFI on NK cells) | | | | | | | Mean top of activation (MedFI on NK cells) | SD top of activation (MedFI on NK cells) |
|---|---|---|---|---|---|---|---|---|---|---|
| | | D091 | D584 | D819 | D018 | D042 | D101 | D236 | | |
| TNFα | NKp46- | 44 | 40 | 41 | 27 | 36 | 37 | 50 | 39 | 7 |
| IFNγ | BCMA_Fc- | 195 | 120 | 138 | 97 | 131 | 132 | 148 | 137 | 30 |
| MIP1β | ADE-DSB | 12923 | 9428 | 7233 | 3679 | 7547 | 16239 | 13968 | 10145 | 4416 |

TABLE 18

$EC_{50}$ values obtained in an NK cell activation assay for MIP1β expression in the presence of NKp46-BCMA_Fc-ADE-DSB and RPMI 8226 MM cells.

| NK cell activation marker | Molecule | $EC_{50}$ (pg/mL) [95% CI] | | | | | | | GeoMean $EC_{50}$ (pg/mL) [95% CI] |
|---|---|---|---|---|---|---|---|---|---|
| | | D091 | D584 | D819 | D018 | D042 | D101 | D236 | |
| MIP1β (% of positive NK cells) | NKp46-BCMA_Fc-ADE-DSB | 92 [73, 116] | 105 [88, 126] | 115 [101, 132] | 134 [97, 186] | 312 [239, 405] | 164 [95, 284] | 126 [87, 183] | 138 [95, 201] |
| MIP1β (MedFI on NK cells) | NKp46-BCMA_Fc-ADE-DSB | 4436 [1650, 19230] | 3276 [2652, 4059] | 2012 [1192, 3480] | 434 [161, 823] | 4237 [2159, 9387] | 1660 [1036, 2669] | 3627 [1377, 13640] | 2283 [1069, 4878] |

| NK cell activation marker | Molecule | $EC_{50}$ (pM) | | | | | | | GeoMean $EC_{50}$ (pM) [95% CI] |
|---|---|---|---|---|---|---|---|---|---|
| | | D091 | D584 | D819 | D018 | D042 | D101 | D236 | |
| MIP1β (% of positive NK cells) | NKp46-BCMA_Fc-ADE-DSB | 0.7 | 0.8 | 0.9 | 1.1 | 2.5 | 1.3 | 1.0 | 1.1 [0.7, 1.6] |
| MIP1β (MedFI on NK cells) | NKp46-BCMA_Fc-ADE-DSB | 35.5 | 26.2 | 16.1 | 3.5 | 33.9 | 13.3 | 29.0 | 18.3 [8.6, 39.0] |

Example 14: In Vitro Cytokine Release Analysis of NKp46-BCMA Fc-ADE-DSB Using Co-Cultured Human Donor Whole Blood Cells and RPMI (Multiple Myeloma) Cell Line Introduction To assess the variability/range of response observed in this assay, whole blood cells were derived from 11 human donors was co-cultured with RPMI-8226-RFP cells which were treated with either NKp46-BCMA_Fc-ADE-DSB or negative or positive controls. Co-cultures were incubated overnight at 37° C. with either 1, 10, 100, and 300 µg/mL of NKp46-BCMA_Fc-ADE-DSB prepared from two different batches (CER or GMP) or with negative or positive controls as detailed in the material and methods section below. Treatment control groups included two negative controls (untreated co-culture and co-culture treated with isotype control at 300 µg/mL), and three positive controls: an human anti-CD3/CD28 T cell activator (25 µg/mL; ImmunoCult™), an anti-CD52 recombinant antibody (alemtuzumab 100 µg/mL; Campath-1H®), and an internal BCMA T cell engager tool compound (TCE-BCMA 100 µg/mL).

Materials and Methods

The RPMI 8226 cell line was obtained from ATCC (American Type Culture Collection, USA) and transfected with red florescent protein (RFP). This modified RPMI 8226-RFP cells were cultured in RPMI 1640 media (Thermo Fisher Scientific, Inc., Waltham, MA, USA) supplemented with 10% fetal bovine serum (Thermo Fisher Scientific, Inc.) and 1% Penicillin-Streptomycin (10,000 U/mL, Thermo Fisher Scientific, Inc.) at +37° C. in a humidified atmosphere of 5% C02.

On the day of the cytokine release assay, cells were counted and assessed for viability on a Cellometer (Nexelcom, Lawrence, MA, USA). RPMI-8226-RFP cells were adjusted to a concentration of 800,000 cells/mL and 25 uL of cells were seeded per well for a final density of 20,000 cells per well in 96-well tissue culture plates (Thermo Fisher Scientific, Inc.).

NKp46-BCMA_Fc-ADE-DSB and controls were dissolved in RPMI 1640 Medium, GlutaMax (Thermo Fisher Scientific, Inc.) supplemented with 10% w/v fetal bovine serum and 1% Penicillin-Streptomycin (10,000 U/mL). 25 µL of NKp46-BCMA_Fc-ADE-DSB and controls were added per well in triplicate. Negative controls were media alone and isotype control at a final concentration of 300 µg/mL. Positive controls with their respective concentrations are listed above as well as labeled in FIG. 28-FIG. 32.

Whole blood from consented 11 donors was by venipuncture into 10 mL vacutainer tubes containing sodium-heparin anticoagulant. Samples were gently mixed and kept under ambient conditions until study initiation. After the addition of RPMI-8226-RFP cells to either a NKp46-BCMA_Fc-ADE-DSB or a treatment control group, fresh whole blood samples (200 µL) from the donors were then added to the wells and the plates were incubated at +37° C. in a humidified atmosphere of 5% C02 for 24 hours.

At the end of the incubation period, plates were centrifuged at 500×g for 10 minutes. Plasma was collected from these plates and then transferred directly to a new 96-well cell culture plate and then centrifuged at 2000×g for 10 minutes to remove remaining cellular debris. The final plasma samples were transferred to new 96-well culture plates and used for immediate assessment of cytokine levels.

Plasma samples were assessed for levels of granulocyte-macrophage colony-stimulating factor (GM-CSF; quantification range of 0.33-10,200 µg/mL), interferon gamma (IFN-γ; quantification range of 9.45-27,000 µg/mL), interleukin-1 beta (IL-1p; quantification range of 0.35-4430 µg/mL), interleukin-2 (IL-2; q quantification range of 1.24-1990 µg/mL), interleukin-4 (IL-4; quantification range of 0.16-1,780 µg/mL), interleukin-6 (IL-6; quantification range of 0.89-2,050 µg/mL), interleukin-8 (IL-8; quantification range of 0.35-2,180 µg/mL), interleukin-10 (IL-10; quantification range of 0.35-3,770 µg/mL), macrophage inflammatory protein 1 alpha (MIP-1a; quantification range of 14.5-5,580 µg/mL), and tumor necrosis factor alpha (TNF-α; quantification range of 0.66-2,940 µg/mL) using a MSD U-PLEX assay (Catalog #K15067L-2; Lot #404471) according to manufacturer instructions (Mesoscale Discovery, Rockville, Maryland, USA).

Cytokine levels were defined using calibration curves for each cytokine by fitting the signals from the calibration standards to a 4-parameter logistic or sigmoidal dose-response model with a $1/Y^2$ weighting. The calculations to determine cytokine concentrations were carried out using the MSD DISCOVERY WORKBENCH analysis version 4.0 (Mesoscale Discovery, Rockville, Maryland, USA) and concentrations were expressed in units of pg/mL.

Cytokine data (in triplicate) were analyzed and the coefficient of variation (% CV) between triplicates was calculated using GraphPad Prism software, version 9.1.2 (GraphPad Software, San Diego, CA, USA). A sigmoidal dose response four parameter variable slope calculation with a bottom constraint set to 0 was used for analysis. Samples where technical errors occurred, and nothing was detected were reported as undetected (UD). Samples with a concentration at or below the lower limit of quantification (LLOQ) were reported as the LLOQ and this value was used in all calculations. Samples with a concentration above the upper limit of quantification (ULOQ) were reported as the extrapolated value obtained, and this value was used in all calculations. A fold change in cytokine level was calculated [overall mean (with SD) and median (with Q1 and Q3: first and third quartiles)] for each treated sample relative to the negative control (untreated co-culture).

Results

As shown in FIG. 28-FIG. 32, positive controls, anti-CD3/CD28 and TCE-BCMA, demonstrate strong increases in cytokine release for IFN-γ (FIG. 28A), MIP-1a (FIG. 28B), TNF-α (FIG. 29A), IL-1β (FIG. 29B), IL-6 (FIG. 30A), IL-8 (FIG. 30B), IL-2 (FIG. 31A), GM-CSF (FIG. 31B), IL-4 (FIG. 32A) and IL-10 (FIG. 32B) when compared to negative controls (untreated and isotype control). Positive control, anti-CD52 induced cytokine release of IFN-γ (FIG. 28A), IL-6 (FIG. 30A), MIP-1α (FIG. 28B), IL-1β (FIG. 29B), and IL-8 (FIG. 30B) but not cytokines typically associated with a T-cell response such as, IL-2 (FIG. 28A), IL-10 (FIG. 31A), GM-CSF (FIG. 31B), or IL-4 (FIG. 32A). Differently, NKp46-BCMA_Fc-ADE-DSB induced secretion of IFN-γ (FIG. 28A) and MIP-1α (FIG. 28B) only; no change in all the other evaluated cytokines was reported.

There was a clear NKp46-BCMA_Fc-ADE-DSB-related increase in IFN-γ and MIP-1a across the donors at all concentrations tested (1, 10, 100, and 300 µg/mL), when compared with the untreated whole blood and RPMI 8226-RFP co-cultures (negative control). IFN-γ levels (FIG. 28A) in samples incubated with NKp46-BCMA_Fc-ADE-DSB (at all tested concentrations) were higher than negative control (3 to 6-fold), but much lower than the positive controls. There was no NKp46-BCMA_Fc-ADE-DSB-related concentration dependence to the increase in IFN-γ, and levels were comparable to the isotype control, suggesting that the IFN-γ secretion was related to NK cell engagement by NKp46-BCMA_Fc-ADE-DSB rather than related to BCMA binding activity. NKp46-BCMA_Fc-ADE-DSB induced MIP-1a (FIG. 28B) levels were slightly higher than the negative control (1 to 3-fold) but strikingly lower than the positive controls. There was no difference in the cytokine release profile between both NKp46-BCMA_Fc-ADE-DSB batches (CER and GMP) tested.

Taken together, the results indicate that the risk of NKp46-BCMA_Fc-ADE-DSB resulting ni CRS in humans is considered low. These results also corroborate those from in vitro cytokine release assay (PBMC) shown in Example 12 supporting the conclusion that NKp46-BCMA_Fc-ADE-DSB has a favorable safety profile.

Example 15: NK Cell Activation and Analysis of MM Cell Lysis in Response to NKp46 Bispecific Antibody Introduction This example assesses the capacity NKp46-BCMA_Fc-ADE-DSB to activate NK cells from MM peripheral blood and to induce MM cell death using flow cytometry Karpas 620 MM cells as target cells were co-incubated with PBMC from MM patients (n=13, Table 18) as effector cells at an E:T ratio 10:1 in presence of increasing concentration of NKp46-BCMA_Fc-ADE-DSB, Isotype control antibody (10 mg/ml) or Daratumumab (10 mg/ml).

To this end, NKp46-BCMA_Fc-ADE-DSB were used to treat Karpas 620 MM cells co-incubated with PBMCs from MM patients either at MM diagnosis (N=2) or were relapsed MM cases (N=11). Samples were analyzed by flow cytometry for MM cell death by the loss of CD138 expression. In parallel, the activation of NK cells (CD3-CD56$^{dim}$) by CD107a and IFNg expression was assessed.

Materials and Methods (1) Cell purification and co-culture conditions. The day before the MM cell lysis assay, PBMCs from MM patients isolated after density gradient centrifugation were immediately stained by CD3-PE and CD56-APC and results were analyzed using flow cytometry prior to NK activation to determine the percentage of CD3−/CD56+ cells. When NK cells represented more than 5% of lymphocytes, PBMC were kept in culture medium containing 10% FCS (FCS from Innate Pharma to preserve NK cells) at 37° C. and 5% C02 overnight. Resting PBMC and MM target cell line at a 10:1 ratio were co-cultured in the presence of tested molecules during 4 hours. Then, (i) expression of activation markers (CD107a) and, intracellular production of cytokines (IFNg) on NK cells and (ii) MM cell death (CD138) were analyzed by flow cytometry.

(2) Cell preparation and treatment and control group conditions. 300,000 PBMC and 30,000 MM target cells (Karpas 620) were collected and counted into each well of a U bottom 96-well plates to obtain an effector: target (E:T) cell ratio of 10:1 ratio. 400,000 PBMC were kept in the incubator for minimal phenotyping (CD56, CD3, CD16, NKp46) of patients NK cells. Cells were centrifuge for 5 minutes at 300 g, resuspended in medium containing BD GolgiSTOP™ solution (1/6000), and dispensed at 300,000 PBMCs and 30,000 MM cells per well. Control conditions were as follows: Negative controls were Karpas 620, PBMC, and Karpas 620+PBMCs with no treatment added. Positive control of NK activation was PBMC treated with 125 ng/ml Phorbol 12-myristate 13-acetate (PMA, Sigma, ref P8139) and 1 mg/ml Ionomycin (Sigma, ref 10634). Treatment groups were isotype control (10 mg/ml), NKp46-BCMA_Fc-ADE-DSB (10 mg/ml) added to the co-culture samples for 4 hours at 37±1° C. and 5±1% C02. Before addition of the treatment, antibodies were centrifuged at 16000×g for 10 minutes at +4° C. to eliminate potential aggregates.

(3) Staining and flow cytometric analysis. After 4 hours of co-incubation at 37±1° C. and 5±1% C02, cells were extracellularly or intracellularly stained for flow cytometric analysis. (3a) Extracellular staining. Cells were transferred to a V-bottom plate and centrifuged for 1 minute at 1900×g, the supernatant was discarded. Cells were washed with 200 μl PBS, and again centrifuged for 1 minute at 1900×g, discarding the supernatant. 50 μl of BD Pharmingen Stain Buffer BSA/Brilliant Stain buffer plus antibody master mix was added to each sample. The antibodies used for NK activation and MM cell death analysis are shown in Table 19 below. Subsequently, cells were incubated for 20 minutes at 4° C. in the dark. Finally, cells were washed with 200 μl of Stain Buffer, centrifuged for 1 minute at 1900 g, and the supernatant was discarded (×2). (3b) Intracellular staining. Cells were resuspended in 100 ml BD Cytofix/Cytoperm and incubated for 20 minutes at 4° C. in dark. Cells were washed two times in 200 μl of 1×BD Perm/Wash buffer (10×BD Perm/Wash buffer in distilled $H_2O$), centrifuged for 1 minute at 1900 g, and the supernatant was discarded. Cells were resuspended in 50 μl of antibody master mix plus BD Perm/Wash buffer and incubated for 30 minutes at 4° C. in dark. Subsequently, cells were washed twice with 200 μl of BD Perm/Wash buffer, centrifuge for 1 minute at 1900 g, and the supernatant was discarded. Finally, cells were resuspended in 200 μl Stain Buffer and flow cytometric analysis was performed. Before acquisition, UltraComp eBeads (Invitrogen) were stained with each antibody fluorophore to set up appropriate fluorescence compensation controls. Results were analyzed using BD FACSymphony A5 and BD FACSDiva Software. The analysis was done using FlowJo software.

TABLE 19

Antibodies for NK activation and MM cell death analysis

| Antibodies | Supplier | Reference | Comments |
| --- | --- | --- | --- |
| Anti- human CD3-PB | BD Biosciences | 625565 | Clone SP34-2, 1/100 dilution |
| Anti-human CD56-BUV737 | BD Biosciences | 612767 | Clone NCAM16.2, 1/200 dilution |
| Anti-human | Miltenyi | 130-119-869 | Clone H4A3, |

TABLE 19-continued

Antibodies for NK activation and MM cell death analysis

| Antibodies | Supplier | Reference | Comments |
| --- | --- | --- | --- |
| CD107a(LAMP-1)-APC | | | 1/100 dilution |
| Anti-human CD69-BV650 | Biolegend | 310934 | Clone FN50, 1/100 dilution |
| Anti-human CD138-PerCP-eF710 | ThermoFisher | 46-1388-41 | Clone MI15, 1/50 dilution |
| Anti-human CD38-BUV395 | BD Biosciences | 563811 | Clone HB7, 1/50 dilution |
| Anti-human MIP1β-PE | BD Biosciences | 550078 | Clone D21-1351, 1/80 dilution |
| Anti-human IFNγ-AF488 | Biolegend | 502515 | Clone 4S.B3, 1/20 dilution |

Results

Karpas 620 MM cell death induced by NKp46-BCMA_Fc-ADE-DSB was first analyzed by measuring the loss of CD138 expression by flow cytometry. NKp46-BCMA_Fc-ADE-DSB demonstrated the induction of Karpas 620 MM cell death when co-cultured with 10 out of 13 MM patient PBMC regardless of the stage of the disease. As expected, Isotype control does not induce MM cell death. Interestingly, the MM cell death induced by NKp46-BCMA_Fc-ADE-DSB at 10 mg/ml was significant ($p=0.0105$, FIG. 33A).

In parallel, the capacity of NKp46-BCMA_Fc-ADE-DSB to induced NK cell activation by the measurement of IFNg and CD107a expression on $NK^{dim}$ cells was assessed (FIG. 33B and FIG. 33C). Expression of IFNg and CD107a is induced more specifically in response to NKp46-BCMA_Fc-ADE-DSB than Isotype control.

Taken together, these results indicate that the NKp46-BCMA_Fc-ADE-DSB has therapeutic potential for treating patients with primary or refractory MM.

Example 16. Ex Vivo Functional Activity of NKp46-BCMA_Fc-ADE-DSB on MM Patient Samples This example assesses the capacity of NKp46-BCMA_Fc-ADE-DSB to induce MM cell death using primary samples from MM patients. Cell death was determined by the decrease of $CD138^+$ MM cells.

Materials and Methods (1) Cell purification and co-culture conditions. On the day of the MM cell death assay, bone marrow mononuclear cells (BMMCs) from MM patients were isolated by gradient density centrifugation using Ficoll-Hypaque and were immediately stained with an anti-CD138-PE monoclonal antibody and analyzed using flow cytometry in order to determine percentage of MM cells ($CD138^+$ cells). BMMC or PBMC were incubated in the presence of negative control or SAR445514 or Daratumumab for 18 hours.

(2) Cell preparation and treatment and control group conditions. 400,000 BM MC were seeded in each well of a U bottom 96-well plates in RPMI containing 5% FCS and 3 ng/ml recombinant human IL-6. 600,000 PBMC were kept in the incubator for minimal phenotyping (CD56, CD3, CD16, NKp46) of patient NK cells and to determine BCMA expression of MM cells. Control conditions were as follows: negative controls were BMMCs or PBMCs with no treatment added. Treatment groups were isotype control (10

µg/ml), NKp46-BCMA_Fc-ADE-DSB (10 µg/ml) added to the samples for 18 hours at 37±1° C. and 5±1% C02. Before addition of the treatment, antibodies were centrifuged at 16000×g for 10 minutes at +4° C. to eliminate potential aggregates.

(3) Staining and flow cytometric analysis. After 18 hours of co-incubation at 37±1° C. and 5±1% C02, cells were extracellularly stained for flow cytometric analysis. (3a) Cells were transferred to a V-bottom plate and centrifuged for 1 minute at 1900×g. The supernatant was discarded, and the cells were washed with 200 µl PBS, and again centrifuged for 1 minute at 1900×g. The supernatant was discarded. 50 µl of BD Pharmingen Stain Buffer BSA/Brilliant Stain buffer plus antibody master mix was added to each sample and incubated for 30 minutes at 4° C. in the dark. Cells were washed with 200 µl of BD Pharmingen Stain Buffer BSA, centrifuged for 1 minute at 1900 g, with the supernatant discarded. This was repeated for a second time. The cells were resuspended in 50 µl at 1% Para-Formaldehyde in PBS and incubated 15 minutes at 4° C. in the dark. The cells were then washed once in 200 µl of BD Pharmingen Stain Buffer BSA ad resuspended in 200 µl of BD Pharmingen Stain Buffer BSA to perform the flow cytometric analysis, Before sample acquisition, UltraComp eBeads (Invitrogen) were stained with each antibody fluorophore to set up appropriate fluorescence compensation controls. Samples and eBeads were acquired using a BD FACSymphony A5 with BD FACSDiva software. The analysis was done using FlowJo software.

NK cell activation was assessed by CD16, CD107a, and CD69 expression on CD3−/CD56$^{dim}$ NK cells. Myeloma cell death was assessed by the disappearance of CD138$^+$ cells.

TABLE 20

Antibodies for NK phenotyping.

| Antibodies | Supplier | Reference | Comments | Batch number |
|---|---|---|---|---|
| Anti-human CD3-PB | BD Biosciences | 625565 | Clone SP34-2, 1/100 dilution | 1050279 |
| Anti-human CD56-APC | Miltenyi | 130-113-310 | Clone REA196, 1/50 dilution | 5211004411 |
| Anti-human CD16-BUV395 | BD Biosciences | 563785 | Clone 3G8, 1/40 dilution | 1228896 |
| Anti-human NKp46-PE | BD Biosciences | 557991 | Clone 9E2, 1/10 dilution | 1209394 |
| Anti-human IgG1-PE | BD Biosciences | 555749 | Clone MOPC-21, 1/10 dilution | 1174457 |

TABLE 21

Antibodies used for NK cell activation and myeloma cell death.

| Antibodies | Supplier | Reference | Comments | Batch number |
|---|---|---|---|---|
| Anti-human CD3-PB | BD Biosciences | 625565 | Clone SP34-2, 1/100 dilution | 1050279 |
| Anti-human CD56-BUV737 | BD Biosciences | 612767 | Clone NCAM16.2, 1/200 dilution | 2047937 |
| Anti-human CD16-BUV615 | BD Biosciences | 751572 | Clone 3G8, 1/100 | 2042713 |
| Anti-human CD107a(LAMP-1)-APC | Miltenyi | 130-119-869 | Clone H4A3, 1/100 dilution | 5220402481-5220509946 |
| Anti-human CD69-BV650 | Biolegend | 310934 | Clone FN50, 1/100 dilution | B356230 |
| Anti-human CD138-PerCP-eF710 | ThermoFisher | 46-1388-41 | Clone MI15, 1/50 dilution | 2403185 |
| Anti-human CD38-BUV395 | BD Biosciences | 563811 | Clone HB7, 1/50 dilution | 2004473 |

TABLE 22

Antibodies used for multiple myeloma cell characterization.

| Antibodies | Supplier | Reference | Comments | Batch number |
|---|---|---|---|---|
| Anti-human CD138-PerCP-eF710 | ThermoFisher | 46-1388-41 | Clone MI15, 1/50 dilution | 2403185 |
| Anti-human CD38-BUV395 | BD Biosciences | 563811 | Clone HB7, 1/50 dilution | 2004473 |
| BCMA-PE-Dazzle594 | Biolegend | 357511 | Clone 19F2, 1/25 dilution | B357269 |
| mIgG2aPE-Dazzle594 | Biolegend | 400276 | Clone MOPC-173, 1/25 dilution | B346418 |

Results

The ex vivo activity of NKp46-BCMA on MM patient samples (N=16) was studied. For this, BMMCs or PBMCs from multiple myeloma patients were untreated, were treated with 10 mg/ml NKp46-BCMA_Fc-ADE-DSB, or were treated with 10 µg/mL of isotype control for 18 hours. MM cell death was measured by by the loss of CD138 expression using flow cytometry. FIG. 16A-16C depicts the results comparing ex vivo NKp46=BCMA_Fc-ADE-DSB NKCE treatment in samples from treatment-naïve patients against those who have received standard of care therapies prior or who were included in clinical trials. Patient samples were more responsive to NKp46-BCMA_Fc-ADE-DSB treatment if treatment-naïve to daratumumab (FIG. 16A), and were slightly less likely to respond if the patient had multiple rounds of relapse (FIG. 16B). FIG. 16C illustrates that samples were less responsive to NKp46-BCMA_Fc-ADE-DSB after relapse >4 TC.

These data demonstrate that NKp46-BCMA_Fc-ADE-DSB NKCE induces MM cell death in samples from MM patients at different stage of the disease (diagnosis or relapse).

Example 17. Combined Pharmacokinetic (PK) and Safety Study Following Repeated Subcutaneous Administration in Cynomolgus Monkeys Methods and Materials A stock solution of NKp46-BCMA_Fc-ADE-DSB was provided at a concentration of 50 mg/mL in 10 mM histidine, pH5.5, 8% sucrose, 0.05% PS80, and 10 µM EDTA.

Dose levels and administration: Non-human primate (NHP) cynomolgus monkeys (*Macaca fascicularis*), both sexes (male and female), were administered NKp46-BCMA_Fc-ADE-DSB via a subcutaneous route (SC, dorsal area) at 1 mL/kg once a week (on Days 1, 8, and 15) for three weeks.

TABLE 23

Dose levels and animal identification per group.

| Dosing regimen and route | Dose level (µg/kg/adm) | Concentration (µg/mL) | Dose volume (mL/kg) | Animal id. Male | Female |
|---|---|---|---|---|---|
| Repeat-dose SC | 25 000 | 25 000 | 1 | 22-23 | — |
| Repeat-dose SC | 50 000 | 50 000 | 1 | — | 24-25 |

Samples collected: Plasma was collected for pharmacokinetics (PK) and for cytokines evaluation.

PK samples: Plasma samples for PK data were collected at: Day 1 at 1, 5, and 24 hours; Day 8 at 0 and 24 hours; and Day 15 at 0, 1, 5, 24, and 144 hours.

Cytokines (INF-g, IL-6, IL-8 and TNF-α) evaluation: Sampling timepoints were before treatment, 5, and 24 hours post each dosing (on Days 1, 8 and 15). The sampling site was from the femoral, saphenous, and/or cephalic vein. The blood samples (0.5 mL) were collected in a K2-EDTA sampling tube. The determination of INF-g, IL-6, IL-8 and TNF-a in monkey plasma samples was done using an exploratory ECLIA (ElectroChemiluminescent ImmunoAssay) method from Mesoscale Discovery (U-PLEX Proinflam Combo 1 (NHP) SECTOR assay kit, Catalog #K15070K-2). All variations are expressed as compared to baseline values (before the first dosing on Day 1). Due to the analytical variability, cytokines increases were considered biologically significant when values were more than 2-fold higher than the corresponding baseline value. The grading was applied as followed: s 2-fold changes: no biological relevant changes; 3 to 10-fold changes: very minimal increase; 11 to 100-fold changes: minimal increase; 101 to 1000-fold changes: moderate increase; and, ≥1001-fold changes: marked increase.

Results

NKp46-BCMA_Fc-ADE-DSB concentrations in plasma were determined using an exploratory immunoassay method running on Gyrolab platform. Descriptive statistics (mean and % CV) NKp46-BCMA_Fc-ADE-DSB PK parameters in plasma after each weekly SC dosing of NKp46-BCMA_Fc-ADE-DSB to cynomolgus monkeys are presented in Table 24. Individual NKp46-BCMA_Fc-ADE-DSB PK parameters are presented in Table 25. Individual (and mean) NKp46-BCMA_Fc-ADE-DSB plasma concentration values) are presented in Table 26.

TABLE 24

Mean and CV % NKp46-BCMA_Fc-ADE-DSB PK parameters in plasma after 3 weekly (n = 2 animals/dose) SC administration of NKp46-BCMA_Fc-ADE-DSB to male and female monkeys.

| Route and dosing regimen | Dose (µg/kg/adm) | Day | Sex | | $C_{max}$ (ug/mL) | $t_{max}$ (day) | $AUC_{last}$ (day*ug/mL) | $t_{last}$ (day) | $AUC_{0-7\ d}$ (day*ug/mL) | $AUC_{0-35\ d}$ (day*ug/mL) |
|---|---|---|---|---|---|---|---|---|---|---|
| Repeated SC | 25 000 | 1 | M | Mean | 182 | 1 | 1070 | 7 | 1070 | NA |
| | | 8 | M | Mean | 301 | 1 | 1730 | 7 | 1730 | NA |
| | | 15 | M | Mean | 391 | 1 | 2100 | 7 | 2100 | NA |
| | 50 000 | 1 | F | Mean | 279 | 7 | 1710 | 7 | 1710 | NA |
| | | 8 | F | Mean | 498 | 1 | 3200 | 7 | 3200 | NA |
| | | 15 | F | Mean | 743 | 1 | 4450 | 7 | 4450 | NA |

Abbreviations:
AUC: area under the concentration versus time curve calculated using the trapezoidal method from time 0 to infinity;
$AUC_{0-x\ d}$: area under the concentration versus time curve calculated using the trapezoidal method from time 0 to x days;
$AUC_{last}$: area under the concentration versus time curve calculated using the trapezoidal method from time 0 to the real time $t_{last}$;
$C_{max}$: maximum observed concentration;
CV: coefficient of variation;
F: female;
M: male;
NA: not applicable;
SC: subcutaneous;
$t_{last}$: time of last measurable concentration
Mean values only at 25 000 and 50 000 µg/kg/adm as n = 2 animals/dose
$AUC_{0-7\ d}$ correspond to NKp46-BCMA_Fc-ADE-DSB exposure not impacted by the presence of ADA on Day 1

After 3 weekly SC administrations, slight NKp46-BCMA_Fc-ADE-DSB accumulation was observed in the plasma on Days 8 and 15, with accumulation ratios ranging from 1.6 to 2.6 at 25,000 and 50,000 µg/kg/adm (i.e., 25 and 50 mg/kg/adm), respectively (FIG. 34A and FIG. 34B).

Overall, after NKp46-BCMA_Fc-ADE-DSB SC dosing in monkeys, bioavailability was close to 90%.

TABLE 25

Individual and mean NKp46-BCMA_Fc-ADE-DSB PK parameters in plasma observed on Days 1, 8, and 15 after 3 weekly SC administration of NKp46-BCMA_Fc-ADE-DSB at 25,000 and 50,000 µg/kg/adm to male and female monkeys.

| Route | Dose (µg/kg/adm) | Day | Sex | Animal Id. | $C_{max}$ (ug/mL) | $t_{max}$ (day) | $AUC_{last}$ (day*ug/mL) | $t_{last}$ (day) | $AUC_{0-7\ d}$ (day*ug/mL) |
|---|---|---|---|---|---|---|---|---|---|
| SC | 25 000 | 1 | M | 22 | 173 | 1 | 1030 | 7 | 1030 |
| | | | | 23 | 190 | 1 | 1110 | 7 | 1110 |
| | | | | Mean | 182 | 1 | 1070 | 7 | 1070 |
| SC | 25 000 | 8 | M | 22 | 308 | 1 | 1770 | 7 | 1770 |
| | | | | 23 | 294 | 1 | 1700 | 7 | 1700 |
| | | | | Mean | 301 | 1 | 1730 | 7 | 1730 |
| SC | 25 000 | 15 | M | 22 | 372 | 1 | 1890 | 7 | 1890 |
| | | | | 23 | 409 | 1 | 2300 | 7 | 2300 |
| | | | | Mean | 391 | 1 | 2100 | 7 | 2100 |
| SC | 50 000 | 1 | F | 24 | 285 | 7 | 1640 | 7 | 1640 |
| | | | | 25 | 273 | 7 | 1780 | 7 | 1780 |
| | | | | Mean | 279 | 7 | 1710 | 7 | 1710 |
| SC | 50 000 | 8 | F | 24 | 517 | 1 | 3380 | 7 | 3380 |
| | | | | 25 | 479 | 1 | 3020 | 7 | 3020 |
| | | | | Mean | 498 | 1 | 3200 | 7 | 3200 |
| SC | 50 000 | 15 | F | 24 | 768 | 1 | 4620 | 7 | 4620 |
| | | | | 25 | 718 | 1 | 4280 | 7 | 4280 |
| | | | | Mean | 743 | 1 | 4450 | 7 | 4450 |

Abbreviations:
$AUC_{0-x\ d}$: area under the concentration versus time curve calculated using the trapezoidal method from time 0 to x days;
$AUC_{last}$: area under the concentration versus time curve calculated using the trapezoidal method from time 0 to the real time $t_{last}$;
$C_{max}$: maximum observed concentration;
F: female;
M: male;
SC: subcutaneous;
$t_{last}$: Time of last measurable concentration;
$t_{max}$: Time of maximum observed concentration
Median for $t_{max}$ and $t_{last}$

TABLE 26

Individual and mean NKp46-BCMA_Fc-ADE-DSB plasma concentration values (μg/mL) observed on Days 1, 8 and 15 after 3 weekly SC administrations of NKp46-BCMA_Fc-ADE-DSB at 25,000 and 50,000 μg/kg/adm to male and female monkeys.

| Route | Dose (ug/kg/adm) | Day | Sex | Animal Id. | Predose | 0.04 | 0.21 | 1 | 6 | 7 |
|---|---|---|---|---|---|---|---|---|---|---|
| | | | | | | Plasma concentrations (ug/mL) | | | | |
| SC | 25 000 | 1 | M | 22 | — | 8.82 | 75.5 | 173 | — | 136$^a$ |
| | | | | 23 | — | 9.20 | 85.0 | 190 | — | 141$^a$ |
| | | | | Mean | NA | 9.01 | 80.3 | 182 | NA | 139$^a$ |
| SC | 25 000 | 8 | M | 22 | 136 | — | — | 308 | — | 208$^b$ |
| | | | | 23 | 141 | — | — | 294 | — | 199$^b$ |
| | | | | Mean | 139 | NA | NA | 301 | NA | 204$^b$ |
| SC | 25 000 | 15 | M | 22 | 208 | 230 | 291 | 372 | 180 | 208$^c$ |
| | | | | 23 | 199 | 240 | 297 | 409 | 282 | 199$^c$ |
| | | | | Mean | 204 | 235 | 294 | 391 | 231 | 204$^c$ |
| SC | 50 000 | 1 | F | 24 | — | 5.02 | 58.9 | 222 | — | 285$^a$ |
| | | | | 25 | — | 14.1 | 127 | 265 | — | 273$^a$ |
| | | | | Mean | NA | 9.56 | 93.0 | 244 | NA | 279$^a$ |
| SC | 50 000 | 8 | F | 24 | 285 | — | — | 517 | — | 477$^b$ |
| | | | | 25 | 273 | — | — | 479 | — | 403$^b$ |
| | | | | Mean | 279 | NA | NA | 498 | NA | 440$^b$ |
| SC | 50 000 | 15 | F | 24 | 477 | 453 | 558 | 768 | 612 | 477$^c$ |
| | | | | 25 | 403 | 463 | 572 | 718 | 555 | 403$^c$ |
| | | | | Mean | 440 | 458 | 565 | 743 | 584 | 440$^c$ |

Abbreviations:
F: female;
M: male;
NA: not applicable;
SC: subcutaneous
—: Not scheduled sample
$^a$Duplicated concentration values obtained at the predose time point on Day 8 before the 2nd injection
$^b$Duplicated concentration values obtained at the predose time point on Day 15 before the 3rd injection
$^c$Duplicated concentration values obtained at the predose time point on Day 15 before the 3rd injection (assuming steady state)

Cytokines (INF-g, IL-6, IL-8 and TNF-a) evaluation: The cytokines (INF-g, IL-6, IL-8 and TNF-a) were measured in plasma samples taken at timepoints specified in the Methods and Materials section. Following weekly SC dosing, no changes in IFN-g and TNF-a levels were observed in any animals. For IL-6 (FIG. 35), only transient and very minimal (up to 10-fold changes in Female No. 25) to minimal (up to 21-fold changes in Female No. 24) increases were observed following the highest dose tested of 50 mg/kg/adm. For IL-8, very minimal increases (up to 6-fold changes) were observed in both animals administered 25 mg/kg/adm.).

Example 18. Study of NKp46-BCMA NKCE Binding Proteins in Patients with Multiple Myeloma This is a first-in-human Phase 1/Phase 2 study for evaluating the NKp46-BCMA NKCE as disclosed herein in participants with relapsed/refractory multiple myeloma (r/r MM).

The study will comprise three parts. First, a dose escalation phase in r/r MM participants that will evaluate several doses administered to determine two doses that will be tested in the dose optimization part. Secondly, a dose optimization phase that will be evaluating two doses determined from the dose escalation phase to determine the preliminary recommended Phase 2 dose (pRP2D) and schedule for the NKp46-BCMA NKCE. Thirdly, a dose expansion phase that will evaluate the preliminary efficacy of the confirmed recommended Phase 2 dose (cRP2D) and schedule for NKp46-BCMA NKCE in r/r MM patients.

Participants will be enrolled and treated by study intervention and separated as such: about 18-30 participants in the first part/dose escalation phase; about 30 participants in the second part/dose optimization phase; and about 15 participants the third part/dose expansion.

The duration of the study for a participant will include a screening period of up to 28 days prior to day 1 of cycle 1 (C1D1), a treatment period where enrolled participants will receive administration of 4 weeks cycles of NKp46-BCMA NKCE subcutaneously. The end of treatment visit will occur 30 days (+/−7 days) from last investigational medicinal product administration or prior initiation of further therapy, whichever comes first.

Primary Outcome Measures:
  Dose escalation: Presence of dose limiting toxicities (DLT). DLTs will be defined using NCI CTCAE version 5.0 or ASTCT criteria for CRS or ICANS.
  Dose optimization: Overall response rate (ORR). ORR is defined as the proportion of participants with stringent complete response (sCR), complete response (CR), very good partial response (VGPR), and partial response (PR) according to the 2016 International Myeloma Working Group (IMWG) criteria, after the last participant is treated for at least 4 cycles or prematurely discontinued.
  Dose expansion: Overall response rate (ORR). ORR is defined as the proportion of participants with stringent complete response (sCR), complete response (CR), very good partial response (VGPR), and partial response (PR) according to the 2016 International Myeloma Working Group (IMWG) criteria.

Secondary Outcome Measures:
  Dose escalation overall response rate (ORR): ORR defined as the proportion of participants with sCR, CR, VGPR, and PR according to the 2016 IMWG criteria.

Dose optimization: Presence of DLT and percentage of participants experiencing treatment-emergent adverse events (TEAEs). TEAEs are defined as adverse events that develop, worsen, or become serious during the treatment period. The treatment period is defined as the time from first dose of study treatment up to 30 days after last dose of study treatment.

Dose optimization and expansion:
  Very good partial response or Better Rate
  Duration of response (DOR). DOR is defined as the time from the date of the first response to the date of the first occurrence of progressive disease (PD as determined by the investigator or death from any cause, whichever happens first. DOR is determined only for participants who have achieved a response (PR or better).
  Time to first response (TT1R): TT1R is defined as the time from the date of the first response to the date of the first occurrence of progressive disease (PD as determined by the investigator or death from any cause, whichever happens first. DOR is determined only for participants who have achieved a response (PR or better).
  Time to best response (TTBR): TTBR is defined as the time from the first administration of the IMP to the date of first occurrence of best overall response (PR or better) that is subsequently confirmed.
  Progression free survival (PFS): PFS is defined as the time from the date of the first administration of the IMP to the date of first documentation of progressive disease or the date of death from any cause, whichever comes first. Responses will be determined according to IMWG criteria. Progression based on paraprotein will be confirmed based on two consecutive assessments.
  Overall survival (OS): OS is defined as the time from the date of the first administration of the IMP to death from any cause.
  Clinical benefit rate (CBR): CBR is the rate of participants with confirmed CR or PR at any time or stable disease (SD) of at least 6 months from the first IMP administration determined by the Investigator per IMWG 2016 criteria.
  Percentage of participants experiencing treatment-emergent adverse events (TEAEs): Treatment-emergent adverse events (Aes) are defined as Aes that develop, worsen, or become serious during the treatment period. The treatment period is defined as the time from first dose of study treatment up to 30 days after last dose of study treatment.
  Incidence rate of infusion associated reactions (IARs)
  Incidence rate of injection site reactions (ISR)
  Incidence of laboratory abnormalities
  Assessment of pharmacokinetics (PK) parameters of NKp46-BCMA NKCE in monotherapy AUClast: Area under the plasma concentration versus time curve calculated using the trapezoidal method from time zero to time of the last concentration observed above the lower limit of quantification (ie, Clast)
  Assessment of pharmacokinetics (PK) parameters of NKp46-BCMA NKCE in monotherapy: Cmax (maximum observed concentration)
  Assessment of pharmacokinetics (PK) parameters of SAR445514 in monotherapy: Tmax (first time to reach Cmax)
  Incidence of anti-drug antibody (ADA) against NKp46-BCMA NKCE in monotherapy
  Minimum Residual Disease (MRD) negativity rate: MRD status in patients with response of VGPR or better Inclusion criteria:
Participants must have:
  A documented diagnosis of multiple myeloma
  Relapsed/refractory mutiple myeloma (r/r MM)
  Measureble disease for r/r MM
  Participants with MM must have received at least 2 prior lines of therapy which must include at least 2 consecutive cycles of a second or third generation immunomodulator, steroid, proteasome inhibitor and anti-CD38 monoclonal antibody
  Must have documented evidence of progressive disease (PD), as per IMWG 2016 criteria
  For dose escalation, body weight within 40 to 120 kg
  Capable of giving signed informed consent Exclusion criteria:
  Primary refractory MM defined as participants who never achieved at least a minimal response with any treatment during the disease course
  Second primary malignancy
  Primary systemic LCA and plasma cell leukemia
  Congestive heart failure
  Uncontrolled infection within 14 days prior to study treatment
  Known acquired immunodeficiency syndrome-related illness or known human immunodeficiency virus (HIV) disease requiring antiviral treatment or active hepatitis A (defined as positive hepatitis A antigen or positive IgM); HIV serology at screening will be tested for participants in countries where it is required by local regulations
  Uncontrolled or active hepatitis B virus (HBV) infection: participants with positive B surface antigen (HBsAg) and/or HBV deoxyribonucleic acid (DNA)
  Active hepatitis C virus (HCV) infection: positive HCV ribonucleic acid (RNA) and negative anti-HCV
  Any anti-MM drug treatment within 14 days before study treatment
  Prior allogenic hematopoietic stem cell (HSC) transplant with active graft-versus-host disease (GvHD) (GvHD any grade and/or being under immunosuppressive treatment within the last 2 months prior to randomization)
  Any major procedure within 14 days before the initiation of the study treatment
  Administration of an anti-CD38 monoclonal antibody (isatuximab or daratumumab) less than 90 days prior to the first administration of study treatment
  Administration of an anti-BCMA agent (including, but not limited to, CAR T-cells, TCEs, antibody drug conjugate) less than 21 days prior to the administration of study treatment
  Unresolved toxicities from prior anticancer therapy, defined as not having resolved to CTCAE Version 5.0 Grade 1.
  Participants with a contraindication to dexamethasone
  Received any other investigational drugs or prohibited therapy for this study within 28 days or 5 half-lives from study treatment, whichever is shorter
  Hemoglobin <8 g/dL (5.0 mmol/L)
  Platelets $<50\times10^9$/L (not permissible to transfuse a participant within 1 weeks prior to the screening platelet count to reach this level)
  Absolute neutrophil count (ANC)<1000 µL ($1\times10^9$/L)

Creatinine clearance <30 mL/min (Modification of Diet in Renal Disease Formula)

Total bilirubin >1.5×upper limit of normal (ULN) (unless the subject has documented Gilbert syndrome in which case direct bilirubin should not be >2.5×ULN)

Aspartate aminotransferase (AST/SGOT) or Alanine aminotransferase (ALT/SGPT)>2.5×ULN Patients with Grade 3 or 4 hypercalcemia (corrected serum calcium of >12.5 mg/dL; >3.1 mmol/L; ionized calcium >1.6 mmol/L; or requiring hospitalization) will not be eligible unless patients recover to Grade 2 or less under anti-hypercalcemia treatment.

Individuals accommodated in an institution because of regulatory or legal order; prisoners or participants who are legally institutionalized Participant not suitable for participation, whatever the reason, as judged by the Investigator Sensitivity to any of the study interventions, or components thereof, or drug or other allergy that, in the opinion of the Investigator, contraindicates participation in the study

Example 19. Study of NKp46-BCMA NKCE Binding Proteins in Patients with Relapsed/Refractory Light Chain Amyloidosis Single and combination chemotherapy agent or immunotherapy regimens used to treat LCA are often difficult for the patient to tolerate and patients often succumb to lasting side effects of the current LCA treatment regimens. Hassan and Sanchorawala (2022), Hemato, vol. 3: 38-46; Sidiqi & Gertz (2021), Blood Cancer Journal, vol. 11: 90.

The natural killer cell engager designed herein is potent but has a favorable toxicity profile in other contexts. Therefore, it is hypothesized the natural killer cell engager will also have therapeutic efficacy for patients with LCA.

A Phase 1 study of the safety, tolerability and feasibility of dosing patients with relapsed/refractory light chain amyloidosis with a NKp46-BCMA NKCE as disclosed herein is performed. This study is to identify the dose and regimen of NKp46-BCMA NKCE that can be safely administered in patients. Patients are monitored throughout the study for toxicity, adverse side effects, and progression of the disease. Patients diagnosed with light chain amyloidosis without a prior diagnosis of multiple myeloma are selected for this study.

Study Overview:

This is a first-in-human, open-label Phase 1/2 study to investigate the safety and efficacy of a NKp46-BCMA NKCE, an NK cell engager targeting B-cell maturation antigen (BCMA), as a monotherapy in patients with relapsed/refractory light-chain amyloidosis (RRLCA).

Inclusion and Exclusion Criteria:

Enrollment of patients who have a documented diagnosis of light chain amyloidosis and who have received at least one prior line of treatment comprising at least one proteasome inhibitor will be allowed. Patients must present with measurable disease according to the International Society of Amyloidosis (ISA) 2012 update, and must have documented evidence of progressive disease (PD), as per ISA 2012 criteria. Patients should have one or more organ impacted by amyloidosis as per the National Comprehensive Cancer Network (NCCN) guidelines.

For dose escalation purposes, the patient's body weight should be between 50 to 100 kg. Patients must also be adults over the age of 18 and must also be capable of giving signed informed consent.

Patients will be excluded from the study if any of the following are demonstrated:

1. Evidence of clinically significant cardiovascular condition, defined as one or more of the following:
   a. N-terminal prohormone of brain natriuretic peptide (NT-proBNP)>8500 ng/mL
   b. New York Heart Association (NYHA) classification IIIb or IV heart failure
   c. Heart failure that, in the opinion of the Investigator, is not primarily related to LCA cardiomyopathy (including, but not limited to, ischemic heart disease, uncorrected valvular disease, infections)
   d. Prior event (history) in the last 6 months of acute coronary syndrome, myocardial infarction or unstable angina as well as participants who during the last 6 months experienced a percutaneous cardiac intervention with stent and/or a coronary artery bypass
   e. Hospitalization in the last 4 weeks prior to treatment related to a cardiovascular event
   f. Prior history of arrhythmia and/or cardiac conduction disorders for which a pacemaker or an implantable cardioverter defibrillator (ICD) is required but has not been placed, including, but may not be limited to, sustained ventricular tachycardia, association of an atrioventricular, or sinoatrial nodal dysfunction
2. A systolic blood pressure of <100 mmHg or a diastolic blood pressure of <55 mmHg
3. Previous or current diagnosis of symptomatic multiple myeloma, including the presence of lytic bone disease, plasmacytomas, ≥60% plasma cells in the bone marrow, or hypercalcemia
4. Uncontrolled infection within 14 days prior to study treatment
5. Known acquired immunodeficiency syndrome-related illness or known human immunodeficiency virus (HIV) disease requiring antiviral treatment or active hepatitis A (defined as positive hepatitis A antigen or positive IgM); HIV serology at screening will be tested for participants in countries where it is required by local regulations
6. Uncontrolled or active hepatitis B virus (HBV) infection: participants with positive B surface antigen (HBsAg) and/or HBV deoxyribonucleic acid (DNA)
7. Active hepatitis C (HCV) infection: positive HCV ribonucleic acid (RNA) and negative anti-HCV
8. Any nonlight-chain amyloidosis
8. Prior/Concomitant therapy:
   a. Any anti-multiple myeloma drug treatment within 14 days before study treatment
   b. Prior allogenic hematopoietic stem cell (HSC) transplant with active graft-versus host disease (GvHD) of any grade and/or being under immunosuppressive treatment within the last 2 months prior to randomization
   c. Any major procedure within 14 days before the initiation of the study treatment
   d. Administration of an anti-CD38 monoclonal antibody (isatuximab or daratumumab) less than 90 days prior to the first administration of study treatment
   e. Administration of an anti-BCMA agent (including, but not limited to, CAR T-cells, TCEs, antibody drug conjugates) less than 21 days prior to the administration of study treatment
   f. Unresolved toxicities from prior anticancer therapy, defined as not having resolved to CTCAE Version 5.0 Grade 1 g. Participants with a contraindication to dexamethasone
9. Prior/Concurrent clinical study experience
   a. Received any other investigational drugs or prohibited therapy for this study within 28 days or 5 half-lives from study treatment, whichever is shorter
10. Diagnostic assessments
    a. Hemoglobin of <8 g/dL (5.0 mmol/L)
    b. Platelets <50×10$^9$/L (not permissible to transfuse a participant within 1 weeks prior to the screening platelet count to reach this level)
    c. Absolute neutrophil count (ANC)<1000 μL (1×10$^9$/L)
    d. Creatinine clearance <30 mL/min (Modification of Diet in Renal Disease Formula)
    e. Total bilirubin >1.5×upper limit of normal (ULN), unless the subject has documented Gilbert syndrome in which case direct bilirubin should not be >2.5× ULN)
    f. Aspartate aminotransferase (AST/SGOT) or Alanine aminotransferase (ALT/SGPT)>2.5×ULN
    g. Patients with Grade 3 or 4 hypercalcemia (corrected serum calcium of >12.5 mg/dL; >3.1 mmol/L; ionized calcium >1.6 mml/L; or requiring hospitalization) will not be eligible unless patients recover to Grade 2 or less under anti-hypercalcemia treatment
11. Other exclusions:
    a. Individuals accommodated in an institution because of regulatory or legal order; prisoners or participants who are legally institutionalized
    b. Participant not suitable for participation, whatever the reason, as judged by the investigator
    c. Sensitivity to any of the study interventions, or components thereof, or drug or other allergy that, in the opinion of the Investigator, contraindicates participation in the study Study Objectives:

The primary objectives of this study are to: 1) determine the recommended Phase 2 dose (RP2D) during dose escalation; and 2) determine the hematological response at the combined recommended Phase 2 dose during dose expansion. The pRP2D will take into account the dose-limiting toxicities (DLTs) at cycle 1, the overall safety profile, the pharmacokinetics (if appropriate), and biomarkers will be taken into account. The hematological response is defined as the proportion of participants with stringent complete response (sCR), complete response (CR), very good partial response (VGPR), and partial response (PR) according to the European Society of Hematology/International Society of Hematology working group criteria.

Secondary objectives for the study are to: 1) assess the potential efficacy of NKp46-BCMA NKCE in participants, 2) assess the safety of NKp46-BCMA NKCE in participants, 3) characterize the pharmacokinetics (PK) of NKp46-BCMA NKCE as a monotherapy, 4) evaluate the potential immunogenicity of NKp46-BCMA NKCE as a monotherapy (incidence of anti-drug antibody (ADA) against NKp46-BCMA NKCE), and 5) to assess the minimum residual disease (MRD) negativity rate of NKp46-BCMA NKCE in patients with a response of VGPR or better.

The tertiary objects for the study are to: 1) evaluate the impact of frailty on the clinical outcome (activities of daily living (ADLs) and instrumental activities of daily living (IADLs) questionnaire); 2) evaluate the impact of NKp46-BCMA NKCE on neurological manifestations in RRLCA patients Study Design:

This is a first-in-human (FIH), open-label study to assess safety and efficacy of NKp46-BCMA NKCE, as a single agent in participants with relapsed/refractory LCA (RRLCA). A dose escalation phase in RRLCA to evaluate two doses to ensure the doses are safe. A dose expansion phase will evaluate the preliminary efficacy of the recommended Phase 2 dose (RP2D) and schedule. During the dose escalation phase and the dose expansion phase, NKp46-BCMA NKCE will be administered to participants using a subcutaneous route.

The study will include:

A screening period of up to 28 days prior to starting the study;

A treatment period when enrolled participants will receive the study medication (4-week cycles, subcutaneous administration)

End of treatment visit. The end of treatment visit will occur approximately 30 days from the last study medication or before initiation of further medication, whichever comes first.

The duration of the study for a participant will include:

A screening period: up to 28 days prior day 1 of cycle 1 (C1D1)

A treatment period: enrolled participants will receive administration of 4 weeks cycles of NKp46-BCMA NKCE subcutaneously.

The end of treatment will occur 30 days (+/−7 days) from the last administration of the investigational medicinal product (IMP) or prior initiation of further therapy, whichever comes first.

The follow-up period will continue until death, upon participant's request to discontinue the study, upon final overall survival analysis or upon cancellation of survival follow-up at the discretion of the Sponsor at any timepoint.

Considerations for dose determination will comprise (but might not be limited to) the DLT at Cycle 1, the overall safety profile, the PK, and biomarkers (such as NK cell count, NK cell activation marker, soluble BCMA) and should not exceed the estimated MTD.

Dose expansion will comprise 14 participants treated at the pRP2D. The primary endpoint for the cohort will be hematological response after the last participant is treated for 4 cycles or is prematurely discontinued. LCA hematological response and progression and organ response and progression will be evaluated locally using the ISA 2012 criteria. All participants treated at the cRP2D during dose escalation and dose expansion (exposed population) will be taken into consideration for primary and secondary endpoints analysis. There will be an update of PFS and OS analysis approximately 15 months after LPI, and the cutoff date for final OS analysis will be approximately 30 months after LPE, also done on exposed population.

Risk Assessment:

In this study, the following important potential risks of NKp46-BCMA_NKCE (taking into account existing biological plausibility and the subcutaneous route of administration): infusion reactions, cytokine release syndrome, neurotoxicity (other than ICANs), hypogammaglobulinemia, B cell depletion and infections, viral reactivations, risks in the context of Coronavirus disease 2019 (COVID-19), injection site reaction, immunogenicity, and second primary malignancies.

Endpoints:

Primary Endpoints:

Observations at the End of Dose Escalation:

Presence of dose limiting toxicities (DLT) at the end of cycle 1 (4 weeks) and the percentage of participants experiencing treatment-emergent adverse events (TEAEs) observed from baseline to the end of follow-up (approximately 15 months).

Hematological response (HR). HR is defined as the proportion of participants with stringent complete response (sCR), complete response (CR), very good partial response (VGPR), and partial response (PR) according to the European Society of Hematology/ International Society of Hematology working group guidelines between Cycles 1 to 4 (4 weeks per cycle).

Secondary Endpoints:

Observations at the End of Dose Escalation:

Overall hematological response (OHR). OHR is defined as the proportion of participants with CR, VGPR, and PR according to the International Society of Amyloidosis guidelines (ISA 2012). OHR will be measured from Cycle 1 to the first progressive disease or end of follow-up, whichever comes first (approximately 15 months with cycle of 28 days).

Observations at the End of Dose Extension:

Hematological complete response rate (HCR). HCR is defined as the proportion of patients with complete response according to the ISA 2012. HCR will be evaluated from Cycle 1 to first progressive disease or end of follow-up whichever comes first (approximately 15 months with cycle of 28 days).

Observations at the End of Dose Expansion:

Overall survival (OS). OS is defined as the time from the date of study entry to death from any cause. OS will be evaluated from Cycle 1 to death or the end of follow-up whichever comes first (approximately 15 months with cycle of 28 days).

Progression-free survival (PFS). PFS is defined as time from first administration of the IMP to any of the following: hematological progression, major organ progression (cardiac, kidney, or liver) according to ISA 2012 criteria or death by any cause. PFS will be evaluated from Cycle 1 to first progressive disease (organ or hematological) or end of follow-up whichever comes first (approximately 15 months with cycle of 28 days).

Time to first hematological response (TT1HR). TT1HR is defined as the time from the first administration of the IMP to the date of first hematological response (PR or better) that is subsequently confirmed. TT1HR will be evaluated from Cycle 1 to first progressive disease or the end of follow-up whichever comes first (approximately 15 months with cycle of 28 days).

Duration of hematological response (DOHR). DOHR is defined as time from first administration to the IMP to any of the following: hematological progression, major organ progression (cardiac, kidney, or liver) according to ISA 2012 criteria or death by any cause. DOHR is evaluated from Cycle 1 to first progressive disease or end of follow-up whichever comes first (approximately 15 months with cycle of 28 days).

Percentage of participants experiencing treatment-emergent adverse events (TEAEs). TEAEs are defined as adverse events that develop, worsen, or become serious during the treatment period. The treatment period is defined as the time from first dose of study treatment up to 30 days after last dose of study treatment. TEAEs are evaluated from the first dose of the study treatment up to 30 days after the last dose of study treatment (approximately 1 year with a cycle of 28 days).

Incidence rate of infusion associated reactions (IARs) will be evaluated from cycle 1 to the end of treatment (approximately 1 year with a cycle of 28 days).

Incidence rate of injection site reactions (ISR) will be evaluated from cycle 1 to the end of treatment (approximately 1 year with a cycle of 28 days).

Incidence of laboratory abnormalities will be evaluated from cycle 1 to the end of treatment (approximately 1 year with a cycle of 28 days).

Assessment of pharmacokinetics (PK) parameters of NKp46-BCMA NKCE in a monotherapy will be evaluated from cycle 1 to the end of treatment (approximately 1 year with a cycle of 28 days).

Incidence of anti-drug antibody (ADA) against NKp46-BCMA NKCE in monotherapy will be evaluated from cycle 1 to the end of treatment (approximately 1 year with a cycle of 28 days).

Tertiary Observations:

Impact of frailty on participant clinical outcome using activities of daily living (ADLs) and instrumental activities of daily living (IADLs) questionnaire.

Orthostatic hypotension response rate defined as the rate of participants in the cohort with an increase of orthostatic hypotension by 10 mmHg in participants in the cohort with orthostatic hypotension at screening, as defined as a decrease of 20 mmHg of orthostatic systolic blood pressure in comparison to supine systolic blood pressure.

Performance status improvement rate in the cohort, defined as the number of participants with an improvement of at least 10 in the Karnofsky performance status index.

Levels of cytokines such as interferon-gamma, tumor necrosis factor-alpha (TNF-$\alpha$), interleukin-6 (IL-6), interleukin-1b (IL-1b), MIP-1b, etc.

Immune cell profiling and BCMA+ tumor cell profiling (blood and bone marrow [BM] aspirate).

Cytogenetic abnormalities (mainly but no limited to t[4; 14], t[14; 16]; del[17p], and [1q21+]).

Explore the PK/pharmacodynamics relationship: relationship between NKp46-BCMA_NKCE PK and biomarkers such as NK cell count, NK cell activation marker, soluble BMA, etc.

Dose-Limiting Toxicities (DLTs):

For this study, DLTs will be evaluated using National Cancer Institute (NCI) Common Terminology Criteria for Adverse Events (CTCAE) version 5.0 criteria during Cycle 1 (28 days) to estimate the probability of maximum tolerated dose (MTD).

To be considered as DLT-evaluable participants, participants must complete the DLT evaluation period and receive at least 75% of the planned dose unless occurrence of a DLT. The DLT evaluation period has been selected to be from the first administration of IMP until the end of the $28^{th}$ day.

Considering the mode of action and previous data collected on BCMA targeting agents, main expected treatment-emergent adverse event (TEAEs) are:

Due to NK-cell engagement: infusion reactions;

Due to BCMA targeting: cytopenia (neutropenia, anemia, and thrombocytopenia) associated or not with infections; B-cell aplasia; and hypgammaglobulinemia.

DLTs for this study will comprise:

Hematological DLTs, any of the following unless due to disease progression or an obviously unless due to disease progression or an obviously unrelated cause:

Grade 4 neutropenia lasting more than 7 consecutive days

Grade 3 or higher febrile neutropenia (ANC<1000/mm^3 and a single temperature of >38.3 C or a sustained temperature of ≥38.0° C.) or Grade 3 or higher neutropenic infection.

Grade ≥3 thrombocytopenia associated with bleeding requiring transfusion.

Grade 4 thrombocytopenia lasting more than 7 consecutive days.

Grade 4 anemia, unexplained by the underlying disease.

Platelet transfusions in the absence of bleeding, if not meeting the previous criteria, will not be considered indicative for a DLT because thrombocytopenia is an anticipated complication of MM and participants can enter the study with pre-existing thrombocytopenia.

Nonhematological DLTs, any of the following unless due to disease progression or an obviously unrelated cause:

Any Grade ≥3 non-hematological IMP-related AE excluding:
  Grade 3 fatigue lasting less than 1 week, or
  Grade 3 laboratory abnormalities (excluding electrolytes) improving at least to Grade 2 in less than one week (of not, related Grade 4 should be considered a DLT), or
  Grade ≥3 isolated electrolyte abnormalities that last up to 72 hours, are not clinically complicated, and resolve spontaneously or respond to conventional medication interventions, or
  Grade 3 nausea/vomiting/diarrhea responsive to optimal medical management within 48 hours, or
  Grade 3 infusion associated reaction or cytokine release syndrome that resolves to Grade ≤1 or baseline within 48 hours. any Grade 4 regardless of duration should be a DLT.

Liver impairment: Any Grade ≥3 elevation in the liver enzymes (ALT or AST)

Delay in the initiation of Cycle 2>14 days due to IMP-related laboratory abnormalities or TEAEs.

Any other AE that the Investigator and the Sponsor deem to be dose-limiting, regardless of its severity, may also be considered as DLT.

Study interventions will be administered according to the following sequence: premedication for NKp46-BCMA NKCE (apart from Montelukast, 30-60 minutes prior to NKCE administration), then NKp46-BCMA NKCE.

Participants will receive study treatment until progression, occurrence of unacceptable toxicity, or other permanent discontinuation criteria.

Participants will receive the following medication for at least 4 administrations (except for montelukast and dexamethasone/methylprednisolone) to prevent or reduce the risk of potential adverse events. Apart from montelukast, all premedication is to be given 15 to 50 minutes prior to NKCE administration.

Montelukast (ATC code: R03DC03) 10 mg PO (to be administered only at Cycle 1 Day 1, Day 8, Day 15): 2 hours prior to NKCE administration.

Dexamethasone (ATC code: H02AB02) 20 mg PO given 30 to 60 min prior administration (Cycle 1 Day 1, Day 8, Day 15). Alternatively, methylprednisolone (ATC code: H02AB04) or equivalent can be given at the dose of 100 mg IV (Cycle 1 Day 1, Day 8, Day 15).

Acetominophen (paracetamol ATC code: N02BE01) 650 mg to 1000 mg PO or IV

Diphenhydramine 50 mg PO (ATC code: R05AA02) or equivalent, e.g., cetirizine, promethazine, dexchlorpheniramine, according to the approval availability, or diphenhydramine 25 to 50 mg IV (or equivalent). Intravenous root is to be preferred for the first four NKCE administrations.

Tociliziumab or other institution-recommended interventions should be always available at the site at all times in the vent a participant requires rapid intervention for the treatment of severe cytokine release syndrome.

Efficacy Assessments:

The primary and secondary endpoints will be assessed based on central laboratory M-protein analysis and local assessment for organ progression/response using ISA2012 criteria.

Laboratory tests will be performed at screening (for eligibility), again within 24 hours prior to the start of study treatment administration at Cycle 1/Day 1 (baseline for response assessment) and then Day 1 of every cycle during treatment up to progression and for participants who discontinue study treatment for reasons other than progression, every 4 weeks during follow-up until PD:

M-protein quantification (serum and 24-hour urine, protein immunoelectrophoresis, and immunofixation). After Cycle 1 Day 1, immunofixation will be done in case of undetectable M-protein (serum and urine).

Serum-free light chain levels.

Quantitative immunoglobulins (IgG, IgA, IgM).

Bone Marrow Aspiration:

For quantification of percentage plasma cells is required at screening/baseline (within 21 days prior to study treatment administration). Repeat to confirm CR or sCR if CR or sCR is suspected.

For MRD assessment at screening, time of confirmed CR, 12 months after C1 D1 (for CR patients) and 6 months after first MRD negativity.

For cytogenetics assessment: at screening, bone marrow aspirate will be collected for fluorescent in situ hybridization (FISH) (including, but may not be limited to, del[17p], t[4; 14], t[14; 16]), 1q21+) analysis.

Bone marrow aspiration for genomic and genetic profiling at screening and at time of progression.

All organ involvement should be evaluated at baseline and during the course of the study. Organ progression/response should be evaluated using ISA 2012 criteria.

SEQUENCE LISTING

| Name | Sequence |
|---|---|
| HCDR1 Anti-BCMA | GFTFSNFGMH (SEQ ID NO: 1) |
| HCDR2 Anti-BCMA | VIWSDETNR (SEQ ID NO: 2) |
| HCDR3 Anti-BCMA | DQQYCSSDSCFTWFDP (SEQ ID NO: 3) |

-continued

SEQUENCE LISTING

| Name | Sequence |
|---|---|
| LCDR1 consensus Anti-BCMA | CX$^1$SSTGX$^2$VTPX$^3$X$^4$YAN (SEQ ID NO: 4), wherein X$^1$ is R or A, X$^2$ is T or A, X$^3$ is S or G, and X$^4$ is N or Y |
| LCDR2 consensus Anti-BCMA | DNNX$^5$X$^6$PP (SEQ ID NO: 5), wherein X$^5$ is S, I, or N and X$^6$ is R or K |
| LCDR3 consensus Anti-BCMA | ALX$^7$X$^8$GX$^9$QWV (SEQ ID NO: 6), wherein X$^7$ is W or Y, X$^8$ is F or Y, and X$^9$ is N or G |
| LCDR1 Anti-BCMA CA 10 v2, v6, v7 | CASSTGTVTPSNYAN (SEQ ID NO: 7) |
| LCDR2 Anti-BCMA CA 10 v2, v6, v7 | DNNSRPP (SEQ ID NO: 8) |
| LCDR3 Anti-BCMA CA10 v2, v6, v7 | ALWFGNQWV (SEQ ID NO: 9) |
| LCDR1 Anti-BCMA CA 10 v1 | CRSSTGTVTPSNYAN (SEQ ID NO: 10) |
| LCDR2 Anti-BCMA CA10 v1 | DNNSRPP (SEQ ID NO: 11) |
| LCDR3 Anti-BCMA CA 10 v1 | ALWFGNQWV (SEQ ID NO: 12) |
| LCDR1 Anti-BCMA CA 10 v3 | CASSTGAVTPSNYAN (SEQ ID NO: 13) |
| LCDR2 Anti-BCMA CA 10 v3 | DNNIKPP (SEQ ID NO: 14) |
| LCDR3 Anti-BCMA CA 10 v3 | ALWYGGQWV (SEQ ID NO: 15) |
| LCDR1 Anti-BCMA CA10 v4 | CASSTGAVTPGYYAN (SEQ ID NO: 16) |
| LCDR2 Anti-BCMA CA 10 v4 | DNNNKPP (SEQ ID NO: 17) |
| LCDR3 Anti-BCMA CA 10 v4 | ALYYGGQWV (SEQ ID NO: 18) |
| HCDR1 Anti-NKp46 3D9 and NKp46-1 | GYTFSDYVIN (SEQ ID NO: 19) |
| HCDR1 (IMGT) Anti-Nkp46 3D9 and NKp46-1 | GYTFSDYV (SEQ ID NO: 87) |
| HCDR1 (Chothia) Anti-Nkp46 3D9 and NKp46-1 | GYTFSDY (SEQ ID NO: 88) |

-continued

SEQUENCE LISTING

| Name | Sequence |
|---|---|
| HCDR1 (Honegger) Anti-Nkp46 3D9 and NKp46-1 | ASGYTFSDYV (SEQ ID NO: 89) |
| HCDR2 Anti-NKp46 3D9 and NKp46-1 | EIYPGSGTN (SEQ ID NO: 20) |
| HCDR2 (IMGT) Anti-Nkp46 3D9 and NKp46-1 | IYPGSGTN (SEQ ID NO: 90) |
| HCDR2 (Chothia) Anti-Nkp46 3D9 and NKp46-1 | PGSG (SEQ ID NO: 91) |
| HCDR2 (Honegger) Anti-Nkp46 3D9 and NKp46-1 | IYPGSGTNYYNEKFKAK (SEQ ID NO: 92) |
| HCDR3 Anti-NKp46 3D9 and NKp46-1 | RGRYGLYAMDY (SEQ ID NO: 21) |
| HCDR3 (IMGT) Anti-Nkp46 3D9 and NKp46-1 | ARRGRYGLYAMDY (SEQ ID NO: 93) |
| HCDR3 (Chothia) Anti-Nkp46 3D9 and NKp46-1 | GRYGLYAMD (SEQ ID NO: 94) |
| HCDR3 (Honegger) Anti-Nkp46 3D9 and NKp46-1 | RGRYGLYAMD (SEQ ID NO: 95) |
| HCDR1 (Kabat) Anti-NKp46 3D9 and NKp46-1 alternative length | DYVIN (SEQ ID NO: 80) |
| HCDR2 (Kabat) Anti-NKp46 3D9 and NKp46-1 Alternative length | EIYPGSGTNYYNEKFKA (SEQ ID NO: 81) |
| HCDR3 (Kabat) Anti-NKp46 3D9 and NKp46-1 Alternative length | RGRYGLYAMDY (SEQ ID NO: 21) |

-continued

| Name | Sequence |
|---|---|
| HCDR1 Anti-NKp46 NKp46-2 and 13G4 | SDYAWN (SEQ ID NO: 22) |
| HCDR2 Anti-NKp46 NKp46-2 and 13G4 | YITYSGSTSYNPSLES (SEQ ID NO: 23) |
| HCDR3 Anti-NKp46 NKp46-2 and 13G4 | GGYYGSSWGVFAY (SEQ ID NO: 24) |
| HCDR1 Anti-NKp46 NKp46-3 | EYTMH (SEQ ID NO: 25) |
| HCDR2 Anti-NKp46 NKp46-3 | GISPNIGGTSYNQKFKG (SEQ ID NO: 26) |
| HCDR3 Anti-NKp46 NKp46-3 | RGGSFDY (SEQ ID NO: 27) |
| HCDR1 Anti-NKp46 NKp46-4 | SFTMH (SEQ ID NO: 28) |
| HCDR2 Anti-NKp46 NKp46-4 | YINPSSGYTEYNQKFKD (SEQ ID NO: 29) |
| HCDR3 Anti-NKp46 NKp46-4 | GSSRGFDY (SEQ ID NO: 30) |
| HCDR1 Anti-NKp46 13G4 | SDYAWN (SEQ ID NO: 31) |
| HCDR2 Anti-NKp46 13G4 | YITYSGSTNYNPSLKS (SEQ ID NO: 32) |
| HCDR3 Anti-NKp46 13G4 | CWDYALYAMDC (SEQ ID NO: 33) |
| LCDR1 (Kabat) Anti-NKp46 3D9 and NKp46-1 | RASQDISNYLN (SEQ ID NO: 34) |
| LCDR1 (IMGT) 3D9 and NKp46-1 | QDISNY (SEQ ID NO: 96) |
| LCDR1 (Chothia) 3D9 and NKp46-1 | SQDISNY (SEQ ID NO: 97) |
| LCDR1 (Honegger) 3D9 and NKp46-1 | ASQDISNY (SEQ ID NO: 98) |
| LCDR2 (Kabat) Anti-NKp46 3D9 and NKp46-1 | YTSRLHS (SEQ ID NO: 35) |

-continued

SEQUENCE LISTING

| Name | Sequence |
|---|---|
| LCDR2 (IMGT) 3D9 and NKp46-1 | YTS (SEQ ID NO: 99) |
| LCDR2 (Chothia) 3D9 and NKp46-1 | YTS (SEQ ID NO: 100) |
| LCDR2 (Honegger) 3D9 and NKp46-1 | YTSRLHSGVPSR (SEQ ID NO: 101) |
| LCDR3 (Kabat) Anti-NKp46 3D9 and NKp46-1 | QQGNTRPWT (SEQ ID NO: 36) |
| LCDR3 (IMGT) Anti-Nkp46 3D9 and NKp46-1 | QQGNTRPWTF (SEQ ID NO: 102) or QQGNTRPWT (SEQ ID NO: 111) |
| LCDR3 (Chothia) Anti-Nkp46 3D9 and NKp46-1 | GNTRPW (SEQ ID NO: 103) |
| LCDR3 (Honegger) Anti-Nkp46 3D9 and NKp46-1 | GNTRPW (SEQ ID NO: 104) |
| LCDR1 Anti-NKp46 NKp46-2 | RVSENIYSYLA (SEQ ID NO: 37) |
| LCDR2 Anti-NKp46 NKp46-2 | NAKTLAE (SEQ ID NO: 38) |
| LCDR3 Anti-NKp46 NKp46-2 | QHHYGTPWT (SEQ ID NO: 39) |
| LCDR1 Anti-NKp46 NKp46-3 | RASQSISDYLH (SEQ ID NO: 40) |
| LCDR2 Anti-NKp46 NKp46-3 | YASQSIS (SEQ ID NO: 41) |
| LCDR3 Anti-NKp46 NKp46-3 | QNGHSFPLT (SEQ ID NO: 42) |
| LCDR1 Anti-NKp46 NKp46-4 | RASENIYSNLA (SEQ ID NO: 43) |
| LCDR2 Anti-NKp46 NKp46-4 | AATNLAD (SEQ ID NO: 44) |
| LCDR3 Anti-NKp46 NKp46-4 | QHFWGTPRT (SEQ ID NO: 45) |

SEQUENCE LISTING

| Name | Sequence |
|---|---|
| LCDR1 Anti-NKp46 13G4 | RTSENIYSYLA (SEQ ID NO: 46) |
| LCDR2 Anti-NKp46 13G4 | NAKTLAE (SEQ ID NO: 47) |
| LCDR3 Anti-NKp46 13G4 | QHHYDTPLT (SEQ ID NO: 48) |
| VH-full length Anti-BCMA | QVQLVESGGGVVQPGRSLRLSCAASGFTFSNFGMHWVRQAPGRGLEWVAVIWSDETNRYYADSVKGRFTVSRDNVKSTVYLQMNSLISEDTAVYYCARDQQYCSSDSCFTWFDPWGQGTLVTVSS (SEQ ID NO: 49) |
| VL-full length Anti-BCMA CA 10 v1 | QTVVTQEPSLTVSPGGTVTLTCRSSTGTVTPSNYANWVQQKPDHFFTGLIGDNNSRPPGVPARFSASLIGDKAALTLSGVQPEDEAEYYCALWFGNQWVFGGGTKLTVL (SEQ ID NO: 50) |
| VL-full length Anti-BCMA CA 10 v2 | QTVVTQEPSLTVSPGGTVTLTCASSTGTVTPSNYANWVQQKPGQAPRGLIGDNNSRPPGTPARFSASLLGGKAALTLSGVQPEDEAEYYCALWFGNQWVFGGGTKLTVL (SEQ ID NO: 51) |
| VL-full length Anti-BCMA CA10 v3 | QTVVTQEPSLTVSPGGTVTLTCASSTGAVTPSNYANWVQQKPGQAPRGLIGDNNIKPPWTPARFSGSLLGGKAALTLSGVQPEDEAEYYCALWYGGQWVFGGGTKLTVL (SEQ ID NO: 51) |
| VL-full length Anti-BCMA CA 10 v4 | QTVVTQEPSLTVSPGGTVTLTCASSTGAVTPGYYANWVQQKPGQAPRGLIGDNNNKPPWTPARFSGSLLGGKAALTLSGVQPEDEAEYYCALYYGGQWVFGGGTKLTVL (SEQ ID NO: 53) |
| VL-full length Anti-BCMA CA 10 v6 | QTVVTQEPSLTVSPGGTVTLTCASSTGTVTPSNYANWVQQKPGQFPRGLIGDNNSRPPGTPARFSASLLGGKAALTLSGVQPEDEAEYYCALWFGNQWVFGGGTKLTVL (SEQ ID NO: 54) |
| VL-full length Anti-BCMA CA 10 v7 | QTVVTQEPSLTVSPGGTVTLTCASSTGTVTPSNYANWVQQKPGQAFRGLIGDNNSRPPGTPARFSASLLGGKAALTLSGVQPEDEAEYYCALWFGNQWVFGGGTKLTVL (SEQ ID NO: 55) |
| VH-full length Anti-NKp46 3D9 | QVQLVQSGAEVKKPGSSVKVSCKASGYTFSDYVINWVRQAPGQGLEWMGEIYPGSGTNYYNEKFKAKATITADKSTSTAYMELSSLRSEDTAVYYCARRGRYGLYAMDYWGQGTTVTVSS (SEQ ID NO: 56) |
| VH-full length Anti-NKp46 NKp46-1 | QVQLQQSGPELVKPGASVKMSCKASGYTFTDYVINWGKQRSGQGLEWIGEIYPGSGTNYYNEKFKAKATLTADKSSNIAYMQLSSLTSEDSAVYFCARRGRYGLYAMDYWGQGTSVTVS (SEQ ID NO: 57) |
| VH-full length Anti-NKp46 NKp46-2 | EVQLQESGPGLVKPSQSLSLTCTVTGYSITSDYAWNWIRQFPGNKLEWMGYITYSGSTSYNPSLESRISITRDTSTNQFFLQLNSVTTEDTATYYCARGGYYGSSWGVFAYWGQGTLVTVSA (SEQ ID NO: 58) |
| VH-full length Anti-NKp46 NKp46-3 | EVQLQQSGPELVKPGASVKISCKTSGYTFTEYTMHWVKQSHGKSLEWIGGISPNIGGTSYNQKFKGKATLTVDKSSSTAYMELRSLTSEDSAVYYCARRGGSFDYWGQGTTLTVSS (SEQ ID NO: 59) |
| VH-full length Anti-NKp46 NKp46-4 | QVQLQQSAVELARPGASVKMSCKASGYTFTSFTMHWVKQRPGQGLEWIGYINPSSGYTEYNQKFKDKTTLTADKSSSTAYMLDSLTSDDSAVYYCVRGSSRGFDYWGQGTLVTVSA (SEQ ID NO: 60) |
| VH-full length Anti-NKp46 10B8 | QVQLQESGPGLVKPSQTLSLTCTVSGYSISSDYAWNWIRQPPGKGLEWIGYITYSGSTSYNPSLESRVTISRDTSKNQFSLKLSSVTAADTAVYYCARGGYYGSSWGVFAYWGQGTLVTVSS (SEQ ID NO: 61) |

SEQUENCE LISTING

| Name | Sequence |
|---|---|
| VH-full length Anti-NKp46 12E12 | QVQLVQSGAEVKKPGASVKVSCKASGYTFTSFTMHWVRQ APGQGLEWIGYINPSSGYTEYNQKFKDRVTITADKSTSTAY MELSSLRSEDTAVYYCVRGSSRGFDYWGQGTLVTVSS (SEQ ID NO: 62) |
| VH-full length Anti-NKp46 13G4 | QVQLQESGPGLVKPSQTLSLTCTVSGYSISSDYAWNWIRQ PPGKGLEWIGYITYSGSTNYNPSLKSRVTISRDTSKNQFSL KLSSVTAADTAVYYCARCWDYALYAMDCWGQGTTVTVSS (SEQ ID NO: 63) |
| VL-full length Anti-NKp46 3D9 | DIQMTQSPSSLSASVGDRVTITCRASQDISNYLNWYQQKP GKAPKLLIYYTSRLHSGVPSRFSGSGSGTDFTFTISSLQPE DIATYFCQQGNTRPWTFGGGTKVEIK (SEQ ID NO: 64) |
| VL-full length Anti-NKp46 NKp46-1 | DIQMTQTTSSLSASLGDRVTISCRASQDISNYLNWYQQKPD GTVKLLIYYTSRLHSGVPSRFSGSGSGTDYSLTINNLEQEDI ATYFCQQGNTRPWTFGGGTKLEIK (SEQ ID NO: 65) |
| VL-full length Anti-NKp46 NKp46-2 | DIQMTQSPASLSASVGETVTITCRVSENIYSYLAWYQQKQG KSPQLLVYNAKTLAEGVPSRFSGSGSGTQFSLKINSLQPED FGSYYCQHHYGTPWTFGGGTKLEIK (SEQ ID NO: 66) |
| VL-full length Anti-NKp46 NKp46-3 | DIVMTQSPATLSVTPGDRVSLSCRASQSISDYLHWYQQKS HESPRLLIKYASQSISGIPSRFSGSGSGSDFTLSINSVEPED VGVYYCQNGHSFPLTFGAGTKLELK (SEQ ID NO: 67) |
| VL-full length Anti-NKp46 NKp46-4 | DIQMIQSPASLSVSVGETVTITCRASENIYSNLAWFQQKQG KSPQLLVYAATNLADGVPSRFSGSGSGTQYSLKINSLQSED FGIYYCQHFWGTPRTFGGGTKLEIK (SEQ ID NO: 68) |
| VL-full length Anti-NKp46 10B8 | DIQMTQSPSSLSASVGDRVTITCRVSENIYSYLAWYQQKPG KAPKLLVYNAKTLAEGVPSRFSGSGSGTDFTLTISSLQPED FATYYCQHHYGTPWTFGGGTKVEIK (SEQ ID NO: 69) |
| VL-full length Anti-NKp46 12E12 | DIQMTQSPSSLSASVGDRVTITCRASENIYSNLAWFQQKPG KAPKLLYAATNLADGVPSRFSGSGSGTDYTLTISSLQPED FATYYCQHFWGTPRTFGGGTKVEIK (SEQ ID NO: 70) |
| VL-full length Anti-NKp46 13G4 | DIQMTQSPSSLSASVGDRVTITCRTSENIYSYLAWCQQKPG KAPKLLIYNAKTLAEGVPSRFSGSGSGTDFTLTISSLQPEDF ATYYCQHHYDTPLTFGQGTKLEIK (SEQ ID NO: 71) |
| Polypeptide Chain (I) (light chain) | QTVVTQEPSLTVSPGGTVTLTCASSTGTVTPSNYANWVQQ KPGQAFRGLIGDNNSRPPGTPARFSASLLGGKAALTLSGV QPEDEAEYYCALWFGNQWVFGGGTKLTVLGGGGSGGGG SDIQMTQSPSSLSASVGDRVTITCRASQDISNYLNWYQQK PGKAPKLLIYYTSRLHSGVPSRFSGSGSGTDFTFTISSLQPE DIATYFCQQGNTRPWTFGGGTKVEIKGGGGSGGGGSRTV AAPSVFIFPPSDEQLKSGTASVVCLLNNFYPREAKVQWKV DNALQSGNSQESVTEQDSKDSTYSLSSTLTLSKADYEKHK VYACEVTHQGLSSPVTKSFNRGEC (SEQ ID NO: 72) |
| Polypeptide Chain (II) Heavy chain, full | QVQLVQSGAEVKKPGSSVKVSCKASGYTFSDYVINWVRQ APGQGLEWMGEIYPGSGTNYYNEKFKAKATITADKSTSTA YMELSSLRSEDTAVYYCARRGRYGLYAMDYWGQGTTVTV SSQVQLVESGGGVVQPGRSLRLSCAASGFTFSNFGMHWV RQAPGRGLEWVAVIWSDETNRYYADSVKGRFTVSRDNVK STVYLQMNSLISEDTAVYYCARDQQYCSSDSCFTWFDPW GQGTLVTVSSASTKGPSVFPLAPSSKSTSGGTAALGCLVK DYFPEPVTVSWNSGALTSGVHTFPAVLQSSGLYSLSSVVT VPSSSLGTQTYICNVNHKPSNTKVDKKVEPKSCDKTHTCP PCPAPELLAGPDVFLFPPKPKDTLMISRTPEVTCVVVDVSH EDPEVKFNWYVDGVEVHNAKTKPCEEQYNSTYRCVSVLT VLHQDWLNGKEYKCKVSNKALPAPEEKTISKAKGQPREPQ VYTLPPCRDELTKNQVSLWCLVKGFYPSDIAVEWESNGQP ENNYKTTPPVLDSDGSFFLYSKLTVDKSRWQQGNVFSCSV MHEALHNHYTQKSLSLSPG (SEQ ID NO: 73) |
| Polypeptide Chain (III) (Fc-only) | DKTHTCPPCPAPELLAGPDVFLFPPKPKDTLMISRTPEVTC VVVDVSHEDPEVKFNWYVDGVEVHNAKTKPCEEQYNSTY RCVSVLTVLHQDWLNGKEYKCKVSNKALPAPEEKTISKAK |

SEQUENCE LISTING

| Name | Sequence |
|---|---|
| | GQPREPQVCTLPPSRDELTKNQVSLSCAVKGFYPSDIAVE WESNGQPENNYKTTPPVLDSDGSFFLVSKLTVDKSRWQQ GNVFSCSVMHEALHNRFTQKSLSLSPG (SEQ ID NO: 74) |
| $C_K$ | RTVAAPSVFIFPPSDEQLKSGTASVVCLLNNFYPREAKVQW KVDNALQSGNSQESVTEQDSKDSTYSLSSTLTLSKADYEK HKVYACEVTHQGLSSPVTKSFNRGEC (SEQ ID NO: 75) |
| CH1-CH2-CH3 (Heavy chain, full) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLAGP DVFLFPPKPKDTLMISRTPEVTCVVVDVSHEDPEVKFNWYV DGVEVHNAKTKPC EEQYNSTYRCVSVLTVLHQDWLNGKEYKCKVSNKALPAPE EKTISKAKGQPREPQVYTLPPCRDELTKNQVSLWCLVKGF YPSDIAVEWESNGQPENNYKTTPPVLDSDGSFFLYSKLTV DKSRWQQGNVFSCSVMHEALHNHYTQKSLSLSPG (SEQ ID NO: 76) |
| CH1-CH2-CH3 (Fc only) | DKTHTCPPCPAPELLAGPDVFLFPPKPKDTLMISRTPEVTC VVVDVSHEDPEVKFNWYVDGVEVHNAKTKPCEEQYNSTY RCVSVLTVLHQDWLNGKEYKCKVSNKALPAPEEKTISKAK GQPREPQVCTLPPSRDELTKNQVSLSCAVKGFYPSDIAVE WESNGQPENNYKTTPPVLDSDGSFFLVSKLTVDKSRWQQ GNVFSCSVMHEALHNRFTQKSLSLSPG (SEQ ID NO: 77) |
| Linker$_1$ (light chain) | GGGGSGGGGS (SEQ ID NO: 78) |
| Linker$_2$ (light chain) | GGGGSGGGGS (SEQ ID NO: 79) |
| Linker | GGGGSGGGGSGGGGS (SEQ ID NO: 82) |
| Linker | TKGPS (SEQ ID NO: 83) |
| Linker | GQPKAAP (SEQ ID NO: 84) |
| Linker | GGSGSSGSGG (SEQ ID NO: 85) |
| peptide on the NKp46-BCMA NKCE_Fc CODV-OL1-ADE-DSB molecule | VYACEVTHQGLSSPVTK (SEQ ID NO: 86) |
| peptide on the NKp46-BCMA NKCE_Fc CODV-OL1-ADE-DSB molecule | GPSVFPLAPSSK (SEQ ID NO: 105) |
| peptide on the NKp46-BCMA NKCE_Fc CODV-OL1-ADE-DSB molecule | TTPPVLDSDGSFFLYSK (SEQ ID NO: 106) |
| Primer | TACGACTCACAAGCTTGCCGCCACCATGTCTTCCACACT CCCTGC (SEQ ID NO: 107) |
| Primer | CCGCCCCGACTCTAGATCAATGGTGATGGTGGTGATGAT TCTGGGCAGTGTGATCCC (SEQ ID NO: 108) |
| Primer | TACGACTCACAAGCTTGCCGCCACCATGTCTTCCACACT CCGTGC (SEQ ID NO: 109) |
| Primer | CCGCCCCGACTCTAGATCACTTGTCATCGTCATCTTTGT AATCATTCTGGGCAGTGTGGTCC (SEQ ID NO: 110) |

The invention claimed is:

1. A binding protein comprising a first antigen binding domain (ABD) with binding specificity to BCMA and a second ABD with binding specificity to NKp46, wherein:
(a) the first ABD comprises:
  (a1) a first immunoglobulin heavy chain variable domain (VH1) comprising:
    (i) an HCDR1 comprising the amino acid sequence GFTFSNFGMH (SEQ ID NO: 1),
    (ii) an HCDR2 comprising the amino acid sequence VIWSDETNR (SEQ ID NO: 2), and
    (iii) an HCDR3 comprising the amino acid DQQYCSSDSCFTWFDP (SEQ ID NO: 3); and
  (a2) a first immunoglobulin light chain variable domain (VL1) comprising:
    (i) an LCDR1 comprising the amino acid sequence CASSTGTVTPSNYAN (SEQ ID NO: 7),
    (ii) an LCDR2 comprising the amino acid sequence DNNSRPP (SEQ ID NO: 8), and
    (iii) an LCDR3 comprising the amino acid sequence ALWFGNQWV (SEQ ID NO: 9); and
(b) the second ABD comprises:
  (b1) a second immunoglobulin heavy chain variable domain (VH2) comprising:
    (i) an HCDR1 comprising the amino acid sequence DYVIN (SEQ ID NO: 80),
    (ii) an HCDR2 comprising the amino acid sequence EIYPGSGTNYYNEKFKA (SEQ ID NO: 81), and
    (iii) an HCDR3 comprising the amino acid sequence RGRYGLYAMDY (SEQ ID NO: 21); and
  (b2) a second immunoglobulin light chain variable domain (VL2) comprising:
    (i) an LCDR1 comprising the amino acid sequence RASQDISNYLN (SEQ ID NO: 34),
    (ii) an LCDR2 comprising the amino acid sequence YTSRLHS (SEQ ID NO: 35), and
    (iii) an LCDR3 comprising the amino acid sequence QQGNTRPWT (SEQ ID NO: 36; or
  (b3) a second immunoglobulin VH2 comprising:
    (i) an HCDR1 comprising the amino acid sequence GYTFSDYVIN (SEQ ID NO: 19),
    (ii) an HCDR2 comprising the amino acid sequence EIYPGSGTN (SEQ ID NO: 20), and
    (iii) an HCDR3 comprising the amino acid sequence RGRYGLYAMDY (SEQ ID NO: 21); and
  (b4) a second immunoglobulin VL2 comprising:
    (i) an LCDR1 comprising the amino acid sequence RASQDISNYLN (SEQ ID NO: 34),
    (ii) an LCDR2 comprising the amino acid sequence YTSRLHS (SEQ ID NO: 35), and
    (iii) an LCDR3 comprising the amino acid sequence QQGNTRPWT (SEQ ID NO: 36); or
  (b5) a second immunoglobulin VH2 comprising:
    (i) an HCDR1 comprising the amino acid sequence SDYAWN (SEQ ID NO: 22),
    (ii) an HCDR2 comprising the amino acid sequence YITYSGSTSYNPSLES (SEQ ID NO: 23), and
    (iii) an HCDR3 comprising the amino acid sequence GGYYGSSWGVFAY (SEQ ID NO: 24); and
  (b6) a second immunoglobulin VL2 comprising:
    (i) an LCDR1 comprising the amino acid sequence RVSENIYSYLA (SEQ ID NO: 37),
    (ii) an LCDR2 comprising the amino acid sequence NAKTLAE (SEQ ID NO: 38), and
    (iii) an LCDR3 comprising the amino acid sequence QHHYGTPWT (SEQ ID NO: 39); or
  (b7) a second immunoglobulin VH2 comprising:
    (i) an HCDR1 comprising the amino acid sequence EYTMH (SEQ ID NO: 25),
    (ii) an HCDR2 comprising the amino acid sequence GISPNIGGTSYNQKFKG (SEQ ID NO: 26), and
    (iii) an HCDR3 comprising the amino acid sequence RGGSFDY (SEQ ID NO: 27); and
  (b8) a second immunoglobulin VL2 comprising:
    (i) an LCDR1 comprising the amino acid sequence RASQSISDYLH (SEQ ID NO: 40),
    (ii) an LCDR2 comprising the amino acid sequence YASQSIS (SEQ ID NO: 41), and
    (iii) an LCDR3 comprising the amino acid sequence QNGHSFPLT (SEQ ID NO: 42); or
  (b9) a second immunoglobulin VH2 comprising:
    (i) an HCDR1 comprising the amino acid sequence SFTMH (SEQ ID NO: 28),
    (ii) an HCDR2 comprising the amino acid sequence YINPSSGYTEYNQKFKD (SEQ ID NO: 29), and
    (iii) an HCDR3 comprising the amino acid sequence GSSRGFDY (SEQ ID NO: 30); and
  (b10) a second immunoglobulin VL2 comprising:
    (i) an LCDR1 comprising the amino acid sequence RASENIYSNLA (SEQ ID NO: 43),
    (ii) an LCDR2 comprising the amino acid sequence AATNLAD (SEQ ID NO: 44), and
    (iii) an LCDR3 comprising the amino acid sequence QHFWGTPRT (SEQ ID NO: 45); or
  (b11) a second immunoglobulin VH2 comprising:
    (i) an HCDR1 comprising the amino acid sequence SDYAWN (SEQ ID NO: 31),
    (ii) an HCDR2 comprising the amino acid sequence YITYSGSTNYNPSLKS (SEQ ID NO: 32), and
    (iii) an HCDR3 comprising the amino acid sequence CWDYALYAMDC (SEQ ID NO: 33); and
  (b12) a second immunoglobulin VL2 comprising:
    (i) an LCDR1 comprising the amino acid sequence RTSENIYSYLA (SEQ ID NO: 46),
    (ii) an LCDR2 comprising the amino acid sequence NAKTLAE (SEQ ID NO: 47), and
    (iii) an LCDR3 comprising the amino acid sequence QHHYDTPLT (SEQ ID NO: 48).

2. The binding protein of claim 1, wherein the VH1 comprises an amino acid sequence that is at least about 90% identical to the amino acid sequence of SEQ ID NO: 49, and wherein the VL1 comprises an amino acid sequence that is at least about 90% identical to the amino acid sequence of SEQ ID NO: 55.

3. The binding protein of claim 1, wherein:
the VH2 comprises an amino acid sequence that is at least about 90% identical to the amino acid sequence of SEQ ID NO: 56, and wherein the VL2 comprises an amino acid sequence that is at least about 90% identical to the amino acid sequence of SEQ ID NO: 64;
the VH2 comprises an amino acid sequence that is at least about 90% identical to the amino acid sequence of SEQ ID NO: 57, and wherein the VL2 comprises an amino acid sequence that is at least about 90% identical to the amino acid sequence of SEQ ID NO: 65;
the VH2 comprises an amino acid sequence that is at least about 90% identical to the amino acid sequence of SEQ ID NO: 58, and wherein the VL2 comprises an amino acid sequence that is at least about 90% identical to the amino acid sequence of SEQ ID NO: 66;
the VH2 comprises an amino acid sequence that is at least about 90% identical to the amino acid sequence of SEQ ID NO: 59, and wherein the VL2 comprises an amino acid sequence that is at least about 90% identical to the amino acid sequence of SEQ ID NO: 67;

the VH2 comprises an amino acid sequence that is at least about 90% identical to the amino acid sequence of SEQ ID NO: 60, and wherein the VL2 comprises an amino acid sequence that is at least about 90% identical to the amino acid sequence of SEQ ID NO: 68;

the VH2 comprises an amino acid sequence that is at least about 90% identical to the amino acid sequence of SEQ ID NO: 61, and wherein the VL2 comprises an amino acid sequence that is at least about 90% identical to the amino acid sequence of SEQ ID NO: 69;

the VH2 comprises an amino acid sequence that is at least about 90% identical to the amino acid sequence of SEQ ID NO: 62, and wherein the VL2 comprises an amino acid sequence that is at least about 90% identical to the amino acid sequence of SEQ ID NO: 70; or the VH2 comprises an amino acid sequence that is at least about 90% identical to the amino acid sequence of SEQ ID NO: 63, and wherein the VL2 comprises an amino acid sequence that is at least about 90% identical to the amino acid sequence of SEQ ID NO: 71.

4. The binding protein of claim 1, further comprising all or part of an immunoglobulin Fc domain or variant thereof.

5. The binding protein of claim 4, wherein the Fc domain or variant thereof comprises a first Fc heavy chain and a second Fc heavy chain.

6. The binding protein of claim 5, wherein at least one Fc heavy chain comprises an engineered intrachain disulfide bond mediated by a pair of cysteines (C) that substitute for:
 (i) a leucine (L) at amino acid position 242 and a lysine (K) at amino acid position 334;
 or
 (iii) an arginine (R) at amino acid position 292 and a valine (V) at amino acid position 302;
 wherein the amino acid positions are according to EU numbering.

7. The binding protein of claim 6, wherein the first and the second Fc heavy chain each comprise both the L242C and K334C substitutions.

8. The binding protein of claim 6, wherein the first and the second Fc heavy chain each comprise both the R292C and V302C substitutions.

9. The binding protein of claim 6, wherein at least one Fc heavy chain comprises a substitution at amino acid position 332, according to EU numbering.

10. The binding protein of claim 6, wherein at least one Fc heavy chain further comprises an aspartic acid (D) at amino acid position 239, and a glutamic acid (E) at amino acid position 332, according to EU numbering.

11. The binding protein of claim 1, comprising at least two polypeptide chains that form at least two antigen binding domains, wherein at least one polypeptide chain comprises a structure represented by the formula:

VL1-L1-VL2-L2-CL  [I];

and at least one polypeptide chain comprises a structure represented by the formula:

VH2-L3-VH1-L4-CH1  [II];

wherein:
CL is an immunoglobulin light chain constant domain;
CH1 is an immunoglobulin CH1 heavy chain constant domain; and
L1, L2, L3, and L4 are amino acid linkers, wherein any one or more of L1, L2, L3, and L4 are optionally absent, and wherein the polypeptides of formula I and the polypeptides of formula II form a cross-over light chain-heavy chain pair.

12. The binding protein of claim 11, wherein:
L1, L2, L3, and L4 each independently are zero amino acids in length or comprise a sequence selected from the group consisting of GGGGSGGGGS (SEQ ID NO: 78), GGGGSGGGGSGGGGS (SEQ ID NO: 82), S, RT, TKGPS (SEQ ID NO: 83), GQPKAAP (SEQ ID NO: 84), and GGSGSSGSGG (SEQ ID NO: 85).

13. The binding protein of claim 1, comprising:
(i) a first polypeptide chain comprising an amino acid sequence of SEQ ID NO: 72;
(ii) a second polypeptide chain comprising an amino acid sequence of SEQ ID NO: 73; and
(iii) a third polypeptide chain comprising an amino acid sequence of SEQ ID NO: 74.

14. A binding protein comprising a first antigen binding domain (ABD) with binding specificity to BCMA and a second ABD with binding specificity to NKp46, wherein:
(a) the first ABD comprises
(a1) a first immunoglobulin heavy chain variable domain (VH1) comprising:
 (i) an HCDR1 sequence from SEQ ID NO: 49, according to Kabat numbering,
 (ii) an HCDR2 sequence from SEQ ID NO: 49, according to Kabat numbering, and
 (iii) an HCDR3 sequence from SEQ ID NO: 49, according to Kabat numbering, and
(a2) a first immunoglobulin light chain variable domain (VL1) comprising:
 (i) an LCDR1 sequence from SEQ ID NO: 55, according to Kabat numbering,
 (ii) an LCDR2 sequence from SEQ ID NO: 55, according to Kabat numbering, and
 (iii) an LCDR3 sequence from SEQ ID NO: 55, according to Kabat numbering, and
(b) the second ABD comprises
(b1) a second immunoglobulin heavy chain variable domain (VH2) comprising:
 (i) an HCDR1 sequence from SEQ ID NO: 56, according to Kabat numbering,
 (ii) an HCDR2 sequence from SEQ ID NO: 56, according to Kabat numbering, and
 (iii) an HCDR3 sequence from SEQ ID NO: 56, according to Kabat numbering, and
(b2) a second immunoglobulin light chain variable domain (VL2) comprising:
 (i) an LCDR1 sequence from SEQ ID NO: 64, according to Kabat numbering,
 (ii) an LCDR2 sequence from SEQ ID NO: 64, according to Kabat numbering, and
 (iii) an LCDR3 sequence from SEQ ID NO: 64, according to Kabat numbering.

15. The binding protein of claim 14, comprising:
(i) a first polypeptide chain comprising an amino acid sequence of SEQ ID NO: 72;
(ii) a second polypeptide chain comprising an amino acid sequence of SEQ ID NO: 73; and
(iii) a third polypeptide chain comprising an amino acid sequence of SEQ ID NO: 74.

16. A binding protein comprising a first antigen binding domain (ABD) with binding specificity to BCMA and a second ABD with binding specificity to NKp46, wherein the binding protein comprises:
(i) a first polypeptide chain consisting of an amino acid sequence of SEQ ID NO: 72;

(ii) a second polypeptide chain consisting of an amino acid sequence of SEQ ID NO: 73; and
(iii) a third polypeptide chain consisting of an amino acid sequence of SEQ ID NO: 74.

17. A pharmaceutical composition comprising the binding protein according to claim 1.

18. The binding protein of claim 4, wherein all or part of the immunoglobulin Fc domain or variant thereof binds to a human Fc-γ receptor.

19. The binding protein of claim 4, wherein all or part of the immunoglobulin Fc domain or variant thereof binds to a human CD16A (FcγRIII) polypeptide.

20. The binding protein of claim 4, wherein the Fc domain comprises a native glycan at amino acid position 297, according to EU numbering.

21. The binding protein of claim 4, wherein the binding protein is N-glycosylated.

22. The binding protein of claim 9, wherein the substitution at amino acid position 332 is a glutamic acid (E).

23. The binding protein of claim 9, wherein at least one Fc heavy chain comprises one or more substitutions at amino acid positions 236, 239, or 330, according to EU numbering.

24. The binding protein of claim 23, wherein the substitution at amino acid position 236 is an alanine (A), the substitution at amino acid position 239 is an aspartic acid (D), and the substitution at amino acid position 330 is a leucine (L).

25. The binding protein of claim 6, wherein at least one Fc heavy chain further comprises an alanine (A) at amino acid position 236, an aspartic acid (D) at amino acid position 239, and a glutamic acid (E) at amino acid position 332, according to EU numbering.

26. The binding protein of claim 6, wherein at least one Fc heavy chain further comprises an alanine (A) at amino acid position 236, an aspartic acid (D) at amino acid position 239, a leucine (L) at amino acid position 330, and a glutamic acid (E) at amino acid position 332, according to EU numbering.

27. The binding protein of claim 1, wherein (b) the second ABD comprises:
(b1) a second immunoglobulin heavy chain variable domain (VH2) comprising:
(i) an HCDR1 comprising the amino acid sequence DYVIN (SEQ ID NO: 80),
(ii) an HCDR2 comprising the amino acid sequence EIYPGSGTNYYNEKFKA (SEQ ID NO: 81), and
(iii) an HCDR3 comprising the amino acid sequence RGRYGLYAMDY (SEQ ID NO: 21); and
(b2) a second immunoglobulin light chain variable domain (VL2) comprising:
(i) an LCDR1 comprising the amino acid sequence RASQDISNYLN (SEQ ID NO: 34),
(ii) an LCDR2 comprising the amino acid sequence YTSRLHS (SEQ ID NO: 35), and
(iii) an LCDR3 comprising the amino acid sequence QQGNTRPWT (SEQ ID NO: 36).

28. The binding protein of claim 11, wherein the binding protein comprises three polypeptide chains that form two antigen binding domains, wherein one polypeptide chain comprises a structure represented by the formula:

VL1-L1-VL2-L2-CL     [I];

one polypeptide chain comprises a structure represented by the formula:

VH2-L3-VH1-L4-CH1-hinge-CH2-CH3     [III]; and one polypeptide chain comprises a structure represented by the formula:

hinge-CH2-CH3     [IV]

wherein:
CL is an immunoglobulin light chain constant domain;
CH1 is an immunoglobulin CHI heavy chain constant domain;
CH2 is an immunoglobulin CH2 heavy chain constant domain;
CH3 is an immunoglobulin CH3 heavy chain constant domain;
hinge is an immunoglobulin hinge region connecting the CH1 and CH2 domains; and
L1, L2, L3, and L4 are amino acid linkers, wherein any one or more of L1, L2, L3, and L4 are optionally absent, and
wherein the polypeptides of formula I and the polypeptides of formula [III] form a cross-over light chain-heavy chain pair.

29. The binding protein of claim 28, wherein L1, L2, L3, and L4 each independently are zero amino acids in length or comprise a sequence selected from the group consisting of GGGGSGGGGS (SEQ ID NO: 78), GGGGSGGGGSGGGGS (SEQ ID NO: 82), S, RT, TKGPS (SEQ ID NO: 83), GQPKAAP (SEQ ID NO: 84), and GGSGSSGSGG (SEQ ID NO: 85).

30. The binding protein of claim 1, wherein the VH1 comprises SEQ ID NO: 49, and wherein the VL1 comprises SEQ ID NO: 55.

31. The binding protein of claim 1, wherein the VH2 comprises SEQ ID NO: 56, and wherein the VL2 comprises SEQ ID NO: 64.

32. The binding protein of claim 1, wherein:
(a) the first ABD comprises the VH1 of SEQ ID NO: 49 and the VL1 of SEQ ID NO: 55; and
(b) the second ABD comprises the VH2 of SEQ ID NO: 56 and the VL2 of SEQ ID NO: 64.

33. A binding protein comprising a first antigen binding domain (ABD) with binding specificity to BCMA and a second ABD with binding specificity to NKp46, wherein:
(a) the first ABD comprises
(a1) a first immunoglobulin heavy chain variable domain (VH1) comprising:
(i) an HCDR1 sequence from SEQ ID NO: 49, according to IMGT numbering,
(ii) an HCDR2 sequence from SEQ ID NO: 49, according to IMGT numbering, and
(iii) an HCDR3 sequence from SEQ ID NO: 49, according to IMGT numbering, and
(a2) a first immunoglobulin light chain variable domain (VL1) comprising:
(i) an LCDR1 sequence from SEQ ID NO: 55, according to IMGT numbering,
(ii) an LCDR2 sequence from SEQ ID NO: 55, according to IMGT numbering, and
(iii) an LCDR3 sequence from SEQ ID NO: 55, according to IMGT numbering; and
(b) the second ABD comprises
(b1) a second immunoglobulin heavy chain variable domain (VH2) comprising:
an HCDR1 sequence from SEQ ID NO: 56, according to IMGT numbering,
an HCDR2 sequence from SEQ ID NO: 56, according to IMGT numbering, and
an HCDR3 sequence from SEQ ID NO: 56, according to IMGT numbering, and (b2) a second immunoglobulin light chain variable domain (VL2) comprising:
an LCDR1 sequence from SEQ ID NO: 64, according to IMGT numbering,
an LCDR2 sequence from SEQ ID NO: 64, according to IMGT numbering, and
an LCDR3 sequence from SEQ ID NO: 64, according to IMGT numbering.

* * * * *

SEQUENCE LISTING

```
Sequence total quantity: 110
SEQ ID NO: 1                moltype = AA   length = 10
FEATURE                     Location/Qualifiers
source                      1..10
                            mol_type = protein
                            organism = synthetic construct
SEQUENCE: 1
GFTFSNFGMH                                                                   10

SEQ ID NO: 2                moltype = AA   length = 9
FEATURE                     Location/Qualifiers
source                      1..9
                            mol_type = protein
                            organism = synthetic construct
SEQUENCE: 2
VIWSDETNR                                                                    9

SEQ ID NO: 3                moltype = AA   length = 16
FEATURE                     Location/Qualifiers
source                      1..16
                            mol_type = protein
                            organism = synthetic construct
SEQUENCE: 3
DQQYCSSDSC FTWFDP                                                            16

SEQ ID NO: 4                moltype = AA   length = 15
FEATURE                     Location/Qualifiers
source                      1..15
                            mol_type = protein
                            organism = synthetic construct
VARIANT                     2
                            note = X can be R or A
VARIANT                     7
                            note = X can be T or A
VARIANT                     11
                            note = X can be S or G
VARIANT                     12
                            note = X can be N or Y
SEQUENCE: 4
CXSSTGXVTP XXYAN                                                             15

SEQ ID NO: 5                moltype = AA   length = 7
FEATURE                     Location/Qualifiers
source                      1..7
                            mol_type = protein
                            organism = synthetic construct
VARIANT                     4
                            note = X can be S, I, or N
VARIANT                     5
                            note = X can be R or K
SEQUENCE: 5
DNNXXPP                                                                      7

SEQ ID NO: 6                moltype = AA   length = 9
FEATURE                     Location/Qualifiers
source                      1..9
                            mol_type = protein
                            organism = synthetic construct
VARIANT                     3
                            note = X can be W or Y
VARIANT                     4
                            note = X can be F or Y
VARIANT                     6
                            note = X can be N or G
SEQUENCE: 6
ALXXGXQWV                                                                    9

SEQ ID NO: 7                moltype = AA   length = 15
FEATURE                     Location/Qualifiers
source                      1..15
                            mol_type = protein
                            organism = synthetic construct
SEQUENCE: 7
CASSTGTVTP SNYAN                                                             15

SEQ ID NO: 8                moltype = AA   length = 7
FEATURE                     Location/Qualifiers
source                      1..7
```

```
                              mol_type = protein
                              organism = synthetic construct
SEQUENCE: 8
DNNSRPP                                                                    7

SEQ ID NO: 9                  moltype = AA   length = 9
FEATURE                       Location/Qualifiers
source                        1..9
                              mol_type = protein
                              organism = synthetic construct
SEQUENCE: 9
ALWFGNQWV                                                                  9

SEQ ID NO: 10                 moltype = AA   length = 15
FEATURE                       Location/Qualifiers
source                        1..15
                              mol_type = protein
                              organism = synthetic construct
SEQUENCE: 10
CRSSTGTVTP SNYAN                                                          15

SEQ ID NO: 11                 moltype = AA   length = 7
FEATURE                       Location/Qualifiers
source                        1..7
                              mol_type = protein
                              organism = synthetic construct
SEQUENCE: 11
DNNSRPP                                                                    7

SEQ ID NO: 12                 moltype = AA   length = 9
FEATURE                       Location/Qualifiers
source                        1..9
                              mol_type = protein
                              organism = synthetic construct
SEQUENCE: 12
ALWFGNQWV                                                                  9

SEQ ID NO: 13                 moltype = AA   length = 15
FEATURE                       Location/Qualifiers
source                        1..15
                              mol_type = protein
                              organism = synthetic construct
SEQUENCE: 13
CASSTGAVTP SNYAN                                                          15

SEQ ID NO: 14                 moltype = AA   length = 7
FEATURE                       Location/Qualifiers
source                        1..7
                              mol_type = protein
                              organism = synthetic construct
SEQUENCE: 14
DNNIKPP                                                                    7

SEQ ID NO: 15                 moltype = AA   length = 9
FEATURE                       Location/Qualifiers
source                        1..9
                              mol_type = protein
                              organism = synthetic construct
SEQUENCE: 15
ALWYGGQWV                                                                  9

SEQ ID NO: 16                 moltype = AA   length = 15
FEATURE                       Location/Qualifiers
source                        1..15
                              mol_type = protein
                              organism = synthetic construct
SEQUENCE: 16
CASSTGAVTP GYYAN                                                          15

SEQ ID NO: 17                 moltype = AA   length = 7
FEATURE                       Location/Qualifiers
source                        1..7
                              mol_type = protein
                              organism = synthetic construct
SEQUENCE: 17
DNNNKPP                                                                    7

SEQ ID NO: 18                 moltype = AA   length = 9
FEATURE                       Location/Qualifiers
```

```
source                   1..9
                         mol_type = protein
                         organism = synthetic construct
SEQUENCE: 18
ALYYGGQWV                                                                9

SEQ ID NO: 19            moltype = AA   length = 10
FEATURE                  Location/Qualifiers
source                   1..10
                         mol_type = protein
                         organism = synthetic construct
SEQUENCE: 19
GYTFSDYVIN                                                              10

SEQ ID NO: 20            moltype = AA   length = 9
FEATURE                  Location/Qualifiers
source                   1..9
                         mol_type = protein
                         organism = synthetic construct
SEQUENCE: 20
EIYPGSGTN                                                                9

SEQ ID NO: 21            moltype = AA   length = 11
FEATURE                  Location/Qualifiers
source                   1..11
                         mol_type = protein
                         organism = synthetic construct
SEQUENCE: 21
RGRYGLYAMD Y                                                            11

SEQ ID NO: 22            moltype = AA   length = 6
FEATURE                  Location/Qualifiers
source                   1..6
                         mol_type = protein
                         organism = synthetic construct
SEQUENCE: 22
SDYAWN                                                                   6

SEQ ID NO: 23            moltype = AA   length = 16
FEATURE                  Location/Qualifiers
source                   1..16
                         mol_type = protein
                         organism = synthetic construct
SEQUENCE: 23
YITYSGSTSY NPSLES                                                       16

SEQ ID NO: 24            moltype = AA   length = 13
FEATURE                  Location/Qualifiers
source                   1..13
                         mol_type = protein
                         organism = synthetic construct
SEQUENCE: 24
GGYYGSSWGV FAY                                                          13

SEQ ID NO: 25            moltype = AA   length = 5
FEATURE                  Location/Qualifiers
source                   1..5
                         mol_type = protein
                         organism = synthetic construct
SEQUENCE: 25
EYTMH                                                                    5

SEQ ID NO: 26            moltype = AA   length = 17
FEATURE                  Location/Qualifiers
source                   1..17
                         mol_type = protein
                         organism = synthetic construct
SEQUENCE: 26
GISPNIGGTS YNQKFKG                                                      17

SEQ ID NO: 27            moltype = AA   length = 7
FEATURE                  Location/Qualifiers
source                   1..7
                         mol_type = protein
                         organism = synthetic construct
SEQUENCE: 27
RGGSFDY                                                                  7

SEQ ID NO: 28            moltype = AA   length = 5
```

```
FEATURE              Location/Qualifiers
source               1..5
                     mol_type = protein
                     organism = synthetic construct
SEQUENCE: 28
SFTMH                                                                    5

SEQ ID NO: 29        moltype = AA   length = 17
FEATURE              Location/Qualifiers
source               1..17
                     mol_type = protein
                     organism = synthetic construct
SEQUENCE: 29
YINPSSGYTE YNQKFKD                                                       17

SEQ ID NO: 30        moltype = AA   length = 8
FEATURE              Location/Qualifiers
source               1..8
                     mol_type = protein
                     organism = synthetic construct
SEQUENCE: 30
GSSRGFDY                                                                 8

SEQ ID NO: 31        moltype = AA   length = 6
FEATURE              Location/Qualifiers
source               1..6
                     mol_type = protein
                     organism = synthetic construct
SEQUENCE: 31
SDYAWN                                                                   6

SEQ ID NO: 32        moltype = AA   length = 16
FEATURE              Location/Qualifiers
source               1..16
                     mol_type = protein
                     organism = synthetic construct
SEQUENCE: 32
YITYSGSTNY NPSLKS                                                        16

SEQ ID NO: 33        moltype = AA   length = 11
FEATURE              Location/Qualifiers
source               1..11
                     mol_type = protein
                     organism = synthetic construct
SEQUENCE: 33
CWDYALYAMD C                                                             11

SEQ ID NO: 34        moltype = AA   length = 11
FEATURE              Location/Qualifiers
source               1..11
                     mol_type = protein
                     organism = synthetic construct
SEQUENCE: 34
RASQDISNYL N                                                             11

SEQ ID NO: 35        moltype = AA   length = 7
FEATURE              Location/Qualifiers
source               1..7
                     mol_type = protein
                     organism = synthetic construct
SEQUENCE: 35
YTSRLHS                                                                  7

SEQ ID NO: 36        moltype = AA   length = 9
FEATURE              Location/Qualifiers
source               1..9
                     mol_type = protein
                     organism = synthetic construct
SEQUENCE: 36
QQGNTRPWT                                                                9

SEQ ID NO: 37        moltype = AA   length = 11
FEATURE              Location/Qualifiers
source               1..11
                     mol_type = protein
                     organism = synthetic construct
SEQUENCE: 37
RVSENIYSYL A                                                             11
```

```
SEQ ID NO: 38            moltype = AA   length = 7
FEATURE                  Location/Qualifiers
source                   1..7
                         mol_type = protein
                         organism = synthetic construct
SEQUENCE: 38
NAKTLAE                                                                    7

SEQ ID NO: 39            moltype = AA   length = 9
FEATURE                  Location/Qualifiers
source                   1..9
                         mol_type = protein
                         organism = synthetic construct
SEQUENCE: 39
QHHYGTPWT                                                                  9

SEQ ID NO: 40            moltype = AA   length = 11
FEATURE                  Location/Qualifiers
source                   1..11
                         mol_type = protein
                         organism = synthetic construct
SEQUENCE: 40
RASQSISDYL H                                                              11

SEQ ID NO: 41            moltype = AA   length = 7
FEATURE                  Location/Qualifiers
source                   1..7
                         mol_type = protein
                         organism = synthetic construct
SEQUENCE: 41
YASQSIS                                                                    7

SEQ ID NO: 42            moltype = AA   length = 9
FEATURE                  Location/Qualifiers
source                   1..9
                         mol_type = protein
                         organism = synthetic construct
SEQUENCE: 42
QNGHSFPLT                                                                  9

SEQ ID NO: 43            moltype = AA   length = 11
FEATURE                  Location/Qualifiers
source                   1..11
                         mol_type = protein
                         organism = synthetic construct
SEQUENCE: 43
RASENIYSNL A                                                              11

SEQ ID NO: 44            moltype = AA   length = 7
FEATURE                  Location/Qualifiers
source                   1..7
                         mol_type = protein
                         organism = synthetic construct
SEQUENCE: 44
AATNLAD                                                                    7

SEQ ID NO: 45            moltype = AA   length = 9
FEATURE                  Location/Qualifiers
source                   1..9
                         mol_type = protein
                         organism = synthetic construct
SEQUENCE: 45
QHFWGTPRT                                                                  9

SEQ ID NO: 46            moltype = AA   length = 11
FEATURE                  Location/Qualifiers
source                   1..11
                         mol_type = protein
                         organism = synthetic construct
SEQUENCE: 46
RTSENIYSYL A                                                              11

SEQ ID NO: 47            moltype = AA   length = 7
FEATURE                  Location/Qualifiers
source                   1..7
                         mol_type = protein
                         organism = synthetic construct
SEQUENCE: 47
NAKTLAE                                                                    7
```

```
SEQ ID NO: 48           moltype = AA  length = 9
FEATURE                 Location/Qualifiers
source                  1..9
                        mol_type = protein
                        organism = synthetic construct
SEQUENCE: 48
QHHYDTPLT                                                                  9

SEQ ID NO: 49           moltype = AA  length = 125
FEATURE                 Location/Qualifiers
source                  1..125
                        mol_type = protein
                        organism = synthetic construct
SEQUENCE: 49
QVQLVESGGG VVQPGRSLRL SCAASGFTFS NFGMHWVRQA PGRGLEWVAV IWSDETNRYY          60
ADSVKGRFTV SRDNVKSTVY LQMNSLISED TAVYYCARDQ QYCSSDSCFT WFDPWGQGTL         120
VTVSS                                                                    125

SEQ ID NO: 50           moltype = AA  length = 109
FEATURE                 Location/Qualifiers
source                  1..109
                        mol_type = protein
                        organism = synthetic construct
SEQUENCE: 50
QTVVTQEPSL TVSPGGTVTL TCRSSTGTVT PSNYANWVQQ KPDHFFTGLI GDNNSRPPGV          60
PARFSASLIG DKAALTLSGV QPEDEAEYYC ALWFGNQWVF GGGTKLTVL                     109

SEQ ID NO: 51           moltype = AA  length = 109
FEATURE                 Location/Qualifiers
source                  1..109
                        mol_type = protein
                        organism = synthetic construct
SEQUENCE: 51
QTVVTQEPSL TVSPGGTVTL TCASSTGTVT PSNYANWVQQ KPGQAPRGLI GDNNSRPPGT          60
PARFSASLLG GKAALTLSGV QPEDEAEYYC ALWFGNQWVF GGGTKLTVL                     109

SEQ ID NO: 52           moltype = AA  length = 109
FEATURE                 Location/Qualifiers
source                  1..109
                        mol_type = protein
                        organism = synthetic construct
SEQUENCE: 52
QTVVTQEPSL TVSPGGTVTL TCASSTGAVT PSNYANWVQQ KPGQAPRGLI GDNNIKPPWT          60
PARFSGSLLG GKAALTLSGV QPEDEAEYYC ALWYGGQWVF GGGTKLTVL                     109

SEQ ID NO: 53           moltype = AA  length = 109
FEATURE                 Location/Qualifiers
source                  1..109
                        mol_type = protein
                        organism = synthetic construct
SEQUENCE: 53
QTVVTQEPSL TVSPGGTVTL TCASSTGAVT PGYYANWVQQ KPGQAPRGLI GDNNNKPPWT          60
PARFSGSLLG GKAALTLSGV QPEDEAEYYC ALYYGGQWVF GGGTKLTVL                     109

SEQ ID NO: 54           moltype = AA  length = 109
FEATURE                 Location/Qualifiers
source                  1..109
                        mol_type = protein
                        organism = synthetic construct
SEQUENCE: 54
QTVVTQEPSL TVSPGGTVTL TCASSTGTVT PSNYANWVQQ KPGQFPRGLI GDNNSRPPGT          60
PARFSASLLG GKAALTLSGV QPEDEAEYYC ALWFGNQWVF GGGTKLTVL                     109

SEQ ID NO: 55           moltype = AA  length = 109
FEATURE                 Location/Qualifiers
source                  1..109
                        mol_type = protein
                        organism = synthetic construct
SEQUENCE: 55
QTVVTQEPSL TVSPGGTVTL TCASSTGTVT PSNYANWVQQ KPGQAFRGLI GDNNSRPPGT          60
PARFSASLLG GKAALTLSGV QPEDEAEYYC ALWFGNQWVF GGGTKLTVL                     109

SEQ ID NO: 56           moltype = AA  length = 120
FEATURE                 Location/Qualifiers
source                  1..120
                        mol_type = protein
                        organism = synthetic construct
SEQUENCE: 56
```

```
QVQLVQSGAE VKKPGSSVKV SCKASGYTFS DYVINWVRQA PGQGLEWMGE IYPGSGTNYY    60
NEKFKAKATI TADKSTSTAY MELSSLRSED TAVYYCARRG RYGLYAMDYW GQGTTVTVSS   120

SEQ ID NO: 57           moltype = AA  length = 120
FEATURE                 Location/Qualifiers
source                  1..120
                        mol_type = protein
                        organism = synthetic construct
SEQUENCE: 57
QVQLQQSGPE LVKPGASVKM SCKASGYTFT DYVINWGKQR SGQGLEWIGE IYPGSGTNYY    60
NEKFKAKATL TADKSSNIAY MQLSSLTSED SAVYFCARRG RYGLYAMDYW GQGTSVTVSS   120

SEQ ID NO: 58           moltype = AA  length = 122
FEATURE                 Location/Qualifiers
source                  1..122
                        mol_type = protein
                        organism = synthetic construct
SEQUENCE: 58
EVQLQESGPG LVKPSQSLSL TCTVTGYSIT SDYAWNWIRQ FPGNKLEWMG YITYSGSTSY    60
NPSLESRISI TRDTSTNQFF LQLNSVTTED TATYYCARGG YYGSSWGVFA YWGQGTLVTV   120
SA                                                                 122

SEQ ID NO: 59           moltype = AA  length = 116
FEATURE                 Location/Qualifiers
source                  1..116
                        mol_type = protein
                        organism = synthetic construct
SEQUENCE: 59
EVQLQQSGPE LVKPGASVKI SCKTSGYTFT EYTMHWVKQS HGKSLEWIGG ISPNIGGTSY    60
NQKFKGKATL TVDKSSSTAY MELRSLTSED SAVYYCARRG GSFDYWGQGT TLTVSS       116

SEQ ID NO: 60           moltype = AA  length = 117
FEATURE                 Location/Qualifiers
source                  1..117
                        mol_type = protein
                        organism = synthetic construct
SEQUENCE: 60
QVQLQQSAVE LARPGASVKM SCKASGYTFT SFTMHWVKQR PGQGLEWIGY INPSSGYTEY    60
NQKFKDKTTL TADKSSSTAY MQLDSLTSDD SAVYYCVRGS SRGFDYWGQG TLVTVSA      117

SEQ ID NO: 61           moltype = AA  length = 122
FEATURE                 Location/Qualifiers
source                  1..122
                        mol_type = protein
                        organism = synthetic construct
SEQUENCE: 61
QVQLQESGPG LVKPSQTLSL TCTVSGYSIS SDYAWNWIRQ PPGKGLEWIG YITYSGSTSY    60
NPSLESRVTI SRDTSKNQFS LKLSSVTAAD TAVYYCARGG YYGSSWGVFA YWGQGTLVTV   120
SS                                                                 122

SEQ ID NO: 62           moltype = AA  length = 117
FEATURE                 Location/Qualifiers
source                  1..117
                        mol_type = protein
                        organism = synthetic construct
SEQUENCE: 62
QVQLVQSGAE VKKPGASVKV SCKASGYTFT SFTMHWVRQA PGQGLEWIGY INPSSGYTEY    60
NQKFKDRVTI TADKSTSTAY MELSSLRSED TAVYYCVRGS SRGFDYWGQG TLVTVSS      117

SEQ ID NO: 63           moltype = AA  length = 120
FEATURE                 Location/Qualifiers
source                  1..120
                        mol_type = protein
                        organism = synthetic construct
SEQUENCE: 63
QVQLQESGPG LVKPSQTLSL TCTVSGYSIS SDYAWNWIRQ PPGKGLEWIG YITYSGSTNY    60
NPSLKSRVTI SRDTSKNQFS LKLSSVTAAD TAVYYCARCW DYALYAMDCW GQGTTVTVSS   120

SEQ ID NO: 64           moltype = AA  length = 107
FEATURE                 Location/Qualifiers
source                  1..107
                        mol_type = protein
                        organism = synthetic construct
SEQUENCE: 64
DIQMTQSPSS LSASVGDRVT ITCRASQDIS NYLNWYQQKP GKAPKLLIYY TSRLHSGVPS    60
RFSGSGSGTD FTFTISSLQP EDIATYFCQQ GNTRPWTFGG GTKVEIK                 107

SEQ ID NO: 65           moltype = AA  length = 107
FEATURE                 Location/Qualifiers
```

```
source                      1..107
                            mol_type = protein
                            organism = synthetic construct
SEQUENCE: 65
DIQMTQTTSS LSASLGDRVT ISCRASQDIS NYLNWYQQKP DGTVKLLIYY TSRLHSGVPS    60
RFSGSGSGTD YSLTINNLEQ EDIATYFCQQ GNTRPWTFGG GTKLEIK                 107

SEQ ID NO: 66               moltype = AA   length = 107
FEATURE                     Location/Qualifiers
source                      1..107
                            mol_type = protein
                            organism = synthetic construct
SEQUENCE: 66
DIQMTQSPAS LSASVGETVT ITCRVSENIY SYLAWYQQKQ GKSPQLLVYN AKTLAEGVPS    60
RFSGSGSGTQ FSLKINSLQP EDFGSYYCQH HYGTPWTFGG GTKLEIK                 107

SEQ ID NO: 67               moltype = AA   length = 107
FEATURE                     Location/Qualifiers
source                      1..107
                            mol_type = protein
                            organism = synthetic construct
SEQUENCE: 67
DIVMTQSPAT LSVTPGDRVS LSCRASQSIS DYLHWYQQKS HESPRLLIKY ASQSISGIPS    60
RFSGSGSGSD FTLSINSVEP EDVGVYYCQN GHSFPLTFGA GTKLELK                 107

SEQ ID NO: 68               moltype = AA   length = 107
FEATURE                     Location/Qualifiers
source                      1..107
                            mol_type = protein
                            organism = synthetic construct
SEQUENCE: 68
DIQMIQSPAS LSVSVGETVT ITCRASENIY SNLAWFQQKQ GKSPQLLVYA ATNLADGVPS    60
RFSGSGSGTQ YSLKINSLQS EDFGIYYCQH FWGTPRTFGG GTKLEIK                 107

SEQ ID NO: 69               moltype = AA   length = 107
FEATURE                     Location/Qualifiers
source                      1..107
                            mol_type = protein
                            organism = synthetic construct
SEQUENCE: 69
DIQMTQSPSS LSASVGDRVT ITCRVSENIY SYLAWYQQKP GKAPKLLVYN AKTLAEGVPS    60
RFSGSGSGTD FTLTISSLQP EDFATYYCQH HYGTPWTFGG GTKVEIK                 107

SEQ ID NO: 70               moltype = AA   length = 107
FEATURE                     Location/Qualifiers
source                      1..107
                            mol_type = protein
                            organism = synthetic construct
SEQUENCE: 70
DIQMTQSPSS LSASVGDRVT ITCRASENIY SNLAWFQQKP GKAPKLLVYA ATNLADGVPS    60
RFSGSGSGTD YTLTISSLQP EDFATYYCQH FWGTPRTFGG GTKVEIK                 107

SEQ ID NO: 71               moltype = AA   length = 107
FEATURE                     Location/Qualifiers
source                      1..107
                            mol_type = protein
                            organism = synthetic construct
SEQUENCE: 71
DIQMTQSPSS LSASVGDRVT ITCRTSENIY SYLAWCQQKP GKAPKLLIYN AKTLAEGVPS    60
RFSGSGSGTD FTLTISSLQP EDFATYYCQH HYDTPLTFGQ GTKLEIK                 107

SEQ ID NO: 72               moltype = AA   length = 343
FEATURE                     Location/Qualifiers
source                      1..343
                            mol_type = protein
                            organism = synthetic construct
SEQUENCE: 72
QTVVTQEPSL TVSPGGTVTL TCASSTGTVT PSNYANWVQQ KPGQAFRGLI GDNNSRPPGT    60
PARFSASLLG GKAALTLSGV QPEDEAEYYC ALWFGNQWVF GGGTKLTVLG GGGSGGGGSD   120
IQMTQSPSSL SASVGDRVTI TCRASQDISN YLNWYQQKPG KAPKLLIYYT SRLHSGVPSR   180
FSGSGSGTDF TFTISSLQPE DIATYFCQQG NTRPWTFGGG TKVEIKGGGG SGGGGSRTVA   240
APSVFIFPPS DEQLKSGTAS VVCLLNNFYP REAKVQWKVD NALQSGNSQE SVTEQDSKDS   300
TYSLSSTLTL SKADYEKHKV YACEVTHQGL SSPVTKSFNR GEC                    343

SEQ ID NO: 73               moltype = AA   length = 574
FEATURE                     Location/Qualifiers
source                      1..574
                            mol_type = protein
                            organism = synthetic construct
```

```
SEQUENCE: 73
QVQLVQSGAE VKKPGSSVKV SCKASGYTFS DYVINWVRQA PGQGLEWMGE IYPGSGTNYY    60
NEKFKAKATI TADKSTSTAY MELSSLRSED TAVYYCARRG RYGLYAMDYW GQGTTVTVSS   120
QVQLVESGGG VVQPGRSLRL SCAASGFTFS NFGMHWVRQA PGRGLEWVAV IWSDETNRYY   180
ADSVKGRFTV SRDNVKSTVY LQMNSLISED TAVYYCARDQ QYCSSDSCFT WFDPWGQGTL   240
VTVSSASTKG PSVFPLAPSS KSTSGGTAAL GCLVKDYFPE PVTVSWNSGA LTSGVHTFPA   300
VLQSSGLYSL SSVVTVPSSS LGTQTYICNV NHKPSNTKVD KKVEPKSCDK THTCPPCPAP   360
ELLAGPDVFL FPPKPKDTLM ISRTPEVTCV VVDVSHEDPE VKFNWYVDGV EVHNAKTKPC   420
EEQYNSTYRC VSVLTVLHQD WLNGKEYKCK VSNKALPAPE EKTISKAKGQ PREPQVYTLP   480
PCRDELTKNQ VSLWCLVKGF YPSDIAVEWE SNGQPENNYK TTPPVLDSDG SFFLYSKLTV   540
DKSRWQQGNV FSCSVMHEAL HNHYTQKSLS LSPG                              574

SEQ ID NO: 74            moltype = AA   length = 226
FEATURE                  Location/Qualifiers
source                   1..226
                         mol_type = protein
                         organism = synthetic construct
SEQUENCE: 74
DKTHTCPPCP APELLAGPDV FLFPPKPKDT LMISRTPEVT CVVVDVSHED PEVKFNWYVD    60
GVEVHNAKTK PCEEQYNSTY RCVSVLTVLH QDWLNGKEYK CKVSNKALPA PEEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNRFTQKS LSLSPG                  226

SEQ ID NO: 75            moltype = AA   length = 107
FEATURE                  Location/Qualifiers
source                   1..107
                         mol_type = protein
                         organism = synthetic construct
SEQUENCE: 75
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 76            moltype = AA   length = 329
FEATURE                  Location/Qualifiers
source                   1..329
                         mol_type = protein
                         organism = synthetic construct
SEQUENCE: 76
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLAG   120
PDVFLFPPKP KDTLMISRTP EVTCVVVDVS HEDPEVKFNW YVDGVEVHNA KTKPCEEQYN   180
STYRCVSVLT VLHQDWLNGK EYCKVSNKA LPAPEEKTIS KAKGQPREPQ VYTLPPCRDE   240
LTKNQVSLWC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 77            moltype = AA   length = 226
FEATURE                  Location/Qualifiers
source                   1..226
                         mol_type = protein
                         organism = synthetic construct
SEQUENCE: 77
DKTHTCPPCP APELLAGPDV FLFPPKPKDT LMISRTPEVT CVVVDVSHED PEVKFNWYVD    60
GVEVHNAKTK PCEEQYNSTY RCVSVLTVLH QDWLNGKEYK CKVSNKALPA PEEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNRFTQKS LSLSPG                  226

SEQ ID NO: 78            moltype = AA   length = 10
FEATURE                  Location/Qualifiers
source                   1..10
                         mol_type = protein
                         organism = synthetic construct
SEQUENCE: 78
GGGGSGGGGS                                                          10

SEQ ID NO: 79            moltype = AA   length = 10
FEATURE                  Location/Qualifiers
source                   1..10
                         mol_type = protein
                         organism = synthetic construct
SEQUENCE: 79
GGGGSGGGGS                                                          10

SEQ ID NO: 80            moltype = AA   length = 5
FEATURE                  Location/Qualifiers
source                   1..5
                         mol_type = protein
                         organism = synthetic construct
SEQUENCE: 80
DYVIN                                                                5
```

```
SEQ ID NO: 81              moltype = AA  length = 17
FEATURE                    Location/Qualifiers
source                     1..17
                           mol_type = protein
                           organism = synthetic construct
SEQUENCE: 81
EIYPGSGTNY YNEKFKA                                                        17

SEQ ID NO: 82              moltype = AA  length = 15
FEATURE                    Location/Qualifiers
source                     1..15
                           mol_type = protein
                           organism = synthetic construct
SEQUENCE: 82
GGGGSGGGGS GGGGS                                                          15

SEQ ID NO: 83              moltype = AA  length = 5
FEATURE                    Location/Qualifiers
source                     1..5
                           mol_type = protein
                           organism = synthetic construct
SEQUENCE: 83
TKGPS                                                                      5

SEQ ID NO: 84              moltype = AA  length = 7
FEATURE                    Location/Qualifiers
source                     1..7
                           mol_type = protein
                           organism = synthetic construct
SEQUENCE: 84
GQPKAAP                                                                    7

SEQ ID NO: 85              moltype = AA  length = 10
FEATURE                    Location/Qualifiers
source                     1..10
                           mol_type = protein
                           organism = synthetic construct
SEQUENCE: 85
GGSGSSGSGG                                                                10

SEQ ID NO: 86              moltype = AA  length = 17
FEATURE                    Location/Qualifiers
source                     1..17
                           mol_type = protein
                           organism = synthetic construct
SEQUENCE: 86
VYACEVTHQG LSSPVTK                                                        17

SEQ ID NO: 87              moltype = AA  length = 8
FEATURE                    Location/Qualifiers
source                     1..8
                           mol_type = protein
                           organism = synthetic construct
SEQUENCE: 87
GYTFSDYV                                                                   8

SEQ ID NO: 88              moltype = AA  length = 7
FEATURE                    Location/Qualifiers
source                     1..7
                           mol_type = protein
                           organism = synthetic construct
SEQUENCE: 88
GYTFSDY                                                                    7

SEQ ID NO: 89              moltype = AA  length = 10
FEATURE                    Location/Qualifiers
source                     1..10
                           mol_type = protein
                           organism = synthetic construct
SEQUENCE: 89
ASGYTFSDYV                                                                10

SEQ ID NO: 90              moltype = AA  length = 8
FEATURE                    Location/Qualifiers
source                     1..8
                           mol_type = protein
                           organism = synthetic construct
SEQUENCE: 90
```

```
IYPGSGTN                                                                               8

SEQ ID NO: 91          moltype = AA  length = 4
FEATURE                Location/Qualifiers
source                 1..4
                       mol_type = protein
                       organism = synthetic construct SEQUENCE: 91
PGSG                                                                                   4

SEQ ID NO: 92          moltype = AA  length = 17
FEATURE                Location/Qualifiers
source                 1..17
                       mol_type = protein
                       organism = synthetic construct SEQUENCE: 92
IYPGSGTNYY NEKFKAK                                                                    17

SEQ ID NO: 93          moltype = AA  length = 13
FEATURE                Location/Qualifiers
source                 1..13
                       mol_type = protein
                       organism = synthetic construct SEQUENCE: 93
ARRGRYGLYA MDY                                                                        13

SEQ ID NO: 94          moltype = AA  length = 9
FEATURE                Location/Qualifiers
source                 1..9
                       mol_type = protein
                       organism = synthetic construct SEQUENCE: 94
GRYGLYAMD                                                                              9

SEQ ID NO: 95          moltype = AA  length = 10
FEATURE                Location/Qualifiers
source                 1..10
                       mol_type = protein
                       organism = synthetic construct SEQUENCE: 95
RGRYGLYAMD                                                                            10

SEQ ID NO: 96          moltype = AA  length = 6
FEATURE                Location/Qualifiers
source                 1..6
                       mol_type = protein
                       organism = synthetic construct SEQUENCE: 96
QDISNY                                                                                 6

SEQ ID NO: 97          moltype = AA  length = 7
FEATURE                Location/Qualifiers
source                 1..7
                       mol_type = protein
                       organism = synthetic construct SEQUENCE: 97
SQDISNY                                                                                7

SEQ ID NO: 98          moltype = AA  length = 8
FEATURE                Location/Qualifiers
source                 1..8
                       mol_type = protein
                       organism = synthetic construct SEQUENCE: 98
ASQDISNY                                                                               8

SEQ ID NO: 99          moltype =     length =
SEQUENCE: 99
000

SEQ ID NO: 100         moltype =     length =
SEQUENCE: 100
000

SEQ ID NO: 101         moltype = AA  length = 12
FEATURE                Location/Qualifiers
source                 1..12
                       mol_type = protein
                       organism = synthetic construct
```

```
SEQUENCE: 101
YTSRLHSGVP SR                                                    12

SEQ ID NO: 102          moltype = AA   length = 10
FEATURE                 Location/Qualifiers
source                  1..10
                        mol_type = protein
                        organism = synthetic construct
SEQUENCE: 102
QQGNTRPWTF                                                       10

SEQ ID NO: 103          moltype = AA   length = 6
FEATURE                 Location/Qualifiers
source                  1..6
                        mol_type = protein
                        organism = synthetic construct
SEQUENCE: 103
GNTRPW                                                            6

SEQ ID NO: 104          moltype = AA   length = 6
FEATURE                 Location/Qualifiers
source                  1..6
                        mol_type = protein
                        organism = synthetic construct
SEQUENCE: 104
GNTRPW                                                            6

SEQ ID NO: 105          moltype = AA   length = 12
FEATURE                 Location/Qualifiers
source                  1..12
                        mol_type = protein
                        organism = synthetic construct
SEQUENCE: 105
GPSVFPLAPS SK                                                    12

SEQ ID NO: 106          moltype = AA   length = 17
FEATURE                 Location/Qualifiers
source                  1..17
                        mol_type = protein
                        organism = synthetic construct
SEQUENCE: 106
TTPPVLDSDG SFFLYSK                                               17

SEQ ID NO: 107          moltype = DNA   length = 45
FEATURE                 Location/Qualifiers
source                  1..45
                        mol_type = other DNA
                        organism = synthetic construct
SEQUENCE: 107
tacgactcac aagcttgccg ccaccatgtc ttccacactc cctgc                45

SEQ ID NO: 108          moltype = DNA   length = 57
FEATURE                 Location/Qualifiers
source                  1..57
                        mol_type = other DNA
                        organism = synthetic construct
SEQUENCE: 108
ccgccccgac tctagatcaa tggtgatggt ggtgatgatt ctgggcagtg tgatccc   57

SEQ ID NO: 109          moltype = DNA   length = 45
FEATURE                 Location/Qualifiers
source                  1..45
                        mol_type = other DNA
                        organism = synthetic construct
SEQUENCE: 109
tacgactcac aagcttgccg ccaccatgtc ttccacactc cgtgc                45

SEQ ID NO: 110          moltype = DNA   length = 62
FEATURE                 Location/Qualifiers
source                  1..62
                        mol_type = other DNA
                        organism = synthetic construct
SEQUENCE: 110
ccgccccgac tctagatcac ttgtcatcgt catctttgta atcattctgg gcagtgtggt 60
cc                                                               62
```